United States Patent
Pullen et al.

(10) Patent No.: US 10,259,872 B2
(45) Date of Patent: Apr. 16, 2019

(54) ANTIBODIES TO MADCAM

(71) Applicants: Pfizer Inc., New York, NY (US);
Amgen Fremont Inc., Thousand Oaks, CA (US)

(72) Inventors: Nicholas Pullen, Sandwich (GB);
Elizabeth Molloy, Sandwich (GB);
Sirid-Aimee Kellermann, Menlo Park, CA (US); Larry L. Green, San Francisco, CA (US); Mary Haak-Frendscho, Newark, CA (US)

(73) Assignees: Pfizer, Inc., New York, NY (US);
Amgen Fremont, Inc., Fremont, CA (US)

( * ) Notice: Subject to any disclaimer, the term of this patent is extended or adjusted under 35 U.S.C. 154(b) by 0 days.

(21) Appl. No.: 15/086,930

(22) Filed: Mar. 31, 2016

(65) Prior Publication Data
US 2017/0051057 A1    Feb. 23, 2017

Related U.S. Application Data

(62) Division of application No. 11/031,485, filed on Jan. 7, 2005, now Pat. No. 9,328,169.

(60) Provisional application No. 60/535,490, filed on Jan. 9, 2004.

(51) Int. Cl.
| | |
|---|---|
| *C12P 21/00* | (2006.01) |
| *C12N 5/20* | (2006.01) |
| *C07K 16/28* | (2006.01) |
| *G01N 33/569* | (2006.01) |
| *G01N 33/68* | (2006.01) |
| *A61K 39/00* | (2006.01) |
| *C07K 14/705* | (2006.01) |

(52) U.S. Cl.
CPC ... *C07K 16/2803* (2013.01); *G01N 33/56972* (2013.01); *G01N 33/6854* (2013.01); *A61K 2039/505* (2013.01); *C07K 14/70503* (2013.01); *C07K 2317/21* (2013.01); *C07K 2317/33* (2013.01); *C07K 2317/34* (2013.01); *C07K 2317/51* (2013.01); *C07K 2317/515* (2013.01); *C07K 2317/56* (2013.01); *C07K 2317/565* (2013.01); *C07K 2317/76* (2013.01); *C07K 2317/92* (2013.01); *G01N 2333/70503* (2013.01); *G01N 2333/70546* (2013.01)

(58) Field of Classification Search
None
See application file for complete search history.

(56) References Cited

U.S. PATENT DOCUMENTS

| | | | |
|---|---|---|---|
| 4,399,216 A | 8/1983 | Axel et al. | |
| 4,510,245 A | 4/1985 | Cousens et al. | |
| 4,634,665 A | 1/1987 | Axel et al. | |
| 4,740,461 A | 4/1988 | Kaufman | |
| 4,912,040 A | 3/1990 | Kaufman et al. | |
| 4,959,455 A | 9/1990 | Clark et al. | |
| 4,968,615 A | 11/1990 | Koszinowski et al. | |
| 5,151,510 A | 9/1992 | Stec et al. | |
| 5,168,062 A | 12/1992 | Stinski | |
| 5,179,017 A | 1/1993 | Axel et al. | |
| 5,223,409 A | 6/1993 | Ladner et al. | |
| 5,530,101 A | 6/1996 | Queen et al. | |
| 5,545,807 A | 8/1996 | Surani et al. | |
| 5,545,806 A | 9/1996 | Lonberg et al. | |
| 5,585,089 A | 12/1996 | Queen et al. | |
| 5,591,669 A | 1/1997 | Krimpenfort et al. | |
| 5,612,205 A | 3/1997 | Kay et al. | |
| 5,625,126 A | 4/1997 | Lonberg et al. | |
| 5,633,425 A | 5/1997 | Lonberg et al. | |
| 5,643,763 A | 7/1997 | Dunn et al. | |
| 5,661,016 A | 8/1997 | Lonberg et al. | |
| 5,693,761 A | 12/1997 | Queen et al. | |

(Continued)

FOREIGN PATENT DOCUMENTS

| | | |
|---|---|---|
| EP | 0216846 | 4/1987 |
| EP | 0256055 | 2/1988 |

(Continued)

OTHER PUBLICATIONS

U.S. Appl. No. 13/871,913, filed Apr. 26, 2013, Pullen.

(Continued)

*Primary Examiner* — Maher M Haddad
(74) *Attorney, Agent, or Firm* — Proskauer Rose LLP; Fangli Chen; Julio J. Mendez

(57) ABSTRACT

The present invention relates to antibodies including human antibodies and antigen-binding portions thereof that specifically bind to MAdCAM, preferably human MAdCAM and that function to inhibit MAdCAM. The invention also relates to human anti-MAdCAM antibodies and antigen-binding portions thereof. The invention also relates to antibodies that are chimeric, bispecific, derivatized, single chain antibodies or portions of fusion proteins. The invention also relates to isolated heavy and light chain immunoglobulins derived from human anti-MAdCAM antibodies and nucleic acid molecules encoding such immunoglobulins. The present invention also relates to methods of making human anti-MAdCAM antibodies, compositions comprising these antibodies and methods of using the antibodies and compositions for diagnosis and treatment. The invention also provides gene therapy methods using nucleic acid molecules encoding the heavy and/or light immunoglobulin molecules that comprise the human anti-MAdCAM antibodies. The invention also relates to transgenic animals or plants comprising nucleic acid molecules of the invention.

8 Claims, 20 Drawing Sheets

Specification includes a Sequence Listing.

(56) References Cited

U.S. PATENT DOCUMENTS

| | | | |
|---|---|---|---|
| 5,693,792 A | 12/1997 | Torii et al. |
| 5,714,350 A | 2/1998 | Co et al. |
| 5,721,367 A | 2/1998 | Kay et al. |
| 5,741,957 A | 4/1998 | Deboer et al. |
| 5,750,172 A | 5/1998 | Meade et al. |
| 5,756,687 A | 5/1998 | Denman et al. |
| 5,770,429 A | 6/1998 | Lonberg et al. |
| 5,777,085 A | 7/1998 | Co et al. |
| 5,789,215 A | 8/1998 | Berns et al. |
| 5,789,650 A | 8/1998 | Lonberg et al. |
| 5,814,318 A | 9/1998 | Lonberg et al. |
| 5,827,690 A | 10/1998 | Meade et al. |
| 5,877,293 A | 3/1999 | Adair et al. |
| 5,886,152 A | 3/1999 | Nakatani et al. |
| 5,916,771 A | 6/1999 | Hori et al. |
| 5,939,598 A | 8/1999 | Kucherlapati et al. |
| 5,959,177 A | 9/1999 | Hein et al. |
| 5,985,615 A | 11/1999 | Jakobovits et al. |
| 5,994,619 A | 11/1999 | Stice et al. |
| 5,998,209 A | 12/1999 | Jokobovits et al. |
| 6,046,037 A | 4/2000 | Hiatt et al. |
| 6,054,297 A | 4/2000 | Carter et al. |
| 6,075,181 A | 6/2000 | Kucherlapati et al. |
| 6,091,001 A | 7/2000 | Jakobovits et al. |
| 6,114,598 A | 9/2000 | Kucherlapati et al. |
| 6,130,364 A | 10/2000 | Jakobovits et al. |
| 6,150,584 A | 11/2000 | Kucherlapati et al. |
| 6,407,213 B1 | 6/2002 | Carter et al. |
| 6,517,529 B1 | 2/2003 | Quinn et al. |
| 6,551,593 B1 | 4/2003 | Ringler et al. |
| 7,932,372 B2 | 4/2011 | Pullen et al. |
| RE45,847 E | 1/2016 | Pullen et al. |
| 2001/0046496 A1 | 11/2001 | Brettman et al. |
| 2002/0065220 A1 | 5/2002 | Young et al. |
| 2002/0147314 A1 | 10/2002 | Briskin et al. |
| 2002/0172679 A1 | 11/2002 | Ringler et al. |
| 2003/0003108 A1 | 1/2003 | Fong et al. |
| 2003/0082182 A1 | 5/2003 | Briskin et al. |
| 2003/0138417 A1 | 7/2003 | Kaisheva et al. |
| 2004/0009169 A1 | 1/2004 | Taylor et al. |
| 2004/0010810 A1 | 1/2004 | Kucherlapati |
| 2005/0232917 A1 | 10/2005 | Pullen |
| 2007/0009536 A1 | 1/2007 | Pullen |
| 2008/0124339 A1 | 5/2008 | Pullen |
| 2008/0248047 A1 | 10/2008 | Chesterfield |
| 2009/0214527 A1 | 8/2009 | Burgess |
| 2009/0214558 A1 | 8/2009 | Pullen |
| 2009/0238820 A1 | 9/2009 | Allan |
| 2010/0119517 A1 | 5/2010 | Burgess |

FOREIGN PATENT DOCUMENTS

| | | |
|---|---|---|
| EP | 0323997 | 7/1989 |
| EP | 0338841 | 10/1989 |
| JP | 2003-089656 | 3/2003 |
| WO | WO-1991010741 | 7/1991 |
| WO | WO-1991017271 | 11/1991 |
| WO | WO-1992001047 | 1/1992 |
| WO | WO-1992002190 | 2/1992 |
| WO | WO-1992009690 | 6/1992 |
| WO | WO-1992015679 | 9/1992 |
| WO | WO-1992018619 | 10/1992 |
| WO | WO-1992020791 | 11/1992 |
| WO | WO-1993001288 | 1/1993 |
| WO | WO-1993006213 | 4/1993 |
| WO | WO-1994002602 | 2/1994 |
| WO | WO-1994013312 | 6/1994 |
| WO | WO-1996024673 | 8/1996 |
| WO | WO-1996033735 | 10/1996 |
| WO | WO-1996034096 | 10/1996 |
| WO | WO-1997025351 | 7/1997 |
| WO | WO-1998006248 | 2/1998 |
| WO | WO-1998016654 | 4/1998 |
| WO | WO-1998024893 | 6/1998 |
| WO | WO-1998050433 | 11/1998 |
| WO | WO-1999045031 | 9/1999 |
| WO | WO-1999053049 | 10/1999 |
| WO | WO-1999058573 | 11/1999 |
| WO | WO-2000009560 | 2/2000 |
| WO | WO-2000037504 | 6/2000 |
| WO | WO-2001018176 | 3/2001 |
| WO | WO-2001078779 | 10/2001 |
| WO | WO-1997007671 | 11/2002 |
| WO | WO-2003039485 | 5/2003 |
| WO | WO-2003072040 | 9/2003 |
| WO | WO-2004081049 | 9/2004 |
| WO | WO-2004091658 | 10/2004 |
| WO | WO-2005076843 | 8/2005 |
| WO | WO-2006096488 | 9/2006 |

OTHER PUBLICATIONS

Altschul et al., "Basic local alignment search tool," *Journal Molecular Biology*, 215(1):403-410 (1990).

Ben-Horin et al., "Characterizing the circulating, gliadin-specific CD4+ memory T cells in patients with celiac disease: linkage between memory function, gut homing and Th1 polarization" *Journal of Leukocyte Biology*, 79(4):676-685 (2006).

Berlin et al., "α4 integrins mediate lymphocyte attachment and rolling under physiologic flow," *Cell*, 80:413-422 (1995).

Berlin et al., "α4β7 integrin mediates lymphocyte binding to the mucosal vascular addressin MAdCAM-1," *Cell*, 74:185-195 (1993).

Bird et al., "Single-chain antigen-binding proteins," *Science*, 242:423-426 (1988).

Bowie et al., "A method to identify protein sequences that fold into a known three-dimensional structure," *Science*, 253:164-170 (1991).

Briskin et al., "Human mucosal addressin cell adhesion molecule-1 is preferentially expressed in intestinal tract and associated lymphoid tissue," *American Journal of Pathology*, 151(1):97-110 (1997).

Celsa, "Written Description: Antibodies," presentation from Biotechnology/Chemical/Pharmaceutical Customer Partnership meeting, Tuesday, Jun. 2, 2009, United States Patent and Trademark Office, Madison Auditorium.

Chan et al, "Adhesion to vascular cell adhesion molecule 1 and fibronectin," *The Journal of Biological Chemistry*, 267(12)8366-8270 (1992).

Cheroutre, H. et al., "Acquired and Natural Memory T Cells Join Forces at the Mucosal Front Line," *Immunology*, 4(4):290-300 (2004).

Chothia et al., "Canonical structures for the hypervariable regions of immunoglobulins," *Journal of Molecular Biology*, 196:901-917 (1987).

Chothia et al., "Conformations of immunoglobulin hypervariable regions," *Nature*, 342:877-883 (1989).

Clackson et al., "Making antibody fragments using phage display libraries," *Nature*, 352:624-628 (1991).

Coligan et al, "Enzyme-linked immunosorbent assays," *Current Protocols In Immunology*, vol. 1, Unit 2.1:2.1.1-2.1.22, John Wiley & Sons, Inc. (1994).

Connor et al., "Expression of mucosal addressin cell adhesion molecule-1 (MAdCAM-1) in acute and chronic inflammation," *Journal of Leukocyte Biology*, 65:349-355 (1999).

Depascalis et al., "Grafting of "abbreviated" complementarity-determining regions containing specificity-determining residues essential for ligand contact to engineer a less immunogenic humanized monoclonal antibody," Journal of Immunology, 169(6):3076-3084 (2002).

Dubroc et al., "Selective a4β7 Integrin Antagonists and Their Potential as Antiinflammatory Agents," *Journal of Medicinal Chemistry*, 45:3451-3457 (2002).

Erle et al., "Expression and function of the MAdCAM-1 receptor, integrin α4β7, on human leukocytes," *The Journal of Immunology*, 153:517-528 (1994).

Evans et al., "Design of nonpeptidal ligands for a peptide receptor: Cholecystokinin antagonists," *Journal of Medicinal Chemistry*, 30:1229-1239 (1987).

Fanger et al., "Production and use of anti-FcR bispecific antibodies," *Immunomethods*, 4:72-81 (1994).

(56) References Cited

OTHER PUBLICATIONS

Fauchere, "Elements for the rational drug design of peptides drugs," *Advances in Drug Research*, 15:29-69 (1986).

Fernekorn, U. et al., "Functional Involvement of P-Selectin and MAdCAM-1 in the Recruitment of a 4β7-Integrin-Expressing Monocyte-Like Cells to the Pregnant Mouse Uterus," *European Journal of Immunology*, 34:3423-3433 (2004).

Fuchs et al., "Targeting recombinant antibodies to the surface of *Escherichia coli*: fusion to a peptidoglycan associated lipoprotein," *Biotechnology*, 9:1369-1372 (1991).

Fujimori et al., "Intravital observation of lymphocyte migration in lamina propria of mouse small intestine," *Digestive Organ and Mucosal Immunology*, 35:92-94 (1998).

Fujisaki et al., "Expression of mucosal addressin cell adhesion molecule-1 (MAdCAM-1) during small-bowel graft rejection in rates," *Scandinavian Journal of Gastroenterology*, 38:437-442 (2003).

Galfre et al., "Preparation of monoclonal antibodies: strategies and procedures," *Methods in Enzymology*, 73:3-46 (1981).

Garrard et al., "$F_{ab}$ assembly and enrichment in a monovalent phage display system," *Biotechnology*, 9:1373-1377 (1991).

Ghosh, "Therapeutic value of alpha-4 integrin blockade in inflammatory bowel disease: the role of natalizumab,." *Expert Opinion on Biological Therapy*, 3(6):995-1000 (2003).

Gonnet et al., "Exhaustive matching of the entire protein sequence database," *Science*, 256:1443-1445 (1992).

Gram et al., "In vitro selection and affinity maturation of antibodies from a naive combinatorial immunoglobulin library," *PNAS*, 89:3576-3580 (1992).

Grant et al., "MAdCAM-1 expressed in chronic inflammatory liver disease supports mucosal lymphocyte adhesion to hepatic endothelium (MAdCAM-1 in chronic inflammatory liver disease)," *Hepatology*, 33:1065-72 (2001).

Green et al., "Antibody engineering via genetic engineering of the mouse: XenoMouse strains are a vehicle for the facile generation of therapeutic human monoclonal antibodies," *Journal of Immunological Methods*, 231:11-23 (1999).

Green et al., "Antigen-specific human monoclonal antibodies from mice engineered with human Ig heavy and light chain YACs," *Nature Genetics*, 7:13-21 (1994).

Green et al., "Regulation of B cell development by variable gene complexity in mice reconstituted with human immunoglobulin yeast artificial chromosomes," *Journal of Experimental Medicine*, 188(3):483-495 (1998).

Griffiths et al., "Human anti-self antibodies with high specificity from phage display libraries," *The EMBO Journal*, 12(2):725-734 (1993).

Hanninen et al., "Mucosal addressin is required for the development of diabetes in nonobese diabetic mice," *The Journal of Immunology*, 160:6018-6025 (1998).

Hatanaka et al., "Increased expression of mucosal addressin cell adhesion molecule-1 (MAdCAM-1) and lymphocyte recruitment in murine gastritis induced by *Helicobacter pylori*," *Clinical and Experimental Immunology*, 130(2):183-189 (2002).

Hawkins et al., "Selection of phage antibodies by binding affinity mimicking affinity maturation," *Journal of Molecular Biology*, 226:889-896 (1992).

Hay et al., "Bacteriophage cloning and *Escherichia coli* expression of a human IgM Fab," *Human Antibodies & Hybridomas*, 3:81-85 (1992).

Hesterberg et al., Rapid resolution of chronic colitis in the cotton-top tamarin with an antibody to a gut-homing integrin α4β7, *Gastroenterology*, 111:1373-1380 (1996).

Hillan et al., Expression of the mucosal vascular addressin, MAdCAM-1, inflammatory liver disease, *Liver*, 19:509-518 (1999).

Hokari et al., "Involvement of mucosal addressin in cell adhesion molecule-1 (MAdCAM-1) in the pathogenesis of granulomatous colitis in rats," *Clinical and Experimental Immunology*, 126(2):259-265 (2001).

Holliger et al., "Diabodies: small bivalent and bispecific antibody fragments," *PNAS*, 90:6444-6448 (1993).

Hoogenboom et al., "Multi-subunit proteins on the surface of filamentous phage: methodologies for displaying antibody (Fab) heavy and light chains," *Nucleic Acids Research*, 19(15):4133-4137 (1991).

Huse et al., "Generation of a large combinatorial library of the immunoglobulin repertoire in phage lambda," *Science*, 246:1275-1281 (1989).

Huston et al., "Protein engineering of antibody binding sites: Recovery of specific activity in an anti-digoxin single-chain Fv analogue produced in *Escherichia coli*," *PNAS*, 85:5879-5883 (1988).

Iizuka et al., "Expression of GALT-specific adhesion molecule MAdCAM-1 in rat intestinal trace," *Digestive Organ and Mucosal Immunology*, 36:39-42 (1999).

Ill et al., "Design and construction of a hybrid immunoglobulin domain with properties of both heavy and light chain variable regions," *Protein Engineering*, 10(8):949-957 (1997).

Johnsson et al., "Comparison of methods for immobilization to carboxymethyl dextran sensor surfaces by analysis of the specific activity of monoclonal antibodies," *Journal of Molecular Recognition*, 8:125-131 (1995).

Johnsson et al., "Immobilization of proteins to a carboxymethyldextran-modified gold surface for biospecific interaction analysis in surface plasmon resonance sensors," *Analytical Biochemistry*, 198:268-277 (1991).

Jonsson et al., "Introducing a biosensor based technology for real-time biospecific interaction analysis," *Annales Biologie Clinique*, 51:19-26 (1993).

Jonsson et al., "Real-time biospecific interaction analysis using surface plasmon resonance and a sensor chip technology," *BioTechniques*, 11(5):620-627 (1991).

Kanwar et al., "Prevention of a chronic progressive form of experimental autoimmune encephalomyelitis by an antibody against mucosal addressin cell adhesion molecule-1, given early in the course of disease progression," *Immunology and Cell Biology*, 78:641-645 (2000).

Kato et al., "Amelioration of murine experimental colitis by inhibition of mucosal addressin cell adhesion molecule-$1^1$," *Journal of Pharmacology and Experimental Therapeutics*, 295(1):183-'89 (2000).

Kawashima, H. et al., "Lymphocyte homing and adhesion molecules," *Ann. Rev. Immunology*, pp. 139-147 (1996).

Klimka et al., "Human anti-CD30 recombinant antibodies by guided phage antibody selection using cell panning," *British Journal of Cancer*, 83(2):252-260 (2000).

Koseki, S. et al., "Examination of Intraepithelial Lymphocyte Adhesion to Microvessels in Small Intestine," *J. Keio Med. Soc.*, 79(3):T407-T419 (2002).

Kraal et al., Expression of the mucosal vascular addressin, MAdCAM-1, on sinus-lining cells in the spleen, *American Journal of Pathology*, 147(3):763-771 (1995).

Laplanche et al., "Phosphorothioate-modified oligodeoxyribonucleotides, III. NMR and UV spectroscopic studies of the $R_p$-$R_p$, $S_p$-$S_p$, and $R_p$-$S_p$ duplexes, [d($GG_5$AATTCC)]$_2$, derived from diastereomeric O-ethyl phosphorothioates," *Nucleic Acids Research*, 14(22):9081-9093 (1986).

Leung et al., "Bioassay detects soluble MAdCAM-1 in body fluids" *Immunology and Cell Biology*, 82(4):400-409 (2004).

MacCallum et al., "Antibody-antigen interactions: contact analysis and binding site topography," Journal of Molecular Biology, 262(5):732-745 (1996).

Marks et al., "Oligonucleotide primers for polymerase chain reaction amplification of human immunoglobulin variable genes and design of family-specific oligonucleotide probes." *European Journal of Immunology*, 21:985-991 (1991).

Martin et al., "Mechanistic population pharmacokinetics (PK) model of PF-00547659, a fully human IgG2 anti-MAdCAM antibody, in ulcerative colitis patients: results of a first in human (FIH) study," Poster presented at American Gastroenterological Association (AGA) Digestive Disease Week, Chicago IL, Jun. 3, 2009.

Martin et al., "The affinity-selection of a minibody polypeptide inhibitor of human interleukin-6," *The EMBO Journal*, 13(22):5303-5309 (1994).

McCafferty et al., "Phage antibodies: filamentous phage displaying antibody variable domains," *Nature*, 348:552-554 (1990).

(56) References Cited

OTHER PUBLICATIONS

Mendez et al., "Functional transplant of megabase human immunoglobulin loci recapitulates human antibody response in mice," *Nature Genetics*, 15:146-156 (1997).

Miura, S. et al., "Protection of Small Intestinal Mucosa and Migration of Lymphoid Cells,"*J. Jap. Soc. Gastroenterology*, 103:275-282 (2006).

Murai et al., "Peyer's patch is the essential site in initiating murine acute and lethal graft-versus-host reaction," *Nature Immunology*, 4(2):154-160 (2003).

Nakache et al., "The mucosal vascular addressin is a tissue-specific endothelial cell adhesion molecule for circulating lymphocytes," *Nature*, 337(12):179-181 (1989).

Noy et al., "Mucosal Addressin Cell Adhesion Molecule (MAdCAM) Is Not Expressed in Normal and MS Brain Tissue," W1209 Poster presented at American Gastroenterological Association (AGA) Digestive Disease Week, Chicago IL, Jun. 3, 2009.

Ogawa et al., "Chronic allergy to dietary ovalbumin induces lymphocyte migration to rat small intestinal mucosa that is inhibited by MAdCAM-1," American Journal of Physiology: Gastrointestinal and Liver Physiology 286(5):G702-G710 (2004).

Pachynski, R., et al., "Secondary Lymphoid-Tissue Chemokine (SLC) Stimulates Integrin $\alpha_4\beta_7$-Mediated Adhesion of Lymphocytes to Mucosal Addresssin Cell Adhesion Molecule-1 (MAdCAM-1) Under Flow," *The Journal of Immunology*, 16(2):952-956 (1998).

Pearson, "Effective protein sequence comparison," *Methods in Enzymology*, 266:227-258 (1996).

Pearson, "Empirical statistical estimates for sequence similarity searches," *Journal of Molecular Biology*, 276:71-84 (1998).

Pearson, "Flexible sequence similarity searching with the FASTA3 program package," *Methods in Molecular Biology*, 132:185-219 (2000).

Pearson, "Rapid and sensitive sequence comparison with FASTP and FASTA," *Methods in Enzymology*, 183:63-98 (1990).

Pearson, "Using the FASTA program to search protein and DNA sequence databases," *Methods in Molecular Biology*, 24:307-331 (1994).

Picarella et al., "Monoclonal antibodies specific for $\beta_7$ integrin and mucosal addressin cell adhesion molecule-1 (MAdCAM-1) reduce inflammation in the colin of scid mice reconstituted with CD45RB$^{high}$ CD4+ T cells," *The Journal of Immunology*, 158:2099-2106 (1997).

Poljak, "Production and structure of diabodies," *Structure*, 2:1121-1123 (1994).

Portolano et al., "Lack of promiscuity in autoantigen-specific H and L chain combinations as revealed by human H and L chain "roulette"," Journal of Immunology, 150(3):880-887 (1993).

Pullen et al., "Pharmacological characterization of PF-00547659, an anti-human MAdCAM monoclonal antibody," British Journal of Pharmacology, 157:281-293.

Reineke et al., "Antigen sequence- and library-based mapping of linear and discontinuous protein-protein-interaction sites by spot synthesis," *Current Topics in Microbiology and Immunology*, 243: 23-36 (1999).

Riechmann et al., "Reshaping human antibodies for therapy," Nature, 332(6162):323-327 (1988).

Rizo et al., "Constrained peptides: models of bioactive peptides and protein substructures," *Annual Review of Biochemistry*, 61:387-418 (1992).

Rott, L. S. et al., "A Fundamental Subdivision of Circulating Lymphocytes Defined by Adhesion to Mucosal Addressin Cell Adhesion Molecule-1," *The Journal of Immunology*, 156:3737-3736 (1996).

Shigematsu et al., "MAdCAM mediates lymphocyte-endothelial cell adhesion in a murine model of chronic colitis," *American Journal of Physiology—Gastrointestinal and Liver Physiology*, 281:G1309-G1315 (2001).

Shyjan et al., Human mucosal addressin cell adhesion molecule-1 (MAdCAM-1) demonstrates structural and functional similarities to the $\alpha_4\beta_7$-integrin binding domains of murine MAdCAM-1, but extreme divergence of mucin-like sequences, *The Journal of Immunology*, 156,2851-2857 (1996).

Simmons, "Cloning cell surface molecules by transient expression in mammalian cells," *Cellular Interactions in Development: A Practical Approach*, 93-127 (D.A. Hartley, Ed., Oxford University Press, Oxford, England) (1993).

Souza et al., "Expression of lymphocyte-endothelial receptor-ligand pairs, $\alpha 4\beta 7$/MAdCAM-1 and OX40/OX40 ligand in the colon and jejunum of patients with inflammatory bowel disease," *Gut*, 45:856-863 (1999).

Stalder et al., "Late-onset chronic inflammatory encephalopathy in immune-competent and severe combined immune-deficient (SCID) mice with astrocyte-targeted expression of tumor necrosis factor," *American Journal of Pathology*, 153(3):767-883 (1998).

Stec et al., "Automated solid-phase synthesis, separation, and stereochemistry of phosphorothioate analogues of oligodeoxyribonucleotides," *Journal of the American Chemical Society*, 106(20):6077-6079 (1984).

Stein et al., "Physiochemical properties of phosphorothioate oligodeoxynucleotides," *Nucleic Acids Research*, 16(8):3209-3221 (1988).

Streeter et al., "A tissue-specific endothelial cell molecule involved in lymphocyte homing," *Nature*, 331:41-46 (1988).

Thornton et al., "Prediction of progress at last," *Nature*, 354(14):105-106 (1991).

Tidswell, M., et al., "Structure-Function Analysis of the Integrin $\beta_7$ Subunit Identification of Domains Involved in Adhesion to MAdCAM-1," *Journal of Immunology*, 159(3): 1497-1505 (1997).

Tomlinson et al., "The repertoire of human germline $V_H$ sequences reveals about fifty groups of $V_H$ segments with different hypervariable loops," *The Journal of Molecular Biology*, 227:776-798 (1992).

Tomlinson et al., "The structural repertoire of the human $V_k$ domain," *The EMBO Journal*, 14(18)4628-4638 (1995).

Tomlinson, et al, "Human immunoglobulin $V_H$ and D segments on chromosomes 15q11.2 and 16p11.2," *Human Molecular Genetics*, 3(6):853-860 (1994).

Traunecker et al., "Bispecific single chain molecules (Janusins) target cytotoxic lymphocytes on HIV infected cells," *The EMBO Journal*, 10(12):3655-3659 (1991).

Traunecker et al., "Janusin: new molecular design for bispecific reagents," *International Journal of Cancer*, 7:51-52 (1992).

Uhlmann et al., "Antisense oligonucleotides: a new therapeutic principle," *Chemical Reviews*, 90(4):543-584 (1990).

Veber et al., "The design of metabolically-stable peptide analogs," *TINS*, 8(9):392-396 (1985).

Vermeire et al., "Safety and Efficacy of Pf-00547,659, a Fully Human Anti-MAdCAM Antibody, in Ulcerative Colitis. Results of a First in Human Study," No. 861 Presentation presented at American Gastroenterological Association.

Vermeire et al., "The mucosal addressin cell adhesion molecule antibody PF-00547,659 in ulcerative colitis: a randomised study," Gut, 60(8):1068-1075 (2011).

Walsh et al., "Integrin $\alpha_4\beta_7$ mediates human eosinophil interaction with MAdCAM-1, VCAM-1 and fibronectin," *Immunology*, 89:112-119 (1996).

Ward et al., "Binding activities of a repertoire of single immunoglobulin variable domains secreted from *Escherichia coli*," *Nature*, 341:544-546 (1989).

Winter et al., "Humanized antibodies," *Immunology Today*, 14(6):243-246 (1993).

Wright et al., "Genetically engineered antibodies: progress and prospects," *Critical Reviews in Immunology*, 12:(3,4)125-168 (1992).

Yang et al., Involvement of $\beta_7$ integrin and mucosal addressin cell adhesion molecule-1 (MAdCAM-1) in the development of diabetes in nonobese diabetic mice, *Diabetes*, 46:1542-1547 (1997).

Zon et al., "Phosphorothioate oligonucleotides," *Oligonucleotides and Analogues: A Practical Approach*, 87-108 (F. Eckstein, Ed., Oxford University Press, Oxford England (1991).

Zon et al., "Phosphorothioate oligonucleotides: chemistry, purification, analysis, scale-up and future directions," *Anti-Cancer Drug Design*, 6:539-568 (1991).

(56) References Cited

OTHER PUBLICATIONS

Allavena et al., CNS Elevation of Vascular and Not Mucosal Addressin Cell Adhesion Molecules in Patients with Multiple Sclerosis, American Journal of Pathology, 176 (2):556-62 (2009).

Altschul et al., "Basic local alignment search tool," *Journal of Molecular Biology*, 215(1):403-410 (1990).

Altschul et al., "Gapped BLAST and PSI-BLAST: a new generation of protein database search programs," *Nucleic Acids Research*, 25(17):3389-3402 (1997).

Arihiro et al., "Differential expression of mucosal addressin cell adhesion molecule-1 (MAdCAM-1) in ulcerative colitis and Crohn's disease," *Pathology International*, 52:367-374 (2002).

Barbas et al., "Assembly of combinatorial antibody libraries on phage surfaces: The gene III site," *PNAS*, 88:7978-7982 (1991).

Barrett et al, "Homing and adhesion molecules in autoimmune gastritis," *Journal of Leukocyte Biology*, 67:169-73 (2000).

Beiboer et al., "Guided selection of a pan carcinoma specific antibody reveals similar binding characteristics yet structural divergence between the original murine antibody and its human equivalent," Journal of Molecular Biology, 296(3):833-849 (2000).

Ben-Horin et al., "Characterizing the circulating, gliadin-specific CD4+ memory T cells in patients with celiac disease: linkage between memory function, gut homing and Th1 polarization" *Journal of Leukocyte Biology*, 79(4):676-685 (2006).

Figure 1A

```
                    CDR1                                              CDR2
VH3-15 Product   EVQLVESGGGLVKPGGSLRLSCAASGFTFSNAWMSWVRQAPGKGLEWVGRIKSKTDGGTTDYAAPVKGRFTISRDDSKNTLYL
1.7.2 Heavy chain
                 EVQLVESGGGLVKPGGSLRLSCVASGFTFTNAWMIWVRQAPGKGLEWVGRIKRKTDGGTTDYAAPVKGRFTISRDDSKNTLYL
1.8.2 Heavy chain
                 EVQLVESGGGLVKPGGSLRLSCVVSGFTFTNAWMIWVRQAPGKGLEWVGRIKRKTDGGTTDYAAPVKGRFTISRDDSKNTLYL CDR3
VH3-15 Product    QMNSLKTEDTAVYYCTT---VA-DYWGQGTLVTVSSA
1.7.2 Heavy chain QMNSLKTEDTAVYYCTTGGVAEDYWGQGTLVTVSSA
1.8.2 Heavy chain QMNSLKTEDTAVYYCTTGGVAEDYWGQGTLVTVSSA
```

Figure 1B

```
                     CDR1                                              CDR2
VH-3-23 Product   EVQLLESGGGLVQPGGSLRLSCAASGFTFSSYAMSWVRQAPGKGLEWVSAISGSGGSTYYADSVKGRFTISRDNSKNTLYLQM
6.14.2 Heavy chain
                  EVQLLESGGGLVQPGGSLRLSCAASGLTFNNSAMTWVRQAPGKGLEWVSTTSGSGGTTYYADSVKGRFTISRDSPKNTLYLQM CDR3
VH-3-23 Product     NSLRAEDTAVYYCAA-GYSYG-----YWGQGTLVTVSSA
6.14.2 Heavy chain  NSLRAEDTAVYYCAARGYSYGTTPYEYWGQGTLVTVSSA
```

Figure 1C

```
                              CDR1                                                    CDR2
VH3-33 Product    QVQLVESGGGVVQPGRSLRLSCAASGFTFSSYGMHWVRQAPGKGLEWVAVIWYDGSNKYYADSVKGRFTISRDNSKNTLYLQ
6.22.2 Heavy chain QVQLVESGGGVVQPGRSLRLSCAASGHTFSSDGMHWVRQAPGKGLEWVAIIWYDGSNKYYADSVKGRFTISRDNSKNTLYLQ
                                                                 CDR3
VH3-33 Product    MNSLRAEDTAVYYCAR---YYYGMDVWGQGTTVTVSSA
6.22.2 Heavy chain MNSLRAEDTAVYYCARDPGYYYYGMDVWGQGTTVTVSSA
```

Figure 1D

```
                              CDR1                                                    CDR2
VH3-30 Product    QVQLVESGGGVVQPGRSLRLSCAASGFTFSSYGMHWVRQAPGKGLEWVAVISYDGSNKYYADSVKGRFTISRDNSKNTLYLQ
6.34.2 Heavy chain QVQLVESGGGVVQPGRSLRLSCAASGFTFSSYGMHWVRQAPGKGLEWVAVISNDGNNKYYADSVKGRFTISRDNSKNTLYLQ
                                                                 CDR3
VH3-30 Product    MNSLRAEDTAVYYCAR--TVVTYYYYGMDVWGQGTTVTVSSA
6.34.2 Heavy chain MNSLSAEDTAVYYCARDSTAITYYYYGMDVWGQGTTVTVSSA
```

Figure 1E

```
                      CDR1                                              CDR2
VH4-4 Product    QVQLQESGPGLVKPSETLSLTCTVSGGSISSYYWSWIRQPAGKGLEWIGRIYTSGSTNYNPSLKSRVTMSVDTSKNQFSLKL
6.67.1 Heavy chain
                 QVQLQESGPGLVKPSETLSLTCTVSGDSISSNYWSWIRQPAGKGLEWIGRIYTSGGTNSNPSLRGRVTILADTSKNQFSLKL CDR3
VH4-4    Product      SSVTAADTAVYYCAR--ITMVRGVI----FDYWGQGTLVTVSSA
6.67.1 Heavy chain    SSVTAADTAVYYCARDRITIIRGLIPSFFDYWGQGTLVTVSSA
```

Figure 1F

```
                      CDR1                                              CDR2
VH3-23 Product   EVQLLESGGGLVQPGGSLRLSCAASGFTFSSYAMSWVRQAPGKGLEWVSAISGSGGSTYYADSVKGRFTISRDNSKNTLYLQ
6.73.2 Heavy chain
                 EVQLLESGGDLVQPGGSLRLSCAASGFTFRSYAMNWVRQAPGKGLEWVSVISGRGGTTYYADSVKGRFTISRDNSKNTLYLQ CDR3
VH3-23 Product        MNSLRAEDTAVYYCA-IAVA----YYYYGMDVWGQGTTVTVSSA
6.73.2 Heavy chain    MNSLRAEDAAVYYCAKIAVAGEGLYYYYGMDVWGQGTTVTVSSA
```

Figure 1G

```
VH3-21 Product        CDR1                                                           CDR2
                EVQLVESGGGLVKPGGSLRLSCAASGFTFSSYSMNWVRQAPGKGLEWVSSISSSSSYIYYADSVKGRFTISRDNAKNSLYLQMN
6.77.1 Heavy chain
                EVQLVESGGGLVKPGGSLRLSCAASGFTFSSYSMNWVRQAPGKGLEWVSSISSSSSYIYYADSVKGRFTISRDNAKNSLYLQMN CDR3
VH3-21 Product       SLRAEDTAVYYCAR--GYSSGW-YYYYYGMDVWGQGTTVTVSSA
6.77.1 Heavy chain   SLRAEDTAVYYCARDGYSSGWSYYYYYGMDVWGQGTTVTVSSA
```

Figure 1H

```
VH1-18 Product        CDR1                                                              CDR2
                QVQLVQSGAEVKKPGASVKVSCKASGYTFTSYGISWVRQAPGQGLEWMGWISAYNGNTNYAQKLQGRVTMTTDTSTSTAYME
7.16.6 Heavy chain
                QVQLVQSGAEVKKPGASVKVSCKASGYTFTSYGINWVRQAPGQGLEWMGWISVYSGNTNYAQKVQGRVTMTADTSTSTAYMD
7.26.4 Heavy chain
                QVQLVQSGAEVKKPGASVKVSCEASGYTFTSYGIDWVRQAPGQGLEWMGWISVYSGNTNYAQKLQGRVTMSTDTSTSTAYME CDR3
VH1-18 Product       LRSLRSDDTAVYYCAR--SSSS--YYYGMDVWGQGTTVTVSSA
7.16.6 Heavy chain   LRSLRSDDTAVYYCAREGSSSSGDYYYGMDVWGQGTTVTVSSA
7.26.4 Heavy chain   LRSLRSDDTAVYYCAREGSSSSGDYYYGMDVWGQGTTVTVSSA
```

Figure 1I

VH4-4 Product
QVQLQESGPGLVKPSETLSLTCTVSGGSISSYYWSWIRQPAGKGLEWIGRIYTSGSTNYNPSLKSRVTMSVDTSKNQFSLKLSS 7.20.5 Heavy chain
QVQLQESGPGLVKPSETLSLTCTVSGSSISSYHWNWIRQPAGKGLEWIGRIYTSGSTNYNPSLKSRVTMSLDTSKNQFSLKLSS

CDR1                   CDR2

VH4-4 Product    VTAADTAVYYCAR----YYYGSGS-YYGMDVWGQGTTVTVSSA 7.20.5 Heavy chain VTAADTAVYYCAREGVRYRYYASGSYYYGLDVWGQGTTVTVSSA

CDR3

Figure 1J

VH3-33 Product
QVQLVESGGGVVQPGRSLRLSCAASGFTFSSYGMHWVRQAPGKGLEWVAVIWYDGSNKYYADSVKGRFTISRDN 9.8.2 Heavy chain
QVQLVESGGGVVQPGRSLRLSCAASGFTFSSYGMHWVRQAPGKGLEWVAVIWYDGSNEYYADSVKGRFTISRDN

CDR1                  CDR2

VH3-33 Product   SKNTLYLQMNSLRAEDTAVYYCA-----FDYWGQGTLVTVSSA 9.8.2 Heavy chain SKNTLYLQMNSLRAEDTAVYYCARGAYHFAYWGQGTLVTVSSA

CDR3

Figure 1K

```
                                    CDR1                                                         CDR2
A3 Product       DIVMTQSPLSLPVTPGEPASISCRSSQSLLQSNGYNYLDWYLQKPGQSPQLLIYLGSNRASGVPDRFSG
1.7.2 Kappa chain DIVMTQSPLSLPVTPGEPASISCRSSQSLLQSNGYNYLDWYLQKPGQSPQLLIYLGSNRASGVPDRFSG
1.8.2 Kappa chain DIVMTQSPLSLPVTPGEPASISCRSSQSLLQSNGFNYLDWYLQKPGQSPQLLIYLGSNRASGVPDRFSG CDR3
A3 Product       SGSGTDFTLKISRVEAEDVGVYYCMQALQTITFGQGTRLEIKR
1.7.2 Kappa chain SGSGTDFTLKISRVEAEDVGVYYCMQALQTITFGQGTRLEIKR
1.8.2 Kappa chain SGSGTDFTLKISRVEAEDVGVYYCMQALQTITFGQGTRLEIKR
```

Figure 1L

```
                                    CDR1                                                         CDR2
O12 Product       DIQMTQSPSSLSASVGDRVTITCRASQSISSYLNWYQQKPGKAPKVLIFAASSLQSGVPSRFSGS
6.14.2 Kappa chain DIQMTQSPSSLSASVGDRVTITCRASRSISSYLNWYQQKPGKAPKVLIFFVSSLQSGVPSRFSGS CDR3
O12 Product       GSGTDFTLTISSLQPEDFATYYCQQSYSTP-TFGQGTRLEIKR
6.14.2 Kappa chain GSGTDFTLTISSLQPEDFATYYCQQNYIPPITFGQGTRLEIRR
```

Figure 1M

```
                                    CDR1                                                         CDR2
A26 Product       EIVLTQSPDFQSVTPKEKVTITCRASQSIGSSLHWYQQKPDQSPKLLIKYASQSFTGVPSRFSGS
6.22.2 Kappa chain EIVLTQSPDFQSVTPKEKVTITCRASQRIGSSLHWYQQKPDQSPKLLIKYASQSFSGVPSRFSGS CDR3
A26 Product       GSGTDFTLTINSLEAEDAATYYCHQSSSL--TFGGGTKVEIKR
6.22.2 Kappa chain GSGTNFTLTINGLEAEDAATYYCHQSGRLPLTFGGGTKVEIKR
```

Figure 1N

```
                                                         CDR1                                    CDR2
O12 Product        DIQMTQSPSSLSASVGDRVTITCRASQSISSYLNWYQQKPGKAPKLLIYAASSLSQGVPSRFSGS
6.34.2 Kappa chain DIQMTQSPSSLSASVGDRVTITCRASQNISSYLNWFQQKPGKAPKLLIYAASGLKRGVPSRFSGS CDR3
O12 Product        GSGTDFTLTISSLQPEDFATYYCQQSYSTPFTFGPGTKVDIKR
6.34.2 Kappa chain GSGTDFTLTIRTLQPDDFATYSCHQSYSLPFTFGPGTKVDIKR
```

Figure 1O

```
                                                         CDR1                                    CDR2
B3 Product         DIVMTQSPDSLAVSLGERATINCKSSQSVLYSSNNKNYLAWYQQKPGQPPKLLIYWASTRESGVPDRFSGSG
6.67.1 Kappa chain DIVMTQSPDSLAVSLGERATINCKSSQSVLYSSNNKTYLAWYQQKPRQPPKLLIYWASIREYGVPDRFSGSG CDR3
B3 Product         SGTDFTLTISSLQAEDVAVYYCQQYYSTP-LTFGGGTKVEIKR
6.67.1 Kappa chain SGTDFTLTISSLQAEDVAVYFCQQYYSIPPLTFGGGTKVEIKR
```

Figure 1P

```
                              CDR1                                              CDR2
O12 Product          DIQMTQSPSSLSASVGDRVTITCRASQSISSYLNWYQQKPGKAPKLLIYAASSLQSGVPSRFSGSGS
6.73.2 Kappa chain   DIQMTQSPSSLSASVGDRVTFTCRASQNITNYLNWYQQKPGKAPKLLIYAASSLPRGVPSRFRGSGS CDR3
O12 Product          GTDFTLTISSLQPEDFATYYCQQSYSTP----FGQGTTLDIKR
6.73.2 Kappa chain   GTDFTLTISSLQPEDFATYYCQQSYSNPPECGFGQGTTLDIKR
```

Figure 1Q

```
                              CDR1                                              CDR2
A2 Product           DIVMTQTPLSLSVTPGQPASISCKSSQSLLHSDGKTYLYWYLQKPGQPPQLLIYEVSNRFSGVPDRFSGS
6.77.1 Kappa chain   DIVMTQTPLSLSVTPGQPASISCNSSQSLLLSDGKTYLNWYLQKPGQPPQLLIYEVSNRFSGVPDRFSGS CDR3
A2 Product           GSGTDFTLKISRVEAEDVGVYYCMQSIQL---FGQGTKLEIKR
6.77.1 Kappa chain   GSGTDFTLKISRVEAEDVGVYSCMQSIQLMCSFGQGTKLEIKR
```

Figure 1R

```
                              CDR1                                              CDR2
A2 product           DIVMTQTPLSLSVTPGQPASISCKSSQSLLHSDGKTYLYWYLQKPGQPPQLLIYEVSNRFSGVPDRFSGS
7.16.6 Kappa chain   DIVMTQTPLSLSVTPGQPASISCKSSQSLLHTDGTTYLYWYLQKPGQPPQLLIYEVSNRFSGVPDRFSGS
7.26.4 Kappa chain   DIVMTQTPLSLSVTPGQPASISCKSNQSLLYSDGKTYLFWYLQKPGQPPQLLIYEVSNRFSGVPDRFSGS CDR3
A2 product           GSGTDFTLKISRVEAEDVGVYYCMQSIQLPWTFGQGTKVEIKR
7.16.6 Kappa chain   GSGTDFTLKISRVEAEDVGIYYCMQNIQLPWTFGQGTKVEIKR
7.26.4 Kappa chain   GSGTDFTLKISRVEAEDVGVYYCMQSIQLPWTFGQGTKVEIKR
```

Figure 1S

```
                                      CDR1                                              CDR2
A3 Product        DIVMTQSPLSLPVTPGEPASISCRSSQSLLHGNGYNYLDWYLQKPGQSPQLLIYLGSNRASGVPDRFSG
7.20.5 Kappa chain DIVMTQSPLSLPVTPGEPASISCRSSQSLLHGNGYNYLDWYLQKPGQSPQLLIYLGSNRASGVPDRFSG CDR3
A3 Product        SGSGTDFTLKISRVEAEDVGVYYCMQALQTLTFGGGTKVEIKR
7.20.5 Kappa chain SGSGTDFTLKISRVEAEDVGVYYCMQALQTLTFGGGTKVEIKR
```

Figure 1T

```
                                      CDR1                                              CDR2
O18 Product       DIQMTQSPSSLSASVGDRVTITCQASQDISNYLNWYQQKPGKAPKLLIYDASNLETGVPSRFSGS
9.8.2 Kappa chain DIQMTQSPSSLSASVGDRVTITCQASQDISNYLNWYQQKPGKAPKLLIYDASNLETGVPSRFSGS CDR3
O18 Product       GSGTDFTFTISSLQPEDIATYYCQQYDNL-ITTFGQGTRLEIKR
9.8.2 Kappa chain GSGTDFTFTISSLQPEDIATYSCQHSDNLSITTFGQGTRLEIKR
```

Figure 2A

| | |
|---|---|
| 1.7.2 | --MRLPAQLLGLLMLWVS--GSSGDIVMTQSPLSLPVTPGEPASISCRSSQSLLQS-NGY |
| 1.8.2 | --MRLPAQLLGLLMLWVS--GSSGDIVMTQSPLSLPVTPGEPASISCRSSQSLLQS-NGF |
| 7.20.5 | --MRLPAQLLGLLMLWVS--GSSGDIVMTQSPLSLPVTPGEPASISCRSSQSLLHG-NGY |
| 7.16.6 | --MRLPAQLLGLLMLWIP--GSSADIVMTQTPLSLSVTPGQPASISCKSSQSLLHT-DGT |
| 7.26.4 | --MRLPAQLLGLLMLWIP--GSSGDIVMTQTPLSLSVTPGQPASISCKSNQSLLYS-DGK |
| 6.77.1 | --MRLPAQLLGLLMLWIP--GSSADIVMTQTPLSLSVTPGQPASISCNSSQSLLLS-DGK |
| 6.67.1 | --MVLQTQVFISLLLWIS--GAYGDIVMTQSPDSLAVSLGERATINCKSSQSVLYSSNNK |
| 6.34.2 | MDMRVPAQLLGLLLLWLR--GARCDIQMTQSPSSLSASVGDRVTITCRASQNISSY---- |
| 6.73.2 | MDMRVPAQLLGLLLLWLR--GARCDIQMTQSPSSLSASVGDRVTFTCRASQNITNY---- |
| 6.14.2 | MDMRVPAQLLGLLLLWLR--GARCDIQMTQSPSSLSASVGDRVTITCRASRSISSY---- |
| 9.8.2 | MDMRVPAQLLGLLLLWLSVAGARCDIQMTQSPSSLSASVGDRVTITCQASQDISNY---- |
| 6.22.2 | ----MLPSQLIGFLLLWVP--ASRGEIVLTQSPDFQSVTPKEKVTITCRASQRIGSS--- |
| | :  *: :   *::*  **:   * **::*  *     |
| | |
| 1.7.2 | NYLDWYLQKPGQSPQLLIYLGSNRASGVPDRFSGSGSGTDFTLKISRVEAEDVGVYYCMQ |
| 1.8.2 | NYLDWYLQKPGQSPQLLIYLGSNRASGVPDRFSGSGSGTDFTLKISRVEAEDVGVYYCMQ |
| 7.20.5 | NYLDWYLQKPGQSPQLLIYLGSNRASGVPDRFSGSGSGTDFTLKISRVEAEDVGVYYCMQ |
| 7.16.6 | TYLYWYLQKPGQPPQLLIYEVSNRFSGVPDRFSGSGSGTDFTLKISRVEAEDVGIYYCMQ |
| 7.26.4 | TYLFWYLQKPGQPPQLLIYEVSNRFSGVPDRFSGSGSGTDFTLKISRVEAEDVGVYYCMQ |
| 6.77.1 | TYLNWYLQKPGQPPQLLIYEVSNRFSGVPDRFSGSGSGTDFTLKISRVEAEDVGVYSCMQ |
| 6.67.1 | TYLAWYQQKPRQPPKLLIYWASIREYGVPDRFSGSGSGTDFTLTISSLQAEDVAVYFCQQ |

Figure 2A (cont.)

```
6.34.2    --LNWFQQKPGKAPKLLIYAASGLKRGVPSRFSGSGSGTDFTLTIRTLQPDDFATYSCHQ
6.73.2    --LNWYQQKPGKAPKLLIYAASSLPRGVPSRFRGSGSGTDFTLTISSLQPEDFATYCQQ
6.14.2    --LNWYQQKPGKAPKVLIFFVSSLQSGVPSRFSGSGSGTDFTLTISSLQPEDFATYCQQ
9.8.2     --LNWYQQKPGKAPKLLIYDASNLETGVPSRFSGSGSGTDFTFTISSLQPEDIATYSCQH
6.22.2    --LHWYQQKPDQSPKLLIKYASQSFSGVPSRFSGSGSGTNFTLTINGLEAEDAATYYCHQ
            *  *:  ***  :. : *::**                *** :** *******::.*   .    *

1.7.2     ALQT---ITFGQGTRLEIKR
1.8.2     ALQT---ITFGQGTRLEIKR
7.20.5    ALQT---LTFGGGTKVEIKR
7.16.6    NIQLP--WTFGQGTKVEIKR
7.26.4    SIQLP--WTFGQGTKVEIKR
6.77.1    SIQLM--CSFGQGTKLEIKR
6.67.1    YYSIPP-LTFGGGTKVEIKR
6.34.2    SYSLP--FTFGPGTKVDIKR
6.73.2    SYSNPPECGFGQGTTLDIKR
6.14.2    NYIPP--ITFGQGTRLEIRR
9.8.2     SDNLS--ITFGQGTRLEIKR
6.22.2    SGRLP--LTFGGGTKVEIKR
                 ** **  ::*:**
```

Figure 2B

```
7.16.6   QVQLVQSG
7.26.4   QVQLVQSGAEVKKPGASVKVSCEASGYTFTSYGIDWVRQAPGQGLEWMGWIS--VYSGNT
1.7.2    EVQLVESGGGLVKPGGSLRLSCVASGFTFTNAWMIWVRQAPGKGLEWVGRIKRKTDGGTT
1.8.2    EVQLVESGGGLVKPGGSLRLSCVVSGFTFTNAWMIWVRQAPGKGLEWVGRIKRKTDGGTT
6.14.2   EVQLLESGGGLVQPGGSLRLSCAASGLTFNNSAMTWVRQAPGKGLEWVSTTS--GSGGTT
6.73.2   EVQLLESGGDLVQPGGSLRLSCAASGFTFRSYAMNWVRQAPGKGLEWVSVIS--GRGGTT
6.77.1   EVQLVESGGGLVKPGGSLRLSCAASGFTFSSYSMNWVRQAPGKGLEWVSSIS--SSSSYI
6.22.2   QVQLVESGGGVVQPGRSLRLSCAASGHTFSSDGMHWVRQAPGKGLEWVAIIW--YDGSNK
6.34.2   QVQLVESGGGVVQPGRSLRLSCAASGFTFSSYGMHWVRQAPGKGLEWVAVIS--NDGNNK
9.8.2    QVQLVESGGGVVQPGRSLRLSCAASGFTFSSYGMHWVRQAPGKGLEWVAVIW--YDGSNE
7.20.5   QVQLQESGPGLVKPSETLSLTCTVSGGSISSYHWNWIRQPAGKGLEWIGRIY---TSGST
6.67.1   QVQLQESGPGLVKPSETLSLTCTVSGDSISSNYWSWIRQPAGKGLEWIGRIY---TSGGT
         :.***..:**  ::   ::*  .  ** :     *  :** . *.:*****:.    .

7.16.6   NYAQKVQGRVTMTADTSTSTAYMDLRSLRSDDTAVYYCAREG-SS--SSGDYYYGMDVWG
7.26.4   NYAQKLQGRVTMSTDDTSTSTAFFLLRSLRSDDTAVYYCAREG-SS--SSGDYYYGMDVWG
1.7.2    DYAAPVKGRFTISRDDSKNTLYLQMNSLKTEDTAVYYCTTGG------VAEDY-----WG
1.8.2    DYAAPVKGRFTISRDDSKNTLYLQMNSLKTEDTAVYYCTTGG------VAEDY-----WG
6.14.2   YYADSVKGRFTISRDSPKNTLYLQMNSLRAEDTAVYYCAARG-YSYGTTPYEY-----WG
6.73.2   YYADSVKGRFTISRDNSKNTLYLQMNSLRAEDAAVYYCAKIA-VAGEGLYYYG-MDVWG
6.77.1   YYADSVKGRFTISRDNAKNSLYLQMNSLRAEDTAVYYCARDG-YSSGWSYYYYYGMDVWG
6.22.2   YYADSVKGRFTISRDNSKNTLYLQMNSLRAEDTAVYYCARD-------PGYYYG-MDVWG
6.34.2   YYADSVKGRFTISRDNSKNTLYLQMNSLRAEDTAVYYCARD-------ITYYYG-MDVWG
9.8.2    YYADSVKGRFTISRDNSKNTLYLSAEDTAVYYCARDS-TA--ITYYYG-MDVWG
7.20.5   YYADSVKGRFTISRDNSKNTLYLQMNSLRAEDTAVYYCARG-------AYH-FAYWG
6.67.1   NYNPSLKKSRVTMSLDTSKNQFSLKLSSVTAADTAVYYCAREGVRYYYASGSYYYGLDVWG
```

Figure 2B (cont.)

```
6.67.1    NSNPSLRGRVTILADTSKNQFSLKLSSVTAADTAVYYCARD--RITIIRGLIPSFFDYWG
          ::.*.*:  .  *    ..  ..: .. *:.******::              **

7.16.6    QGTTVTVSSA
7.26.4    QGTTVTVSSA
1.7.2     QGTLVTVSSA
1.8.2     QGTLVTVSSA
6.14.2    QGTTVTVSSA
6.73.2    QGTLVTVSSA
6.77.1    QGTTVTVSSA
6.22.2    QGTLVTVSSA
6.34.2    QGTTVTVSSA
9.8.2     QGTTVTVSSA
7.20.5    QGTLVTVSSA
6.67.1    QGTLVTVSSA
          *** *******
```

Figure 3

Domain 1

```
                                                                A                   A'                  B
cyno MAdCAM   MDRGLALLLAGLLGLLQPGCGQSLQVKPLQVEPPEPVVAVALGASRQLTCRLDCADGGAT
human MAdCAM  MDFGLALLLAGLLGLLL---GQSLQVKPLQVEPPEPVVAVALGASRQLTCRLACADRGAS
              **:************    ********************************:*** **:;

C        D         E                  F                     G
cyno MAdCAM   VQWRGLDTSLGAVQSDAGRSVLTVRNASLSAAGTRVCVGSCGGRTFQHTVRLLVYAFPDQ
human MAdCAM  VQWRGLDTSLGAVQSDTGRSVLTVRNASLSAAGTRVCVGSCGGRTFQHTVQLLVYAFPDQ
              ****************:*******************************:.:*********
```

Domain 2

```
               A     A'             B                         C      C'           D
cyno MAdCAM   LTISPAALVPGDPEVACTAHKVTPVDPNALSFSLLLGDQELEGAQALGPEVEEEEE-PQE
human MAdCAM  LTVSPAALVPGDPEVACTAHKVTPVDPNALSFSLLVGGQELEGAQALGPEVQEEEEEPQG
              **:****************************** *.*************:.*:.***  *

E                     F                       G
cyno MAdCAM   EEDVLFRVTERWRLPTLATPVLPALYCQATMRLPGLELSHRQAIPVLH
human MAdCAM  DEDVLFRVTERWRLPPLGTPVPPALYCQATMRLPGLELSHRQAIPVLH
              :*************.*.:** ***************************
```

ANTIBODIES TO MADCAM

This application is a divisional application of U.S. patent application Ser. No. 11/031,485, filed Jan. 7, 2005, now U.S. Pat. No. 9,328,169, issued May 3, 2016, which claims the benefit of U.S. provisional Application 60/535,490, filed Jan. 9, 2004, which applications are incorporated herein by reference in their entirety.

SEQUENCE LISTING

The Sequence Listing associated with this application is provided in text format in lieu of a paper copy, and is hereby incorporated by reference into the specification. The name of the text file containing the Sequence Listing is 000659-0055-101-SL. The text file is 191,159 bytes in size, was created on Mar. 31, 2016, and is being submitted electronically via EFS Web.

BACKGROUND OF THE INVENTION

Mucosal addressin cell adhesion molecule (MAdCAM) is a member of the immunoglobulin superfamily of cell adhesion receptors. The selectivity of lymphocyte homing to specialized lymphoid tissue and mucosal sites of the gastrointestinal tract is determined by the endothelial expression of MAdCAM (Berlin, C. et al., *Cell,* 80:413-422(1994); Berlin, C., et al., *Cell,* 74:185-195 (1993); and Erle, D. J., et al., *J. Immunol.,* 153: 517-528 (1994)). MAdCAM is uniquely expressed on the cell surface of high endothelial venules of organized intestinal lymphoid tissue, such as Peyer's patches and mesenteric lymph nodes (Streeter et al., *Nature,* 331:41-6 (1988); Nakache et al., *Nature,* 337:179-81 (1989); Briskin et al., *Am. J. Pathol.* 151-97-110 (1997)), but also in other lymphoid organs, such as pancreas, gall bladder and splenic venules and marginal sinus of the splenic white pulp (Briskin et al (1997), supra; Kraal et al., *Am. J. Path.,* 147: 763-771 (1995)).

While MAdCAM plays a physiological role in gut immune surveillance, it appears to facilitate excessive lymphocyte extravasation in inflammatory bowel disease under conditions of chronic gastrointestinal tract inflammation. TNFα and other pro-inflammatory cytokines increase endothelial MAdCAM expression and, in biopsy specimens taken from patients with Crohn's disease and ulcerative colitis, there is an approximate 2-3 fold focal increase in MAdCAM expression at sites of inflammation (Briskin et al. (1997), Souza et al., Gut, 45:856-63 (1999); Arihiro et al., *Pathol Int.,* 52:367-74 (2002)). Similar patterns of elevated expression have been observed in experimental models of colitis (Hesterberg et al., Gastroenterology, 111:1373-1380 (1997); Picarella et al., *J. Immunol.,* 158: 2099-2106 (1997); Connor et al., *J Leukoc Biol.,* 65:349-55 (1999); Kato et al., *J Pharmacol Exp Ther.,* 295:183-9 (2000); Hokari et al., *Clin Exp Immunol.,* 26:259-65 (2001); Shigematsu et al., *Am J Physiol Gastrointest Liver Physiol.,* 281:G1309-15 (2001)). In other pre-clinical models for inflammatory conditions, such as insulin-dependent diabetes (Yang et al. *Diabetes,* 46:1542-7 (1997); Hanninen et al., *J Immunol.,* 160:6018-25 (1998)), graft versus host disease (Fujisaki et al., *Scand J Gastroenterol.,* 38:437-42 (2003), Murai et al., *Nat Immunol.,* 4:154-60 (2003)), chronic liver disease (Hillan et al., *Liver,* 19:509-18 (1999); Grant et al., *Hepatology,* 33:1065-72 (2001)), inflammatory encephalopathy (Stalder et al., *Am J Pathol.,* 153:767-83 (1998); Kanawar et al; *Immunol Cell Biol.,* 78:641-5 (2000)), and gastritis (Barrett et al., *J Leukoc Biol.,* 67:169-73 (2000); Hatanaka et al., *Clin Exp Immunol.,* 130:183-9 (2002)), there is also reawakening of fetal MAdCAM expression and participation of activated $\alpha_4\beta_7$-lymphocytes in disease pathogenesis. In these inflammatory models as well as hapten-mediated (e.g., TNBS, DSS, etc.) or adoptive transfer (CD4$^+$CD45Rb$^{high}$) mouse colitic models, the rat anti-mouse MAdCAM monoclonal antibody (mAb), MECA-367, which blocks the binding of $\alpha_4\beta_7^+$ lymphocytes to MAdCAM, reduces the lymphocyte recruitment, tissue extravasation, inflammation and disease severity. Mouse monoclonal antibodies (mAbs) against human MAdCAM also have been reported (see, e.g., WO 96/24673 and WO 99/58573).

Given the role of MAdCAM in inflammatory bowel disease (IBD) and other inflammatory diseases associated with the gastrointestinal tract or other tissues, a means for inhibiting $\alpha_4\beta_7$ binding and MAdCAM-mediated leukocyte recruitment is desirable. It further would be desirable to have such therapeutic means with advantageous properties including but not limited to the absence of unwanted interactions with other medications in patients and favorable physicochemical properties such as pK/pD values in humans, solubility, stability, shelf-life and in vivo half-life. A therapeutic protein, such as an antibody, would advantageously be free of unwanted post-translational modifications or aggregate formation. Accordingly, there is a critical need for therapeutic anti-MAdCAM antibodies.

SUMMARY OF THE INVENTION

The present invention provides an isolated antibody that specifically binds MAdCAM, wherein at least the CDR sequences of said antibody are human CDR sequences, or an antigen-binding portion of said antibody. In some embodiments the antibody is a human antibody, preferably an antibody that acts as a MAdCAM antagonist. Also provided are compositions comprising said antibodies or portions.

The invention also provides a composition comprising the heavy and/or light chain of said anti-MAdCAM antagonist antibody or the variable region or other antigen-binding portion thereof or nucleic acid molecules encoding any of the foregoing and a pharmaceutically acceptable carrier. Compositions of the invention may further comprise another component, such as a therapeutic agent or a diagnostic agent. Diagnostic and therapeutic methods are also provided by the invention.

The invention further provides an isolated cell line, that produces said anti-MAdCAM antibody or antigen-binding portion thereof.

The invention also provides nucleic acid molecules encoding the heavy and/or light chain of said anti-MAdCAM antibody or the variable region thereof or antigen-binding portion thereof.

The invention provides vectors and host cells comprising said nucleic acid molecules, as well as methods of recombinantly producing the polypeptides encoded by the nucleic acid molecules.

Non-human transgenic animals or plants that express the heavy and/or light chain of said anti-MAdCAM antibody, or antigen-binding portion thereof, are also provided.

BRIEF DESCRIPTION OF THE DRAWINGS

FIG. 1 is an alignment of the predicted amino acid sequences of the heavy and kappa light chain variable regions of twelve human anti-MAdCAM monoclonal antibodies with the germline amino acid sequences of the corresponding human genes.

FIG. 1A shows an alignment of the predicted amino acid sequence of the heavy chain for antibodies 1.7.2 and 1.8.2 with the germline human VH 3-15 gene product.

FIG. 1B shows an alignment of the predicted amino acid sequence of the heavy chain for antibody 6.14.2 with the germline human VH 3-23 gene product.

FIG. 1C shows an alignment of the predicted amino acid sequence of the heavy chain for antibody 6.22.2 with the germline human VH 3-33 gene product.

FIG. 1D shows an alignment of the predicted amino acid sequence of the heavy chain for antibody 6.34.2 with the germline human VH 3-30 gene product FIG. 1E shows an alignment of the predicted amino acid sequence of the heavy chain for antibody 6.67.1 with the germline human VH 4-4 gene product.

FIG. 1F shows an alignment of the predicted amino acid sequence of the heavy chain for antibody 6.73.2 with the germline human VH 3-23 gene product.

FIG. 1G shows an alignment of the predicted amino acid sequence of the heavy chain for antibody 6.77.1 with the germline human VH 3-21 gene product.

FIG. 1H shows an alignment of the predicted amino acid sequence of the heavy chain for antibodies 7.16.6 and 7.26.4 with the germline human VH 1-18 gene product.

FIG. 1I shows an alignment of the predicted amino acid sequence of the heavy chain for antibody 7.20.5 with the germline human VH 4-4 gene product.

FIG. 1J shows an alignment of the predicted amino acid sequence of the heavy chain for antibody 9.8.2 with the germline human VH 3-33 gene product.

FIG. 1K shows an alignment of the predicted amino acid sequence of the light kappa chain for antibodies 1.7.2 and 1.8.2 with the germline human A3 gene product.

FIG. 1L shows an alignment of the predicted amino acid sequence of the kappa light chain for antibody 6.14.2 with the germline human O12 gene product.

FIG. 1M shows an alignment of the predicted amino acid sequence of the kappa light chain for antibody 6.22.2 with the germline human A26 gene product.

FIG. 1N shows an alignment of the predicted amino acid sequence of the kappa light chain for antibody 6.34.2 with the germline human O12 gene product.

FIG. 1O shows an alignment of the predicted amino acid sequence of the kappa light chain for antibody 6.67.1 with the germline human B3 gene product.

FIG. 1P shows an alignment of the predicted amino acid sequence of the kappa light chain for antibody 6.73.2 with the germline human O12 gene product.

FIG. 1Q shows an alignment of the predicted amino acid sequence of the kappa light chain for antibody 6.77.1 with the germline human A2 gene product.

FIG. 1R shows an alignment of the predicted amino acid sequence of the kappa light chain for antibodies 7.16.6 and 7.26.4 with the germline human A2 gene product.

FIG. 1S shows an alignment of the predicted amino acid sequence of the kappa light chain for antibody 7.20.5 with the germline human A3 gene product.

FIG. 1T shows an alignment of the predicted amino acid sequence of the kappa light chain for antibody 9.8.2 with the germline human 018 gene product.

FIG. 2 are CLUSTAL alignments of the predicted heavy and kappa light chain amino acid sequences of human anti-MAdCAM antibodies.

FIG. 3 is an amino acid sequence CLUSTAL alignment of the 2 N-terminal domains of cynomolgus and human MAdCAM which form the $\alpha_4\beta_7$ binding domain. The β-strands are aligned according to Tan et al., Structure (1998) 6:793-801.

DETAILED DESCRIPTION OF THE INVENTION

Definitions and General Techniques

Figure 2A:
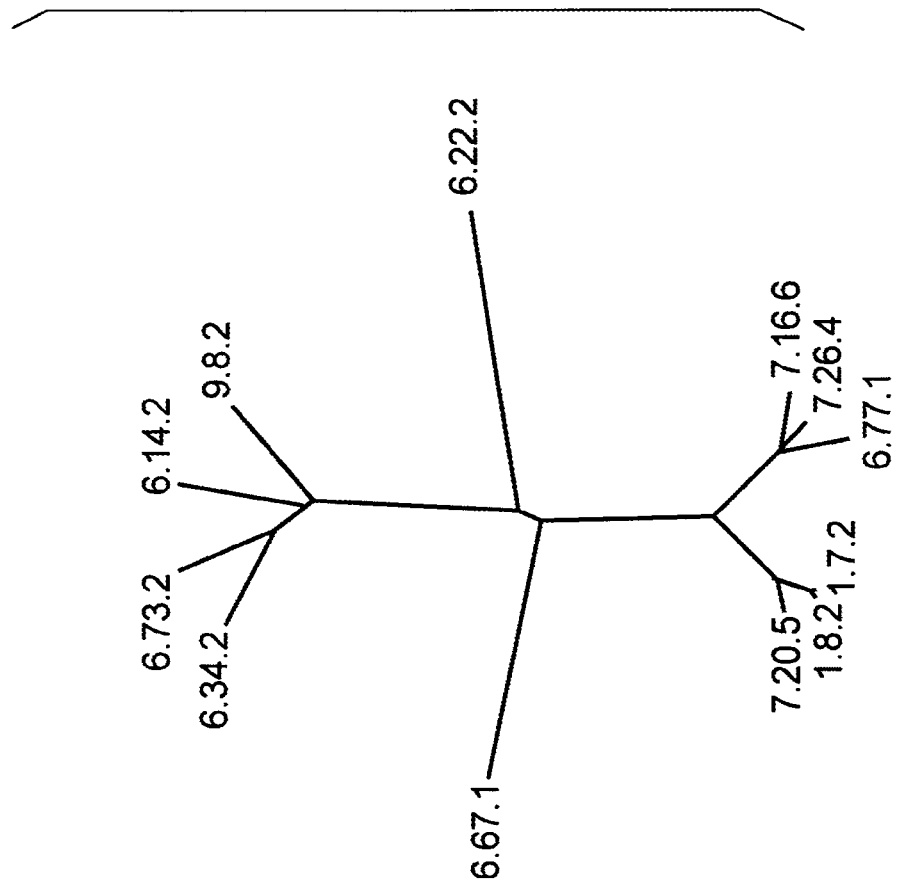
FIG. 2A is a CLUSTAL alignment and radial tree of the predicted kappa light chain amino acid sequences, showing the degree of similarity between the anti-MAdCAM antibody kappa light chains.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics, protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al., *Molecular Cloning: A Laboratory Manual*, 2nd ed., Cold Spring Harbor Laboratory Press, Cold Spring Harbor, N.Y. (1989) and Ausubel et al., *Current Protocols in Molecular Biology*, Greene Publishing Associates (1992), and Harlow and Lane, *Antibodies: A Laboratory Manual*, Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. Standard techniques are used for chemical syntheses, chemical analyses, pharmaceutical preparation, formulation, and delivery, and treatment of patients.

The following terms, unless otherwise indicated, shall be understood to have the following meanings:

The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation (1) is not associated with naturally associated components that accompany it in its native state, (2) is free of other proteins from the same species (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

A protein or polypeptide is "substantially pure," "substantially homogeneous" or "substantially purified" when at least about 60 to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "polypeptide fragment" as used herein refers to a polypeptide that has an amino-terminal and/or carboxy-terminal deletion, but where the remaining amino acid sequence is identical to the corresponding positions in the naturally-occurring sequence. In some embodiments, fragments are at least 5, 6, 8 or 10 amino acids long. In other embodiments, the fragments are at least 14 amino acids long, more preferably at least 20 amino acids long, usually at least 50 amino acids long, even more preferably at least 70, 80, 90, 100, 150 or 200 amino acids long.

The term "polypeptide analog" as used herein refers to a polypeptide that comprises a segment of at least 25 amino acids that has substantial identity to a portion of an amino acid sequence and that has at least one of the following properties: (1) specific binding to MAdCAM under suitable binding conditions, (2) ability to inhibit $\alpha_4\beta_7$ integrin and/or L-selectin binding to MAdCAM, or (3) ability to reduce MAdCAM cell surface expression in vitro or in vivo. Typically, polypeptide analogs comprise a conservative amino acid substitution (or insertion or deletion) with respect to the naturally-occurring sequence. Analogs typically are at least 20 amino acids long, preferably at least 50, 60, 70, 80, 90, 100, 150 or 200 amino acids long or longer, and can often be as long as a full-length naturally-occurring polypeptide.

Preferred amino acid substitutions are those which: (1) reduce susceptibility to proteolysis, (2) reduce susceptibility to oxidation, (3) alter binding affinity for forming protein complexes, (4) alter binding affinities, or (5) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et al., *Nature,* 354:105 (1991), which are each incorporated herein by reference.

Non-peptide analogs are commonly used in the pharmaceutical industry as drugs with properties analogous to those of the template peptide. These types of non-peptide compound are termed "peptide mimetics" or "peptidomimetics". Fauchere, *J. Adv. Drug Res.,* 15:29(1986); Veber and Freidinger, *TINS*, p. 392(1985); and Evans et al., *J. Med. Chem.,* 30:1229(1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a desired biochemical property or pharmacological activity), such as a human antibody, but have one or more peptide linkages optionally replaced by a linkage such as: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

An "immunoglobulin" is a tetrameric molecule. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as κ and λ light chains. Heavy chains are classified as μ, δ, γ, α, or ε, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 or more amino acids. See generally, *Fundamental Immunology*, Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Immunoglobulin chains exhibit the same general structure of relatively conserved framework regions (FR) joined by three hypervariable regions, also called complementarity determining regions or CDRs. The CDRs from the two chains of each pair are aligned by the framework regions to form an epitope-specific binding site. From N-terminus to C-terminus, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md. (1987 and 1991)), or Chothia & Lesk, *J. Mol. Biol.*, 196:901-917(1987); Chothia et al., *Nature*, 342:878-883(1989), each of which is incorporated herein by reference in their entirety.

An "antibody" refers to an intact immunoglobulin or to an antigen-binding portion thereof that competes with the intact antibody for specific binding. In some embodiments, an antibody is an antigen-binding portion thereof. Antigen-binding portions may be produced by recombinant DNA techniques or by enzymatic or chemical cleavage of intact antibodies. Antigen-binding portions include, inter alia, Fab, Fab', F(ab')$_2$, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide. A Fab fragment is a monovalent fragment consisting of the VL, VH, CL and CH1 domains; a F(ab)$_2$ fragment is a bivalent fragment comprising two Fab fragments linked by a disulfide bridge at the hinge region; a Fd fragment consists of the VH and CH1 domains; an Fv fragment consists of the VL and VH domains of a single arm of an antibody; and a dAb fragment (Ward et al., *Nature*, 341:544-546(1989)) consists of a VH domain.

As used herein, an antibody that is referred to as, e.g., 1.7.2, 1.8.2, 6.14.2, 6.34.2, 6.67.1, 6.77.2, 7.16.6, 7.20.5, 7.26.4 or 9.8.2, is a monoclonal antibody that is produced by the hybridoma of the same name. For example, antibody 1.7.2 is produced by hybridoma 1.7.2. An antibody that is referred to as 6.22.2-mod, 6.34.2-mod, 6.67.1-mod, 6.77.1-mod or 7.26.4-mod is a monoclonal antibody whose sequence has been modified from its corresponding parent by site-directed mutagenesis.

A single-chain antibody (scFv) is an antibody in which VL and VH regions are paired to form a monovalent molecule via a synthetic linker that enables them to be made as a single protein chain (Bird et al., *Science*, 242:423-426 (1988) and Huston et al., *Proc. Natl. Acad. Sci. USA*, 85:5879-5883 (1988)). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al., *Proc. Natl. Acad. Sci. USA*, 90: 6444-6448 (1993) and Poljak, R. J., et al., *Structure*, 2:1121-1123 (1994)). One or more CDRs from an antibody of the invention may be incorporated into a molecule either covalently or noncovalently to make it an immunoadhesin that specifically binds to MAdCAM. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a "bispecific" or "bifunctional" antibody (diabody) has two different binding sites.

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature. Examples of isolated antibodies include an anti-MAdCAM antibody that has been affinity purified using MAdCAM, an anti-MAdCAM antibody that has been produced by a hybridoma or other cell line in vitro, and a human anti-MAdCAM antibody derived from a transgenic mammal or plant.

As used herein, the term "human antibody" means an antibody in which the variable and constant region sequences are human sequences. The term encompasses antibodies with sequences derived from human genes, but which have been changed, e.g., to decrease possible immunogenicity, increase affinity, eliminate cysteines or glycosylation sites that might cause undesirable folding, etc. The term encompasses such antibodies produced recombinantly in non-human cells which might impart glycosylation not typical of human cells. The term also encompasses antibodies which have been raised in a transgenic mouse which comprises some or all of the human immunoglobulin heavy and light chain loci.

In one aspect, the invention provides a humanized antibody. In some embodiments, the humanized antibody is an antibody that is derived from a non-human species, in which certain amino acids in the framework and constant domains of the heavy and light chains have been mutated so as to avoid or abrogate an immune response in humans. In some embodiments, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293. In some embodiments, a humanized anti-MAdCAM antibody of the invention comprises the amino acid sequence of one or more framework regions of one or more human anti-MAdCAM antibodies of the invention.

In another aspect, the invention includes a "chimeric antibody". In some embodiments the chimeric antibody refers to an antibody that contains one or more regions from one antibody and one or more regions from one or more other antibodies. In a preferred embodiment, one or more of the CDRs are derived from a human anti-MAdCAM antibody of the invention. In a more preferred embodiment, all of the CDRs are derived from a human anti-MAdCAM antibody of the invention. In another preferred embodiment, the CDRs from more than one human anti-MAdCAM antibody of the invention are mixed and matched in a chimeric antibody. For instance, a chimeric antibody may comprise a CDR1 from the light chain of a first human anti-MAdCAM antibody may be combined with CDR2 and CDR3 from the light chain of a second human anti-MAdCAM antibody, and the CDRs from the heavy chain may be derived from a third anti-MAdCAM antibody. Further, the framework regions may be derived from one of the same anti-MAdCAM antibodies, from one or more different antibodies, such as a human antibody, or from a humanized antibody.

A "neutralizing antibody," "an inhibitory antibody" or antagonist antibody is an antibody that inhibits the binding of $\alpha_4\beta_7$ or $\alpha_4\beta_7$-expressing cells, or any other cognate ligand or cognate ligand-expressing cells, to MAdCAM by at least about 20%. In a preferred embodiment, the antibody reduces inhibits the binding of $\alpha_4\beta_7$ integrin or $\alpha_4\beta_7$-expressing cells to MAdCAM by at least 40%, more preferably by 60%, even more preferably by 80%, 85%, 90%, 95% or 100%. The binding reduction may be measured by any means known to one of ordinary skill in the art, for example, as measured in an in vitro competitive binding assay. An example of measuring the reduction in binding of $\alpha_4\beta_7$-expressing cells to MAdCAM is presented in Example I.

Fragments or analogs of antibodies can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known (Bowie et al., *Science,* 253:164 (1991)).

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al., *Ann. Biol. Clin.,* 51:19-26 (1993); Jonsson, U., et al., *Biotechniques,* 11:620-627 (1991); Johnsson, B., et al., *J. Mol. Recognit.,* 8:125-131 (1995); and Johnnson, B., et al., *Anal. Biochem.,* 198:268-277 (1991).

The term "$k_{off}$" refers to the off rate constant for dissociation of an antibody from the antibody/antigen complex.

The term "$K_d$" refers to the dissociation constant of a particular antibody-antigen interaction. An antibody is said to bind an antigen when the dissociation constant is $\leq 1$ µM, preferably $\leq 100$ nM and most preferably $\leq 10$ nM.

The term "epitope" includes any protein determinant capable of specific binding to an immunoglobulin or T-cell receptor or otherwise interacting with a molecule. Epitopic determinants usually consist of chemically active surface groupings of molecules such as amino acids or carbohydrate side chains and usually have specific three dimensional structural characteristics, as well as specific charge characteristics. An epitope may be "linear" or "conformational." In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another.

As used herein, the twenty conventional amino acids and their abbreviations follow conventional usage. See *Immunology—A Synthesis* (2nd Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes; although oligonucleotides may be double stranded, e.g., for use in the construction of a gene mutant. Oligonucleotides of the invention can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., *Nucl. Acids Res.* 14:9081 (1986); Stec et al., *J. Am. Chem. Soc.* 106:6077(1984); Stein et al., *Nucl. Acids Res.,* 16:3209 (1988); Zon et al., *Anti-Cancer Drug Design* 6:539(1991); Zon et al., *Oligonucleotides and Analogues: A Practical Approach,* pp. 87-108 (F. Eckstein, Ed., Oxford University Press, Oxford England (1991)); Stec et al., U.S. Pat. No. 5,151,510; Uhlmann and Peyman, *Chemical Reviews,* 90:543(1990), the disclosures of which are hereby incorporated by reference. An oligonucleotide can include a label for detection, if desired.

"Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. "High stringency" or "highly stringent" conditions can be used to achieve selective hybridization conditions as known in the art and discussed herein. An example of "high stringency" or "highly stringent" conditions is a method of incubating a polynucleotide with another polynucleotide, wherein one polynucleotide may be affixed to a solid surface such as a membrane, in a hybridization buffer of 6×SSPE or SSC, 50% formamide, 5×Denhardt's reagent, 0.5% SDS, 100 µg/ml denatured, fragmented salmon sperm DNA at a hybridization temperature of 42° C. for 12-16 hours, followed by twice washing at 55° C. using a wash buffer of 1×SSC, 0.5% SDS. See also Sambrook et al., supra, pp. 9.50-9.55.

The term "percent sequence identity" in the context of nucleotide sequences refers to the residues in two sequences which are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.3, Accelrys, San Diego, Calif. FASTA, which includes, e.g., the programs FASTA2 and FASTA3, provides alignments and percent sequence identity of the regions of the best overlap between the query and search sequences (Pearson, *Methods Enzymol.*, 183: 63-98 (1990); Pearson, *Methods Mol. Biol.*, 132: 185-219 (2000); Pearson, *Methods Enzymol.*, 266: 227-258 (1996); Pearson, *J. Mol. Biol.*, 276: 71-84 (1998); herein incorporated by reference). Unless otherwise specified, default parameters for a particular program or algorithm are used. For instance, percent sequence identity between nucleotide sequences can be determined using FASTA with its default parameters (a word size of 6 and the NOPAM factor for the scoring matrix) or using Gap with its default parameters as provided in Wisconsin Package Version 10.3, herein incorporated by reference.

A reference to a nucleotide sequence encompasses its complement unless otherwise specified. Thus, a reference to a nucleic acid molecule having a particular sequence should be understood to encompass its complementary strand, with its complementary sequence.

In the molecular biology art, researchers use the terms "percent sequence identity", "percent sequence similarity" and "percent sequence homology" interchangeably. In this application, these terms shall have the same meaning with respect to nucleotide sequences only.

The term "substantial similarity" or "substantial sequence similarity," when referring to a nucleic acid or fragment thereof, indicates that, when optimally aligned with appropriate nucleotide insertions or deletions with another nucleic acid (or its complementary strand), there is nucleotide sequence identity in at least about 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

As applied to polypeptides, the term "substantial identity" means that two peptide sequences, when optimally aligned, such as by the programs GAP or BESTFIT using default gap weights, share at least 75% or 80% sequence identity, preferably at least 90% or 95% sequence identity, even more preferably at least 98% or 99% sequence identity. Preferably, residue positions that are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, *Methods Mol. Biol.*, 24: 307-31 (1994), herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; and 6) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., *Science*, 256: 1443-45 (1992), herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., Wisconsin package Version 10.3. Polypeptide sequences also can be compared using FASTA using default or recommended parameters, a program in Wisconsin package Version 10.3. FASTA (e.g., FASTA2 and FASTA3) provides alignments and percent sequence identity of the regions of the best overlap between the query and search sequences (Pearson (1990); Pearson (2000)). Another preferred algorithm when comparing a sequence of the invention to a database containing a large number of sequences from different organisms is the computer program BLAST, especially blastp or tblastn, using default parameters. See, e.g., Altschul et al., *J. Mol. Biol.* 215: 403-410 (1990); Altschul et al., *Nucleic Acids Res.* 25:3389-402 (1997); herein incorporated by reference.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

The term "agent" is used herein to denote a chemical compound, a mixture of chemical compounds, a biological macromolecule, or an extract made from biological materials. The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), incorporated herein by reference).

The term "anti-inflammatory" or "immuno-modulatory" agent is used herein to refer to agents that have the functional property of inhibiting inflammation, including inflammatory disease in a subject, including in a human. In various embodiments of this invention, the inflammatory disease may be, but is not limited to inflammatory diseases of the gastrointestinal tract including Crohn's disease, ulcerative colitis, diverticula disease, gastritis, liver disease, primary biliary sclerosis, sclerosing cholangitis. Inflammatory diseases also include but are not limited to abdominal disease (including peritonitis, appendicitis, biliary tract disease), acute transverse myelitis, allergic dermatitis (including allergic skin, allergic eczema, skin atopy, atopic eczema, atopic dermatitis, cutaneous inflammation, inflammatory eczema, inflammatory dermatitis, flea skin, miliary dermatitis, miliary eczema, house dust mite skin), ankylosing spondylitis (Reiters syndrome), asthma, airway inflammation, atherosclerosis, arteriosclerosis, biliary atresia, bladder inflammation, breast cancer, cardiovascular inflammation (including vasculitis, rheumatoid nail-fold infarcts, leg ulcers, polymyositis, chronic vascular inflammation, pericarditis, chronic obstructive pulmonary disease), chronic pancreatitis, perineural inflammation, colitis (including amoebic colitis, infective colitis, bacterial colitis, Crohn's colitis, ischemic colitis, ulcerative colitis, idiopathic proctocolitis, inflammatory bowel disease, pseudomembranous colitis), collagen vascular disorders (rheumatoid arthritis, SLE, progressive systemic sclerosis, mixed connective tissue disease, diabetes mellitus), Crohn's disease (regional enteritis, granulomatous ileitis, ileocolitis, digestive system inflammation), demyelinating disease (including myelitis, multiple sclerosis, disseminated sclerosis, acute disseminated encephalomyelitis, perivenous demyelination, vitamin B12 deficiency, Guillain-Barre syndrome, MS-associated retrovirus), dermatomyositis, diverticulitis, exudative diarrhea, gastritis, granulomatous hepatitis, granulomatous inflammation, cholecystitis, insulin-dependent diabetes mellitus, liver inflammatory diseases (liver fibrosis primary biliary cirrhosis, hepatitis, sclerosing cholangitis), lung inflammation (idiopathic pulmonary fibrosis, eosinophilic granuloma of the lung, pulmonary histiocytosis X, peribronchiolar inflammation, acute bronchitis), lymphogranuloma venereum, malignant melanoma, mouth/tooth disease (including gingivitis, periodontal disease), mucositis, musculoskeletal system inflammation (myositis), nonalcoholic steatohepatitis (nonalcoholic fatty liver disease), ocular & orbital inflammation (including uveitis, optic neuritis, peripheral rheumatoid ulceration, peripheral corneal inflammation), osteoarthritis, osteomyelitis, pharyngeal inflammation, polyarthritis, proctitis, psoriasis, radiation injury, sarcoidosis, sickle cell necropathy, superficial thrombophlebitis, systemic inflammatory response syndrome, thyroiditis, systemic lupus erythematosus, graft versus host disease, acute burn injury, Behçet's syndrome, Sjögren's syndrome.

The terms patient and subject include human and veterinary subjects.

Human Anti-MAdCAM Antibodies and Characterization Thereof

In one embodiment, the invention provides anti-MAdCAM antibodies comprising human CDR sequences. In a preferred embodiment, the invention provides human anti-MAdCAM antibodies. In some embodiments, human anti-MAdCAM antibodies are produced by immunizing a non-human transgenic animal, e.g., a rodent, whose genome comprises human immunoglobulin genes so that the transgenic animal produces human antibodies. In some embodiments, the invention provides an anti-MAdCAM antibody that does not bind complement.

In a preferred embodiment, the anti-MAdCAM antibody is 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In another preferred embodiment, the anti-MAdCAM antibody comprises a light chain comprising an amino acid sequence selected from SEQ ID NO: 4, 8, 12, 16, 20, 24, 28, 32, 36, 40, 44, 48, 54, 58, 62, 66 or 68 (with or without the signal sequence) or the variable region of any one of said amino acid sequences, or one or more CDRs from these amino acid sequences. In another preferred embodiment, the anti-MAdCAM antibody comprises a heavy chain comprising an amino acid sequence selected from SEQ ID NO: 2, 6, 10, 14, 18, 22, 26, 30, 34, 38, 42, 46, 52, 56, 60 or 64 (with or without the signal sequence) or the amino acid sequence of the variable region, or of one or more CDRs from said amino acid sequences. Also included in the invention are human anti-MAdCAM antibodies comprising the amino acid sequence from the beginning of the CDR1 to the end of the CDR3 of any one of the above-mentioned sequences. The invention further provides an anti-MAdCAM antibody comprising one or more FR regions of any of the above-mentioned sequences.

The invention further provides an anti-MAdCAM antibody comprising one of the afore-mentioned amino acid sequences in which one or more modifications have been made. In some embodiments, cysteines in the antibody, which may be chemically reactive, are substituted with another residue, such as, without limitation, alanine or serine. In one embodiment, the substitution is at a non-canonical cysteine. The substitution can be made in a CDR or framework region of a variable domain or in the constant domain of an antibody. In some embodiments, the cysteine is canonical.

In some embodiments, an amino acid substitution is made to eliminate potential proteolytic sites in the antibody. Such sites may occur in a CDR or framework region of a variable domain or in the constant domain of an antibody. Substitution of cysteine residues and removal of proteolytic sites may decrease the heterogeneity in the antibody product. In some embodiments, asparagine-glycine pairs, which form potential deamidation sites, are eliminated by altering one or both of the residues. In some embodiments, an amino acid substitution is made to add or to remove potential glycosylation sites in the variable region of an antibody of the invention.

In some embodiments, the C-terminal lysine of the heavy chain of the anti-MAdCAM antibody of the invention is cleaved. In various embodiments of the invention, the heavy and light chains of the anti-MAdCAM antibodies may optionally include a signal sequence.

In one aspect, the invention provides twelve inhibitory human anti-MAdCAM monoclonal antibodies and the hybridoma cell lines that produce them. Table 1 lists the sequence identifiers (SEQ ID NO:) of the nucleic acids encoding the full-length heavy and light chains (including signal sequence), and the corresponding full-length deduced amino acid sequences.

TABLE 1

HUMAN ANTI-MAdCAM ANTIBODIES

| Monoclonal Antibody | SEQUENCE IDENTIFIER (SEQ ID NO:) Full Length | | | |
|---|---|---|---|---|
| | Heavy | | Light | |
| | DNA | Protein | DNA | Protein |
| 1.7.2 | 1 | 2 | 3 | 4 |
| 1.8.2 | 5 | 6 | 7 | 8 |
| 6.14.2 | 9 | 10 | 11 | 12 |
| 6.22.2 | 13 | 14 | 15 | 16 |
| 6.34.2 | 17 | 18 | 19 | 20 |
| 6.67.1 | 21 | 22 | 23 | 24 |
| 6.73.2 | 25 | 26 | 27 | 28 |
| 6.77.1 | 29 | 30 | 31 | 32 |
| 7.16.6 | 33 | 34 | 35 | 36 |
| 7.20.5 | 37 | 38 | 39 | 40 |
| 7.26.4 | 41 | 42 | 43 | 44 |
| 9.8.2 | 45 | 46 | 47 | 48 |

In another aspect, the invention provides a modified version of certain of the above-identified human anti-MAdCAM monoclonal antibodies. Table 2 lists the sequence identifiers for the DNA and protein sequences of the modified antibodies.

TABLE 2

HUMAN ANTI-MAdCAM ANTIBODIES

| Modified Monoclonal Antibody | SEQUENCE IDENTIFIER (SEQ ID NO:) Full Length | | | |
|---|---|---|---|---|
| | Heavy | | Light | |
| | DNA | Protein | DNA | Protein |
| 6.22.2-mod | 51 | 52 | 53 | 54 |
| 6.34.2-mod | 55 | 56 | 57 | 58 |
| 6.67.1-mod | 59 | 60 | 61 | 62 |
| 6.77.1-mod | 63 | 64 | 65 | 66 |
| 7.26.4-mod | 41 | 42 | 67 | 68 |

Class and Subclass of anti-MAdCAM Antibodies

The antibody may be an IgG, an IgM, an IgE, an IgA or an IgD molecule. In a preferred embodiment, the antibody is an IgG class and is an $IgG_1$, $IgG_2$, $IgG_3$ or $IgG_4$ subclass. In a more preferred embodiment, the anti-MAdCAM antibody is subclass $IgG_2$ or $IgG_4$. In another preferred embodiment, the anti-MAdCAM antibody is the same class and subclass as antibody 1.7.2, 1.8.2, 7.16.6, 7.20.5, 7.26.4, 6.22.2-mod, 6.34.2-mod, 6.67.1-mod, 6.77.1-mod or 7.26.4-mod which is $IgG_2$, or 6.14.2, 6.22.2, 6.34.2, 6.67.1, 6.73.2, 6.77.1 or 9.8.2, which is $IgG_4$.

The class and subclass of anti-MAdCAM antibodies may be determined by any method known in the art. In general, the class and subclass of an antibody may be determined using antibodies that are specific for a particular class and subclass of antibody. Such antibodies are available commercially. ELISA, Western Blot as well as other techniques can determine the class and subclass. Alternatively, the class and subclass may be determined by sequencing all or a portion of the constant domains of the heavy and/or light chains of the antibodies, comparing their amino acid sequences to the known amino acid sequences of various classes and subclasses of immunoglobulins, and determining the class and subclass of the antibodies as the class showing the highest sequence identity.

Species and Molecule Selectivity

In another aspect of the invention, the anti-MAdCAM antibody demonstrates both species and molecule selectivity. In one embodiment, the anti-MAdCAM antibody binds to human, cynomolgus or dog MAdCAM. In some embodiments, the anti-MAdCAM antibody does not bind to a New World monkey species such as a marmoset. Following the teachings of the specification, one may determine the species selectivity for the anti-MAdCAM antibody using methods well known in the art. For instance, one may determine species selectivity using Western blot, FACS, ELISA or immunohistochemistry. In a preferred embodiment, one may determine the species selectivity using immunohistochemistry.

In some embodiments, an anti-MAdCAM antibody that specifically binds MAdCAM has selectivity for MAdCAM over VCAM, fibronectin or any other antigen that is at least 10 fold, preferably at least 20, 30, 40, 50, 60, 70, 80 or 90 fold, most preferably at least 100 fold. In a preferred embodiment, the anti-MAdCAM antibody does not exhibit any appreciable binding to VCAM, fibronectin or any other antigen other than MAdCAM. One may determine the selectivity of the anti-MAdCAM antibody for MAdCAM using methods well known in the art following the teachings of the specification. For instance, one may determine the selectivity using Western blot, FACS, ELISA, or immunohistochemistry.

Binding Affinity of Anti-MAdCAM Antibodies to MAdCAM

In another aspect of the invention, the anti-MAdCAM antibodies specifically bind to MAdCAM with high affinity. In one embodiment, the anti-MAdCAM antibody specifically binds to MAdCAM with a $K_d$ of $3 \times 10^{-8}$ M or less, as measured by surface plasmon resonance, such as BIAcore. In more preferred embodiments, the antibody specifically binds to MAdCAM with a $K_d$ of $1 \times 10^{-8}$ or less or $1 \times 10^{-9}$ M or less. In an even more preferred embodiment, the antibody specifically binds to MAdCAM with a $K_d$ or $1 \times 10^{-10}$ M or less. In other preferred embodiments, an antibody of the invention specifically binds to MAdCAM with a $K_d$ of $2.66 \times 10^{-10}$ M or less, $2.35 \times 10^{-11}$ M or less or $9 \times 10^{-12}$ M or less. In another preferred embodiment, the antibody specifically binds to MAdCAM with a $K_d$ or $1 \times 10^{-11}$ M or less. In another preferred embodiment, the antibody specifically binds to MAdCAM with substantially the same $K_d$ as an antibody selected from 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. An antibody with "substantially the same $K_d$" as a reference antibody has a $K_d$ that is ±100 µM, preferably ±50 µM, more preferably ±20 µM, still more preferably ±10 µM, ±5 µM or ±2 µM, compared to the $K_d$ of the reference antibody in the same experiment. In another preferred embodiment, the antibody binds to MAdCAM with substantially the same $K_d$ as an antibody that comprises one or more variable domains or one or more CDRs from an antibody selected from 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In still another preferred embodiment, the antibody binds to MAdCAM with substantially the same $K_d$ as an antibody that comprises one of the amino acid sequences selected from SEQ ID NOS: 2, 4, 6, 8, 10, 12, 14, 16, 18, 20, 22, 24, 26, 28, 30, 32, 34, 36, 38, 40, 42, 44, 46 48, 52, 54, 56, 58, 62, 64, 66 or 68 (with or without the signal sequence), or the variable domain thereof. In another preferred embodiment, the antibody binds to MAdCAM with substantially the same $K_d$ as an antibody that comprises one or more CDRs from an antibody that comprises an amino acid sequence selected from SEQ ID NOS: 2, 4, 6, 8, 10, 12, 14, 16, 18, 20, 22, 24, 26, 28, 30, 32, 34, 36, 38, 40, 42, 44, 46 48, 52, 54, 56, 58, 62, 64, 66 or 68.

The binding affinity of an anti-MAdCAM antibody to MAdCAM may be determined by any method known in the art. In one embodiment, the binding affinity can be measured by competitive ELISAs, RIAs or surface plasmon resonance, such as BIAcore. In a more preferred embodiment, the binding affinity is measured by surface plasmon resonance. In an even more preferred embodiment, the binding affinity and dissociation rate is measured using a BIAcore. An example of determining binding affinity is described below in Example II.

Half-Life of Anti-MAdCAM Antibodies

According to another object of the invention, the anti-MAdCAM antibody has a half-life of at least one day in vitro or in vivo. In a preferred embodiment, the antibody or portion thereof has a half-life of at least three days. In a more preferred embodiment, the antibody or portion thereof has a half-life of four days or longer. In another embodiment, the antibody or portion thereof has a half-life of eight days or longer. In another embodiment, the antibody or antigen-binding portion thereof is derivatized or modified such that it has a longer half-life, as discussed below. In another preferred embodiment, the antibody may contain point mutations to increase serum half life, such as described WO 00/09560, published Feb. 24, 2000.

The antibody half-life may be measured by any means known to one having ordinary skill in the art. For instance, the antibody half life may be measured by Western blot, ELISA or RIA over an appropriate period of time. The antibody half-life may be measured in any appropriate animal, such as a primate, e.g., cynomolgus monkey, or a human.

Identification of MAdCAM Epitopes Recognized by Anti-MAdCAM Antibody

The invention also provides a human anti-MAdCAM antibody that binds the same antigen or epitope as a human anti-MAdCAM antibody provided herein. Further, the invention provides a human anti-MAdCAM antibody that competes or cross-competes with a human anti-MAdCAM antibody. In a preferred embodiment, the human anti-MAdCAM antibody is 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In another preferred embodiment, the human anti-MAdCAM antibody comprises one or more variable domains or one or more CDRs from an antibody selected from 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In still another preferred embodiment, the human anti-MAdCAM antibody comprises one of the amino acid sequences selected from SEQ ID NOS: 2, 4, 6, 8, 10, 12, 14, 16, 18, 20, 22, 24, 26, 28, 30, 32, 34, 36, 38, 40, 42, 44, 46 48, 52, 54, 56, 58, 62, 64, 66 or 68 (with or without the signal sequence), or a variable domain thereof. In another preferred embodiment, the human anti-MAdCAM antibody comprises one or more CDRs from an antibody that comprises one of the amino acid sequences selected from SEQ ID NOS: 2, 4, 6, 8, 10, 12, 14, 16, 18, 20, 22, 24, 26, 28, 30, 32, 34, 36, 38, 40, 42, 44, 46 48, 52, 54, 56, 58, 62, 64, 66 or 68. In a highly preferred embodiment, the anti-MAdCAM antibody is another human antibody.

One may determine whether an anti-MAdCAM antibody binds to the same antigen as another anti-MAdCAM antibody using a variety of methods known in the art. For instance, one can use a known anti-MAdCAM antibody to capture the antigen, elute the antigen from the anti-MAdCAM antibody, and then determine whether the test antibody will bind to the eluted antigen. One may determine whether an antibody competes with an anti-MAdCAM antibody by binding the anti-MAdCAM antibody to MAdCAM under saturating conditions, and then measuring the ability of the test antibody to bind to MAdCAM. If the test antibody is able to bind to the MAdCAM at the same time as the anti-MAdCAM antibody, then the test antibody binds to a different epitope than the anti-MAdCAM antibody. However, if the test antibody is not able to bind to the MAdCAM at the same time, then the test antibody competes with the human anti-MAdCAM antibody. This experiment may be performed using ELISA, or surface plasmon resonance or, preferably, BIAcore. To test whether an anti-MAdCAM antibody cross-competes with another anti-MAdCAM antibody, one may use the competition method described above in two directions, i.e. determining if the known antibody blocks the test antibody and vice versa.

Light and Heavy Chain Gene Usage

The invention also provides an anti-MAdCAM antibody that comprises a light chain variable region encoded by a human κ gene. In a preferred embodiment, the light chain variable region is encoded by a human Vκ A2, A3, A26, B3, O12 or O18 gene family. In various embodiments, the light chain comprises no more than eleven, no more than six or no more than three amino acid substitutions from the germline human Vκ A2, A3, A26, B3, O12 or O18 sequence. In a preferred embodiment, the amino acid substitutions are conservative substitutions.

SEQ ID NOS: 4, 8, 12, 16, 20, 24, 28, 32, 36, 40, 44 and 48 provide the amino acid sequences of the full-length kappa light chains of twelve anti-MAdCAM antibodies, 1.7.2, 1.8.2, 6.14.2, 6.22.2, 6.34.2, 6.67.1, 6.73.2, 6.77.1, 7.16.6, 7.20.5, 7.26.4 and 9.8.2. FIGS. 1K-1T are alignments of the amino acid sequences of the light chain variable domains of twelve anti-MAdCAM antibodies with the germline sequences from which they are derived. FIG. 2A shows an alignment of the amino acid sequences of the light chain variable domains of the kappa light chains of twelve anti-MAdCAM antibodies to each other. Following the teachings of this specification, one of ordinary skill in the art could determine the differences between the germline sequences and the antibody sequences of additional anti-MAdCAM antibodies. SEQ ID NOS: 54, 58, 62, 66 or 68 provide the amino acid sequences of the full length kappa light chains of five additional anti-MAdCAM antibodies, 6.22.2-mod, 6.34.2-mod, 6.67.1-mod, 6.77.1-mod and 7.26.4-mod, modified by amino acid substitution from their parent anti-MAdCAM antibodies, 6.22.2, 6.34.2, 6.67.1, 6.77.1 or 7.26.4, respectively.

In a preferred embodiment, the VL of the anti-MAdCAM antibody contains the same mutations, relative to the germline amino acid sequence, as any one or more of the VL of antibodies 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. The invention includes an anti-MAdCAM antibody that utilizes the same human Vκ and human Jk genes as an exemplified antibody. In some embodiments, the antibody comprises one or more of the same mutations from germline as one or more exemplified antibodies. In some embodiments, the antibody comprises different substitutions at one or more of the same positions as one or more of the exemplified antibodies. For example, the VL of the anti-MAdCAM antibody may contain one or more amino acid substitutions that are the same as those present in antibody 7.16.6, and another amino acid substitution that is the same as antibody 7.26.4. In this manner, one can mix and match different features of antibody binding in order to alter, e.g., the affinity of the antibody for MAdCAM or its dissociation rate from the antigen. In another embodiment, the mutations are made in the same position as those found in any one or more of the VL of antibodies 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod, but conservative amino acid substitutions are made rather than using the same amino acid. For example, if the amino acid substitution compared to the germline in one of the antibodies 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod is glutamate, one may conservatively substitute aspartate. Similarly, if the amino acid substitution is serine, one may conservatively substitute threonine.

In another preferred embodiment, the light chain comprises an amino acid sequence that is the same as the amino acid sequence of the VL of 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In another highly preferred embodiment, the light chain comprises amino acid sequences that are the same as the CDR regions of the light chain of 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In another preferred embodiment, the light chain comprises an amino acid sequence with at least one CDR region of the light chain of 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In another preferred embodiment, the light chain comprises amino acid sequences with CDRs from different light chains that use the same $V_K$ and $J_K$ genes. In a more preferred embodiment, the CDRs from different light chains are obtained from 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In another preferred embodiment, the light chain comprises an amino acid sequence selected from SEQ ID NOS: 4, 8, 12, 16, 20, 24, 28, 32, 36, 40, 44, 48, 54, 58, 62, 64, 66 or 68 with or without the signal sequence. In another embodiment, the light chain comprises an amino acid sequence encoded by a nucleotide sequence selected from SEQ ID NOS: 3, 7, 11, 15, 19, 23, 27, 31, 35, 39, 43, 47, 53, 57, 61, 65 or 67 (with or without the signal sequence), or a nucleotide sequence that encodes an amino acid sequence having 1-11 amino acid insertions, deletions or substitutions therefrom. Preferably, the amino acid substitutions are conservative amino acid substitutions. In another embodiment, the antibody or portion thereof comprises a lambda light chain.

The present invention also provides an anti-MAdCAM antibody or portion thereof that comprises a human VH gene sequence or a sequence derived from a human VH gene. In one embodiment, the heavy chain amino acid sequence is derived from a human VH 1-18, 3-15, 3-21, 3-23, 3-30, 3-33 or 4-4 gene family. In various embodiments, the heavy chain comprises no more than fifteen, no more than six or no more than three amino acid changes from germline human VH 1-18, 3-15, 3-21, 3-23, 3-30, 3-33 or 4-4 gene sequence.

Figure 2B:
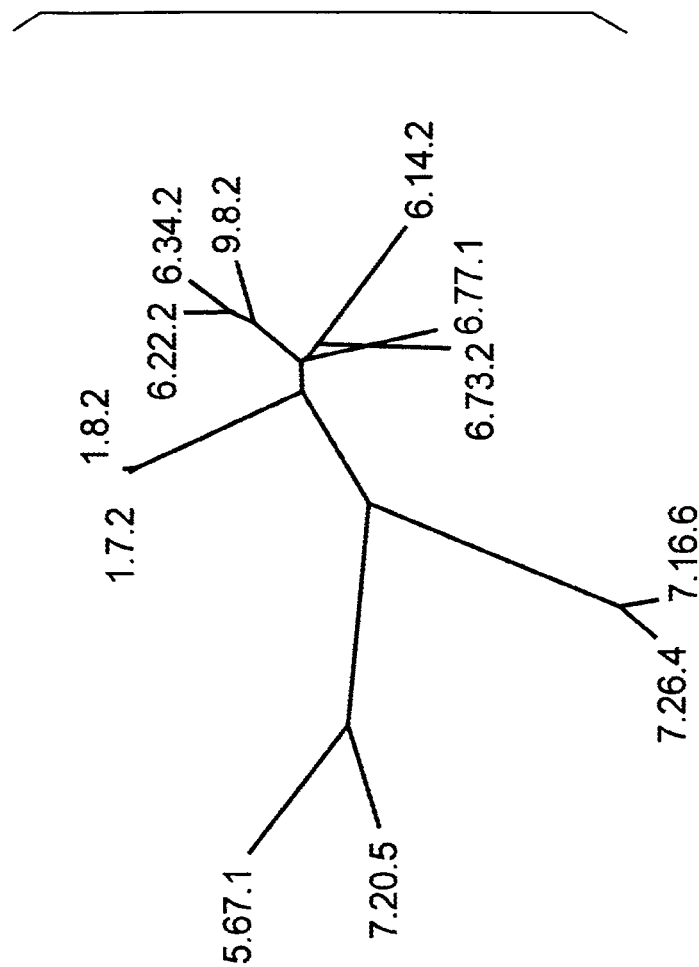
FIG. 2B is a CLUSTAL alignment and radial tree of the predicted heavy amino acid sequences, showing the degree of similarity between the anti-MAdCAM antibody heavy chains.

SEQ ID NOS: 2, 6, 10, 14, 18, 22, 26, 30, 34, 38, 42 and 46 provide the amino acid sequences of the full-length heavy chains of twelve anti-MAdCAM antibodies. FIGS. 1A-1J are alignments of the amino acid sequences of the heavy chain variable regions of twelve anti-MAdCAM antibodies with the germline sequences from which they are derived. FIG. 2B shows the alignments of the amino acid sequences of the heavy chain variable regions of twelve anti-MAdCAM antibodies to each other. Following the teachings of this specification and the nucleotide sequences of the invention, one of ordinary skill in the art could determine the encoded amino acid sequence of the twelve anti-MAdCAM heavy chains and the germline heavy chains and determine the differences between the germline sequences and the antibody sequences. SEQ ID NOS: 52, 56, 60 and 64 provide the amino acid sequences of the full length heavy chains of anti-MAdCAM antibodies, 6.22.2-mod, 6.34.2-mod and 6.67.1-mod, modified by amino acid substitution from their parent anti-MAdCAM antibodies, 6.22.2, 6.34.2 and 6.67.1 respectively. One further modified anti-MAdCAM antibody, 7.26.4-mod, has a full length heavy chain amino acid sequence which is SEQ ID NO: 42.

In a preferred embodiment, the VH of the anti-MAdCAM antibody contains the same mutations, relative to the germline amino acid sequence, as any one or more of the VH of antibodies 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. Similar to that discussed above, the antibody comprises one or more of the same mutations from germline as one or more exemplified antibodies. In some embodiments, the antibody comprises different substitutions at one or more of the same positions as one or more of the exemplified antibodies. For example, the VH of the anti-MAdCAM antibody may contain one or more amino acid substitutions that are the same as those present in antibody 7.16.6, and another amino acid substitution that is the same as antibody 7.26.4. In this manner, one can mix and match different features of antibody binding in order to alter, e.g., the affinity of the antibody for MAdCAM or its dissociation rate from the antigen. In another embodiment, an amino acid substitution compared to germline is made at the same position as a substitution from germline as found in any one or more of the VH of reference antibody 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod, but the position is substituted with a different residue, which is a conservative substitution compared to the reference antibody.

In another preferred embodiment, the heavy chain comprises an amino acid sequence that is the same as the amino acid sequence of the VH of 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In another highly preferred embodiment, the heavy chain comprises amino acid sequences that are the same as the CDR regions of the heavy chain of 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In another preferred embodiment, the heavy chain comprises an amino acid sequence from at least one CDR region of the heavy chain of 1.7.2, 1.8.2, 6.14.2, 6.22.2, 6.34.2, 6.67.1, 6.73.2, 6.77.1, 7.16.6, 7.20.4, 7.26.4, 9.8.2, 6.22.2-mod, 6.34.2-mod, 6.67.1-mod, 6.77.1-mod or 7.26.4-mod. In another preferred embodiment, the heavy chain comprises amino acid sequences with CDRs from different heavy chains. In a more preferred embodiment, the CDRs from different heavy chains are obtained from 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In another preferred embodiment, the heavy chain comprises an amino acid sequence selected from SEQ ID NOS: 2, 6, 10, 14, 18, 22, 26, 30, 34, 38, 42, 46, 52, 56, 60 or 64 with or without the signal sequence. In another embodiment, the heavy chain comprises an amino acid sequence encoded by a nucleotide sequence selected from SEQ ID NOS: 1, 5, 9, 13, 17, 21, 25, 29, 33, 37, 41, 45, 51, 55, 59 or 63, or a nucleotide sequence that encodes an amino acid sequence having 1-15 amino acid insertions, deletions or substitutions therefrom. In another embodiment, the substitutions are conservative amino acid substitutions.

Methods of Producing Antibodies and Antibody-Producing Cell Lines

Immunization

In one embodiment of the instant invention, human antibodies are produced by immunizing a non-human animal comprising some or all of the human immunoglobulin heavy and light chain loci with an MAdCAM antigen. In a preferred embodiment, the non-human animal is a XENOMOUSE™ animal, which is an engineered mouse strain that comprises large fragments of the human immunoglobulin loci and is deficient in mouse antibody production. See, e.g., Green et al., *Nature Genetics* 7:13-21 (1994) and U.S. Pat. Nos. 5,916,771, 5,939,598, 5,985,615, 5,998,209, 6,075,181, 6,091,001, 6,114,598 and 6,130,364. See also WO 91/10741, WO 94/02602, WO 96/34096 and WO 96/33735, WO 98/16654, WO 98/24893, WO 98/50433, WO 99/45031, WO 99/53049, WO 00 09560 and WO 00/037504. The XENOMOUSE™ animal produces an adult-like human repertoire of fully human antibodies and generates antigen-specific human mAbs. A second generation XENOMOUSE™ animal contains approximately 80% of the human antibody V gene repertoire through introduction of megabase sized, germline configuration YAC fragments of the human heavy chain loci and κ light chain loci. In other embodiments, XENOMOUSE™ mice contain approximately all of the human heavy chain and λ light chain locus. See Mendez et al., *Nature Genetics* 15:146-156 (1997), Green and Jakobovits, *J. Exp. Med.* 188:483-495 (1998), the disclosures of which are hereby incorporated by reference.

The invention also provides a method for making anti-MAdCAM antibodies from non-human, non-mouse animals by immunizing non-human transgenic animals that comprise human immunoglobulin loci. One may produce such animals using the methods described immediately above. The methods disclosed in these documents can be modified as described in U.S. Pat. No. 5,994,619 (the "'619 patent"), which is here in incorporated by reference. The '619 patent describes methods for producing novel cultured inner cell mass (CICM) cells and cell lines, derived from pigs and cows, and transgenic CICM cells into which heterologous DNA has been inserted. CICM transgenic cells can be used to produce cloned transgenic embryos, fetuses, and offspring. The '619 patent also describes methods of producing transgenic animals that are capable of transmitting the heterologous DNA to their progeny. In a preferred embodiment, the non-human animals may be rats, sheep, pigs, goats, cattle or horses.

In another embodiment, the non-human animal comprising human immunoglobulin loci are animals that have a "minilocus" of human immunoglobulins. In the minilocus approach, an exogenous Ig locus is mimicked through the inclusion of individual genes from the Ig locus. Thus, one or more VH genes, one or more DH genes, one or more JH genes, a μ constant domain(s), and a second constant domain(s) (preferably a gamma constant domain(s) are formed into a construct for insertion into an animal. This approach is described, inter alia, in U.S. Pat. Nos. 5,545,807, 5,545,806, 5,625,126, 5,633,425, 5,661,016, 5,770,429, 5,789,650, 5,814,318, 5,591,669, 5,612,205, 5,721,367, 5,789,215, and 5,643,763, hereby incorporated by reference.

An advantage of the minilocus approach is the rapidity with which constructs including portions of the Ig locus can be generated and introduced into animals. However, a potential disadvantage of the minilocus approach is that there may not be sufficient immunoglobulin diversity to support full B-cell development, such that there may be lower antibody production.

To produce a human anti-MAdCAM antibody, a non-human animal comprising some or all of the human immunoglobulin loci is immunized with a MAdCAM antigen and an antibody or the antibody-producing cell is isolated from the animal. The MAdCAM antigen may be isolated and/or purified MAdCAM and is preferably a human MAdCAM. In another embodiment, the MAdCAM antigen is a fragment of MAdCAM, preferably the extracellular domain of MAdCAM. In another embodiment, the MAdCAM antigen is a fragment that comprises at least one epitope of MAdCAM. In another embodiment, the MAdCAM antigen is a cell that expresses MAdCAM on its cell surface, preferably a cell that overexpresses MAdCAM on its cell surface.

Immunization of animals may be done by any method known in the art. See, e.g., Harlow and Lane, *Antibodies: A Laboratory Manual*, New York: Cold Spring Harbor Press (1990). Methods for immunizing non-human animals such as mice, rats, sheep, goats, pigs, cattle and horses are well known in the art. See, e.g., Harlow and Lane and U.S. Pat. No. 5,994,619. In a preferred embodiment, the MAdCAM antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

Example I provides a protocol for immunizing a XENOMOUSE™ animal with full-length human MAdCAM in phosphate-buffered saline.

Production of Antibodies and Antibody-Producing Cell Lines

After immunization of an animal with a MAdCAM antigen, antibodies and/or antibody-producing cells may be obtained from the animal. An anti-MAdCAM antibody-containing serum is obtained from the animal by bleeding or sacrificing the animal. The serum may be used as it is obtained from the animal, an immunoglobulin fraction may be obtained from the serum, or the anti-MAdCAM antibodies may be purified from the serum.

In another embodiment, antibody-producing immortalized cell lines may be prepared from the immunized animal. After immunization, the animal is sacrificed and B cells are immortalized using methods well-known in the art. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. In embodiments involving the myeloma cells, the myeloma cells do not secrete immunoglobulin polypeptides (a non-secretory cell line). After immortalization and antibiotic selection, the immortalized cells, or culture supernatants thereof, are screened using MAdCAM, a portion thereof, or a cell expressing MAdCAM. In a preferred embodiment, the initial screening is performed using an enzyme-linked immunoassay (ELISA) or a radioimmunoassay (RIA), preferably an ELISA. An example of ELISA screening is provided in PCT Publication No. WO 00/37504, herein incorporated by reference.

In another embodiment, antibody-producing cells may be prepared from a human who has an autoimmune disorder and who expresses anti-MAdCAM antibodies. Cells expressing the anti-MAdCAM antibodies may be isolated by isolating white blood cells and subjecting them to fluorescence-activated cell sorting (FACS) or by panning on plates coated with MAdCAM or a portion thereof. These cells may be fused with a human non-secretory myeloma to produce human hybridomas expressing human anti-MAdCAM antibodies. In general, this is a less preferred embodiment because it is likely that the anti-MAdCAM antibodies will have a low affinity for MAdCAM.

Anti-MAdCAM antibody-producing cells, e.g., hybridomas are selected, cloned and further screened for desirable characteristics, including robust cell growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

Preferably, the immunized animal is a non-human animal that expresses human immunoglobulin genes and the splenic B cells are fused to a myeloma derived from the same species as the non-human animal. More preferably, the immunized animal is a XENOMOUSE™ animal and the myeloma cell line is a non-secretory mouse myeloma, such as the myeloma cell line is P3-X63-AG8-653 (ATCC). See, e.g., Example I.

Thus, in one embodiment, the invention provides methods for producing a cell line that produces a human monoclonal antibody or a fragment thereof directed to MAdCAM comprising (a) immunizing a non-human transgenic animal described herein with MAdCAM, a portion of MAdCAM or a cell or tissue expressing MAdCAM; (h) allowing the transgenic animal to mount an immune response to MAd-CAM; (c) isolating antibody-producing cells from transgenic animal; (d) immortalizing the antibody-producing cells; (e) creating individual monoclonal populations of the immortalized antibody-producing cells; and (f) screening the immortalized antibody-producing cells or culture supernatants thereof to identify an antibody directed to MAdCAM.

In one aspect, the invention provides hybridomas that produce human anti-MAdCAM antibodies. In a preferred embodiment, the hybridomas are mouse hybridomas, as described above. In another embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an anti-MAdCAM antibody.

Nucleic Acids, Vectors, Host Cells and Recombinant Methods of Making Antibodies

Nucleic Acids

Nucleic acid molecules encoding anti-MAdCAM antibodies of the invention are provided. In one embodiment, the nucleic acid molecule encodes a heavy and/or light chain of an anti-MAdCAM immunoglobulin. In a preferred embodiment, a single nucleic acid molecule encodes a heavy chain of an anti-MAdCAM immunoglobulin and another nucleic acid molecule encodes the light chain of an anti-MAdCAM immunoglobulin. In a more preferred embodiment, the encoded immunoglobulin is a human immunoglobulin, preferably a human IgG. The encoded light chain may be a λ chain or a κ chain, preferably a κ chain.

In a preferred embodiment the nucleic acid molecule encoding the variable region of the light chain comprises the germline sequence of a human Vκ the A2, A3, A26, B3, O12 or O18 gene or a variant of said sequence. In a preferred embodiment, the nucleic acid molecule encoding the light chain comprises a sequence derived from a human Jκ1, Jκ2, Jκ3, Jκ4 or Jκ5 gene. In a preferred embodiment, the nucleic acid molecule encoding the light chain encodes no more than eleven amino acid changes from the germline A2, A3, A26, B3, O12 or O18 Vκ gene, preferably no more than six amino acid changes, and even more preferably no more than three amino acid changes. In a more preferred embodiment, the nucleic acid encoding the light chain is the germline sequence.

The invention provides a nucleic acid molecule that encodes a variable region of the light chain (VL) containing up to eleven amino acid changes compared to the germline sequence, wherein the amino acid changes are identical to amino acid changes from the germline sequence from the VL of one of the antibodies 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. The invention also provides a nucleic acid molecule comprising a nucleotide sequence that encodes the amino acid sequence of the variable region of the light chain of 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. The invention also provides a nucleic acid molecule comprising a nucleotide sequence that encodes the amino acid sequence of one or more of the CDRs of any one of the light chains of 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In a preferred embodiment, the nucleic acid molecule comprises a nucleotide sequence that encodes the amino acid sequence of all of the CDRs of any one of the light chains of 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In another embodiment, the nucleic acid molecule comprises a nucleotide sequence that encodes the amino acid sequence of one of SEQ ID NOS: 4, 8, 12, 16, 20, 24, 28, 32, 36, 40, 44, 48, 54, 58, 62, 66, 68 or comprises a nucleotide sequence of one of SEQ ID NOS: 3, 7, 11, 15, 19, 23, 27, 31, 35, 39, 43, 47, 53, 57, 61, 65 or 67. In another preferred embodiment, the nucleic acid molecule comprises a nucleotide sequence that encodes the amino acid sequence of one or more of the CDRs of any one of SEQ ID NOS: 4, 8, 12, 16, 20, 24, 28, 32, 36, 40, 44, 48, 54, 58, 62, 66, 68 or comprises a nucleotide sequence of one or more of the CDRs of any one of SEQ ID NOS: 3, 7, 11, 15, 19, 23, 27, 31, 35, 39, 43, 47, 53, 57, 61, 65, or 67. In a more preferred embodiment, the nucleic acid molecule comprises a nucleotide sequence that encodes the amino acid sequence of all of the CDRs of any one of SEQ ID NOS: 4, 8, 12, 16, 20, 24, 28, 32, 36, 40, 44, 48, 54, 58, 62, 66, 68 or comprises a the nucleotide sequence of all the CDRs of any one of SEQ ID NOS: 3, 7, 11, 15, 19, 23, 27, 31, 35, 39, 43, 47, 53, 57, 61, 65, or 67.

The invention also provides a nucleic acid molecule that encodes an amino acid sequence of a VL that has an amino acid sequence that is at least 70%, 75%, 80%, 85%, 90%, 95%, 96%, 97%, 98% or 99% identical to a VL described above, particularly to a VL that comprises an amino acid sequence of one of SEQ ID NOS: 4, 8, 12, 16, 20, 24, 28, 32, 36, 40, 44, 48, 54, 58, 62, 66 or 68. The invention also provides a nucleotide sequence that is at least 70%, 75%, 80%, 85%, 90%, 95%, 96%, 97%, 98% or 99% identical to a nucleotide sequence of one of SEQ ID NOS: 3, 7, 11, 15, 19, 23, 27, 31, 35, 39, 43, 47, 53, 57, 61, 65 or 67.

In another embodiment, the invention provides a nucleic acid molecule that hybridizes under highly stringent conditions to a nucleic acid molecule encoding a VL as described above, particularly a nucleic acid molecule that comprises a nucleotide sequence encoding an amino acid sequence of SEQ ID NOS: 4, 8, 12, 16, 20, 24, 28, 32, 36, 40, 44, 48, 54, 58, 62, 66 or 68. The invention also provides a nucleic acid molecule that hybridizes under highly stringent conditions to a nucleic acid molecule comprising a nucleotide sequence of one of SEQ ID NOS: 3, 7, 11, 15, 19, 23, 27, 31, 35, 39, 43, 47, 53, 57, 61, 65 or 67.

The invention also provides a nucleic acid molecule encoding a heavy chain variable region (VH) that utilizes a human VH 1-18, 3-15, 3-21, 3-23, 3-30, 3-33 or 4-4 VH gene. In some embodiments, the nucleic acid molecule encoding the VH gene further utilizes a human JH4 or JH6 family gene. In some embodiments, the nucleic acid molecule encoding the VH gene utilize the human JH4b or JH6b gene. In another embodiment, the nucleic acid molecule comprises a sequence derived from a human D 3-10, 4-23, 5-5, 6-6 or 6-19 gene. In an even more preferred embodiment, the nucleic acid molecule encoding the VH contains no more than fifteen amino acid changes from the germline VH 1-18, 3-15, 3-21, 3-23, 3-30, 3-33 or 4-4 genes, preferably no more than six amino acid changes, and even more preferably no more than three amino acid changes. In a highly preferred embodiment, the nucleic acid molecule encoding the VH contains at least one amino acid change compared to the germline sequence, wherein the amino acid change is identical to an amino acid change from the germline sequence from the heavy chain of one of the antibodies 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In an even more preferred embodiment, the VH contains no more than fifteen amino acid changes compared to the germline sequences, wherein the changes are identical to those changes from the germline sequence from the VH of one of the antibodies 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod.

In one embodiment, the nucleic acid molecule comprises a nucleotide sequence that encodes the amino acid sequence of the VH of 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In another embodiment, the nucleic acid molecule comprises a nucleotide sequence that encodes the amino acid sequence of one or more of the CDRs of the heavy chain of 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In a preferred embodiment, the nucleic acid molecule comprises nucleotide sequences that encode the amino acid sequences of all of the CDRs of the heavy chain of 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In another preferred embodiment, the nucleic acid molecule comprises a nucleotide sequence that encodes the amino acid sequence of one of SEQ ID NOS: 2, 6, 10, 14, 18, 22, 26, 30, 34, 38, 42, 46, 52, 56, 60 or 64 or that comprises a nucleotide sequence of one of SEQ ID NOS: 1, 5, 9, 13, 17, 21, 25, 29, 33, 37, 41, 45, 51, 55, 59 or 63. In another preferred embodiment, the nucleic acid molecule comprises a nucleotide sequence that encodes the amino acid sequence of one or more of the CDRs of any one of SEQ ID NOS: 2, 6, 10, 14, 18, 22, 26, 30, 34, 38, 42, 46, 52, 56, 60 or 64 or comprises a nucleotide sequence of one or more of the CDRs of any one of SEQ ID NOS: 1, 5, 9, 13, 17, 21, 25, 29, 33, 37, 41, 45, 51, 55, 59 or 63. In a preferred embodiment, the nucleic acid molecule comprises a nucleotide sequence that encodes the amino acid sequences of all of the CDRs of any one of SEQ ID NOS: 2, 6, 10, 14, 18, 22, 26, 30, 34, 38, 42, 46, 52, 56, 60 or 64 or comprises a nucleotide sequence of all of the CDRs of any one of SEQ ID NOS: 1, 5, 9, 13, 17, 21, 25, 29, 33, 37, 41 45, 51, 55, 59 or 63. In some embodiments the nucleic acid molecule comprises a nucleotide sequence encoding a contiguous region from the beginning of CDR1 to the end of CDR3 of a heavy or light chain of any of the above-mentioned anti-MAdCAM antibodies.

In another embodiment, the nucleic acid molecule encodes an amino acid sequence of a VH that is at least 70%, 75%, 80%, 85%, 90%, 95%, 96%, 97%, 98% or 99% identical to one of the amino acid sequences encoding a VH as described immediately above, particularly to a VH that comprises an amino acid sequence of one of SEQ ID NOS: 2, 6, 10, 14, 18, 22, 26, 30, 34, 38, 42, 46, 52, 56, 60 or 64. The invention also provides a nucleotide sequence that is at least 70%, 75%, 80%, 85%, 90%, 95%, 96%, 97%, 98% or 99% identical to a nucleotide sequence of one of SEQ ID NOS: 1, 5, 9, 13, 17, 21, 25, 29, 33, 37, 41, 45, 51, 55, 59 or 63.

In another embodiment, the nucleic acid molecule encoding a VH is one that hybridizes under highly stringent conditions to a nucleotide sequence encoding a VH as described above, particularly to a VH that comprises an amino acid sequence of one of SEQ ID NOS: 2, 6, 10, 14, 18, 22, 26, 30, 34, 38, 42, 46, 52, 56, 60 or 64. The invention also provides a nucleotide sequence encoding a VH that hybridizes under highly stringent conditions to a nucleic acid molecule comprising a nucleotide sequence of one of SEQ ID NOS: 1, 5, 9, 13, 17, 21, 25, 29, 33, 37, 41, 45, 51, 55, 59 or 63.

The nucleotide sequence encoding either or both of the entire heavy and light chains of an anti-MAdCAM antibody or the variable regions thereof may be obtained from any source that produces an anti-MAdCAM antibody. Methods of isolating mRNA encoding an antibody are well-known in the art. See, e.g., Sambrook et al., *Molecular Cloning: A Laboratory Manual,* 2d ed., Cold Spring Harbor Laboratory Press, Cold Spring Harbor, N.Y. (1989). The mRNA may be used to produce cDNA for use in the polymerase chain reaction (PCR) or cDNA cloning of antibody genes. In one embodiment of the invention, the nucleic acid molecules may be obtained from a hybridoma that expresses an anti-MAdCAM antibody, as described above, preferably a hybridoma that has as one of its fusion partners a transgenic animal cell that expresses human immunoglobulin genes, such as a XENOMOUSE™ animal, a non-human mouse transgenic animal or a non-human, non-mouse transgenic animal. In another embodiment, the hybridoma is derived from a non-human, non-transgenic animal, which may be used, e.g., for humanized antibodies.

A nucleic acid molecule encoding the entire heavy chain of an anti-MAdCAM antibody may be constructed by fusing a nucleic acid molecule encoding the entire variable domain of a heavy chain or an antigen-binding domain thereof with a constant domain of a heavy chain. Similarly, a nucleic acid molecule encoding the light chain of an anti-MAdCAM antibody may be constructed by fusing a nucleic acid molecule encoding the variable domain of a light chain or an antigen-binding domain thereof with a constant domain of a light chain. Nucleic acid molecules encoding the VH and VL regions may be converted to full-length antibody genes by inserting them into expression vectors already encoding heavy chain constant and light chain constant regions, respectively, such that the VH segment is operatively linked to the heavy chain constant region (CH) segment(s) within the vector and the VL segment is operatively linked to the light chain constant region (CL) segment within the vector. Alternatively, the nucleic acid molecules encoding the VH or VL chains are converted into full-length antibody genes by linking, e.g., ligating, the nucleic acid molecule encoding a VH chain to a nucleic acid molecule encoding a CH chain using standard molecular biological techniques. The same may be achieved using nucleic acid molecules encoding VL and CL chains. The sequences of human heavy and light chain constant region genes are known in the art. See, e.g., Kabat et al., *Sequences of Proteins of Immunological Interest,* 5th Ed., NIH Publ. No. 91-3242 (1991). Nucleic acid molecules encoding the full-length heavy and/or light chains may then be expressed from a cell into which they have been introduced and the anti-MAdCAM antibody isolated.

In a preferred embodiment, the nucleic acid encoding the variable region of the heavy chain encodes the variable region of amino acid sequences of SEQ ID NOS: 2, 6, 10, 14, 18, 22, 26, 30, 34, 38, 42, 46, 52, 56, 60 or 64, and the nucleic acid molecule encoding the variable region of the light chains encodes the variable region of amino acid sequence of SEQ ID NOS: 4, 8, 12, 16, 20, 24, 28, 32, 36, 40, 44, 48, 54, 58, 62, 66 or 68.

In one embodiment, a nucleic acid molecule encoding either the heavy chain of an anti-MAdCAM antibody or an antigen-binding portion thereof, or the light chain of an anti-MAdCAM antibody or an antigen-binding portion thereof may be isolated from a non-human, non-mouse animal that expresses human immunoglobulin genes and has been immunized with a MAdCAM antigen. In other embodiment, the nucleic acid molecule may be isolated from an anti-MAdCAM antibody-producing cell derived from a non-transgenic animal or from a human patient who produces anti-MAdCAM antibodies. mRNA from the anti-MAdCAM antibody-producing cells may be isolated by standard techniques, cloned and/or amplified using PCR and library construction techniques, and screened using standard protocols to obtain nucleic acid molecules encoding anti-MAdCAM heavy and light chains.

The nucleic acid molecules may be used to recombinantly express large quantities of anti-MAdCAM antibodies, as described below. The nucleic acid molecules may also be used to produce chimeric antibodies, single chain antibodies, immunoadhesins, diabodies, mutated antibodies and antibody derivatives, as described further below. If the nucleic acid molecules are derived from a non-human, non-transgenic animal, the nucleic acid molecules may be used for antibody humanization, also as described below.

In another embodiment, the nucleic acid molecules of the invention may be used as probes or PCR primers for specific antibody sequences. For instance, a nucleic acid molecule probe may be used in diagnostic methods or a nucleic acid molecule PCR primer may be used to amplify regions of DNA that could be used, inter alia, to isolate nucleotide sequences for use in producing variable domains of anti-MAdCAM antibodies. In a preferred embodiment, the nucleic acid molecules are oligonucleotides. In a more preferred embodiment, the oligonucleotides are from highly variable regions of the heavy and light chains of the antibody of interest. In an even more preferred embodiment, the oligonucleotides encode all or a part of one or more of the CDRs.

Vectors

The invention provides vectors comprising the nucleic acid molecules of the invention that encode the heavy chain or the antigen-binding portion thereof. The invention also provides vectors comprising the nucleic acid molecules of the invention that encode the light chain or antigen-binding portion thereof. The invention also provides vectors comprising nucleic acid molecules encoding fusion proteins, modified antibodies, antibody fragments, and probes thereof.

To express the antibodies, or antibody portions of the invention, DNAs encoding partial or full-length light and heavy chains, obtained as described above, are inserted into expression vectors such that the genes are operatively linked to transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human CH or CL immunoglobulin sequence, with appropriate restriction sites engineered so that any VH or VL sequence can be easily inserted and expressed, as described above. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The recombinant expression vector can also encode a signal peptide that facilitates secretion of the antibody chain from a host cell. The antibody chain gene may be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245, and 4,968,615, each of which is hereby incorporated by reference. Methods for expressing antibodies in plants, including a description of promoters and vectors, as well as transformation of plants are known in the art. See, e.g, U.S. Pat. No. 6,517,529. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection), and the glutamate synthetase gene Non-Hybridoma Host Cells and Methods of Recombinantly Producing Protein Nucleic acid molecules encoding the heavy chain or an antigen-binding portion thereof and/or the light chain or an antigen-binding portion thereof of an anti-MAdCAM antibody, and vectors comprising these nucleic acid molecules, can be used for transformation of a suitable mammalian plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455 (which patents are hereby incorporated herein by reference). Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NS0, SP2 cells, HEK-293T cells, NIH-3T3 cells, HeLa cells, baby hamster kidney (BHK) cells, monkey kidney cells (COS), human hepatocellular carcinoma cells (e.g., Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen-binding portion thereof, the light chain and/or antigen-binding portion thereof are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Plant host cells include, e.g., *Nicotiana, Arabidopsis*, duckweed, corn, wheat, potato, etc. Bacterial host cells include *E. coli* and *Streptomyces* species. Yeast host cells include *Schizosaccharomyces pombe, Saccharomyces cerevisiae* and *Pichia pastoris*.

Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, 0 338 841 and 0 323 997.

It is likely that antibodies expressed by different cell lines or in transgenic animals will have different glycosylation from each other. However, all antibodies encoded by the nucleic acid molecules provided herein, or comprising the amino acid sequences provided herein are part of the instant invention, regardless of the glycosylation of the antibodies.

Transgenic Animals and Plants

The invention also provides transgenic non-human animals and transgenic plants comprising one or more nucleic acid molecules of the invention that may be used to produce antibodies of the invention. Antibodies can be produced in and recovered from tissue or bodily fluids, such as milk, blood or urine, of goats, cows, horses, pigs, rats, mice, rabbits, hamsters or other mammals. See, e.g., U.S. Pat. Nos. 5,827,690, 5,756,687, 5,750,172, and 5,741,957. As described above, non-human transgenic animals that comprise human immunoglobulin loci can be immunized with MAdCAM or a portion thereof. Methods for making antibodies in plants are described, e.g., in U.S. Pat. Nos. 6,046,037 and 5,959,177, incorporated herein by reference.

In another embodiment, non-human transgenic animals and transgenic plants are produced by introducing one or more nucleic acid molecules of the invention into the animal or plant by standard transgenic techniques. See Hogan, supra. The transgenic cells used for making the transgenic animal can be embryonic stem cells, somatic cells or fertilized egg cells. The transgenic non-human organisms can be chimeric, nonchimeric heterozygotes, and nonchimeric homozygotes. See, e.g., Hogan et al., *Manipulating the Mouse Embryo: A Laboratory Manual* 2ed., Cold Spring Harbor Press (1999); Jackson et al., *Mouse Genetics and Transgenics: A Practical Approach*, Oxford University Press (2000); and Pinkert, *Transgenic Animal Technology: A Laboratory Handbook*, Academic Press (1999). In another embodiment, the transgenic non-human organisms may have a targeted disruption and replacement that encodes a heavy chain and/or a light chain of interest. In a preferred embodiment, the transgenic animals or plants comprise and express nucleic acid molecules encoding heavy and light chains that combine to bind specifically to MAdCAM, preferably human MAdCAM. In another embodiment, the transgenic animals or plants comprise nucleic acid molecules encoding a modified antibody such as a single-chain antibody, a chimeric antibody or a humanized antibody. The anti-MAdCAM antibodies may be made in any transgenic animal. In a preferred embodiment, the non-human animals are mice, rats, sheep, pigs, goats, cattle or horses. The non-human transgenic animal expresses said encoded polypeptides in blood, milk, urine, saliva, tears, mucus and other bodily fluids.

Phage Display Libraries

The invention provides a method for producing an anti-MAdCAM antibody or antigen-binding portion thereof comprising the steps of synthesizing a library of human antibodies on phage, screening the library with a MAdCAM or a portion thereof, isolating phage that bind MAdCAM, and obtaining the antibody from the phage. One method to prepare the library of antibodies comprises the steps of immunizing a non-human host animal comprising a human immunoglobulin locus with MAdCAM or an antigenic portion thereof to create an immune response, extracting cells from the host animal the cells that are responsible for production of antibodies; isolating RNA from the extracted cells, reverse transcribing the RNA to produce cDNA, amplifying the cDNA using a primer, and inserting the cDNA into phage display vector such that antibodies are expressed on the phage. Recombinant anti-MAdCAM antibodies of the invention may be obtained in this way.

Recombinant anti-MAdCAM human antibodies of the invention in addition to the anti-MAdCAM antibodies disclosed herein can be isolated by screening of a recombinant combinatorial antibody library, preferably a scFv phage display library, prepared using human VL and VH cDNAs prepared from mRNA isolated from human lymphocytes. Methodologies for preparing and screening such libraries are known in the art. There are commercially available kits for generating phage display libraries (e.g., the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, e.g., U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; Fuchs et al. (1991), *Biotechnology*, 9:1369-1372; Hay et al., *Hum. Antibod. Hybridomas*, 3:81-85 (1992); Huse et al., *Science*, 246:1275-1281 (1989); McCafferty et al., *Nature*, 348:552-554 (1990); Griffiths et al., *EMBO J*, 12:725-734 (1993); Hawkins et al., *J. Mol. Biol.*, 226:889-896 (1992); Clackson et al., *Nature*, 352:624-628 (1991); Gram et al., *Proc. Natl. Acad. Sci. USA*, 89:3576-3580 (1992); Garrad et al., *Biotechnology*, 9:1373-1377 (1991); Hoogenboom et al., *Nuc Acid Res*, 19:4133-4137 (1991); and Barbas et al., *Proc. Natl. Acad. Sci. USA*, 88:7978-7982 (1991).

In a preferred embodiment, to isolate human anti-MAdCAM antibodies with the desired characteristics, a human anti-MAdCAM antibody as described herein is first used to select human heavy and light chain sequences having similar binding activity toward MAdCAM, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al., *Nature*, 348:552-554 (1990); and Griffiths et al., *EMBO J*, 12:725-734 (1993). The scFv antibody libraries preferably are screened using human MAdCAM as the antigen.

Once initial human VL and VH segments are selected, "mix and match" experiments, in which different pairs of the initially selected VL and VH segments are screened for MAdCAM binding, are performed to select preferred VL/VH pair combinations. Additionally, to further improve the quality of the antibody, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to MAdCAM.

Following screening and isolation of an anti-MAdCAM antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention, as described below. To express a recombinant human antibody isolated by screening of a combinatorial library, the DNA encoding the antibody is cloned into a recombinant expression vector and introduced into a mammalian host cells, as described above.

Class Switching

Another aspect of the instant invention is to provide a mechanism by which the class of an anti-MAdCAM antibody may be switched with another. In one aspect of the invention, a nucleic acid molecule encoding VL or VH is isolated using methods well-known in the art such that it does not include any nucleotide sequences encoding CL or CH. The nucleic acid molecule encoding VL or VH is then operatively linked to a nucleotide sequence encoding a CL or CH from a different class of immunoglobulin molecule. This may be achieved using a vector or nucleic acid molecule that comprises a CL or CH encoding sequence, as described above. For example, an anti-MAdCAM antibody that was originally IgM may be class switched to an IgG. Further, the class switching may be used to convert one IgG subclass to another, e.g., from $IgG_4$ to $IgG_2$. A preferred method for producing an antibody of the invention comprising a desired isotype or antibody subclass comprises the steps of isolating a nucleic acid encoding the heavy chain of an anti-MAdCAM antibody and a nucleic acid encoding the light chain of an anti-MAdCAM antibody, obtaining the variable region of the heavy chain, ligating the variable region of the heavy chain with the constant domain of a heavy chain of the desired isotype, expressing the light chain and the ligated heavy chain in a cell, and collecting the anti-MAdCAM antibody with the desired isotype.

Antibody Derivatives

One may use the nucleic acid molecules described above to generate antibody derivatives using techniques and methods known to one of ordinary skill in the art.

Humanized Antibodies

The immunogenicity of non-human antibodies can be reduced to some extent using techniques of humanization, potentially employing display techniques using appropriate libraries. It will be appreciated that murine antibodies or antibodies from other species can be humanized or primatized using techniques well known in the art. See, e.g., Winter and Harris, *Immunol Today*, 14:43-46 (1993) and Wright et al., *Crit. Reviews in Immunol.*, 12125-168 (1992). The antibody of interest may be engineered by recombinant DNA techniques to substitute the $C_H1$, CH2, $C_H3$, hinge domains, and/or the framework domain with the corresponding human sequence (see WO 92/02190 and U.S. Pat. Nos. 5,530,101, 5,585,089, 5,693,761, 5,693,792, 5,714,350, and 5,777,085). In another embodiment, a non-human anti-MAdCAM antibody can be humanized by substituting the $C_H1$, hinge domain, $C_H2$, $C_H3$, and/or the framework domains with the corresponding human sequence of a anti-MAdCAM antibody of the invention.

Mutated Antibodies

In another embodiment, the nucleic acid molecules, vectors and host cells may be used to make mutated anti-MAdCAM antibodies. The antibodies may be mutated in the variable domains of the heavy and/or light chains to alter a binding property of the antibody. For example, a mutation may be made in one or more of the CDR regions to increase or decrease the $K_d$ of the antibody for MAdCAM. Techniques in site-directed mutagenesis are well-known in the art. See, e.g., Sambrook et al., and Ausubel et al., supra. In a preferred embodiment, mutations are made at an amino acid residue that is known to be changed compared to germline in a variable region of an anti-MAdCAM antibody. In a more preferred embodiment, one or more mutations are made at an amino acid residue that is known to be changed compared to the germline in a variable region or CDR region of one of the anti-MAdCAM antibodies 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In another embodiment, one or more mutations are made at an amino acid residue that is known to be changed compared to the germline in a variable region or CDR region whose amino acid sequence is presented in SEQ ID NOS: 2, 4, 6, 8, 10, 12, 14, 16, 18, 20, 22, 24, 26, 28, 30, 32, 34, 36, 38, 40, 42, 44, 46, 48, 52, 54, 56, 58, 62, 64, 66 or 68, or whose nucleotide sequence is presented in SEQ ID NOS: 1, 3, 5, 7, 9, 11, 13, 15, 17, 19, 21, 23, 25, 27, 29, 31, 33, 35, 37, 39, 41, 43, 45, 47, 51, 53, 55, 57, 61, 63, 65 or 67. In another embodiment, the nucleic acid molecules are mutated in one or more of the framework regions. A mutation may be made in a framework region or constant domain to increase the half-life of the anti-MAdCAM antibody. See, e.g., WO 00/09560, published Feb. 24, 2000, herein incorporated by reference. In one embodiment, there may be one, three or five or ten point mutations and no more than fifteen point mutations. A mutation in a framework region or constant domain may also be made to alter the immunogenicity of the antibody, to provide a site for covalent or non-covalent binding to another molecule, or to alter such properties as complement fixation. Mutations may be made in each of the framework regions, the constant domain and the variable regions in a single mutated antibody. Alternatively, mutations may be made in only one of the framework regions, the variable regions or the constant domain in a single mutated antibody.

In one embodiment, there are no greater than fifteen amino acid changes in either the VH or VL regions of the mutated anti-MAdCAM antibody compared to the anti-MAdCAM antibody prior to mutation. In a more preferred embodiment, there is no more than ten amino acid changes in either the VH or VL regions of the mutated anti-MAdCAM antibody, more preferably no more than five amino acid changes, or even more preferably no more than three amino acid changes. In another embodiment, there are no more than fifteen amino acid changes in the constant domains, more preferably, no more than ten amino acid changes, even more preferably, no more than five amino acid changes.

Modified Antibodies

In another embodiment, a fusion antibody or immunoadhesin may be made which comprises all or a portion of an anti-MAdCAM antibody linked to another polypeptide. In a preferred embodiment, only the variable regions of the anti-MAdCAM antibody are linked to the polypeptide. In another preferred embodiment, the VH domain of an anti-MAdCAM antibody are linked to a first polypeptide, while the VL domain of an anti-MAdCAM antibody are linked to a second polypeptide that associates with the first polypeptide in a manner in which the VH and VL domains can interact with one another to form an antibody binding site. In another preferred embodiment, the VH domain is separated from the VL domain by a linker such that the VH and VL domains can interact with one another (see below under Single Chain Antibodies). The VH-linker-VL antibody is then linked to the polypeptide of interest. The fusion antibody is useful to directing a polypeptide to a MAdCAM-expressing cell or tissue. The polypeptide may be a therapeutic agent, such as a toxin, growth factor or other regulatory protein, or may be a diagnostic agent, such as an enzyme that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody.

To create a single chain antibody, (scFv) the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see, e.g., Bird et al., Science, 242:423-426 (1988); Huston et al., Proc. Natl. Acad. Sci. USA, 85:5879-5883 (1988); McCafferty et al., Nature, 348:552-554 (1990)). The single chain antibody may be monovalent, if only a single VH and VL are used, bivalent, if two VH and VL are used, or polyvalent, if more than two VH and VL are used.

In another embodiment, other modified antibodies may be prepared using anti-MAdCAM-encoding nucleic acid molecules. For instance, "Kappa bodies" (Ill et al., Protein Eng, 10: 949-57(1997)), "Minibodies" (Martin et al., EMBO J, 13: 5303-9(1994)), "Diahodies" (Holliger et al., PNAS USA, 90: 6444-6448(1993)), or "Janusins" (Traunecker et al., EMBO J, 10:3655-3659 (1991) and Traunecker et al., "Janusin: new molecular design for bispecific reagents," Int J Cancer Suppl, 7:51-52 (1992)) may be prepared using standard molecular biological techniques following the teachings of the specification.

In another aspect, chimeric and bispecific antibodies can be generated. A chimeric antibody may be made that comprises CDRs and framework regions from different antibodies. In a preferred embodiment, the CDRs of the chimeric antibody comprises all of the CDRs of the variable region of a light chain or heavy chain of a human anti-MAdCAM antibody, while the framework regions are derived from one or more different antibodies. In a more preferred embodiment, the CDRs of the chimeric antibody comprise all of the CDRs of the variable regions of the light chain and the heavy chain of a human anti-MAdCAM antibody. The framework regions may be from another species and may, in a preferred embodiment, be humanized. Alternatively, the framework regions may be from another human antibody.

A bispecific antibody can be generated that binds specifically to MAdCAM through one binding domain and to a second molecule through a second binding domain. The bispecific antibody can be produced through recombinant molecular biological techniques, or may be physically conjugated together. In addition, a single chain antibody containing more than one VH and VL may be generated that binds specifically to MAdCAM and to another molecule. Such bispecific antibodies can be generated using techniques that are well known for example, in connection with (i) and (ii) see, e.g., Fanger et al., Immunol Methods 4: 72-81 (1994) and Wright and Harris, supra. and in connection with (iii) see, e.g., Traunecker et al., Int. J. Cancer (Suppl.) 7: 51-52 (1992). In a preferred embodiment, the bispecific antibody binds to MAdCAM and to another molecule expressed at high level on endothelial cells. In a more preferred embodiment, the other molecule is VCAM, ICAM or L-selectin.

In various embodiments, the modified antibodies described above are prepared using one or more of the variable regions or one or more CDR regions from one of the antibodies selected from 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod or 7.26.4-mod. In another embodiment, the modified antibodies are prepared using one or more of the variable regions or one or more CDR regions whose amino acid sequence is presented in SEQ ID NOS: 2, 4, 6, 8, 10, 12, 14, 16, 18, 20, 22, 24, 26, 28, 30, 32, 34, 36, 38, 40, 42, 44, 46, 48, 52, 54, 56, 58, 62, 64, 66 or 68 or whose nucleotide sequence is presented in SEQ ID NOS: 1, 3, 5, 7, 9, 11, 13, 15, 17, 19, 21, 23, 25, 27, 29, 31, 33, 35, 37, 39, 41, 43, 45, 47, 51, 53, 55, 57, 61, 63, 65 or 67.

Derivatized and Labeled Antibodies

An antibody or antibody portion of the invention can be derivatized or linked to another molecule (e.g., another peptide or protein). In general, the antibodies or portions thereof are derivatized such that the MAdCAM binding is not affected adversely by the derivatization or labeling. Accordingly, the antibodies and antibody portions of the invention are intended to include both intact and modified forms of the human anti-MAdCAM antibodies described herein. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a cytotoxic agent, a pharmaceutical agent, and/or a protein or peptide that can mediate association of the antibody or antibody portion with another molecule (such as a streptavidin core region or a polyhistidine tag).

One type of derivatized antibody is produced by cross-linking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Another type of derivatized antibody is a labeled antibody. Useful detection agents with which an antibody or antibody portion of the invention may be derivatized include fluorescent compounds, including fluorescein, fluorescein isothiocyanate, rhodamine, 5-di methylamine-1-napthalenesulfonyl chloride, phycoerythrin, lanthanide phosphors and the like. An antibody may also be labeled with enzymes that are useful for detection, such as horseradish peroxidase, β-galactosidase, luciferase, alkaline phosphatase, glucose oxidase and the like. When an antibody is labeled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody may also be labeled with biotin, and detected through indirect measurement of avidin or streptavidin binding. An antibody may be labeled with a magnetic agent, such as gadolinium. An antibody may also be labeled with a predetermined polypeptide epitope recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

An anti-MAdCAM antibody may also be labeled with a radiolabeled amino acid. The radiolabel may be used for both diagnostic and therapeutic purposes. For instance, the radiolabel may be used to detect MAdCAM-expressing tissues by x-ray or other diagnostic techniques. Further, the radiolabel may be used therapeutically as a toxin for diseased tissue or MAdCAM expressing tumors. Examples of labels for polypeptides include, but are not limited to, the following radioisotopes or radionuclides—$^{3}$H, $^{14}$C, $^{15}$N, $^{35}$S, $^{90}$Y, $^{99}$Tc, $^{111}$In, $^{125}$I, $^{131}$I.

An anti-MAdCAM antibody may also be derivatized with a chemical group such as polyethylene glycol (PEG), a methyl or ethyl group, or a carbohydrate group. These groups may be useful to improve the biological characteristics of the antibody, e.g., to increase serum half-life or to increase tissue binding. This methodology would also apply to any antigen-binding fragments or versions of anti-MAdCAM antibodies.

Pharmaceutical Compositions and Kits

In a further aspect, the invention provides compositions comprising an inhibitory human anti-MAdCAM antibody and methods for treating subjects with such compositions. In some embodiments, the subject of treatment is human. In other embodiments, the subject is a veterinary subject. In some embodiments, the veterinary subject is a dog or a non-human primate.

Treatment may involve administration of one or more inhibitory anti-MAdCAM monoclonal antibodies of the invention, or antigen-binding fragments thereof, alone or with a pharmaceutically acceptable carrier. Inhibitory anti-MAdCAM antibodies of the invention and compositions comprising them, can be administered in combination with one or more other therapeutic, diagnostic or prophylactic agents. Additional therapeutic agents include anti-inflammatory or immunomodulatory agents. These agents include, but are not limited to, the topical and oral corticosteroids such as prednisolone, methylprednisolone, NCX-1015 or budesonide; the aminosalicylates such as mesalazine, olsalazine, balsalazide or NCX-456; the class of immunomodulators such as azathioprine, 6-mercaptopurine, methotrexate, cyclosporin, FK506, IL-10 (Ilodecakin), IL-11 (Oprelevkin), IL-12, MIF/CD74 antagonists, CD40 antagonists, such as TNX-100/5-D12, OX40L antagonists, GM-CSF, pimecrolimus or rapamycin; the class of anti-TNFα agents such as infliximab, adalimumab, CDP-870, onercept, etanercept; the class of anti-inflammatory agents, such as PDE-4 inhibitors (roflumilast, etc), TACE inhibitors (DPC-333, RDP-58, etc) and ICE inhibitors (VX-740, etc) as well as IL-2 receptor antagonists, such as daclizumab, the class of selective adhesion molecule antagonists, such as natalizumab, MLN-02, or alicaforsen, classes of analgesic agents such as, but not limited to, COX-2 inhibitors, such as rofecoxib, valdecoxib, celecoxib, P/Q-type voltage sensitize channel (α2δ) modulators, such as gabapentin and pregabalin, NK-1 receptor antagonists, cannabinoid receptor modulators, and delta opioid receptor agonists, as well as anti-neoplastic, anti-tumor, anti-angiogenic or chemotherapeutic agents Such additional agents may be included in the same composition or administered separately. In some embodiments, one or more inhibitory anti-MAdCAM antibodies of the invention can be used as a vaccine or as adjuvants to a vaccine. In particular, because MAdCAM is expressed in lymphoid tissue, vaccine antigens can be advantageously targeted to lymphoid tissue by conjugating the antigen to an anti-MAdCAM antibody of the invention.

As used herein, "pharmaceutically acceptable carrier" means any and all solvents, dispersion media, coatings, antibacterial and antifungal agents, isotonic and absorption enhancing or delaying agents, and the like that are physiologically compatible. Some examples of pharmaceutically acceptable carriers are water, saline, phosphate buffered saline, acetate buffer with sodium chloride, dextrose, glycerol, Polyethylene glycol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are surfactants, wetting agents or minor amounts of auxiliary substances such as wetting or emulsifying agents, preservatives or buffers, which enhance the shelf life or effectiveness of the antibody.

The compositions of this invention may be in a variety of forms, for example, liquid, semi-solid and solid dosage forms, such as liquid solutions (e.g., injectable and infusible solutions), dispersions or suspensions, tablets, pills, lyophilized cake, dry powders, liposomes and suppositories.

The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular, intradermal). In a preferred embodiment, the antibody is administered by intravenous infusion or injection. In another preferred embodiment, the antibody is administered by intramuscular, intradermal or subcutaneous injection.

Therapeutic compositions typically must be sterile and stable under the conditions of manufacture and storage. The composition can be formulated as a solution, lyophilized cake, dry powder, microemulsion, dispersion, liposome, or other ordered structure suitable to high drug concentration. Sterile injectable solutions can be prepared by incorporating the anti-MAdCAM antibody in the required amount in an appropriate solvent with one or a combination of ingredients enumerated above, as required, followed by sterilization. In the case of sterile powders for the preparation of sterile injectable solutions, the preferred methods of preparation are vacuum drying and freeze-drying that yields a powder of the active ingredient plus any additional desired ingredient from a previously sterile solution thereof. Generally, dispersions are prepared by incorporating the active compound into a sterile vehicle that contains a basic dispersion medium and the required other ingredients from those enumerated above. The desired characteristics of a solution can be maintained, for example, by the use of surfactants and the required particle size in the case of dispersion by the use of surfactants, phospholipids and polymers. Prolonged absorption of injectable compositions can be brought about by including in the composition an agent that delays absorption, for example, monostearate salts, polymeric materials, oils and gelatin.

The antibodies of the present invention can be administered by a variety of methods known in the art, although for many therapeutic applications, the preferred route/mode of administration is subcutaneous, intramuscular, intradermal or intravenous infusion. As will be appreciated by the skilled artisan, the route and/or mode of administration will vary depending upon the desired results.

In certain embodiments, the antibody compositions may be prepared with a carrier that will protect the antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems* (J. R. Robinson, ed., Marcel Dekker, Inc., New York (1978)).

In certain embodiments, an anti-MAdCAM antibody of the invention can be orally administered, for example, with an inert diluent or an assimilable edible carrier. The compound (and other ingredients, if desired) can also be enclosed in a hard or soft shell gelatin capsule, compressed into tablets, or incorporated directly into the subject's diet. For oral therapeutic administration, the anti-MAdCAM antibodies can be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

The compositions of the invention may include a "therapeutically effective amount" or a "prophylactically effective amount" of an antibody or antigen-binding portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a pre-determined quantity of active compound calculated to produce the desired therapeutic effect in association with the required pharmaceutical carrier. The specification for the dosage unit forms of the invention are dictated by and directly dependent on (a) the unique characteristics of the anti-MAdCAM antibody or portion thereof and the particular therapeutic or prophylactic effect to be achieved, and (b) the limitations inherent in the art of compounding such an antibody for the treatment of sensitivity in individuals.

An exemplary, non-limiting range for a therapeutically or prophylactically effective amount of an antibody or antibody portion of the invention is 0.025 to 50 mg/kg, more preferably 0.1 to 50 mg/kg, more preferably 0.1-25, 0.1 to 10 or 0.1 to 3 mg/kg. In some embodiments, a formulation contains 5 mg/mL of antibody in a buffer of 20 mM sodium acetate, pH 5.5, 140 mM NaCl, and 0.2 mg/mL polysorbate 80. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Another aspect of the present invention provides kits comprising an anti-MAdCAM antibody or antibody portion of the invention or a composition comprising such an antibody. A kit may include, in addition to the antibody or composition, diagnostic or therapeutic agents. A kit can also include instructions for use in a diagnostic or therapeutic method. In a preferred embodiment, the kit includes the antibody or a composition comprising it and a diagnostic agent that can be used in a method described below. In another preferred embodiment, the kit includes the antibody or a composition comprising it and one or more therapeutic agents that can be used in a method described below.

Gene Therapy

The nucleic acid molecules of the instant invention can be administered to a patient in need thereof via gene therapy. The therapy may be either in vivo or ex vivo. In a preferred embodiment, nucleic acid molecules encoding both a heavy chain and a light chain are administered to a patient. In a more preferred embodiment, the nucleic acid molecules are administered such that they are stably integrated into chromosomes of B cells because these cells are specialized for producing antibodies. In a preferred embodiment, precursor B cells are transfected or infected ex vivo and re-transplanted into a patient in need thereof. In another embodiment, precursor B cells or other cells are infected in vivo using a recombinant virus known to infect the cell type of interest. Typical vectors used for gene therapy include liposomes, plasmids and viral vectors. Exemplary viral vectors are retroviruses, adenoviruses and adeno-associated viruses. After infection either in vivo or ex vivo, levels of antibody expression can be monitored by taking a sample from the treated patient and using any immunoassay known in the art or discussed herein.

In a preferred embodiment, the gene therapy method comprises the steps of administering an isolated nucleic acid molecule encoding the heavy chain or an antigen-binding portion thereof of an anti-MAdCAM antibody and expressing the nucleic acid molecule. In another embodiment, the gene therapy method comprises the steps of administering an isolated nucleic acid molecule encoding the light chain or an antigen-binding portion thereof of an anti-MAdCAM antibody and expressing the nucleic acid molecule. In a more preferred method, the gene therapy method comprises the steps of administering of an isolated nucleic acid molecule encoding the heavy chain or an antigen-binding portion thereof and an isolated nucleic acid molecule encoding the light chain or the antigen-binding portion thereof of an anti-MAdCAM antibody of the invention and expressing the nucleic acid molecules. The gene therapy method may also comprise the step of administering another anti-inflammatory or immunomodulatory agent.

Diagnostic Methods of Use

The anti-MAdCAM antibodies may be used to detect MAdCAM in a biological sample in vitro or in vivo. The anti-MAdCAM antibodies may be used in a conventional immunoassay, including, without limitation, an ELISA, an RIA, FACS, tissue immunohistochemistry, Western blot or immunoprecipitation. The anti-MAdCAM antibodies of the invention may be used to detect MAdCAM from humans. In another embodiment, the anti-MAdCAM antibodies may be used to detect MAdCAM from Old World primates such as cynomolgus and rhesus monkeys, chimpanzees and apes. The invention provides a method for detecting MAdCAM in a biological sample comprising contacting a biological sample with an anti-MAdCAM antibody of the invention and detecting the antibody bound to MAdCAM. In one embodiment, the anti-MAdCAM antibody is directlyderivatized with a detectable label. In another embodiment, the anti-MAdCAM antibody (the first antibody) is unlabeled and a second antibody or other molecule that can bind the anti-MAdCAM antibody is labeled. As is well known to one of skill in the art, a second antibody is chosen that is able to specifically hind the specific species and class of the first antibody. For example, if the anti-MAdCAM antibody is a human IgG, then the secondary antibody may be an anti-human-IgG. Other molecules that can bind to antibodies include, without limitation, Protein A and Protein G, both of which are available commercially, e.g., from Pierce Chemical Co.

Suitable labels for the antibody or secondary have been disclosed supra, and include various enzymes, prosthetic groups, fluorescent materials, luminescent materials, magnetic agents and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; an example of a magnetic agent includes gadolinium; and examples of suitable radioactive material include $^{125}I$, $^{131}I$, $^{35}S$ or $^{3}H$.

In an alternative embodiment, MAdCAM can be assayed in a biological sample by a competition immunoassay utilizing MAdCAM standards labeled with a detectable substance and an unlabeled anti-MAdCAM antibody. In this assay, the biological sample, the labeled MAdCAM standards and the anti-MAdCAM antibody are combined and the amount of labeled MAdCAM standard bound to the unlabeled antibody is determined. The amount of MAdCAM in the biological sample is inversely proportional to the amount of labeled MAdCAM standard bound to the anti-MAdCAM antibody.

One may use the immunoassays disclosed above for a number of purposes. In one embodiment, the anti-MAdCAM antibodies may be used to detect MAdCAM in cells in cell culture. In a preferred embodiment, the anti-MAdCAM antibodies may be used to determine the level of cell surface MAdCAM expression after treatment of the cells with various compounds. This method can be used to test compounds that may be used to activate or inhibit MAdCAM. In this method, one sample of cells is treated with a test compound for a period of time while another sample is left untreated, cell surface expression could then be determined by flow cytometry, immunohistochemistry, Western blot, ELISA or RIA. In addition, the immunoassays may be scaled up for high throughput screening in order to test a large number of compounds for either activation or inhibition of MAdCAM.

The anti-MAdCAM antibodies of the invention may also be used to determine the levels of MAdCAM on a tissue or in cells derived from the tissue. In a preferred embodiment, the tissue is a diseased tissue. In a more preferred embodiment, the tissue is inflamed gastrointestinal tract or a biopsy thereof. In a preferred embodiment of the method, a tissue or a biopsy thereof is excised from a patient. The tissue or biopsy is then used in an immunoassay to determine, e.g., MAdCAM levels, cell surface levels of MAdCAM, or localization of MAdCAM by the methods discussed above. The method can be used to determine if an inflamed tissue expresses MAdCAM at a high level.

The above-described diagnostic method can be used to determine whether a tissue expresses high levels of MAdCAM, which may be indicative that the tissue will respond well to treatment with anti-MAdCAM antibody. Further, the diagnostic method may also be used to determine whether treatment with anti-MAdCAM antibody (see below) is causing a tissue to express lower levels of MAdCAM and thus can be used to determine whether the treatment is successful.

The antibodies of the present invention may also be used in vivo to localize tissues and organs that express MAd- CAM. In a preferred embodiment, the anti-MAdCAM antibodies can be used to localize inflamed tissue. The advantage of the anti-MAdCAM antibodies of the present invention is that they will not generate an immune response upon administration. The method comprises the steps of administering an anti-MAdCAM antibody or a pharmaceutical composition thereof to a patient in need of such a diagnostic test and subjecting the patient to imaging analysis determine the location of the MAdCAM-expressing tissues. Imaging analysis is well known in the medical art, and includes, without limitation, x-ray analysis, gamma scintigraphy, magnetic resonance imaging (MRI), positron emission tomography or computed tomography (CT). In another embodiment of the method, a biopsy is obtained from the patient to determine whether the tissue of interest expresses MAdCAM rather than subjecting the patient to imaging analysis. In a preferred embodiment, the anti-MAdCAM antibodies may be labeled with a detectable agent that can be imaged in a patient. For example, the antibody may be labeled with a contrast agent, such as barium, which can be used for x-ray analysis, or a magnetic contrast agent, such as a gadolinium chelate, which can be used for MRI or CT. Other labeling agents include, without limitation, radioisotopes, such as $^{99}$Tc. In another embodiment, the anti-MAdCAM antibody will be unlabeled and will be imaged by administering a second antibody or other molecule that is detectable and that can bind the anti-MAdCAM antibody.

The anti-MAdCAM antibodies of the invention may also be used to determine the levels of soluble MAdCAM present in donor blood, serum, plasma, or other biofluid, including, but not limited to, stool, urine, sputum or biopsy sample. In a preferred embodiment, the biofluid is plasma. The biofluid is then used in an immunoassay to determine levels of soluble MAdCAM. Soluble MAdCAM could be a surrogate marker for ongoing gastrointestinal inflammation and the method of detection could be used as a diagnostic marker to measure disease severity.

The above-described diagnostic method can be used to determine whether an individual expresses high levels of soluble MAdCAM, which may be indicative that the individual will respond well to treatment with an anti-MAdCAM antibody. Further, the diagnostic method may also be used to determine whether treatment with anti-MAdCAM antibody (see below) or other pharmaceutical agent of the disease is causing an individual to express lower levels of MAdCAM and thus can be used to determine whether the treatment is successful Inhibition of $\alpha_4\beta_7$/MAdCAM-Dependent Adhesion by Anti-MAdCAM Antibody:

In another embodiment, the invention provides an anti-MAdCAM antibody that binds MAdCAM and inhibits the binding and adhesion of $\alpha_4\beta_7$-integrin bearing cells to MAdCAM or other cognate ligands, such as L-selectin, to MAdCAM. In a preferred embodiment, the MAdCAM is human and is either a soluble form, or expressed on the surface of a cell. In another preferred embodiment, the anti-MAdCAM antibody is a human antibody. In another embodiment, the antibody or portion thereof inhibits binding between $\alpha_4\beta_7$ and MAdCAM with an IC$_{50}$ value of no more than 50 nM. In a preferred embodiment, the IC$_{50}$ value is no more than 5 nM. In a more preferred embodiment, the IC$_{50}$ value is less than 5 nM. In a more preferred embodiment, the IC$_{50}$ value is less than 0.05 µg/mL, 0.04 µg/mL or 0.03 µg/mL. In another preferred embodiment the IC$_{50}$ value is less than 0.5 µg/mL, 0.4 µg/mL or 0.3 µg/mL. The IC$_{50}$ value can be measured by any method known in the art. Typically, an IC$_{50}$ value can be measured by ELISA or adhesion assay. In a preferred embodiment, the IC$_{50}$ value is measured by adhesion assay using either cells or tissue which natively express MAdCAM or cells or tissue which have been engineered to express MAdCAM.

Inhibition of Lymphocyte Recruitment to Gut-Associated Lymphoid Tissue by Anti-MAdCAM Antibodies In another embodiment, the invention provides an anti-MAdCAM antibody that binds natively expressed MAdCAM and inhibits the binding of lymphocytes to specialised gastrointestinal lymphoid tissue. In a preferred embodiment, the natively-expressed MAdCAM is human or primate MAdCAM and is either a soluble form, or expressed on the surface of a cell. In another preferred embodiment, the anti-MAdCAM antibody is a human antibody. In another embodiment, the antibody or portion thereof inhibits the recruitment of gut-trophic $\alpha_4\beta_7^+$ lymphocytes to tissues expressing MAdCAM with an IC$_{50}$ value of no more than 5 mg/kg. In a preferred embodiment, the IC$_{50}$ value is no more than 1 mg/kg. In a more preferred embodiment, the IC$_{50}$ value is less than 0.1 mg/kg. In one embodiment, the IC$_{50}$ value can be determined by measuring the dose effect relationship of recruitment of technetium-labeled peripheral blood lymphocytes to the gastrointestinal tract using gamma scintigraphy or single photon emission computed tomography. In an another embodiment, the IC$_{50}$ value can be determined by measuring the increase in gut-trophic $\alpha_4\beta_7^+$ lymphocytes, such as, but not limited to, CD4$^+$ $\alpha_4\beta_7^+$ memory T-cells, in the peripheral circulation using flow cytometry as a function of the dose of anti-MAdCAM antibody.

In order that this invention may be better understood, the following examples are set forth. These examples are for purposes of illustration only and are not to be construed as limiting the scope of the invention in any manner.

Example 1

Generation of Anti-MAdCAM Producing Hybridomas

Antibodies of the invention were prepared, assayed and selected in accordance with the present Example Primary Immunogen Preparation:

Two immunogens were prepared for immunisation of the XenoMouse™ mice: (i) a MAdCAM-IgG$_1$ Fc fusion protein and (ii) cell membranes prepared from cells stably transfected with MAdCAM.

(i) MAdCAM-IgG$_1$ Fc Fusion Protein

Expression Vector Construction:

An EcoRI/BglII cDNA fragment encoding the mature extracellular, immunoglobulin-like domain of MAdCAM was excised from a pINCY Incyte clone (3279276) and cloned into EcoRI/BamHI sites of the pIG1 vector (Simmons, D. L. (1993) in *Cellular Interactions in Development: A Practical Approach*, ed. Hartley, D. A. (Oxford Univ. Press, Oxford), pp. 93-127.)) to generate an in frame IgG$_1$ Fc fusion. The resulting insert was excised with EcoRI/NotI and cloned into pCDNA3.1+ (Invitrogen). The MAdCAM-IgG$_1$ Fc cDNA in the vector was sequence confirmed. The amino acid sequence of the MAdCAM-IgG$_1$ Fc fusion protein is shown below:

MAdCAM-IgG$_1$ Fc Fusion Protein:

(SEQ ID NO: 107)
<u>MDFGLALLLAGLLGLLLGQSLQVKPLQVEPPEPVVAVALGASRQLTCRLA</u>

CADRGASVQWRGLDTSLGAVQSDTGRSVLTVRNASLSAAGTRVCVGSCGG

RTFQHTVQLLVYAFPDQLTVSPAALVPGDPEVACTAHKVTPVDPNALSFS

LLVGGQELEGAQALGPEVQEEEEEPQGDEDVLFRVTERWRLPPLGTPVPP

ALYCQATMRLPGLELSHRQAIPVLHSPTSPEPPDTTSPESPDTTSPESPD

TTSQEPPDTTSQEPPDTTSQEPPDTTSPEPPDKTSPEPAPQQGSTHTPRS

PGSTRTRRPEIQPKSCDKTHTCPPCPAPELLGGPSVFLFPPKPKDTLMIS

RTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPS

RDELTKNQVSLTCLVKGFYPSDIAVEWESNGQPENNYKATPPVLDSDGSF

FLYSKLTVDKSRWQQGNVFSCSVMHEALHNHYTQKSLSLSPGK

Underline: signal peptide
Bold: MAdCAM extracellular domain

Recombinant Protein Expression/Purification:

CHO-DHFR cells were transfected with pCDNA3.1+ vector containing MAdCAM-IgG$_1$ Fc fusion protein cDNA and stable clones expressing MAdCAM-IgG$_1$ Fc fusion protein selected in Iscove's media containing 600 µg/mL G418 and 100 ng/mL methotrexate. For protein expression, a hollow fibre bioreactor was seeded with stably expressing MAdCAM-IgG$_1$ Fc CHO cells in Iscove's media containing 10% low IgG fetal bovine serum (Gibco), non essential amino acids (Gibco), 2 mM glutamine (Gibco), sodium pyruvate (Gibco), 100 µg/mL G418 and 100 ng/mL methotrexate, and used to generate concentrated media supernatant. The MAdCAM-IgG$_1$ Fc fusion protein was purified from the harvested supernatant by affinity chromatography. Briefly, supernatant was applied to a HiTrap Protein G Sepharose (5 mL, Pharmacia) column (2 mL/min), washed with 25 mM Tris pH 8, 150 mM NaCl (5 column volumes) and eluted with 100 mM glycine pH 2.5 (1 mL/min), immediately neutralising fractions to pH 7.5 with 1M Tris pH 8. Fractions containing MAdCAM-IgG$_1$ Fc fusion protein were identified by SDS-PAGE, pooled together and applied to a Sephacryl S100 column (Pharmacia), pre-equilibrated with 35 mM BisTris pH 6.5, 150 mM NaCl. The gel filtration was performed at 0.35 mL/min, collecting a peak of MAdCAM-IgG$_1$ Fc fusion protein in ca. 3×5 mL fractions. These samples were pooled and applied to a Resource Q (6 mL, Pharmacia) column, pre-equilibrated in 35 mM BisTris pH6.5. The column was washed with 5 column volumes of 35 mM Bis Tris pH 6.5, 150 mM NaCl (6 mL/min) and MAdCAM-IgG$_1$ Fc fusion protein eluted into a 4-6 mL fraction with 35 mM Bis Tris pH 6.5, 400 mM NaCl. At this stage the protein was 90% pure and migrating as a single band at approximately 68 kD by SDS-PAGE. For use as an immunogen and all subsequent assays, the material was buffer exchanged into 25 mM HEPES pH 7.5, 1 mM EDTA, 1 mM DTT, 100 mM NaCl, 50% glycerol and stored as aliquots at −80° C.

(ii) Cell Membranes Stably Expressing MAdCAM

A SacI/NotI fragment comprising nucleotides 645-1222 of the published MAdCAM sequence (Shyjan A M, et al., *J Immunol.*, 156, 2851-7 (1996)) was PCR amplified from a colon cDNA library and cloned into SacI/NotI sites of pIND-Hygro vector (Invitrogen). A SacI fragment, comprising the additional 5' coding sequence was sub-cloned into this construct from pCDNA3.1 MAdCAM-IgG$_1$ Fc, to generate the full length MAdCAM cDNA. A KpnI/NotI fragment containing the MAdCAM cDNA was then cloned into corresponding sites in a pEF5FRTV5GWCAT vector (Invitrogen) and replacing the CAT coding sequence. The cDNA insert was sequence verified and used in transfections to generate single stably expressing clones in FlpIn NIH 3T3 cells (Invitrogen) by Flp recombinase technology, according to the manufacturer's instructions. Stably expressing clones were selected by their ability to support the binding of $\alpha_4\beta_7^+$ JY human B lymphoblastoid cell line (Chan B M, et al, *J. Biol. Chem.*, 267:8366-70 (1992)), outlined below. Stable clones of CHO cells expressing MAdCAM were prepared in the same way, using FlpIn CHO cells (Invitrogen).

MAdCAM-expressing FlpIn NIH-3T3 cells were grown in Dulbecco's modified Eagles Medium (Gibco), containing 2 mM L-glutamine, 10% Donor calf serum (Gibco) and 200 µg/mL Hygromycin B (Invitrogen) and expanded in roller bottles. MAdCAM-expressing FlpIn CHO cells were grown in Ham's F12/Dulbecco's modified Eagles Medium (Gibco), containing 2 mM L-glutamine, 10% Donor calf serum (Gibco) and 350 µg/mL Hygromycin B (Invitrogen) and expanded in roller bottles. Cells were harvested by use of a non-enzymatic cell dissociation solution (Sigma) and scraping, washing in phosphate buffered saline by centrifugation. Cell membranes were prepared from the cell pellet by two rounds of polytron homogenization in 25 mM Bis Tris pH 8, 10 mM MgCl$_2$, 0.015% (w/v) aprotinin, 100 U/mL bacitracin and centrifugation. The final pellet was resuspended in the same buffer, and 50×10$^6$ cell equivalents aliquoted into thick-walled eppendorfs and spun at >100,000 g to generate cell membrane pellets for XenoMouse mice immunisations. Supernatant was decanted and membranes were stored in eppendorfs at −80° C. until required. Confirmation of protein expression in the cell membranes was determined by SDS-PAGE and Western blotting with a rabbit anti-peptide antibody raised against the N-terminal residues of MAdCAM ([C]-KPLQVEPPEP).

Immunization and Hybridoma Generation:

Eight to ten week old XENOMOUSE™ mice were immunized intraperitoneally or in their hind footpads with either the purified recombinant MAdCAM-IgG$_1$ Fc fusion protein (10 µg/dose/mouse), or cell membranes prepared from either stably expressing MAdCAM-CHO or NIH 3T3 cells (10× 10$^6$ cells/dose/mouse). This dose was repeated five to seven times over a three to eight week period. Four days before fusion, the mice received a final injection of the extracellular domain of human MAdCAM in PBS. Spleen and lymph node lymphocytes from immunized mice were fused with the non-secretory myeloma P3-X63-Ag8.653 cell line and were subjected to HAT selection as previously described (Galfre and Milstein, *Methods Enzymol.* 73:3-46 (1981)). A panel of hybridomas all secreting MAdCAM specific human IgG$_2$κ and IgG$_4$κ antibodies were recovered and sub-cloned. Twelve hybridoma sub-clones, 1.7.2, 1.8.2, 6.14.2, 6.22.2, 6.34.2, 6.67.1, 6.73.2, 6.77.1, 7.16.6, 7.20.5, 7.26.4 and 9.8.2, producing monoclonal antibodies specific for MAdCAM were recovered and detected with assays described below. The parental lines 1.7, 1.8, 6.14, 6.22, 6.34, 6.67, 6.73, 6.77, 7.16, 7.20, 7.26 and 9.8, from which the sub-clone hybridoma lines, 1.7.2, 1.8.2, 6.14.2, 6.22.2, 6.34.2, 6.67.1, 6.73.2, 6.77.1, 7.16.6, 7.20.5, 7.26.4 and 9.8.2, were derived all had anti-MAdCAM activity.

ELISA Assays:

Detection of antigen-specific antibodies in mouse serum and hybridoma supernatant was determined by ELISA as described (Coligan et al., Unit 2.1 "Enzyme-linked immunosorbent assays," in *Current Protocols in Immunology* (1994)) using MAdCAM-IgG$_1$ Fc fusion protein to capture the antibodies. For animals that were immunised with MAd-CAM-IgG$_1$ Fc fusion protein, antibodies were screened for non-specific reactivity against human IgG$_1$ and for the ability to bind to FlpIn CHO MAdCAM cells by flow cytometry.

In a preferred ELISA assay, the following techniques are used: ELISA plates were coated overnight at 4° C. with 100 µL/well of MAdCAM-IgG$_1$ Fc fusion (4.5 µg/mL) in plate containing buffer (100 mM sodium carbonate/bicarbonate buffer pH 9.6). After incubation, coating buffer was removed and the plate blocked with 200 µL/well blocking buffer (5% BSA, 0.1% Tween 20, in phosphate buffered saline) and incubated at room temperature for 1 hour. Blocking buffer was removed and 50 µL/well of hybridoma supernatant or other serum or supernatant (e.g., positive control) added for 2 hours at room temperature. After incubation the plate was washed with PBS (3×100 µL/well) and the binding of the hybridoma mAb detected with HRP-conjugated secondary antibodies (i.e. 1:1000 mouse anti-human IgG$_2$-HRP (SB Cat. No. 9060-05) for IgG$_2$ antibodies or 1:1000 mouse anti-human IgG$_4$-HRP (Zymed Cat. No. 3840) for IgG$_4$ antibodies) diluted in PBS. The plates were incubated at room temperature for 1 hour, washed in PBS (3×100 µL/well) and finally developed with 100 µL OPD (o-phenylenediamine (DAKO S2405)+5 µL 30% H$_2$O$_2$/12 mL). The plates were allowed to develop 10-20 mins, stopping the reaction with 100 µL 2M H$_2$SO$_4$. The plates were read at 490 nm.

Adhesion Assays:

Antibodies that demonstrated binding to MAdCAM-IgG$_1$ Fc fusion protein by ELISA, were assessed for antagonist activity in an adhesion assays with $\alpha_4\beta_7^+$ JY cells and either (i) MAdCAM-IgG$_1$ Fc fusion protein or (ii) MAdCAM-CHO cells.

(i) MAdCAM-IgG$_1$ Fc Fusion Assay

100 µL of a 4.5 µg/mL solution of purified MAdCAM-IgG$_1$ Fc fusion protein in Dulbecco's PBS was adsorbed to 96 well Black Microfluor "B" u-bottom (Dynex #7805) plates overnight at 4° C. The MAdCAM coated plates were then inverted and excess liquid blotted off, prior to blocking at 37° C. for at least 1 hour in 10% BSA/PBS. During this time cultured JY cells were counted using tryptan blue exclusion (should be approximately 8×10$^5$ cells/mL) and 20×10$^6$ cells/assay plate pipetted into a 50 mL centrifuge tube. JY cells were cultured in RPMI1640 media (Gibco), containing 2 mM L-glutamine and 10% heat-inactivated fetal bovine serum (Life Technologies #10108-165) and seeded at 1-2×10$^5$/mL every 2-3 days to prevent the culture from differentiating. The cells were washed twice with RPMI 1640 media (Gibco) containing 2 mM L-glutamine (Gibco) by centrifugation (240 g), resuspending the final cell pellet at 2×10$^6$ cells/mL in RPMI 1640 for Calcein AM loading. Calcein AM (Molecular Probes #C-3099) was added to the cells as a 1:200 dilution in DMSO (ca. final concentration 5 µM) and the cells protected from light during the course of the incubation (37° C. for 30 min). During this cell incubation step the antibodies to be tested, were diluted as follows: for single dose testing, the antibodies were made up to 3 µg/mL (11 µg/mL final) in 0.1 mg/mL BSA (Sigma#A3059) in PBS; for full IC$_{50}$ curves, the antibodies were diluted in 0.1 mg/mL BSA/PBS, with 3 µg/mL (1 µg/mL final) being the top concentration, then doubling dilutions (1:2 ratio) across the plate. The final well of the row was used for determining total binding, so 0.1 mg/ml BSA in PBS was used.

After blocking, the plate contents were flicked out and 50 µL of antibodies/controls were added to each well and the plate incubated at 37° C. for 20 min. During this time, Calcein-loaded JY cells were washed once with RPMI 1640 media containing 10% fetal bovine serum and once with 1 mg/mL BSA/PBS by centrifugation, resuspending the final cell pellet to 1×10$^6$/mL in 1 mg/mL BSA/PBS. 100 µL of cells were added to each well of the U bottomed plate, the plate sealed, briefly centrifuged (1000 rpm for 2 min) and the plate then incubated at 37° C. for 45 min. At the end of this time, the plates were washed with a Skatron plate washer and fluorescence measured using a Wallac Victor$^2$ 1420 Multilabel Reader (excitation λ 485 nm, emission λ 535 nm count from top, 8 mm from bottom of plate, for 0.1 sec with normal emission aperture). For each antibody concentration, percent adhesion was expressed as a percentage of maximal fluorescence response in the absence of any antibody minus fluorescence associated with non-specific binding. The IC$_{50}$ value is defined as the anti-MAdCAM antibody concentration at which the adhesion response is decreased to 50% of the response in the absence of anti-MAdCAM antibody. Antibodies that were able to inhibit the binding of JY cells to MAdCAM-IgG$_1$ Fc fusion with an IC$_{50}$ value <0.1 µg/mL, were considered to have potent antagonist activity and were progressed to the MAdCAM-CHO adhesion assay. All twelve of the tested Abs showed potent antagonist activity (Table 3). Monoclonal antibodies 1.7.2, 1.8.2, 7.16.6, 7.20.5 and 7.26.4 were derived from IgG$_2$κ lineages, and monoclonal antibodies 6.14.2, 6.22.2, 6.34.2, 6.67.1, 6.73.2, 6.77.1 and 9.8.2 were derived from IgG$_4$κ lineages.

(ii) MAdCAM-CHO Cell Adhesion Assay.

JY cells were cultured as above. MAdCAM-expressing CHO cells were generated with the pEF5FRT MAdCAM cDNA construct and using the Flp recombinase technology (Invitrogen) as described above. Single stable clones of MAdCAM-expressing CHO cells were selected based on their ability to support the adhesion of JY cells and the binding, by flow cytometry, of the rabbit anti-peptide antibody, raised against the N-terminus of MAdCAM and described above. MAdCAM-expressing CHO cells were cultured in a DMEM/F12 media (Gibco #21331-020) containing 2 mM L-glutamine, 10% fetal bovine serum (Gibco) and 350 µg/mL Hygromycin B (Invitrogen), splitting 1:5 every 2/3 days. For the adhesion assay, MAdCAM-expressing CHO cells were seeded at 4×10$^4$ cells/well in 96 well black plates—clear bottom (Costar #3904) in 200 µL culture medium and cultured overnight at 37° C./5% CO$_2$.

The following day, hybridoma supernatant or purified monoclonal antibody was diluted from a starting concentration of 30 µg/mL (equivalent to a final concentration of 10 µg/mL) in 1 mg/mL BSA/PBS, as described above. For the MAdCAM CHO plates, the plate contents were flicked out and 50 µL of antibodies/controls were added to each well and the plate incubated at 37° C. for 20 min. The final well of the row was used for determining total binding, so 0.1 mg/mL BSA in PBS was used. Calcein AM-loaded JY cells, to a final concentration of 1×10$^6$/mL in 1 mg/mL BSA/PBS, were prepared as above, then 100 µL added to the plate after the 20 min incubation period with the antibody. The plate was then incubated at 37° C. for 45 min, then washed on a Tecan plate washer (PW 384) and fluorescence measured using the Wallac plate reader as described above. For each antibody concentration, percent adhesion was expressed as a percentage of maximal fluorescence response in the absence of any antibody minus fluorescence associated with non-specific binding. Antibodies that were able to inhibit the binding of JY cells to MAdCAM CHO cells with an $IC_{50}$ value <1 µg/mL were considered to have potent antagonist activity. As before, the $IC_{50}$ value is defined as the anti-MAdCAM antibody concentration at which the adhesion response had decreased to 50% of the response in the absence of anti-MAdCAM antibody. The $IC_{50}$ potencies for 1.7.2, 1.8.2, 6.14.2, 6.22.2, 6.34.2, 6.67.1, 6.73.2, 6.77.1, 7.16.6, 7.20.5, 7.26.4 and 9.8.2 in this assay are described below in Table 3.

TABLE 3

$IC_{50}$ values of exemplified anti-MAdCAM antibodies

| Clone | MAdCAM IgG1 Fc fusion Mean IC50 (µg/mL) | n | MAdCAM FlpIn CHO Assay Mean IC50 (µg/mL) | n |
|---|---|---|---|---|
| IgG2 | | | | |
| 1.7.2 | 0.030 ± 0.011 | 6 | 0.052 ± 0.280 | 9 |
| 1.8.2 | 0.027 ± 0.011 | 4 | 0.424 ± 0.107 | 8 |
| 7.16.6 | 0.019 ± 0.009 | 7 | 0.389 ± 0.093 | 16 |
| 7.20.5 | 0.025 ± 0.027 | 7 | 0.387 ± 0.202 | 9 |
| 7.26.4 | 0.021 ± 0.040 | 4 | 0.574 ± 0.099 | 15 |
| IgG4 | | | | |
| 6.14.2 | 0.011 ± 0.005 | 4 | 0.291 ± 0.096 | 6 |
| 6.22.2 | 0.018 ± 0.011 | 4 | 0.573 ± 0.168 | 7 |
| 6.34.2 | 0.013 ± 0.008 | 4 | 0.285 ± 0.073 | 7 |
| 6.67.1 | 0.013 ± 0.070 | 4 | 0.298 ± 0.115 | 8 |
| 6.73.2 | 0.020 ± 0.010 | 4 | 0.369 ± 0.103 | 8 |
| 6.77.1 | 0.022 ± 0.004 | 4 | 0.520 ± 0.100 | 4 |
| 9.8.2 | 0.020 ± 0.050 | 4 | 0.440 ± 0.342 | 8 |

To measure the antagonist potency of anti-MAdCAM mAbs in flow-based assays, under sheer stress conditions that are designed to mimic the microvascular environment on the high endothelial venules which serve the gut associated lymphoid tissue, CHO cells expressing MAdCAM were plated in glass microslides (50×4 mm) and allowed to adhere to form a confluent monolayer (Ca. $2.5 \times 10^5$ cells). The cells were then incubated with affinity-purified mAb over a range of concentrations (0.1-10 µg/mL) for 20 mins at 37° C., before being connected to the flow assay system. An isotype matched $IgG_2$ or $IgG_4$ mAb (10 µg/mL) was used as a negative control. Normal donor peripheral blood lymphocytes (PBLs) were perfused over the cell monolayer at a constant shear stress of 0.05 Pa. Experiments were videoed and total adhesion of lymphocytes (rolling+firm adhesion) was calculated. All of the tested monoclonal antibodies were shown to be potent antagonists under the conditions described.

(iii) Stamper-Woodruff Assays

To visualise MAdCAM⁺ vessels, biotinylated anti-MAd-CAM mAb was generated on 1-2 mg of affinity-purified protein, using a 20 molar excess of biotin-NHS (Pierce) in phosphate buffer saline, according to manufacturer's instructions. The reaction was allowed to sit at room temperature (30 min), and desalted with a PD-10 (Pharmacia) column and the protein concentration determined.

Normal liver lymph node was removed from a donor organ, snap-frozen in liquid nitrogen and stored at −70° C. until use. 10 µm cryostat sections were cut, air-dried on poly-L lysine coated slides, and fixed in acetone prior to the assay. Sections were blocked using an avidin-biotin blocking system (DAKO), and then incubated with biotinylated anti-MAdCAM mAb over a range of concentrations (1-50 µg/mL) at room temperature (2 hrs). An isotype matched $IgG_2$ or $IgG_4$ mAb (50 µg/mL) was used as a negative control and a blocking anti-$\beta_7$ antibody (50 µg/mL) as a positive control.

Figure 4:
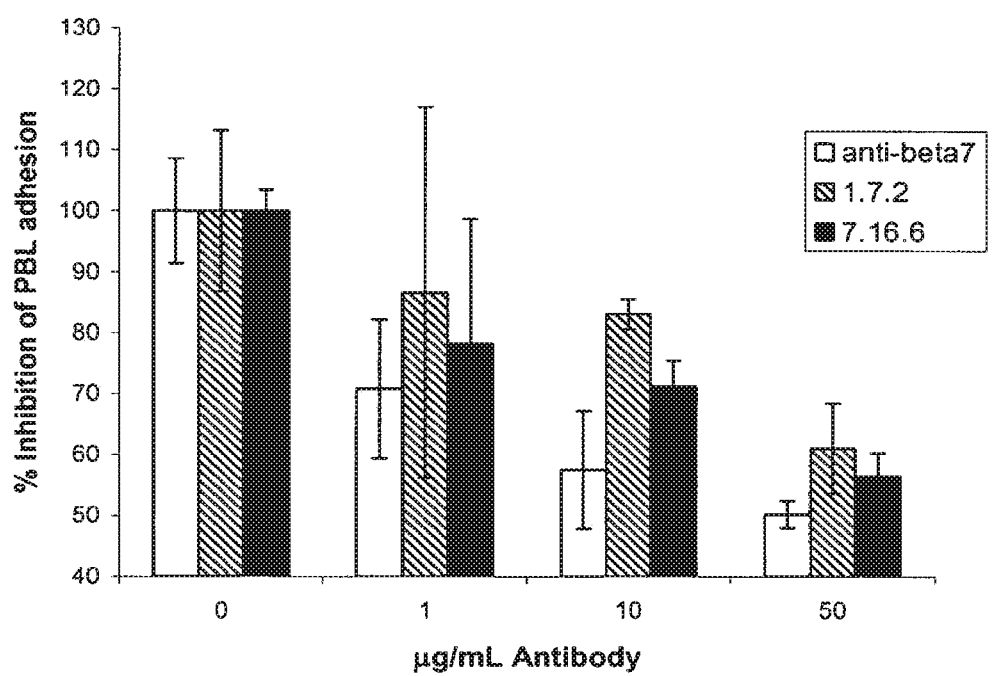
FIG. 4 is a graph representing the dose effects of purified biotinylated 1.7.2 and 7.16.6 on the adhesion of human peripheral blood lymphocytes to sections of MAdCAM-expressing frozen human liver endothelium.

Peripheral blood lymphocytes, taken from normal donors, were labeled with a mouse anti-human CD2 mAb (DAKO) to allow subsequent visualisation of adherent cells. $5 \times 10^5$ PBLs were added to each lymph node section and incubated for 30 mins before being gently rinsed off to avoid detachment of adherent cells. Sections were then re-fixed in acetone, and re-incubated with biotinylated anti-MAdCAM mAh (10 µg/mL), followed by biotinylated goat-anti-mouse mAb (to recognise CD2 labeled PBLs and unstained MAd-CAM⁺ vessels) and then streptABcomplex/HRP (DAKO). Finally MAdCAM⁺ vessels & CD2 labeled PBLs were visualised by addition of DAB substrate (DAKO) to the sections, with a brown reaction product showing areas of positive staining. Lymphocyte adhesion was quantified by counting the number of lymphocytes adhering to 50 MAd-CAM-1⁺ vessels of portal tracts, veins or sinusoids. Data, expressed as mean values, were then normalised to percent adhesion, using the adhesion of PBLs in the absence of any antibody taken as 100%. The data were compiled on the basis of n=3 different PBL donors and for different liver lymph node donors. Representative data for biotinylated purified monoclonal antibodies 1.7.2 and 7.16.6 are depicted in FIG. 4 compared to a blocking anti-$\beta_7$ antibody control.

Selectivity Assays:

VCAM and fibronectin are close structural and sequence homologues to MAdCAM. Affinity-purified anti-MAdCAM mAbs were assessed for MAdCAM-specificity by determining their ability to block the binding of $\alpha_4\beta_1^+/\alpha_5\beta_1^+$ Jurkat T-cells (ATCC) to their cognate cell adhesion molecule. 100 µL of a 4.5 µg/mL solution of Fibronectin cell binding fragment (110 Kd, Europa Bioproducts Ltd, Cat. No. UBF4215-18) or VCAM (Panvera) in Dulbecco's PBS was adsorbed to 96 well Black Microfluor "B" u-bottom (Dynex #7805) plates overnight at 4° C. The coated plates were then inverted and excess liquid blotted off, prior to blocking at 37° C. for at least 1 hour in 10% BSA/PBS. During this time cultured Jurkat T cells were counted using tryptan blue exclusion and loaded with Calcein AM dye as previously described for JY cells above. The antibodies to be tested, were diluted from a top concentration of 10 µg/mL in 0.1 mg/ml BSA in PBS. The final well of the row was used for determining total binding, so 0.1 mg/ml BSA in PBS was used. Echistatin (Bachem, Cat. No. H-9010) prepared in PBS was used at a top concentration of 100 nM to block the $\alpha_5\beta_1$/Fibronectin interaction. An anti-CD106 mAb (Clone 51-10C9, BD Pharmingen Cat. No. 555645) at a top concentration of 1 µg/mL was used to block the $\alpha_4\beta_1$/VCAM interaction.

After blocking, the plate contents were flicked out and 50 µL of antibodies/controls were added to each well and the plate incubated at 37° C. for 20 min. Calcein-loaded Jurkat T cells were washed once as before, resuspending the final cell pellet to $1 \times 10^6$/mL in 1 mg/mL BSA/PBS. 100 µL of cells were added to each well of the U bottomed plate, the plate sealed, briefly centrifuged (1000 rpm for 2 min) and the plate then incubated at 37° C. for 45 min. At the end of this time, the plates were washed with a Skatron plate washer and fluorescence measured using a Wallac Victor² 1420 Multilabel Reader (excitation λ485 nm, emission λ535 nm count from top, 8 mm from bottom of plate, for 0.1 sec with normal emission aperture). For each antibody, the degree of inhibition is expressed below pictorially, in Table 4 (− negligible inhibition of adhesion, *** complete inhibition of adhesion). All mAbs exemplified are potent and selective anti-MAdCAM antagonists, demonstrating substantially greater than 100 fold selectivity for MAdCAM over VCAM and fibronectin.

TABLE 4

Comparative selectivity of anti-MAdCAM antibody for MAdCAM over other cell adhesion molecules, Fibronectin and VCAM

| Clone | Inhibition in $\alpha 5\beta 1$/Fibronectin assay (10 µg/mL) | Inhibition in $\alpha 4\beta 1$/VCAM assay (10 µg/mL) | Inhibition in $\alpha 4\beta 7$/MAdCAM assay (0.1 µg/mL) |
|---|---|---|---|
| IgG2 | | | |
| 1.7.2 | − | − | *** |
| 1.8.2 | − | − | *** |
| 7.16.6 | − | − | *** |
| 7.20.5 | − | − | *** |
| 7.26.4 | − | − | *** |
| IgG4 | | | |
| 6.14.2 | − | − | *** |
| 6.22.2 | − | − | *** |
| 6.34.2 | − | − | *** |
| 6.67.1 | − | − | *** |
| 6.73.2 | − | − | *** |
| 6.77.1 | − | − | *** |
| 9.8.2 | − | − | *** |
| | − | | |

Hybridomas were deposited in the European Collection of Cell Cultures (ECACC), H.P.A at CAMR, Porton Down, Salisbury, Wiltshire SP4 0JG on 9 Sep. 2003 with the following deposit numbers:

| Hybridoma | Deposit No. |
|---|---|
| 1.7.2 | 03090901 |
| 1.8.2 | 03090902 |
| 6.14.2 | 03090903 |
| 6.22.2 | 03090904 |
| 6.34.2 | 03090905 |
| 6.67.1 | 03090906 |
| 6.73.2 | 03090907 |
| 6.77.1 | 03090908 |
| 7.16.6 | 03090909 |
| 7.20.5 | 03090910 |
| 7.26.4 | 03090911 |
| 9.8.2 | 03090912 |

Example II

Determination of Affinity Constants ($K_d$) of Fully Human Anti-MAdCAM Monoclonal Antibodies by BIAcore We performed affinity measures of purified antibodies by surface plasmon resonance using the BIAcore 3000 instrument, following the manufacturer's protocols.
Protocol 1
To perform kinetic analyses, a high density mouse anti-human (IgG$_2$ and IgG$_4$) antibody surface over a CM5 BIAcore sensor chip was prepared using routine amine coupling. Hybridoma supernatants were diluted 10, 5, 2-fold in HBS-P (10 mM HEPES pH 7.4, 150 mM NaCl, 0.005% Surfactant P20) running buffer containing 100 µg/mL BSA and 10 mg/mL carboxymethyldextran or used neat. Each mAb was captured onto a separate surface using a 1 min contact time and a 5 mM wash for stabilization of the mAb baseline. MAdCAM-IgG$_1$ Fc (141 nM) fusion protein was then injected at over all surfaces for one minute, followed by a 3 min dissociation. The data were normalized for the amount of antibody captured on each surface and evaluated with global fit Langmuir 1:1, using baseline drift models available on the BIAevaluation software provided by BIAcore.
Protocol 2
Affinity-purified mAb were immobilized onto the dextran layer of a CM5 biosensor chip using amine coupling. Chips were prepared using pH 4.5 acetate buffer as the immobilization buffer and protein densities of 2.5-5.5 kRU were achieved. Samples of MAdCAM-IgG$_1$ Fc fusion protein in running buffer were prepared at concentrations ranging from 0.2-55 nM (a 0 nM solution comprising running buffer alone was included as a zero reference). Samples were randomized and injected in duplicate for 3 min each across 4 flow cells using HBS-EP (10 mM HEPES pH 7.4, 150 mM NaCl, 3 mM EDTA, 0.005% Surfactant P20) as running buffer. A flow rate of 100 µL/min was used to minimize mass transport limitations. Dissociation of MAdCAM-IgG$_1$ Fc fusion protein was monitored for 180 mins, the surface regenerated by a 6 sec injection of 25 mM H$_3$PO$_4$ (50 µL/min), or 10 mM (6.22.2), 20 mM (6.67.1, 6.73.2, 6.77.1) to 25 mM (6.34.2) and 45 mM NaOH (6.14.2) and the data analysed using the BIAevaluation (v3.1) software package.

Table 5 lists affinity measurements for representative anti-MAdCAM antibodies of the present invention:

TABLE 5

Determination of affinity constant, $K_d$, by surface plasmon resonance (BIAcore)

| | Protocol 1 | | | Protocol 2 | | |
|---|---|---|---|---|---|---|
| CLONE | $K_{on}$ (1/Ms) | $K_{off}$ (1/s) | $K_D$ (pM) | $K_{on}$ (1/MS) | $K_{off}$ (1/s) | $K_D$ (pM) |
| IgG2 | | | | | | |
| 1.7.2 | $2.4 \times 10^5$ | $1 \times 10^{-5}$ | 42 | $5.5 \times 10^3$ | $1.3 \times 10^{-7}$ | 23.6 |
| 1.8.2 | $2.9 \times 10^5$ | $1 \times 10^{-5}$ | 35 | $1.8 \times 10^5$ | $2.3 \times 10^{-5}$ | 128 |
| 7.16.6 | $1.5 \times 10^6$ | $2.2 \times 10^{-6}$ | 1.5 | $2.9 \times 10^5$ | $1.4 \times 10^{-6}$ | 4.8 |
| 7.20.5 | $4.5 \times 10^5$ | $1.9 \times 10^{-5}$ | 42.2 | $1.6 \times 10^5$ | $1.2 \times 10^{-5}$ | 75 |
| 7.26.4 | $9.6 \times 10^5$ | $2.6 \times 10^{-4}$ | 271 | $1.5 \times 10^5$ | $1.2 \times 10^{-5}$ | 80 |
| IgG4 | | | | | | |
| 6.14.2 | $1.3 \times 10^5$ | $1 \times 10^{-5}$ | 7.7 | $5 \times 10^5$ | $<5 \times 10^{-6}$ | <10 |
| 6.22.2 | $1.5 \times 10^6$ | $1.4 \times 10^{-5}$ | 9.3 | $2.3 \times 10^5$ | $8.7 \times 10^{-7}$ | 3.8 |
| 6.34.2 | $1.2 \times 10^6$ | $1.9 \times 10^{-5}$ | 15.8 | $3.3 \times 10^5$ | $<5 \times 10^{-6}$ | <15 |
| 6.67.1 | $5.9 \times 10^5$ | $1 \times 10^{-5}$ | 17 | $2.4 \times 10^5$ | $<5 \times 10^{-6}$ | <20 |
| 6.73.2 | $1.4 \times 10^5$ | $1.3 \times 10^{-4}$ | 93 | | | |
| 6.77.1 | $1.5 \times 10^5$ | $1 \times 10^{-5}$ | 6.7 | | | |
| 9.8.2 | $2.3 \times 10^6$ | $2.3 \times 10^{-4}$ | 100 | $4.4 \times 10^5$ | $1.4 \times 10^{-5}$ | 32.5 |

The kinetic analyses indicate that the antibodies prepared in accordance with the invention possess high affinities and strong binding constants for the extracellular domain of MAdCAM.

Example III

Identification of Epitope Selectivity and Species Cross-Reactivity of Anti-MAdCAM mAbs Antibodies recognize surface-exposed epitopes on antigens as regions of linear (primary) sequence or structural (secondary) sequence. Luminex epitope binning, BIAcore binning and species immunohistochemical analysis were used in concert, in order to define the functional epitope landscape of the anti-MAdCAM antibodies.

Luminex-Based Epitope Binning:

MxhIgG 2,3,4-conjugated beads (Calbiochem Ml 1427) were coupled to the primary unknown anti-MAdCAM antibody. We added 150 µL of primary unknown antibody dilution (0.1 µg/mL diluted in hybridoma medium) to the well of a 96-well tissue culture plate. The bead stock was gently vortexed and diluted in supernatant to a concentration of $0.5 \times 10^5$ heads/mL. The beads were incubated in the supernatant on a shaker overnight in the dark at 4° C.

Each well of a 96-well microtiter filter plate (Millipore # MABVN1250) was pre-wetted by adding 200 µL wash buffer (PBS containing 0.05% Tween20) and removed by aspiration. Next, 50 µL/well of the $0.5 \times 10^5$ beads/mL stock was added to the filter plate, and the wells washed with wash buffer (2×100 µL/well). 60 µL/well of MAdCAM-IgG$_1$ Fc antigen diluted in hybridoma medium (0.1 µg/mL) was added. The plates were covered and incubated at room temperature with gentle shaking for one hour. The wells were washed twice by addition of 100 µL/well wash buffer followed by aspiration. Next, we added 60 µL/well of secondary unknown anti-MAdCAM antibody diluted in hybridoma medium (0.1 µg/mL). The plates were shaken at room temperature in the dark for two hours. Next, the wells were washed twice by addition of 100 µL/well wash buffer followed by aspiration. Next, 60 µL/well of biotinylated MxhIgG 2,3,4 (0.5 µg/mL) was added. The plates were shaken at room temperature in the dark for one hour. The wells were washed twice by addition of 100 µL/well wash buffer followed by aspiration. To each well, 60 µL of 1 µg/mL MxhIgG 2,3,4 Streptavidin-PE (Pharmacia #554061) diluted in hydridoma medium was added. The plates were shaken at room temperature in the dark for twenty minutes. The wells were washed twice by addition of 100 µL/well wash buffer followed by aspiration. Next, each well was resuspended in 80 µL blocking buffer (PBS with 0.5% bovine serum albumin, 0.1% TWEEN and 0.01% Thimerosal) carefully pipetted up and down to resuspend the beads.

Using Luminex 100 and its accompanying software (Luminex® Corporation) the plates were read to determine luminescence readings. Based on the luminescence data obtained for the various anti-MAdCAM antibodies tested, the anti-MAdCAM antibodies were grouped according to their binding specificities. The anti-MAdCAM antibodies that were tested fall into a series of epitope bins, represented in Table 8.

BIAcore Binning:

In a similar method to that described above, BIAcore can also be used to determine the epitope exclusivity of the anti-MAdCAM antibodies exemplified by this invention. Nine anti-MAdCAM antibody clones, 6.22.2, 6.34.2, 6.67.1, 6.77.1, 7.20.5, 9.8.2, 1.7.2, 7.26.4 and 7.16.6, were immobilized onto the dextran layer of separate flow cells of a CM5 biosensor chip using amine coupling. The immobilization buffer was either 10 mM acetate buffer pH 4.5 (clones 6.22.2, 6.34.2, 7.20.5, 9.8.2, 1.7.2, 7.26.4 and 7.16.6) or 10 mM acetate buffer pH 5.5 (clones 6.67.1 and 6.77.1). A protein density of approximately 3750 RU was achieved in all cases. Deactivation of unreacted N-hydroxysuccinimide esters was performed using 1 M ethanolamine hydrochloride, pH 8.5.

MAdCAM-IgG$_1$ Fc fusion protein was diluted to a concentration of 1.5 µg/mL (approximately 25 nM) in HBS-EP running buffer (0.01 M HEPES pH 7.4, 0.15 M NaCl, 3 mM EDTA, 0.005% Polysorbate 20). It was then injected across the first flow cell, in a volume of 50 µL at a rate of 5 µL/min.

After the injection was complete, the first antibody probe was added to the same flow cell. All test antibodies were diluted to a concentration of approximately 20 µg/mL in HBS-EP, and also injected in a volume of 50 µL at a flow rate of 5 µL/min. When no binding of the test antibody was observed, the next test clone was injected immediately afterwards. When binding did occur, the sensor surface was regenerated to remove both the MAdCAM-IgG$_1$ Fc fusion protein and the test antibody. A variety of regeneration solutions were used depending upon the immobilized antibody and the test antibody present. A summary of the regeneration conditions used is depicted in Table 6.

TABLE 6

Summary of regeneration conditions used to perform BIAcore epiope mapping

| Immobilised antibody | Antibody probe to be removed | Regeneration solution | Injection volume |
|---|---|---|---|
| 7.16.6 | 6.22.2 | 40 mM Phosphoric Acid | 20 µL |
|  | 6.34.2 | 40 mM Phosphoric Acid | 40 µL |
|  | 7.20.5 | 40 mM Phosphoric Acid | 20 µL |
| 6.77.1 | 9.8.2 | 40 mM Phosphoric Acid | 10 µL |
|  | 1.7.2 | 40 mM Phosphoric Acid | 5 µL |
|  | 7.16.6 | 40 mM Phosphoric Acid | 10 µL |
| 1.7.2 | 6.77.1 | 25 mM Phosphoric Acid | 5 µL |
|  | 9.8.2 | 25 mM Phosphoric Acid | 5 µL |
|  | 7.20.5 | 25 mM Phosphoric Acid | 5 µL |
|  | 6.22.2 | 25 mM Phosphoric Acid | 5 µL |
|  | 6.34.2 | 25 mM Sodium Hydroxide | 5 µL |
|  | 6.67.1 | 25 mM Sodium Hydroxide | 5 µL |
| 6.22.2 | 9.8.2 | 25 mM Sodium Hydroxide | 20 µL |
|  | 7.26.4 | 25 mM Sodium Hydroxide | 5 µL |
| 6.34.2 | 9.8.2 | 25 mM Sodium Hydroxide | 70 µL |
|  | 1.7.2 | 40 mM Sodium Hydroxide | 5 µL |
|  | 7.26.4 | 40 mM Sodium Hydroxide | 5 µL |
| 6.67.1 | 9.8.2 | 40 mM Sodium Hydroxide | 5 µL |
|  | 1.7.2 | 40 mM Sodium Hydroxide | 5 µL |
| 7.20.5 | 9.8.2 | 25 mM Phosphoric Acid | 5 µL |
|  | 1.7.2 | 25 mM Phosphoric Acid | 5 µL |
|  | 7.26.4 | 25 mM Phosphoric Acid | 5 µL |
| 7.26.4 | 9.8.2 | 40 mM Sodium Hydroxide | 20 µL |
|  | 6.22.2 | 75 mM Phosphoric Acid | 20 µL |
|  | 7.20.5 | 75 mM Phosphoric Acid | 20 µL |
|  | 7.16.6 | 75 mM Phosphoric Acid | 20 µL |
| 9.8.2 | 9.8.2 | 25 mM Phosphoric Acid | 15 µL |
|  | 6.22.2 | 25 mM Phosphoric Acid | 10 µL |
|  | 7.20.5 | 25 mM Phosphoric Acid | 20 µL |
|  | 7.16.6 | 25 mM Phosphoric Acid | 10 µL |

(Flow rate was 50 µL/min during all regeneration procedures)

After regeneration, MAdCAM-IgG$_1$ Fc fusion protein was hound again and further test antibodies were injected. These procedures were carried out until the entire panel of clones had been injected over the surface of the immobilised antibody, with bound MAdCAM-IgG$_1$ Fc fusion protein. A new flow cell with a different immobilised antibody and bound MAdCAM was then used for probing with the nine test clones. Anti-MAdCAM antibodies 1.7.2 and 1.8.2 were expected to recognise the same MAdCAM epitope, based on the close primary amino acid sequence homology of their heavy and kappa light chains, SEQ ID NOS: 2, 4, 6, 8 respectively. Accordingly, only 1.7.2 was assessed though the BIAcore response matrix. Antibodies 6.14.2 and 6.73.2 were omitted from this analysis, but all other combinations of anti-MAdCAM antibody pairs were tested in this way. An arbitrary level of 100 RU was chosen as the threshold between binding/non-binding and a response matrix, (Table 7), was created based on whether binding was observed.

TABLE 7

BIAcore epitope binning response matrix

| Immobilised anti-body | Secondary antibody | | | | | | | | |
|---|---|---|---|---|---|---|---|---|---|
| | 6.22.2 | 6.34.2 | 6.67.1 | 6.77.1 | 7.20.5 | 9.8.2 | 1.7.2 | 7.26.4 | 7.16.6 |
| 6.22.2 | – | – | – | – | – | x | x | x | x |
| 6.34.2 | – | – | – | – | – | x | x | x | x |
| 6.67.1 | – | – | – | – | – | x | x | – | – |
| 6.77.1 | – | – | – | – | – | x | x | – | x |
| 7.20.5 | – | – | – | – | – | x | x | x | x |
| 9.8.2 | x | x | x | x | x | x | – | – | x |
| 1.7.2 | x | x | x | x | x | x | – | – | x |
| 7.26.4 | x | x | – | – | x | x | – | – | x |
| 7.16.6 | x | x | – | – | x | – | – | – | x |

Response matrix for all combinations of antibody pairs.
– indicates no binding of the antibody probe, x indicates binding was observed (above a chosen threshold level of 100 RU).

The matrix diagonal in Table 7 (shaded grey) holds the binding data for identical probe pairs. In all instances, except for the two clones 7.16.6 and 9.8.2, the antibodies were self-blocking. Antibodies 7.16.6 and 9.8.2 do not cross compete. The lack of self-blocking could be due to a mAb-induced conformational change in the fusion protein that permits additional binding of the mAb to a second site on MAdCAM-IgFc.

Figure 5:
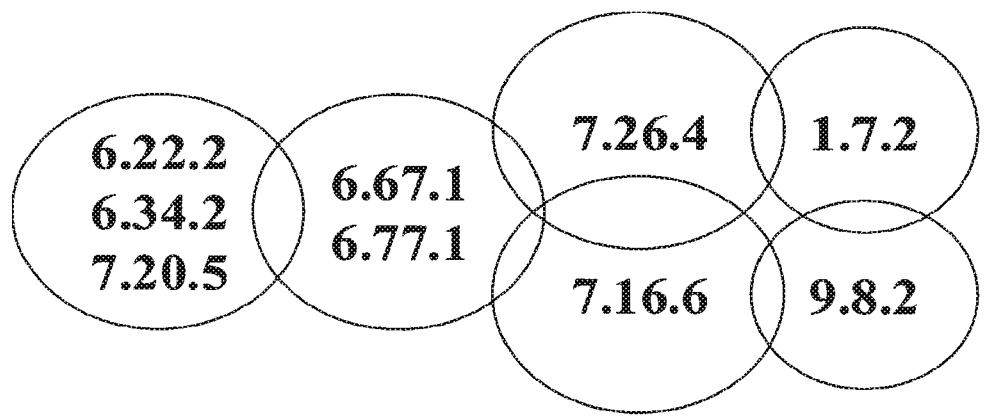
FIG. 5 shows a two dimensional graphical representation based on the data captured in Table 7 of the diversity of MAdCAM epitopes to which the anti-MAdCAM antibodies, 1.7.2, 6.22.2, 6.34.2, 6.67.1, 6.77.1, 7.16.6, 7.20.5, 7.26.4, 9.8.2 bind. Anti-MAdCAM antibodies within the same circle show the same reactivity pattern, belong in the same epitope bin and are likely to recognize the same epitope on MAdCAM. Anti-MAdCAM antibody clones within overlapping circles are unable to bind simultaneously and are, therefore, likely to recognize an overlapping epitope on MAdCAM. Non-integrating circles represent anti-MAdCAM antibody clones with distinct spatial epitope separation.

Grouping the clones that show the same reactivity pattern gives rise to at least six different epitope bins, as shown in the graphical representation, FIG. 5).

Further precise identification of the MAdCAM epitope sequences with which an anti-MAdCAM antibody interacts can be determined by any of a number of methods, including, but not limited to, Western analysis of spotted peptide library arrays (Reineke et al., *Curr. Topics in Microbiol. and Immunol* 243: 23-36 (1999), M. Famulok, E-L Winnacker, C-H Wong eds., Springer-Verlag, Berlin), phage or bacterial flagellin/fliC expression library display, or simple MALDI-TOF analysis of bound protein fragments following limited proteolysis.

Immunohistochemical Assays:

OCT or sucrose-embedded frozen tissue specimens of ileum (Peyer's patches), mesenteric lymph node, spleen, stomach, duodenum, jejunum and colon were used as a positive staining controls for the anti-MAdCAM mAbs. For staining human sections with human $IgG_2$ mAbs, biotinylated derivatives of the anti-MAdCAM mAbs were generated. 10 μm frozen tissue sections were cut onto poly L-lysine coated slides, placed directly into 100% acetone 4° C. (10 min), then 3% hydrogen peroxide in methanol (10 min), washing between steps with PBS. The slides were blocked with Biotin Blocking System (DAKO Cat. No. X0590), prior to incubation with the primary antibody (1:100-1:1000) in PBS (1 hr), washed with PBS-Tween 20 (0.05%) and then binding developed with HRP-Streptavidin (BD Bioscience Cat. No. 550946, 30 mm) and DAB substrate (Sigma Cat. No. D5905). For $IgG_4$ mAbs, an HRP-conjugated, mouse anti-human $IgG_4$ (Zymed Cat. No. 3840) secondary was used. The slides were counterstained with Mayer's Haemalum (1 min), washed and then mounted in DPX.

Binding affinity was compared for a number of species (mouse, rat, rabbit, dog, pig, cynomolgus and human tissue). There was no reactivity for rat, rabbit and pig tissue by immunohistochemistry and no cross-reactivity of the anti-MAdCAM antibodies for recombinant mouse MAdCAM, when analyzed by ELISA. The data for human, cynomolgus and dog tissue are presented in table form, Table 8 below:

TABLE 8

Pattern of cross reactivity of anti-MAdCAM antibodies to MAdCAM species orthologues

| | | IHC cross-reactivity | | | |
|---|---|---|---|---|---|
| CLONE | Luminex BIN | human ileum | cyno ileum | marmoset ileum | dog ileum |
| IgG2 | | | | | |
| 1.7.2 | 3a | Binding | No Binding | No Binding | No Binding |
| 1.8.2 | 3a | Binding | No Binding | No Binding | No Binding |
| 7.16.6 | 3b | Binding | Binding | No Binding | No Binding No Binding |
| 7.20.5 | 2b | Binding | Binding | N.D. | No Binding |
| 7.26.4 | 3b | Binding | Binding | N.D. | No Binding |
| IgG4 | | | | | |
| 6.14.2 | 2 | Binding | Binding | N.D. | Binding |
| 6.22.2 | 2 | Binding | Binding | N.D. | No Binding |
| 6.34.2 | 6 | Binding | Binding | N.D. | No Binding |
| 6.67.1 | 5 | Binding | Binding | N.D. | Binding |
| 6.73.2 | 3 | Binding | N.D. | N.D. | No Binding |
| 6.77.1 | 1 | Binding | Binding | N.D. | No Binding |
| 9.8.2 | 3a | Binding | N.D. | No Binding | No Binding |

Anti-MAdCAM binding to specialised endothelial structures and lymphoid tissue is indicated by the shading, according to the key. The epitope bin based on Luminex epitope analysis and the pattern of MAdCAM cross-reactivity are indicated for each antibody. Luminex epitope binning data for anti-MAdCAM antibodies 6.14.2, 6.22.2, 6.34.2, 6.67.1, 6.73.3 and 6.77.1 (italics) were derived from separate experiments than that for 1.7.2, 1.8.2, 7.16.6, 7.20.5, 7.26.4 and 9.8.2 (bold type), as indicated by the difference in font character.

All anti-MAdCAM antibodies tested had the ability to recognize a human MAdCAM epitope expressed on vascular endothelial compartments of the gastrointestinal tract. Apart from 1.7.2 and 1.8.2, all other anti-MAdCAM antibodies tested were able to specifically bind the vascular endothelial compartments of the cynomolgus gastrointestinal tract Certain other anti-MAdCAM antibodies, namely 6.14.2 and 6.67.1 also had the ability to specifically recognize the dog MAdCAM orthologue as well as cynomolgus MAdCAM.

Generation of a Functionally Active Chimeric Cynomolgus/Human MAdCAM-Expressing CHO Cell Line:

The differences in binding affinity of certain anti-MAdCAM antibodies for human and cynomolgus MAdCAM led us to determine whether a structural basis for this observation could be made.

Based on the published amino acid sequence for Macaque MAdCAM (Shyjan A M, et al., *J Immunol.*, 156, 2851-7 (1996)), primers were designed to PCR amplify the cynomolgus MAdCAM $\alpha_4\beta_7$ binding domain sequence. Total RNA was prepared from frozen excised cynomolgus mesenteric lymph node (Ca. 200 mg) using the Trizol method (Invitrogen) according to the manufacturer's instructions. 1-2 μg was oligo-dT primed and reverse transcribed with AMV reverse transcriptase (Promega). A proportion of the reverse transcribed product was subjected to PCR with forward 5'-AGC ATG GAT CGG GGC CTG GCC-3' (SEQ ID NO: 67) and reverse 5'-GTG CAG GAC CGG GAT GGC CTG-3' (SEQ ID NO: 68) primers with GC-2 polymerase in 1M GC melt (Clontech) and at an annealing temperature of 62° C. An RT-PCR product of the appropriate size was excised and purified from a 1% agarose gel after electrophoresis, then TOPO-TA cloned (Invitrogen) between EcoRI sites of pCR2.1. The insert was sequence confirmed. The nucleotide and predicted translated amino acid sequences are shown in SEQ ID NOS 49 and 50, respectively.

The predicted human and cynomolgus MAdCAM amino acid sequences for the $\alpha_4\beta_7$ binding domain show a high degree of sequence identity (90.8%) when aligned (FIG. 3 provides this sequence alignment). To generate a functionally active cynomolgus MAdCAM-expressing cell line, which mimicked the anti-MAdCAM binding pattern represented by Table 8, a SacI fragment corresponding to the cynomolgus $\alpha_4\beta_7$ binding domain sequence in pCR2.1, was subcloned directly into the C-terminal human MAdCAM pIND-Hygro construct containing carboxyl-terminal mucin stalk and transmembrane domain, described above. The sequence and orientation was verified, then a KpnI/NotI fragment was cloned into pEF5FRTV5GWCAT vector (Invitrogen), replacing the CAT coding sequence and used in transfections to generate single stably expressing clones in Flp In CHO cells (Invitrogen), according to the manufacturer's instructions.

The binding of anti-MAdCAM antibody clones to the CHO cells expressing cynomolgus/human MAdCAM chimera was assessed by flow cytometry and the functional activity of anti-MAdCAM antibodies was determined using a very similar JY cell adhesion assay as that described above. The binding and functional activity of anti-MAdCAM antibodies are expressed in Table 9.

TABLE 9

Correlation between the functional activity in the cynomolgus/human MAdCAM-CHO/JY adhesion assay and human and cynomolgus/human MAdCAM CHO cell binding, as measured by FACS, for a range of anti-MAdCAM antibodies.

| Clone | Functional IC$_{50}$ (µg/mL) | FACS binding human | FACS binding cyno/human |
|---|---|---|---|
| IgG2 | | | |
| 1.7.2 | inactive | Binding | No Binding |
| 1.8.2 | inactive | Binding | No Binding |
| 7.16.6 | 0.72 | Binding | Binding |
| 7.20.5 | 0.62 | Binding | Binding |
| 7.26.4 | 0.96 | Binding | Binding |
| IgG4 | | | |
| 6.14.2 | 0.53 | Binding | Binding |
| 6.22.2 | 0.83 | Binding | Binding |
| 6.34.2 | 0.47 | Binding | Binding |
| 6.67.1 | 0.75 | Binding | Binding |
| 6.73.2 | Inactive | Binding | No Binding |
| 6.77.1 | 0.64 | Binding | Binding |
| 9.8.2 | 0.83 | Binding | Binding |

Taken together, there is a good correlation between the ability of a given anti-MAdCAM antibody to bind human or cynomolgus MAdCAM, as detected by immunohistochemistry (Table 8), with recombinant cell-based binding and functional activity (Table 9). Anti-MAdCAM antibodies 1.7.2, 1.8.2 and 6.73.2, for instance, demonstrated a consistent lack of binding to cynomolgus tissue and cells expressing a chimeric cynomolgus/human MAdCAM protein. Anti-MAdCAM antibodies 1.7.2, 1.8.2 and 6.73.2 also did not have the ability to detect functional blocking activity in the cynomolgus/human MAdCAM/JY adhesion assay.

Similar approaches could be used to define the epitope of the anti-MAdCAM antibodies 6.14.2 and 6.67.1 that recognise dog MAdCAM.

Example IV

Use of Anti-MAdCAM mAbs in the Detection of Circulating Soluble MAdCAM as a Method of Disease Diagnosis Anti-MAdCAM antibodies can be used for the detection of circulating soluble MAdCAM (sMAdCAM). Detection of sMAdCAM in clinical plasma, serum samples or other biofluid, such as, but not limited to, stool, urine, sputum. is likely to be a useful surrogate disease biomarker for underlying disease, including, but not limited to, inflammatory bowel disease.

Based on the epitope binning data (Tables 7 and 8), anti-MAdCAM antibodies 1.7.2 and 7.16.6 appear to recognise different epitopes on human MAdCAM. ELISA plates were coated overnight at 4° C. with 100 µL/well of a 50 µg/mL solution of 1.7.2 in phosphate buffered saline (PBS). After incubation the plate was blocked for 1.5 hours with a PBS blocking buffer containing 10% milk (200 µL/well). After incubation the plate was washed with PBS (2×100 µL/well) and serial dilutions of MAdCAM-IgG$_1$-Fc fusion protein, from a top concentration of 50 µg/mL down to approximately 5 ng/mL in PBS, to a final volume of 100 µL, were added to the plate for incubation of 2 hours at room temperature. In a similar approach the MAdCAM-IgG$_1$-Fc protein can be diluted in plasma or serum, or some other such relevant biofluid and used to determine the expression of soluble MAdCAM in a clinical sample, as described below. As a negative control, only buffer was added to the wells containing the primary anti-MAdCAM antibody. After this time, the plate was washed with PBS (3×100 µL/well) and the plate then incubated in the dark with an Alexa488-labelled 7.16.6 (100 µL, 5 µg/mL). The Alexa488-labelled 7.16.6 was generated using a commercially available kit (Molecular Probes, A-20181), following Manufacturer's protocols.

Figure 6:
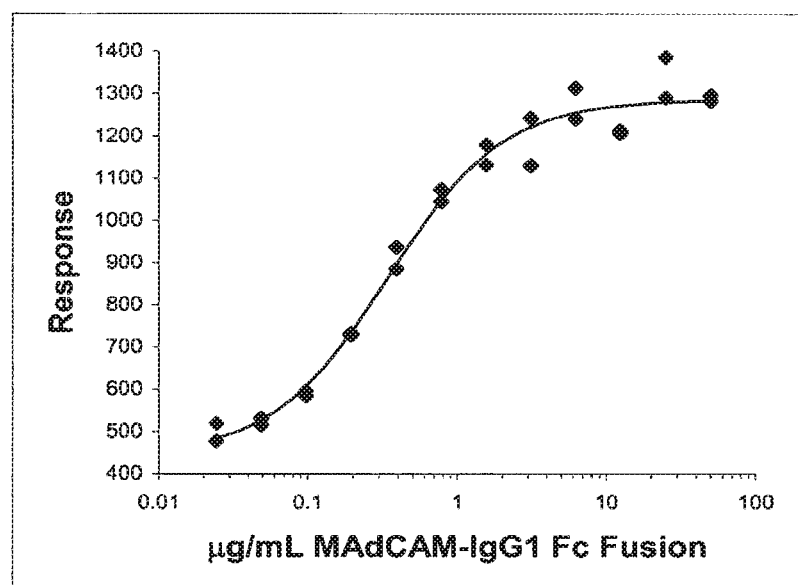
FIG. 6 shows sandwich ELISA data with anti-MAdCAM antibodies 1.7.2 and an Alexa 488-labelled 7.16.6, showing that two antibodies that are able to detect different epitopes on MAdCAM could be used to detect soluble MAdCAM for diagnostic purposes.

The plate was washed with PBS containing 0.05% Tween-20, and binding of labeled 7.16.6 to captured soluble MAdCAM determined by measuring the fluorescence (Wallac Victor$^2$ 1420 Multilabel Reader, excitation λ485 nm, emission λ535 nm count from top, 3 mm from bottom of plate, for 0.1 sec with normal emission aperture). When fluorescence is plotted as a function of the concentration of MAdCAM-IgG$_1$-Fc fusion protein, FIG. 6, it indicates that 1.7.2 and a labeled 7.16.6 can be used for diagnostic purposes to determine the level of circulating soluble MAdCAM expressed in a biofluid or clinical sample. This sandwich ELISA approach is not restricted to the use of 1.7.2 and 7.16.6, but any combination of anti-MAdCAM antibodies that recognise different epitopes on MAdCAM, as outlined by the data and interpretation of table 7 and FIG. 5. Similar strategies could be applied to the development of similar assays, such as immunohistochemistry and Western Blot, with the other anti-MAdCAM antibodies described, using different partners, variants, labels, etc.

Example V

Amino Acid Structure of Anti-MAdCAM mAbs Prepared in Accordance to the Invention In the following discussion, structural information related to the anti-MAdCAM mAbs prepared in accordance with the invention is provided.

To analyze structures of mAbs produced in accordance with the invention, we cloned the genes encoding the heavy and light chain fragments out of the specific hybridoma clone. Gene cloning and sequencing was accomplished as follows:

Poly(A)+ mRNA was isolated from approximately $2\times10^5$ hybridoma cells derived from immunized XenoMouse mice using Fast-Track kit (Invitrogen). The generation of random primed cDNA was followed by PCR. Human VH or Vκ family specific primers (Marks et al., 'Oligonucleotide primers for polymerase chain reaction amplification of human immunoglobulin variable genese and design of family-specific oligonucleotide probes'; *Eur. J. Immunol.*, 21, 985-991 (1991)) or a universal human VH primer, MG-30 (5'-CAG GTG CAG CTG GAG CAG TCI GG-3' (SEQ ID NO: 108) was used in conjunction with primers specific for the human Cγ2, MG40-d (5'-GCT GAG GGA GTA GAG TCC TGA GGA-3' (SEQ ID NO: 109) or Cγ4 constant region, MG-40d (5'GCT GAG GGA GTA GAG TCC TGA GGA CTG T-3' (SEQ ID NO: 110), or Cκ constant region (hκP2; as previously described in Green et al., 1994). Sequences of the human mAb-derived heavy and kappa chain transcripts from hybridomas were obtained by direct sequencing of PCR products generated from poly (A+) RNA using the primers described above. PCR products were cloned into pCR2.1 using a TOPO-TA cloning kit (Invitrogen) and both strands were sequenced using Prism dye terminator sequencing kits and an ABI 377 sequencing machine. All sequences were analysed by alignments to the 'V BASE sequence directory' (Tomlinson, et al, *J. Mol. Biol.*, 227, 776-798 (1992); *Hum. Mol. Genet.*, 3, 853-860 (1994); *EMBO J.*, 14, 4628-4638 (1995).)

Further each of the antibodies, 1.7.2, 1.8.2, 6.14.2, 6.22.2, 6.34.2, 6.67.1, 6.73.2, 6.77.1, 7.16.6, 7.20.5, 7.26.4, 9.8.2, 6.22.2-mod, 6.34.2-mod, 6.67.1-mod, 6.77.1-mod and 7.26.4-mod, were subjected to full length DNA sequencing. For such, total RNA was isolated from approximately 3-6× $10^6$ hybridoma cells using an RNeasy kit (Qiagen). The mRNA was reverse transcribed using oligo-dT and an AMV-based reverse transcriptase system (Promega). V BASE was used to design 5' specific amplification primers, containing an optimal Kozak sequence and ATG start codon (underlined) and 3' reverse primers for the specific heavy and kappa chains as depicted in Table 10.

TABLE 10

PCR primer pairs for cDNA amplification from anti-MAdCAM mAb-expressing hybridomas and primers used in the construction of modified versions of anti-MAdCAM antibodies.

| | Oligo sequence |
|---|---|
| VH1-18 | 5' TATCTAAGCTTCTAGACTCGAGCGCCACCATGG ACTGGACCTGGAGCATCCTT 3' (SEQ ID NO: 70) |
| VH3-15 | 5' TATCTAAGCTTCTAGACTCGAGCGCCACCATGG AGTTTGGGCTGAGCTGGATT 3' (SEQ ID NO: 71) |
| VH3-21 | 5' TATCTAAGCTTCTAGACTCGAGCGCCACCATGG AACTGGGGCTCCGCTGGGTT 3' (SEQ ID NO: 72) |
| VH3-23 | 5' TATCTAAGCTTCTAGACTCGAGCGCCACCATGG AGTTTGGGCTGAGCTGGCTT 3' (SEQ ID NO: 73) |

TABLE 10-continued

PCR primer pairs for cDNA amplification from anti-MAdCAM mAb-expressing hybridomas and primers used in the construction of modified versions of anti-MAdCAM antibodies.

| | Oligo sequence |
|---|---|
| VH3-30 | 5' TATCTAAGCTTCTAGACTCGAGCGCCACCATGG AGTTTGGGCTGAGCTGGGTT 3' (SEQ ID NO: 74) |
| VH3-33 | 5' TATCTAAGCTTCTAGACTCGAGCGCCACCATGG AGTTTGGGCTGAGCTGGGTT 3' (SEQ ID NO: 75) |
| VH4-4 | 5' TATCTAAGCTTCTAGACTCGAGCGCCACCATGA AACACCTGTGGTTCTTCCTC 3' (SEQ ID NO: 76) |
| A2/A3 | 5' TATCTAAGCTTCTAGACCCGGGCGCCACCATGA GGCTCCCTGCTCAGCTCCTG 3' (SEQ ID NO: 77) |
| A26 | 5' TATCTAAGCTTCTAGACCCGGGCGCCACCATGT TGCCATCACAACTCATTGGG 3' (SEQ ID NO: 78) |
| B3 | 5' TATCTAAGCTTCTAGACCCGGGCGCCACCATGG TGTTGCAGACCCAGGTCTTC 3' (SEQ ID NO: 79) |
| O12 | 5' TATCTAAGCTTCTAGACCCGGGCGCCACCATGG ACATGAGGGTCCCCGCTCAG 3' (SEQ ID NO: 80) |
| O18 | 5' TATCTAAGCTTCTAGACCCGGGCGCCACCATGG ACATGAGGGTCCCTGCTCAG 3' (SEQ ID NO: 81) |
| RevIgG2 | 5' TTCTCTGATCAGAATTCCTATCATTTACCCGGA GACAGGGAGAG 3' (SEQ ID NO: 82) |
| RevIgG4 | 5' TTCTTTGATCAGAATTCTCACTAACACTCTCCC CTGTTGAAGC 3' (SEQ ID NO: 83) |
| RevKappa | 5' TTCTCTGATCAGAATTCCTATCATTTACCCAGA GACAGGGAGAG 3' (SEQ ID NO: 84) |
| 6.22.2VK_F1 | 5'-GGA TCT GGG ACA GAT TTC ACC CTC ACC ATC AAT AGC CTG GAA GC-3' (SEQ ID NO: 85) |
| 6.22.2VK_R1 | 5'-GCT TCC AGG CTA TTG ATG GTG AGG GTG AAA TCT GTC CCA GAT CC-3' (SEQ ID NO: 86) |
| 6.22.2VH_F1 | 5'-GCA GCG TCT GGA TTC ACC TTC AGT AGC-3' (SEQ ID NO: 87) |
| 6.22.2VH_R1 | 5'-GCT ACT GAA GGT GAA TCC AGA CGC TGC-3' (SEQ ID NO: 88) |
| 6.22.2VH_CS* | 5'-CGG AGG TGC TTC TAG AGC AGG GCG-3' (SEQ ID NO: 89) |
| 6.34.2VK_F1 | 5'-GCA AGT CAG AGT ATT AGT AGC TAT TTA AAT TGG TAT CAG CAG AAA CC-3' (SEQ ID NO: 90) |
| 6.34.2VK_R1 | 5'-GGT TTC TGC TGA TAC CAA TTT AAA TAG CTA CTA ATA CTC TGA CTT GC-3' (SEQ ID NO: 91) |

TABLE 10-continued

PCR primer pairs for cDNA amplification from anti-MAdCAM mAb-expressing hybridomas and primers used in the construction of modified versions of anti-MAdCAM antibodies.

| | Oligo sequence |
|---|---|
| 6.34.2VK_F2 | 5'-CCA TCA GTT CTC TGC AAC CTG AGG ATT TTG CAA CTT ACT ACT GTC ACC-3' (SEQ ID NO: 92) |
| 6.34.2VK_R3 | 5'-GGT GAC AGT AGT AAG TTG CAA AAT CCT CAG GTT GCA GAG AAC TGA TGG-3' (SEQ ID NO: 93) |
| 6.34.2VH_F1 | 5'-GCA AAT GAA CAG CCT GCG CGC TGA GGA CAC G-3' (SEQ ID NO: 94) |
| 6.34.2VH_R1 | 5'-CGT GTC CTC AGC GCG CAG GCT GTT CAT TTG C-3' (SEQ ID NO: 95) |
| 6.67.1VK_F1 | 5'-CAA TAA GAA CTA CTT AGC TTG GTA CCA ACA GAA ACC AGG ACA GCC-3' (SEQ ID NO: 96) |
| 6.67.1VK_R1 | 5'-GGC TGT CCT GGT TTC TGT TGG TAC CAA GCT AAG TAG TTC TTA TTG-3' (SEQ ID NO: 97) |
| 6.67.1VH_F1 | 5'-CCC TCA GGG GTC GAG TCA CCA TGT CAG TAG ACA CGT CCA AGA ACC-3' (SEQ ID NO: 98) |
| 6.67.1VH_R1 | 5'-GGT TCT TGG ACG TGT CTA CTG ACA TGG TGA CTC GAC CCC TGA GGG-3' (SEQ ID NO: 99) |
| 6.67.1VH_CS* | 5'-ATT CTA GAG CAG GGC GCC AGG-3' (SEQ ID NO: 100) |
| 6.77.1VK_F1 | 5'-CCA TCT CCT GCA AGT CTA GTC AGA GCC TCC-3' (SEQ ID NO: 101) |
| 6.77.1VK_R1 | 5'-GGA GGC TCT GAC TAG ACT TGC AGG AGA TGG-3' (SEQ ID NO: 102) |
| 6.77.1VK_F2 | 5'-GGT TTA TTA CTG CAT GCA AGT ATA CAG CTA TGT CAG TTT TGG CC-3' (SEQ ID NO: 103) |
| 6.77.1VK_R2 | 5'-GGC CAA AAC TGG ACA TAA GCT GTA TAC TTT GCA TGC AGT AAT AAA CC-3' (SEQ ID NO: 104) |
| 7.26.4K_F1 | 5'-CCT GCA AGT CTA GTC AGA GCC TCC-3' (SEQ ID NO: 105) |
| 7.26.4K_R1 | 5'-GGA GGC TCT GAC TAG ACT TGC AGG-3' (SEQ ID NO: 106) |

The primers pairs were used to amplify the cDNAs using Expand High Fidelity Taq polymerase (Roche), and the PCR products cloned into pCR2.1 TOPO-TA (Invitrogen) for subsequent sequencing. Heavy and kappa light chain sequence verified clones were then cloned into pEE6.1 and pEE12.1 vectors (LONZA) using XbaI/EcoRI and HindIII/EcoRI sites respectively.

Gene Utilization Analysis

Table 11 displays the heavy and kappa light chain gene utilization for each hybridoma outlined in the invention.

TABLE 11

Heavy and Kappa light chain Gene Utilization

| | Heavy Chain | | | Kappa light Chain | |
|---|---|---|---|---|---|
| Clone | VH | D | JH | $V_K$ | $J_K$ |
| IgG2 | | | | | |
| 1.7.2 | VH3-15 | D6-19 | JH4b | A3 | JK5 |
| 1.8.2 | VH3-15 | D6-19 | JH4b | A3 | JK5 |
| 7.16.6 | VH1-18 | D6-6 | JH6b | A2 | JK1 |
| 7.20.5 | VH4-4 | D3-10 | JH6b | A3 | JK4 |
| 7.26.4 | VH1-18 | D6-6 | JH6b | A2 | JK1 |
| IgG4 | | | | | |
| 6.14.2 | VH3-23 | D5-5 | JH4b | O12 | JK5 |
| 6.22.2 | VH3-33 | D5-12 | JH6b | A26 | JK4 |
| 6.34.2 | VH3-30 | D4-23 | JH6b | O12 | JK3 |
| 6.67.1 | VH4-4 | D3-10 | JH4b | B3 | JK4 |
| 6.73.2 | VH3-23 | D6-19 | JH6b | O12 | JK2 |
| 6.77.1 | VH3-21 | D6-19 | JH6b | A2 | JK2 |
| 9.8.2 | VH3-33 | D3-10 or D3-16 | JH6b | O18 | JK5 |

Sequence Analysis

To further examine antibody structure predicted amino acid sequences of the antibodies were obtained from the cDNAs obtained from the clones.

Sequence identifier numbers (SEQ ID NO:) 1-48 and 51-68 provide the nucleotide and amino acid sequences of the heavy and kappa light chains of the anti-MAdCAM antibodies 1.7.2 (SEQ ID NOS 1-4), 1.8.2 (SEQ ID NOS 5-8), 6.14.2 (SEQ ID NOS 9-12), 6.22.2 (SEQ ID NOS 13-16), 6.34.2 (SEQ ID NOS 17-20), 6.67.1 (SEQ ID NOS 21-24), 6.73.2 (SEQ ID NOS 25-28), 6.77.1 (SEQ ID NOS 29-32), 7.16.6 (SEQ ID NOS 33-36), 7.20.5 (SEQ ID NOS 37-40), 7.26.4 (SEQ ID NOS 41-44), 9.8.2 (SEQ ID NOS 45-48) and the modified anti-MAdCAM antibodies 6.22.2-mod (SEQ ID NOS 51-54), 6.34.2-mod (SEQ ID NOS 55-58), 6.67.1-mod (SEQ ID NOS 59-62) and 6.77.1-mod (SEQ ID NOS 63-66) and 7.26.4-mod (SEQ ID NOS 41-42, 67-68). For each anti-MAdCAM antibody sequence cloned, the sequences of the signal peptide sequence (or the bases encoding the same) are indicated in lower case and underlined.

FIGS. 1A-1J provide sequence alignments between the predicted heavy chain amino acid sequences of antibodies 1.7.2, 1.8.2, 6.14.2, 6.22.2, 6.34.2, 6.67.1, 6.73.2, 6.77.1, 7.16.6, 7.20.5, 7.26.4 and 9.8.2 and the amino acid sequence of the respective germline gene products. The positions of the CDR1, CDR2 and CDR3 sequences of the antibodies are underlined, differences between the expressed sequence the corresponding germline sequence are indicated in bold and where there are additions in the expressed sequence compared to the germline these are indicated as a (–) in the germline sequence.

FIGS. 1K-1T provide sequence alignments between the predicted kappa light chain amino acid sequences of the antibodies 1.7.2, 1.8.2, 6.14.2, 6.22.2, 6.34.2, 6.67.1, 6.73.2, 6.77.1, 7.16.6, 7.20.5, 7.26.4 and 9.8.2 and the amino acid sequence of the respective germline gene products. The positions of the CDR1, CDR2 and CDR3 sequences of the antibodies are underlined, differences between the expressed sequence the corresponding germline they are indicated in bold and where there are additions in the expressed sequence compared to the germline these are indicated as a (–) in the germline sequence.

Presence of Post-Translational Modification: Glycosylation and Deamidation:

The effect of some of the changes in the expressed anti-MAdCAM antibody sequence, compared with the derived germline sequence, is to introduce residues that potentially could be subject to N-linked glycosylation (Asn-X-Ser/Thr) and/or deamidation (Asn-Gly) (see Table 12). The nucleic acid sequences encoding the kappa light chain variable domain amino acid sequences of the anti-MAd-CAM antibodies 6.22.2, 6.34.2, 6.67.1, 6.73.2, 6.77.1, 7.26.4 and 9.8.2, (SEQ ID NOS: 16, 20, 24, 28, 32, 44 and 48) and the heavy chain variable domain of antibody 6.14.2, (SEQ ID NO: 10), predict the presence of N-linked glycosylation. The presence of this post-translational modification was investigated using a combination of SDS-PAGE and Pro-Q® Emerald 488 Glycoprotein (Molecular Probes) staining with mAbs 6.22.2, 6.34.2, 6.67.1, 6.73.2, 6.77.1, 7.26.4 and 9.8.2.

Briefly, approximately 2 μg of reduced anti-MAdCAM antibody was loaded onto a 4-12% SDS-polyacrylamide gel using a MOPS buffer. Following electrophoresis, the gel was fixed in 50% MeOH, 5% acetic acid and washed in 3% acetic acid. Any carbohydrates on the gel were then oxidised with periodic acid and stained using Pro-Q® Emerald 488 Glycoprotein Stain Kit (Molecular Probes). After a final wash step, glycoprotein staining was visualised using a fluorescence scanner set at a wavelength of 473 nm.

After glycoprotein staining, the gel was stained for total protein using SYPRO Ruby protein gel stain and analysed using a fluorescence scanner set at a wavelength of 473 nm. The kappa light chains of anti-MAdCAM antibodies, 6.22.2, 6.34.2, 6.67.1, 6.73.2, 6.77.1, 7.26.4 and 9.8.2, all stained positively for the presence of glycosylation. As an additional confirmation, anti-MAdCAM antibody 7.26.4, was subjected to tryptic/chymotrypic digestion, the LC-MS/MS analysis confirmed the presence of a modified tryptic peptide and provided additional confirmation of kappa light chain glycosylation.

7.20.5, the presence of deamidated Asn-isoaspartate residues was assessed by mass spectroscopy following trapping the isoaspartate side chain with MeOH.

In brief, for the anti-MAdCAM antibody 1.7.2, the status of the tryptic/Asp-N peptide SSQSLLQSNGYNYL (SEQ ID NO: 69) (1573.7 Da) was selected for monitoring by LC-MS/MS. Anti-MAdCAM antibody 1.7.2 was reduced in 10 mM DTT, alkylated in 5 mM Na iodoacetate and subsequently buffer exchanged into trypsin digestion buffer (50 mM Tris-HCl, 1 mM $CaCl_2$, pH 7.6). The antibody was then mixed with sequencing grade modified trypsin (Promega) in a protease:protein ratio of 1:20. Protein was digested in trypsin for 15 hours at 30° C., and the resulting peptides separated by HPLC using a C-18 RPC on an Ettan LC system. The $^{33}$Asn-containing peptide (4032 Da) was collected from the column and diluted in Asp-N digestion buffer (50 mM sodium phosphate buffer, pH 8.0). Endoproteinase Asp-N(Roche) was then added at an approximate peptide: enzyme ratio of 10:1.

Acetyl chloride (100 μL) was added to a sample of methanol (1 mL, −20° C.), the mixture warmed to room temperature. The tryptic+Asp-N digest was dried in a Speed-Vac and then 5 μL of the methanol/acetyl chloride was added (45 min, room temp), then dried again in a Speed-Vac. The resulting residue was re-constituted in 0.1% TFA and peptides were analysed initially on the Voyager-DE STR MALDI-TOF mass spectrometer using either the nitrocellulose thin layer sample preparation method or reverse phase purification using C18 ZipTips (Millipore) followed by droplet mixing with α-cyano matrix. The methylated peptide mixture was also analysed using LC-MS/MS on a Deca XP Plus Ion Trap Mass Spectrometer as above. The elution was plumbed straight into the Ion Trap MS and peptides were subsequently analysed by MS and MS/MS. The MS was set to analyse all ions between 300 and 2000 Da. The strongest ion in any particular scan was then subjected to MS/MS analysis.

TABLE 12

Post-translational modification of anti-MAdCAM antibodies

| | Heavy Chain | | Kappa light chain | | | |
|---|---|---|---|---|---|---|
| Clone | Glycosylation (NXS/T) | Confirmed | Glycosylation (NXS/T) | Confirmed | Deamidation (NG) | Confirmed |
| IgG2 | | | | | | |
| 1.7.2 | | | | | LQSNGYN | MS |
| 1.8.2 | | | | | LQSNGYN | MS |
| 7.16.6 | | | | | | |
| 7.20.5 | | | | | HGNGYNY | MS |
| 7.26.4 | | | CKSNQSLLY | MS/PAGE | | |
| IgG4 | | | | | | |
| 6.14.2 | TFNNSAMT | N.D. | | | | |
| 6.22.2 | | | SGTNFTLTI | PAGE | LTINGLEA | N.D |
| 6.34.2 | | | ASQNISSYL | PAGE | | |
| 6.67.1 | | | SSNNKTYLA | PAGE | | |
| 6.73.2 | | | RASQNITN | PAGE | | |
| 6.77.1 | | | SCNSSQSL | PAGE | | |
| 9.8.2 | | | HSDNLSIT | PAGE | | |

Specific Asn-Gly sequences in the CDR1 regions of anti-MAdCAM antibodies, 1.7.2, 1.8.2, 6.22.2 and 7.20.5, render these regions sensitive to deamidation. Deamidation at neutral pH introduces a negative charge and can also lead to β-isomerisation, which could affect the properties of an antibody. For anti-MAdCAM antibodies 1.7.2, 1.8.2 and Mutagenesis Studies:

The primary amino acid sequence of the anti-MAdCAM antibodies exemplified in this invention can be modified, by site-directed mutagenesis, to remove potential sites of post-translational modification (e.g., glycosylation, deamidation) or to alter the isotype background, or to engineer other changes which may improve the therapeutic utility. As an example, PCR was used to engineer changes to the anti-MAdCAM antibodies 6.22.2, 6.34.2, 6.67.1, 6.77.1 and 7.26.4, to revert certain framework sequences to germline, to remove potential glycosylation sites and/or to change the isotype background to a human IgG$_2$. pCR2.1 TOPO-TA cloned cDNAs (100 ng), corresponding to heavy chain nucleotide SEQ ID NOS: 13, 17, 21 and 29, and kappa light nucleotide SEQ ID NOS: 15, 19, 23, 31 and 43, were used as a template in a series of PCRs using overlap-extension and a panel of primer sets described in Table 10.

6.22.2 Heavy Chain:

PCR primer sets 6.22.2_VH_F1 and 6.22.2VH_CS* (1) and VH3-33 and 6.22.2_VH_R1 (2) were used to generate separate PCR products (1) and (2), using an Expand Taq polymerase and a pCR2.1 TOPO-TA cDNA template (100 ng) represented by nucleotide sequence SEQ ID NO: 13. Products (1) and (2) were purified and combined in a third PCR step (ca. 50 ng each) along with VH3-33 and VK6.22.2_CS* primers, to generate the modified 6.22.2 heavy chain V-domain. This modified version contains a His/Phe mutation in FR1 and introduces an XbaI restriction site to enable in frame cloning into a pEE6.1 derived vector, termed pEE6.1CH, which contains the corresponding human IgG$_2$ constant domain. The final PCR fragment was cloned into the XbaI site of pEE6.1CH, checked for orientation and the insert full sequence verified. The nucleotide sequence for the modified 6.22.2 heavy chain is found in SEQ ID NO: 51 and the corresponding amino acid sequence in SEQ ID NO: 52. The changes in the nucleotide and amino acid sequences compared with the parent are indicated.

6.22.2 Kappa Light Chain:

PCR primer sets 6.22.2_VK_F1 and revKappa (1), and A26 and 6.22.2_VK_R1 (2) were used to generate separate PCR products (1) and (2), using an Expand Taq polymerase and a pCR2.1 TOPO-TA cDNA template (100 ng) represented by nucleotide sequence SEQ ID NO: 15. Products (1) and (2) were purified and combined in a third PCR step (ca. 50 ng each) along with A26 and revKappa primers, to generate the modified 6.22.2 kappa light chain V-domain. This modified version contains Asn/Asp and Gly/Ser changes to the FR3 sequence. The resultant PCR product was cloned into pEE12.1 using HindIII/EcoR1 sites and fully sequence verified. The nucleotide sequence for the modified 6.22.2 kappa light chain is found in SEQ ID NO: 53 and the corresponding amino acid sequence in SEQ ID NO: 54. The changes in the nucleotide and amino acid sequences compared with the parent are indicated.

6.34.2 Heavy Chain:

PCR primer sets 6.34.2_VH_F1 and 6.22.2VH_CS* (1) and VH3-30 and 6.34.2_VH_R1 (2) were used to generate separate PCR products (1) and (2), using an Expand Taq polymerase and a pCR2.1 TOPO-TA cDNA template (100 ng) represented by nucleotide sequence SEQ ID NO: 17. Products (1) and (2) were purified and combined in a third PCR step (ca. 50 ng each) along with VH3-30 and VK6.22.2_CS* primers, to generate the modified 6.34.2 heavy chain V-domain. This modified version contains a Ser/Arg mutation in FR3 and introduces an XbaI restriction site to enable in frame cloning into a pEE6.1 derived vector, termed pEE6.1CH, which contains the corresponding human IgG$_2$ constant domain. The final PCR fragment was cloned into the XbaI site of pEE6.1CH, checked for orientation and the insert full sequence verified. The nucleotide sequence for the modified 6.34.2 heavy chain is found in SEQ ID NO: 55 and the corresponding amino acid sequence in SEQ ID NO: 56. The changes in the nucleotide and amino acid sequences compared with the parent are indicated.

6.34.2 Kappa Light Chain:

PCR primer sets 012 and 6.34.2_VK_R1 (1), 6.34.2_VK_F1 and 6.34.2_VK_R2 (2), as well as 6.34.2_VK_F2 and revKappa (3) were used to generate separate PCR products (1), (2) and (3), using an Expand Taq polymerase and a pCR2.1 TOPO-TA cDNA template (100 ng) represented by nucleotide sequence SEQ ID NO: 19. Products (1), (2) and (3) were purified and (1) and (2) were combined in a third PCR step (ca. 50 ng each), along with 012 and 6.34.2_VK_R2 primers, to generate the PCR product (4). PCR products (2) and (3) were combined in a fourth PCR step (ca. 50 ng each), along with 6.34.2_VK_F1 and revKappa, to generate the PCR product (5). PCR products (4) and (5) were purified and combined together (ca. 50 ng each) with primers 012 and revKappa to generate the modified 6.34.2 kappa light chain V-domain. This modified version contains an Asn/Ser change in CDR1, a Phe/Tyr change in FR2 and Arg-Thr/Ser-Ser, Asp/Glu and Ser/Tyr changes to the FR3 sequence. The resultant PCR product was cloned into pEE12.1 using HindIII/EcoR1 sites and fully sequence verified. The nucleotide sequence for the modified 6.34.2 kappa light chain is found in SEQ ID NO: 57 and the corresponding amino acid sequence in SEQ ID NO: 58. The changes in the nucleotide and amino acid sequences compared with the parent are indicated.

6.67.1 Heavy Chain:

PCR primer sets 6.67.1_VH_F1 and 6.67.1VH_CS* (1) and VH4-4 and 6.67.1_VH_R1 (2) were used to generate separate PCR products (1) and (2), using an Expand Taq polymerase and a pCR2.1 TOPO-TA cDNA template (100 ng) represented by nucleotide sequence SEQ ID NO: 21. Products (1) and (2) were purified and combined in a third PCR step (ca. 50 ng each) along with VH4-4 and VK6.67.1_CS* primers, to generate the modified 6.67.1 heavy chain V-domain. This modified version contains an Ile-Leu-Ala/Met-Ser-Val conversion in FR3 and introduces an XbaI restriction site to enable in frame cloning into a pEE6.1 derived vector, termed pEE6.1CH, which contains the corresponding human IgG$_2$ constant domain. The final PCR fragment was cloned into the XbaI site of pEE6.1CH, checked for orientation and the insert full sequence verified. The nucleotide sequence for the modified 6.67.1 heavy chain is found in SEQ ID NO: 59 and the corresponding amino acid sequence in SEQ ID NO: 60. The changes in the nucleotide and amino acid sequences compared with the parent are indicated.

6.67.1 Kappa Light Chain:

PCR primer sets 6.67.1_VK_F1 and revKappa (1), and B3 and 6.67.1_VK_R1 (2) were used to generate separate PCR products (1) and (2), using an Expand Taq polymerase and a pCR2.1 TOPO-TA cDNA template (100 ng) represented by nucleotide sequence SEQ ID NO: 23. Products (1) and (2) were purified and combined in a third PCR step (ca. 50 ng each) along with B3 and revKappa primers, to generate the modified 6.67.1 kappa light chain V-domain. This modified version contains a Thr/Asn change in CDR1 and an Arg/Gly change in FR2. The resultant PCR product was cloned into pEE12.1 using HindIII/EcoR1 sites and fully sequence verified. The nucleotide sequence for the modified 6.67.1 kappa light chain is found in SEQ ID NO: 61 and the corresponding amino acid sequence in SEQ ID NO: 62. The changes in the nucleotide and amino acid sequences compared with the parent are indicated.

6.77.1 Heavy Chain:

PCR primer sets VH 3-21 and 6.22.2VH_CS* were used to generate a single PCR product using an Expand Taq polymerase and a pCR2.1 TOPO-TA cDNA template (100 ng) represented by nucleotide sequence SEQ ID NO: 29. The PCR products were digested with XbaI, gel purified and cloned into the XbaI site of pEE6.1CH, checking for orientation. The insert was fully sequence verified. The nucleotide sequence for the modified 6.77.1 heavy chain is found in SEQ ID NO: 63 and the corresponding amino acid sequence in SEQ ID NO: 64. The changes in the nucleotide and amino acid sequences compared with the parent are indicated.

6.77.1 Kappa Light Chain:

PCR primer sets A2 and 6.77.1_VK_R1 (1), 6.77.1_VK_VK_F1 and 6.77.1_R2 (2), as well as 6.77.1_VK_F2 and revKappa (3) were used to generate separate PCR products (1), (2) and (3), using an Expand Taq polymerase and a pCR2.1 TOPO-TA cDNA template (100 ng) represented by nucleotide sequence SEQ ID NO: 31. Products (1), (2) and (3) were purified and, (1) and (2) were combined in a third PCR step (ca. 50 ng each) along with A2 and 6.77.1_VK_R2 primers, to generate PCR product (4). PCR product (2) and (3) were combined in a fourth PCR step (ca. 50 ng each) along with 6.77.1_VK_F1 and revKappa primers, to generate PCR product (5). PCR products (4) and (5) were purified and combined together (ca. 50 ng each) with primers A2 and JK2 to generate the modified 6.77.1 kappa light chain V-domain. This modified version contains an Asn/Lys change in CDR1, a Ser/Tyr change in FR3 and a Cys/Ser residue change in CDR3 sequence. The resultant PCR product was cloned into pEE12.1 using HindIII/EcoR1 sites and fully sequence verified. The nucleotide sequence for the modified 6.77.1 kappa light chain is found in SEQ ID NO: 65 and the corresponding amino acid sequence in SEQ ID NO: 66. The changes in the nucleotide and amino acid sequences compared with the parent are indicated.

7.26.4 Kappa Light Chain:

PCR primer sets 7.26.4_VK_F1 and revKappa (1), and A2 and 7.26.4_VK_R1 (2) were used to generate separate PCR products (1) and (2), using an Expand Taq polymerase and a pCR2.1 TOPO-TA cDNA template (100 ng) represented by nucleotide sequence SEQ ID NO: 43. Products (1) and (2) were purified and combined in a third PCR step (ca. 50 ng each) along with A2 and revKappa primers, to generate the modified 7.26.4 kappa light chain V-domain. This modified version contains an Asn/Ser change in CDR1. The resultant PCR product was cloned into pEE12.1 using HindIII/EcoR1 sites and fully sequence verified. The nucleotide sequence for the modified 7.26.4 kappa light chain is found in SEQ ID NO: 67 and the corresponding amino acid sequence in SEQ ID NO: 68. The changes in the nucleotide and amino acid sequences compared with the parent are indicated.

A functional eukaryotic expression vector for each of the modified versions of 6.22.2, 6.34.2, 6.67.1, 6.77.1 and 7.26.4, referred to as 6.22.2-mod, 6.34.2-mod, 6.67.1-mod, 6.77.1-mod and 7.26.4-mod, and representing respectively the heavy chain nucleotide sequences SEQ ID NOS: 51, 55, 59, 63 and 41, and corresponding amino acid sequences SEQ ID NOS: 52, 56, 60, 64 and 42, as well as the kappa light chain nucleotide sequences SEQ ID NOS: 53, 57, 61, 65 and 67, and the corresponding amino acid sequences SEQ ID NOS: 54, 58, 62, 66 and 68 were assembled as follows: The heavy chain cDNA inserts corresponding to 6.22.2-mod, 6.34.2-mod, 6.67.1-mod and 6.77.1-mod were excised from the pEE6.1CH vector with NotI/SalI, the parental version of the heavy chains of 7.26.4 was excised from the pEE6.1 vector with NotI/SalI, and the purified fragments were cloned into identical sites into the corresponding pEE12.1 vector containing the modified versions of the kappa light chain sequences 6.22.2-mod, 6.34.2-mod, 6.67.1-mod, 6.77.1-mod and 7.26.4-mod. The sequences of the vectors were confirmed, and purified amounts used in transient transfections with HEK 293T cells. Briefly, $9 \times 10^6$ HEK 293T cells, seeded in a T165 flask the day before transfection and washed into Optimem, were transiently transfected with vector cDNAs corresponding to 6.22.2-mod, 6.34.2-mod, 6.67.1-mod, 6.77.1-mod and 7.26.4-mod (40 μg) using Lipofectamine PLUS (Invitrogen) according to manufacturer's instructions. The cells were incubated for 3 hrs, then the transfection media replaced with DMEM (Invitrogen 21969-035) media containing 10% ultra-low IgG fetal calf serum (Invitrogen 16250-078) and L-Glutamine (50 mL). The media supernatant was harvested 5 days later, filter sterilised and the anti-MAdCAM antibody purified using protein G sepharose affinity chromatography, in a similar manner as to that described above. The amount of antibody recovered (20-100 μg) was quantified by a Bradford assay.

The anti-MAdCAM activity of affinity purified antibody corresponding to 6.22.2-mod, 6.34.2-mod, 6.67.1-mod, 6.77.1-mod and 7.26.4-mod was assessed in the MAdCAM-IgG$_1$-Fc fusion assay as described previously. The IC$_{50}$ values of these anti-MADCAM antibodies compared with the parental anti-MAdCAM antibodies from which they were derived are presented in Table 13. There was minimal effect of the amino acid substitutions described above on the activity of the modified anti-MAdCAM antibodies compared with their parents was minimal. The antibodies also maintained their binding to CHO cells expressing recombinant human MAdCAM or the cynomolgus/human MAdCAM chimera.

TABLE 13

Activity of modified versions of anti-MAdCAM antibodies, 6.22.2-mod, 6.34.2-mod, 6.67.1-mod, 6.77.1-mod and 7.26.4-mod compared with their parents.

| CLONE | MAdCAM IgG1 Fc fusion Assay Mean IC50 (μg/mL) | |
|---|---|---|
| | Parent | Modified |
| 6.22.2 | 0.018 | 0.058 |
| 6.34.2 | 0.013 | 0.049 |
| 6.67.1 | 0.013 | 0.037 |
| 6.77.1 | 0.022 | 0.077 |
| 7.26.4 | 0.021 | 0.033 |

Example VI

Increase in $\beta_7^+$ Lymphocytes in the Peripheral Circulation by Blocking Anti-MAdCAM Antibodies An assay was developed to identify and correlate a mechanistic effect of an anti-MAdCAM antibody and its circulating level in blood. An inhibitory anti-MAdCAM antibody should have the effect of inhibiting the recruitment of leukocytes expressing the $\alpha_4\beta_7$ integrin to the gastrointestinal tract. Classes of $\alpha_4\beta_7$ integrin-bearing leukocytes should, therefore, be restricted to the peripheral circulation This was demonstrated with a fully human anti-human MAdCAM mAb 7.16.6, in cynomolgus.

Purified anti-human MAdCAM mAb 7.16.6 (1 mg/kg) or vehicle (20 mM NaAcetate, 0.2 mg/mL polysorbate 80, 45 mg/mL mannitol, and 0.02 mg/mL EDTA at pH 5.5) were assessed in a similar manner by intravenous administration via the saphenous vein to two groups of cynomolgus monkeys (n=4/group). At day 3 post-dosing blood samples were collected in EDTA tubes by femoral venipuncture. LPAM specific antibodies, which crossreact with the cynomolgus $\alpha_4\beta_7$ integrin, are not commercially available, so an anti-$\beta_7$ antibody (recognising $\alpha_4\beta_7$ and $\alpha_E\beta_7$ integrin) was used instead. Antibodies (30 μL), according to the following table, table 15, were added to tubes containing 100 μL of cynomolgus blood, mixed by gentle vortexing and incubated for 20-30 mins at 4° C.

TABLE 15

Antibodies (BD Pharmingen) used in immunophenotyping of cynomologus blood

| Catalogue Number | Antibody or Isotype |
| --- | --- |
| 555748 | mIgG1, k-FITC |
| 555844 | mIgG2a, k-PE |
| 559425 | mIgG1 - PerCP |
| 555751 | mIgG1, k-APC |
| 555728 | CD 28-FITC |
| 555945 | β7-PE |
| 558814 | CD 95-APC |
| 550631 | CD 4-PerCP |

Figure 7:
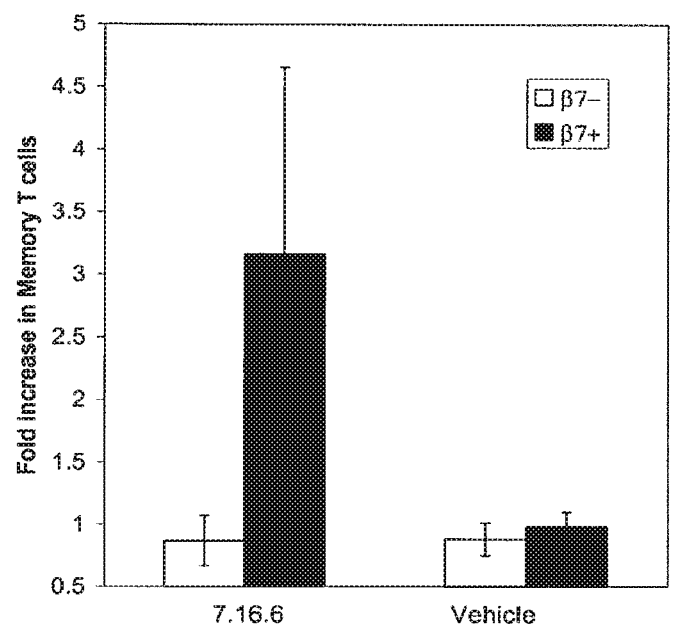
FIG. 7 shows the effect of an inhibitory anti-MAdCAM antibody (1 mg/kg) on the number of circulating peripheral $\alpha_4\beta_7^+$ lymphocytes, expressed as a fold increase over control IgG2a mAb or vehicle, using anti-MAdCAM mAb 7.16.6 in a cynomolgus monkey model.

To each tube, 1 mL of 1:10 FACSlyse solution (BD #349202) was added, mixed by gentle vortex and incubated at room temperature for approximately 12 minutes in the dark until red blood cell lysis was complete. Then 2 mL of BD stain buffer (#554656) was added to each tube, mixed and centrifuged at 250×g for 6-7 mins at room temperature. The supernatant was decanted and the pellet resuspended in 3 mL of stain buffer, mixed again and centrifuged at 250×g for 6-7 mins at room temperature. Cytofix buffer (BD #554655), containing w/v paraformaldehyde (100 μL) was added to the cell pellets from monkey peripheral blood and mixed thoroughly by low/moderate speed of vortexer. The samples were kept at 4° C. in the dark until they acquired on the FACSCalibur. Just prior to acquisition, PBS (100 μL) was added to all tubes immediately before acquisition. The absolute cell numbers of CD4$^+$β$_7$$^+$CD95loCD28$^+$ (naïve), CD4$^+$β$_7$+CD95hiCD28$^+$ (central memory), CD4$^+$β$_7$-CD95hiCD28$^+$ (central memory), CD4$^+$β$_7$$^+$CD95hiCD28$^-$ (effector memory) were acquired by appropriate gating and quandrant analyses. Other T cell subsets for example, CD8$^+$ T central memory cell (β$_7$$^+$CD8$^+$CD28$^+$CD95$^+$) and any other leukocytes bearing a MAdCAM ligand, may also be analyzed by this method with the appropriate antibodies. Compared with the vehicle control, anti-MAdCAM mAb 7.16.6 caused an approximate 3 fold increase in the levels of circulating CD4$^+$β$_7$$^+$CD95hiCD28$^+$ central memory T cells, as shown in FIG. 7. There were no effects on the population of circulating CD4$^+$β$_7$-CD95hiCD28$^+$ central memory T cells, indicating that the effect of anti-MAdCAM mAb 7.16.6 is specific for gut homing T cells. The effects of anti-MAdCAM mAb 7.16.6, in cynomolgus, on populations of circulating ($\alpha_4$)β$_7$$^+$ lymphocytes indicates that this is a robust surrogate proof of mechanism biomarker, particularly in the context of practical application in a clinical setting.

Sequences

SEQ ID NO: 1-48 and 51-68 provide nucleotide and amino acid sequences of the heavy and kappa light chains for twelve human anti-MAdCAM antibodies, nucleotide and amino acid sequences of cynomolgus MAdCAM $\alpha_4\beta_7$ binding domain sequences and nucleotide and amino acid sequences of five modified human anti-MAdCAM antibodies.

SEQ ID NO: 1-48 provide the heavy and kappa light chain nucleotide and amino acid sequences of twelve human monoclonal anti-MAdCAM antibodies: 1.7.2 (SEQ ID NO: 1-4), 1.8.2 (SEQ ID NO: 5-8), 6.14.2 (SEQ ID NO: 9-12), 6.22.2 (SEQ ID NO: 13-16), 6.34.2 (SEQ ID NO: 17-20), 6.67.1 (SEQ ID NO: 21-24), 6.73.2 (SEQ ID NO: 25-28), 6.77.1 (SEQ ID NO: 29-32), 7.16.6 (SEQ ID NO: 33-36), 7.20.5 (SEQ ID NO: 37-40), 7.26.4 (SEQ ID NO: 41-44), and 9.8.2 (SEQ ID NO: 45-48).

SEQ ID NO: 49-50 provide the nucleotide and amino acid sequences of a cynomolgus MAdCAM $\alpha_4\beta_7$ binding domain.

SEQ ID NO: 51-68 provide the heavy and kappa light chain nucleotide and amino acid sequences for the modified monoclonal anti-MAdCAM antibodies: 6.22.2 (SEQ ID NO: 51-54), modified 6.34.2 (SEQ ID NO: 55-58), modified 6.67.1 (SEQ ID NO: 59-62), modified 6.77.1 (SEQ ID NO: 63-66) and the kappa light chain nucleotide and amino acid sequences of modified monoclonal anti-MAdCAM antibody: modified 7.26.4 (SEQ ID NO: 67-68). SEQ ID NOS: 70-106 and 108-110 provide various primer sequences.

Key:
Signal sequence: underlined lower case
Amino acid changes in modified anti-MAdCAM antibodies sequence compared to parent: underlined upper case

```
1.7.2 Heavy Chain Nucleotide Sequence
                                                     SEQ ID NO. 1
  1 atggagtttg ggctgagctg gattttcctt gctgctattt taaaaggtgt 51 ccagtgtGAG GTGCAGCTGG TGGAGTCTGG GGGAGGCTTG GTGAAGCCTG

101 GGGGGTCCCT TAGACTCTCC TGTGTAGCCT CTGGATTCAC TTTCACTAAC

151 GCCTGGATGA TCTGGGTCCG CCAGGCTCCA GGGAAGGGGC TGGAGTGGGT

201 TGGCCGTATT AAAAGGAAAA CTGATGGTGG GACAACAGAC TACGCTGCAC

251 CCGTGAAAGG CAGATTCACC ATCTCAAGAG ATGATTCAAA AAACACGCTG

301 TATCTGCAAA TGAACAGCCT GAAAACCGAG GACACAGCCG TGTATTACTG

351 TACCACAGGG GGAGTGGCTG AGGACTACTG GGGCCAGGGA ACCCTGGTCA

401 CCGTCTCCTC AGCCTCCACC AAGGGCCCAT CGGTCTTCCC CCTGGCGCCC
```

```
451 TGCTCCAGGA GCACCTCCGA GAGCACAGCG GCCCTGGGCT GCCTGGTCAA

501 GGACTACTTC CCCGAACCGG TGACGGTGTC GTGGAACTCA GGCGCTCTGA

551 CCAGCGGCGT GCACACCTTC CCAGCTGTCC TACAGTCCTC AGGACTCTAC

601 TCCCTCAGCA GCGTGGTGAC CGTGCCCTCC AGCAACTTCG GCACCCAGAC

651 CTACACCTGC AACGTAGATC ACAAGCCCAG CAACACCAAG GTGGACAAGA

701 CAGTTGAGCG CAAATGTTGT GTCGAGTGCC CACCGTGCCC AGCACCACCT

751 GTGGCAGGAC CGTCAGTCTT CCTCTTCCCC CCAAAACCCA AGGACACCCT

801 CATGATCTCC CGGACCCCTG AGGTCACGTG CGTGGTGGTG GACGTGAGCC

851 ACGAAGACCC CGAGGTCCAG TTCAACTGGT ACGTGGACGG CGTGGAGGTG

901 CATAATGCCA AGACAAAGCC ACGGGAGGAG CAGTTCAACA GCACGTTCCG

951 TGTGGTCAGC GTCCTCACCG TTGTGCACCA GGACTGGCTG AACGGCAAGG

1001 AGTACAAGTG CAAGGTCTCC AACAAAGGCC TCCCAGCCCC CATCGAGAAA

1051 ACCATCTCCA AACCAAAGG GCAGCCCCGA GAACCACAGG TGTACACCCT

1101 GCCCCCATCC CGGGAGGAGA TGACCAAGAA CCAGGTCAGC CTGACCTGCC

1151 TGGTCAAAGG CTTCTACCCC AGCGACATCG CCGTGGAGTG GGAGAGCAAT

1201 GGGCAGCCGG AGAACAACTA CAAGACCACA CCTCCCATGC TGGACTCCGA

1251 CGGCTCCTTC TTCCTCTACA GCAAGCTCAC CGTGGACAAG AGCAGGTGGC

1301 AGCAGGGGAA CGTCTTCTCA TGCTCCGTGA TGCATGAGGC TCTGCACAAC

1351 CACTACACGC AGAAGAGCCT CCCCTGTCT CCGGGTAAAT GA
```

1.7.2 Predicted Heavy Chain Protein Sequence

SEQ ID NO. 2

```
  1 mefglswifl aailkgvqcE VQLVESGGGL VKPGGSLRLS CVASGFTFTN

51 AWMIWVRQAP GKGLEWVGRI KRKTDGGTTD YAAPVKGRFT ISRDDSKNTL

101 YLQMNSLKTE DTAVYYCTTG GVAEDYWGQG TLVTVSSAST KGPSVFPLAP

151 CSRSTSESTA ALGCLVKDYF PEPVTVSWNS GALTSGVHTF PAVLQSSGLY

201 SLSSVVTVPS SNFGTQTYTC NVDHKPSNTK VDKTVERKCC VECPPCPAPP

251 VAGPSVFLFP PKPKDTLMIS RTPEVTCVVV DVSHEDPEVQ FNWYVDGVEV

301 HNAKTKPREE QFNSTFRVVS VLTVVHQDWL NGKEYKCKVS NKGLPAPIEK

351 TISKTKGQPR EPQVYTLPPS REEMTKNQVS LTCLVKGFYP SDIAVEWESN

401 GQPENNYKTT PPMLDSDGSF FLYSKLTVDK SRWQQGNVFS CSVMHEALHN

451 HYTQKSLSLS PGK
```

1.7.2 Kappa Light Chain Nucleotide Sequence

SEQ ID NO. 3

```
  1 atgaggctcc ctgctcagct cctggggctg ctaatgctct gggtctctgg 51 atccagtggg GATATTGTGA TGACTCAGTC TCCACTCTCC CTGCCCGTCA

101 CCCCTGGAGA GCCGGCCTCC ATCTCCTGCA GGTCTAGTCA GAGCCTCCTG

151 CAAAGTAATG GATACAACTA TTTGGATTGG TACCTGCAGA AGCCAGGGCA

201 GTCTCCACAG CTCCTGATCT ATTTGGGTTC TAATCGGGCC TCCGGGGTCC

251 CTGACAGGTT CAGTGGCAGT GGATCAGGCA CAGATTTTAC ACTGAAAATC

301 AGCAGAGTGG AGGCTGAGGA TGTTGGGGTT TATTACTGCA TGCAAGCTCT

351 ACAAACTATC ACCTTCGGCC AAGGGACACG ACTGGAGATT AAACGAACTG

401 TGGCTGCACC ATCTGTCTTC ATCTTCCCGC CATCTGATGA GCAGTTGAAA

451 TCTGGAACTG CCTCTGTTGT GTGCCTGCTG AATAACTTCT ATCCCAGAGA
```

```
501 GGCCAAAGTA CAGTGGAAGG TGGATAACGC CCTCCAATCG GGTAACTCCC

551 AGGAGAGTGT CACAGAGCAG ACAGCAAGG ACAGCACCTA CAGCCTCAGC

601 AGCACCCTGA CGCTGAGCAA AGCAGACTAC GAGAAACACA AAGTCTACGC

651 CTGCGAAGTC ACCCATCAGG GCCTGAGCTC GCCCGTCACA AAGAGCTTCA

701 ACAGGGGAGA GTGTTAGTGA
```

1.7.2 Predicted Kappa Light Chain Protein Sequence

SEQ ID NO. 4

```
  1 mrlpaqllgl lmlwvsgssq DIVMTQSPLS LPVTPGEPAS ISCRSSQSLL

51 QSNGYNYLDW YLQKPGQSPQ LLIYLGSNRA SGVPDRFSGS GSGTDFTLKI

101 SRVEAEDVGV YYCMQALQTI TFGQGTRLEI KRTVAAPSVF IFPPSDEQLK

151 SGTASVVCLL NNFYPREAKV QWKVDNALQS GNSQESVTEQ DSKDSTYSLS

202 STLTLSKADY EKHKVYACEV THQGLSSPVT KSFNRGEC
```

1.8.2 Heavy Chain Nucleotide Sequence

SEQ ID NO. 5

```
  1 atggagtttg ggctgagctg gattttcctt gctgctattt taaaaggtgt 51 ccagtgtGAG GTGCAGCTGG TGGAGTCTGG GGGAGGCTTG GTGAAGCCTG

101 GGGGGTCCCT TAGACTCTCC TGTGTAGTCT CTGGATTCAC TTTCACTAAC

151 GCCTGGATGA TCTGGGTCCG CCAGGCTCCA GGGAAGGGGC TGGAGTGGGT

201 TGGCCGTATT AAAAGGAAAA CTGATGGTGG ACAACAGAC TACGCTGCAC

251 CCGTGAAAGG CAGATTCACC ATCTCAAGAG ATGATTCAAA AAACACGCTG

301 TATCTGCAAA TGAACAGCCT GAAAACCGAG GACACAGCCG TGTATTACTG

351 TACCACAGGG GGAGTGGCTG AGGACTACTG GGGCCAGGGA ACCCTGGTCA

401 CCGTCTCCTC AGCCTCCACC AAGGGCCCAT CGGTCTTCCC CCTGGCGCCC

451 TGCTCCAGGA GCACCTCCGA GAGCACAGCG GCCCTGGGCT GCCTGGTCAA

501 GGACTACTTC CCCGAACCGG TGACGGTGTC GTGGAACTCA GGCGCTCTGA

551 CCAGCGGCGT GCACACCTTC CCAGCTGTCC TACAGTCCTC AGGACTCTAC

601 TCCCTCAGCA GCGTGGTGAC CGTGCCCTCC AGCAACTTCG GCACCCAGAC

651 CTACACCTGC AACGTAGATC ACAAGCCCAG CAACACCAAG GTGGACAAGA

701 CAGTTGAGCG CAAATGTTGT GTCGAGTGCC CACCGTGCCC AGCACCACCT

751 GTGGCAGGAC CGTCAGTCTT CCTCTTCCCC CCAAAACCCA AGGACACCCT

801 CATGATCTCC CGGACCCCTG AGGTCACGTG CGTGGTGGTG GACGTGAGCC

851 ACGAAGACCC CGAGGTCCAG TTCAACTGGT ACGTGGACGG CGTGGAGGTG

901 CATAATGCCA AGACAAAGCC ACGGGAGGAG CAGTTCAACA GCACGTTCCG

951 TGTGGTCAGC GTCCTCACCG TTGTGCACCA GGACTGGCTG AACGGCAAGG

1001 AGTACAAGTG CAAGGTCTCC AACAAAGGCC TCCCAGCCCC CATCGAGAAA

1051 ACCATCTCCA AAACCAAAGG GCAGCCCCGA GAACCACAGG TGTACACCCT

1101 GCCCCCATCC CGGGAGGAGA TGACCAAGAA CCAGGTCAGC CTGACCTGCC

1151 TGGTCAAAGG CTTCTACCCC AGCGACATCG CCGTGGAGTG GGAGAGCAAT

1201 GGGCAGCCGG AGAACAACTA CAAGACCACA CCTCCCATGC TGGACTCCGA

1251 CGGCTCCTTC TTCCTCTACA GCAAGCTCAC CGTGGACAAG AGCAGGTGGC

1301 AGCAGGGGAA CGTCTTCTCA TGCTCCGTGA TGCATGAGGC TCTGCACAAC

1351 CACTACACGC AGAAGAGCCT CTCCCTGTCT CCGGGTAAAT GA
```

1.8.2 Predicted Heavy Chain Protein Sequence

SEQ ID NO. 6
```
  1 mefglswifl aailkqvqcE VQLVESGGGL VKPGGSLRLS CVVSGFTFTN
 51 AWMIWVRQAP GKGLEWVGRI KRKTDGGTTD YAAPVKGRFT ISRDDSKNTL
101 YLQMNSLKTE DTAVYYCTTG GVAEDYWGQG TLVTVSSAST KGPSVFPLAP
151 CSRSTSESTA ALGCLVKDYF PEPVTVSWNS GALTSGVHTF PAVLQSSGLY
201 SLSSVVTVPS SNFGTQTYTC NVDHKPSNTK VDKTVERKCC VECPPCPAPP
251 VAGPSVFLFP PKPKDTLMIS RTPEVTCVVV DVSHEDPEVQ FNWYVDGVEV
301 HNAKTKPREE QFNSTFRVVS VLTVVHQDWL NGKEYKCKVS NKGLPAPIEK
351 TISKTKGQPR EPQVYTLPPS REEMTKNQVS LTCLVKGFYP SDIAVEWESN
401 GQPENNYKTT PPMLDSDGSF FLYSKLTVDK SRWQQGNVFS CSVMHEALHN
451 HYTQKSLSLS PGK
```

1.8.2 Kappa Light Chain Nucleotide Sequence

SEQ ID NO. 7
```
  1 atgaggctcc ctgctcagct cctggggctg ctaatgctct gggtctctgg
 51 atccagtggg GATATTGTGA TGACTCAGTC TCCACTCTCC CTGCCCGTCA
101 CCCCTGGAGA GCCGGCCTCC ATCTCCTGCA GGTCTAGTCA GAGCCTCCTG
151 CAAAGTAATG GATTCAACTA TTTGGATTGG TACCTGCAGA AGCCAGGGCA
201 GTCTCCACAG CTCCTGATCT ATTTGGGTTC TAATCGGGCC TCCGGGGTCC
251 CTGACAGGTT CAGTGGCAGT GGGTCAGGCA CAGATTTTAC ACTGAAAATC
301 AGCAGAGTGG AGGCTGAGGA TGTTGGGGTT TATTACTGCA TGCAAGCTCT
351 ACAAACTATC ACCTTCGGCC AAGGGACACG ACTGGAGATT AAACGAACTG
401 TGGCTGCACC ATCTGTCTTC ATCTTCCCGC CATCTGATGA GCAGTTGAAA
451 TCTGGAACTG CCTCTGTTGT GTGCCTGCTG AATAACTTCT ATCCCAGAGA
501 GGCCAAAGTA CAGTGGAAGG TGGATAACGC CCTCCAATCG GGTAACTCCC
551 AGGAGAGTGT CACAGAGCAG GACAGCAAGG ACAGCACCTA CAGCCTCAGC
601 AGCACCCTGA CGCTGAGCAA AGCAGACTAC GAGAAACACA AAGTCTACGC
651 CTGCGAAGTC ACCCATCAGG GCCTGAGCTC GCCCGTCACA AAGAGCTTCA
701 ACAGGGGAGA GTGTTAGTGA
```

1.8.2 Predicted Kappa Light Chain Protein Sequence

SEQ ID NO. 8
```
  1 mrlpaqllgl lmlwvsgssg DIVMTQSPLS LPVTPGEPAS ISCRSSQSLL
 51 QSNGFNYLDW YLQKPGQSPQ LLIYLGSNRA SGVPDRFSGS GSGTDFTLKI
101 SRVEAEDVGV YYCMQALQTI TFGQGTRLEI KRTVAAPSVF IFPPSDEQLK
151 SGTASVVCLL NNFYPREAKV QWKVDNALQS GNSQESVTEQ DSKDSTYSLS
202 STLTLSKADY EKHKVYACEV THQGLSSPVT KSFNRGEC
```

6.14.2 Heavy Chain Nucleotide Sequence

SEQ ID NO. 9
```
  1 atggagtttg ggctgagctg gcttttttctt gtggctattt taaaaggtgt
 51 ccagtgtGAG GTGCAGCTGT TGGAGTCTGG GGGAGGCTTG GTACAGCCTG
101 GGGGGTCCCT GAGACTCTCC TGTGCAGCCT CTGGACTCAC CTTTAACAAT
151 TCTGCCATGA CCTGGGTCCG CCAGGCTCCA GGGAAGGGGC TGGAGTGGGT
201 CTCAACTACT AGTGGAAGTG GTGGTACCAC ATACTACGCA GACTCCGTGA
251 AGGGCCGGTT CACCATCTCC AGAGACTCTC CAAGAACACG CTCTATCTG
301 CAAATGAACA GCCTGAGAGC CGAGGACACG GCCGTATATT ACTGTGCGGC
```

```
 351 CCGTGGATAC AGCTATGGTA CGACCCCCTA TGAGTACTGG GGCCAGGGAA
 401 CCCTGGTCAC CGTCTCCTCA GCTTCCACCA AGGGCCCATC CGTCTTCCCC
 451 CTGGCGCCCT GTTCCAGGAG CACCTCCGAG AGCACAGCCG CCCTGGGCTG
 501 CCTGGTCAAG GACTACTTCC CCGAACCGGT GACGGTGTCG TGGAACTCAG
 551 GCGCCCTGAC CAGCGGCGTG CACACCTTCC CGGCTGTCCT ACAGTCCTCA
 601 GGACTCTACT CCCTCAGCAG CGTGGTGACC GTGCCCTCCA GCAGCTTGGG
 651 CACGAAGACC TACACCTGCA ACGTAGATCA CAAGCCCAGC AACACCAAGG
 701 TGGACAAGAG AGTTGAGTCC AAATATGGTC CCCCATGCCC ATCATGCCCA
 751 GCACCTGAGT TCCTGGGGGG ACCATCAGTC TTCCTGTTCC CCCCAAAACC
 801 CAAGGACACT CTCATGATCT CCCGGACCCC TGAGGTCACG TGCGTGGTGG
 851 TGGACGTGAG CCAGGAAGAC CCCGAGGTCC AGTTCAACTG GTACGTGGAT
 901 GGCGTGGAGG TGCATAATGC CAAGACAAAG CCGCGGGAGG AGCAGTTCAA
 951 CAGCACGTAC CGTGTGGTCA GCGTCCTCAC CGTCCTGCAC CAGGACTGGC
1001 TGAACGGCAA GGAGTACAAG TGCAAGGTCT CCAACAAAGG CCTCCCGTCC
1051 TCCATCGAGA AAACCATCTC CAAAGCCAAA GGGCAGCCCC GAGAGCCACA
1101 GGTGTACACC CTGCCCCCAT CCCAGGAGGA GATGACCAAG AACCAGGTCA
1151 GCCTGACCTG CCTGGTCAAA GGCTTCTACC CCAGCGACAT CGCCGTGGAG
1201 TGGGAGAGCA ATGGGCAGCC GGAGAACAAC TACAAGACCA CGCCTCCCGT
1251 GCTGGACTCC GACGGCTCCT TCTTCCTCTA CAGCAGGCTA ACCGTGGACA
1301 AGAGCAGGTG GCAGGAGGGG AATGTCTTCT CATGCTCCGT GATGCATGAG
1351 GCTCTGCACA ACCACTACAC ACAGAAGAGC CTCTCCCTGT CTCTGGGTAA
1401 ATGA
```

6.14.2 Predicted Heavy Chain Protein Sequence
SEQ ID NO. 10
```
  1 mefglswlfl vailkgvqcE VQLLESGGGL VQPGGSLRLS CAASGLTFNN
 51 SAMTWVRQAP GKGLEWVSTT SGSGGTTYYA DSVKGRFTIS RDSPKNTLYL
101 QMNSLRAEDT AVYYCAARGY SYGTTPYEYW GQGTLVTVSS ASTKGPSVFP
151 LAPCSRSTSE STAALGCLVK DYFPEPVTVS WNSGALTSGV HTFPAVLQSS
201 GLYSLSSVVT VPSSSLGTKT YTCNVDHKPS NTKVDKRVES KYGPPCPSCP
251 APEFLGGPSV FLFPPKPKDT LMISRTPEVT CVVVDVSQED PEVQFNWYVD
301 GVEVHNAKTK PREEQFNSTY RVVSVLTVLH QDWLNGKEYK CKVSNKGLPS
351 SIEKTISKAK GQPREPQVYT LPPSQEEMTK NQVSLTCLVK GFYPSDIAVE
401 WESNGQPENN YKTTPPVLDS DGSFFLYSRL TVDKSRWQEG NVFSCSVMHE
451 ALHNHYTQKS LSLSLGK
```

6.14.2 Kappa Light Chain Nucleotide Sequence
SEQ ID NO. 11
```
  1 atggacatga gggtccccgc tcagctcctg gggctcctgc tactctggct
 51 ccgaggggcc agatgtGACA TCCAGATGAC CCAGTCTCCA TCCTCCCTGT
101 CTGCATCTGT AGGAGACAGA GTCACCATCA CTTGCCGGGC AAGTCGGAGC
151 ATTAGCAGCT ATTTAAATTG GTATCAGCAG AAACCAGGGA AAGCCCCTAA
201 AGTCCTGATC TTTTTTGTGT CCAGTTTGCA AAGTGGGGTC CCATCAAGGT
251 TCAGTGGCAG TGGCTCTGGG ACAGATTTCA CTCTCACCAT CAGCAGTCTG
```

```
301 CAACCTGAAG ATTTTGCAAC TTACTACTGT CAACAGAATT ACATTCCCCC

351 TATTACCTTC GGCCAGGGGA CACGACTGGA GATCAGACGA ACTGTGGCTG

401 CACCATCTGT CTTCATCTTC CCGCCATCTG ATGAGCAGTT GAAATCTGGA

451 ACTGCCTCTG TTGTGTGCCT GCTGAATAAC TTCTATCCCA GAGAGGCCAA

501 AGTACAGTGG AAGGTGGATA ACGCCCTCCA ATCGGGTAAC TCCCAGGAGA

551 GTGTCACAGA GCAGGACAGC AAGGACAGCA CCTACAGCCT CAGCAGCACC

601 CTGACGCTGA GCAAAGCAGA CTACGAGAAA CACAAAGTCT ACGCCTGCGA

651 AGTCACCCAT CAGGGCCTGA GCTCGCCCGT CACAAAGAGC TTCAACAGGG

701 GAGAGTGTTA G
```

6.14.2 Predicted Kappa Light Chain Protein Sequence

```
                                               SEQ ID NO. 12
  1 mdmrvpaqll glllwlrga rcDIQMTQSP SSLSASVGDR VTITCRASRS

51 ISSYLNWYQQ KPGKAPKVLI FFVSSLQSGV PSRFSGSGSG TDFTLTISSL

101 QPEDFATYYC QQNYIPPITF GQGTRLEIRR TVAAPSVFIF PPSDEQLKSG

151 TASVVCLLNN FYPREAKVQW KVDNALQSGN SQESVTEQDS KDSTYSLSST

202 LTLSKADYEK HKVYACEVTH QGLSSPVTKS FNRGEC
```

6.22.2 Heavy Chain Nucleotide Sequence

```
                                               SEQ ID NO. 13
   1 atggagtttg ggctgagctg ggttttcctc gttgctcttt taagaggtgt 51 ccagtgtCAG GTGCAGCTGG TGGAGTCTGG GGGAGGCGTG GTCCAGCCTG

101 GGAGGTCCCT GAGACTCTCC TGTGCAGCGT CTGGACACAC CTTCAGTAGC

151 GATGGCATGC ACTGGGTCCG CCAGGCTCCA GGCAAGGGGC TGGAGTGGGT

201 GGCAATTATA TGGTATGATG GAAGTAATAA ATATTATGCA GACTCCGTGA

251 AGGGCCGATT CACCATCTCC AGAGACAATT CCAAGAACAC GCTGTATCTG

301 CAAATGAACA GCCTGAGAGC CGAGGACACG GCTGTATATT ACTGTGCGAG

351 AGATCCCGGC TACTATTACG GTATGGACGT CTGGGGCCAA GGGACCACGG

401 TCACCGTCTC CTCAGCTTCC ACCAAGGGCC CATCCGTCTT CCCCCTGGCG

451 CCCTGCTCCA GGAGCACCTC CGAGAGCACA GCCGCCCTGG GCTGCCTGGT

501 CAAGGACTAC TTCCCCGAAC CGGTGACGGT GTCGTGGAAC TCAGGCGCCC

551 TGACCAGCGG CGTGCACACC TTCCCGGCTG TCCTACAGTC CTCAGGACTC

601 TACTCCCTCA GCAGCGTGGT GACCGTGCCC TCCAGCAGCT TGGGCACGAA

651 GACCTACACC TGCAACGTAG ATCACAAGCC CAGCAACACC AAGGTGGACA

701 AGAGAGTTGA GTCCAAATAT GGTCCCCCAT GCCCATCATG CCCAGCACCT

751 GAGTTCCTGG GGGGACCATC AGTCTTCCTG TTCCCCCCAA AACCCAAGGA

801 CACTCTCATG ATCTCCCGGA CCCCTGAGGT CACGTGCGTG GTGGTGGACG

851 TGAGCCAGGA AGACCCCGAG GTCCAGTTCA ACTGGTACGT GGATGGCGTG

901 GAGGTGCATA ATGCCAAGAC AAAGCCGCGG GAGGAGCAGT TCAACAGCAC

951 GTACCGTGTG GTCAGCGTCC TCACCGTCCT GCACCAGGAC TGGCTGAACG

1001 GCAAGGAGTA CAAGTGCAAG GTCTCCAACA AAGGCCTCCC GTCCTCCATC

1051 GAGAAAACCA TCTCCAAAGC CAAAGGGCAG CCCCGAGAGC CACAGGTGTA

1101 CACCCTGCCC CCATCCCAGG AGGAGATGAC CAAGAACCAG GTCAGCCTGA

1151 CCTGCCTGGT CAAAGGCTTC TACCCCAGCG ACATCGCCGT GGAGTGGGAG

1201 AGCAATGGGC AGCCGGAGAA CAACTACAAG ACCGCGCCTC CCGTGCTGGA
```

```
1251 CTCCGACGGC TCCTTCTTCC TCTACAGCAG GCTAACCGTG ACAAGAGCA

1301 GGTGGCAGGA GGGGAATGTC TTCTCATGCT CCGTGATGCA TGAGGCTCTG

1351 CACAACCACT ACACACAGAA GAGCCTCTCC CTGTCTCTGG GTAAATGA
```

6.22.2 Predicted Heavy Chain Protein Sequence
SEQ ID NO. 14
```
  1 mefglswvfl vallrqvqcQ VQLVESGGGV VQPGRSLRLS CAASGHTFSS

51 DGMHWVRQAP GKGLEWVAII WYDGSNKYYA DSVKGRFTIS RDNSKNTLYL

101 QMNSLRAEDT AVYYCARDPG YYYGMDVWGQ GTTVTVSSAS TKGPSVFPLA

151 PCSRSTSEST AALGCLVKDY FPEPVTVSWN SGALTSGVHT FPAVLQSSGL

201 YSLSSVVTVP SSSLGTKTYT CNVDHKPSNT KVDKRVESKY GPPCPSCPAP

251 EFLGGPSVFL FPPKPKDTLM ISRTPEVTCV VVDVSQEDPE VQFNWYVDGV

301 EVHNAKTKPR EEQFNSTYRV VSVLTVLHQD WLNGKEYKCK VSNKGLPSSI

351 EKTISKAKGQ PREPQVYTLP PSQEEMTKNQ VSLTCLVKGF YPSDIAVEWE

401 SNGQPENNYK TAPPVLDSDG SFFLYSRLTV DKSRWQEGNV FSCSVMHEAL

451 HNHYTQKSLS LSLGK
```

6.22.2 Kappa Light Chain Nucleotide Sequence
SEQ ID NO. 15
```
  1 atgttgccat cacaactcat tgggtttctg ctgctctggg ttccagcttc 51 cagggqtGAA ATTGTGCTGA CTCAGTCTCC AGACTTTCAG TCTGTGACTC

101 CAAAAGAGAA AGTCACCATC ACCTGCCGGG CCAGTCAGAG AATTGGTAGT

151 AGCTTACACT GGTACCAGCA GAAACCAGAT CAGTCTCCAA AACTCCTCAT

201 CAAGTATGCT TCCCAGTCCT TCTCAGGGGT CCCCTCGAGG TTCAGTGGCA

251 GTGGATCTGG GACAAATTTC ACCCTCACCA TCAATGGCCT GGAAGCTGAA

301 GATGCTGCAA CTTATTACTG TCATCAGAGT GGTCGTTTAC CGCTCACTTT

351 CGGCGGAGGG ACCAAGGTGG AGATCAAACG AACTGTGGCT GCACCATCTG

401 TCTTCATCTT CCCGCCATCT GATGAGCAGT TGAAATCTGG AACTGCCTCT

451 GTTGTGTGCC TGCTGAATAA CTTCTATCCC AGAGAGGCCA AAGTACAGTG

501 GAAGGTGGAT AACGCCCTCC AATCGGGTAA CTCCCAGGAG AGTGTCACAG

551 AGCAGGACAG CAAGGACAGC ACCTACAGCC TCAGCAGCAC CCTGACGCTG

601 AGCAAAGCAG ACTACGAGAA ACACAAAGTC TACGCCTGCG AAGTCACCCA

651 TCAGGGCCTG AGCTCGCCCG TCACAAAGAG CTTCAACAGG GGAGAGTGTT

701 AGTGA
```

6.22.2 Predicted Kappa Light Chain Protein Sequence
SEQ ID NO. 16
```
  1 mlpsqliqfl llwvpasrqE IVLTQSPDFQ SVTPKEKVTI TCRASQRIGS

51 SLHWYQQKPD QSPKLLIKYA SQSFSGVPSR FSGSGSGTNF TLTINGLEAE

101 DAATYYCHQS GRLPLTFGGG TKVEIKRTVA APSVFIFPPS DEQLKSGTAS

151 VVCLLNNFYP REAKVQWKVD NALQSGNSQE SVTEQDSKDS TYSLSSTLTL

201 SKADYEKHKV YACEVTHQGL SSPVTKSFNR GEC
```

6.34.2 Heavy Chain Nucleotide Sequence
SEQ ID NO. 17
```
  1 atggagtttg ggctgagctg ggttttcctc gttgctcttt taagaggtgt 51 ccagtgtCAG GTGCAGCTGG TGGAGTCTGG GGGAGGCGTG GTCCAGCCTG

101 GGAGGTCCCT GAGACTCTCC TGTGCAGCCT CTGGATTCAC CTTCAGTAGC
```

```
151 TATGGCATGC ACTGGGTCCG CCAGGCTCCA GGCAAGGGGC TGGAGTGGGT

201 GGCAGTTATA TCAAATGATG GAAATAATAA ATACTATGCA GACTCCGTGA

251 AGGGCCGATT CACCATCTCC AGAGACAATT CCAAAAACAC GCTGTATCTG

301 CAAATGAACA GCCTGAGCGC TGAGGACACG GCTGTGTATT ACTGTGCGAG

351 AGATAGTACG GCGATAACCT ACTACTACTA CGGAATGGAC GTCTGGGGCC

401 AAGGGACCAC GGTCACCGTC TCCTCAGCTT CCACCAAGGG CCCATCCGTC

451 TTCCCCCTGG CGCCCTGCTC CAGGAGCACC TCCGAGAGCA CAGCCGCCCT

501 GGGCTGCCTG GTCAAGGACT ACTTCCCCGA ACCGGTGACG GTGTCGTGGA

551 ACTCAGGCGC CCTGACCAGC GGCGTGCACA CCTTCCCGGC TGTCCTACAG

601 TCCTCAGGAC TCTACTCCCT CAGCAGCGTG GTGACCGTGC CCTCCAGCAG

651 CTTGGGCACG AAGACCTACA CCTGCAACGT AGATCACAAG CCCAGCAACA

701 CCAAGGTGGA CAAGAGAGTT GAGTCCAAAT ATGGTCCCCC ATGCCCATCA

751 TGCCCAGCAC CTGAGTTCCT GGGGGGACCA TCAGTCTTCC TGTTCCCCCC

801 AAAACCCAAG GACACTCTCA TGATCTCCCG GACCCCTGAG GTCACGTGCG

851 TGGTGGTGGA CGTGAGCCAG GAAGACCCCG AGGTCCAGTT CAACTGGTAC

901 GTGGATGGCG TGGAGGTGCA TAATGCCAAG ACAAAGCCGC GGGAGGAGCA

951 GTTCAACAGC ACGTACCGTG TGGTCAGCGT CCTCACCGTC CTGCACCAGG

1001 ACTGGCTGAA CGGCAAGGAG TACAAGTGCA AGGTCTCCAA CAAAGGCCTC

1051 CCGTCCTCCA TCGAGAAAAC CATCTCCAAA GCCAAAGGGC AGCCCCGAGA

1101 GCCACAGGTG TACACCCTGC CCCCATCCCA GGAGGAGATG ACCAAGAACC

1151 AGGTCAGCCT GACCTGCCTG GTCAAAGGCT TCTACCCCAG CGACATCGCC

1201 GTGGAGTGGG AGAGCAATGG ACAGCCGGAG AACAACTACA AGACCACGCC

1251 TCCCGTGCTG GACTCCGACG GCTCCTTCTT CCTCTACAGC AGGCTAACCG

1301 TGGACAAGAG CAGGTGGCAG GAGGGGAATG TCTTCTCATG CTCCGTGATG

1351 CATGAGGCTC TGCACAACCA CTACACACAG AAGAGCCTCT CCCTGTCTCT

1401 GGGTAAATGA
```

6.34.2 Predicted Heavy Chain Protein Sequence

SEQ ID NO. 18

```
  1 mefglswvfl vallrgvqcQ VQLVESGGGV VQPGRSLRLS CAASGFTFSS

51 YGMHWVRQAP GKGLEWVAVI SNDGNNKYYA DSVKGRFTIS RDNSKNTLYL

101 QMNSLSAEDT AVYYCARDST AITYYYYGMD VWGQGTTVTV SSASTKGPSV

151 FPLAPCSRST SESTAALGCL VKDYFPEPVT VSWNSGALTS GVHTFPAVLQ

201 SSGLYSLSSV VTVPSSSLGT KTYTCNVDHK PSNTKVDKRV ESKYGPPCPS

251 CPAPEFLGGP SVFLFPPKPK DTLMISRTPE VTCVVVDVSQ EDPEVQFNWY

301 VDGVEVHNAK TKPREEQFNS TYRVVSVLTV LHQDWLNGKE YKCKVSNKGL

351 PSSIEKTISK AKGQPREPQV YTLPPSQEEM TKNQVSLTCL VKGFYPSDIA

401 VEWESNGQPE NNYKTTPPVL DSDGSFFLYS RLTVDKSRWQ EGNVFSCSVM

451 HEALHNHYTQ KSLSLSLGK
```

6.34.2 Kappa Light Chain Nucleotide Sequence

SEQ ID NO. 19

```
  1 atggacatga gggtccccgc tcagctcctg gggctcctgc tactctggct 51 ccgaggtgcc agatgtGACA TCCAGATGAC CCAGTCTCCA TCCTCCCTGT

101 CTGCATCTGT CGGAGACAGA GTCACCATCA CTTGCCGGGC AAGTCAGAAT
```

```
151 ATTAGTAGCT ATTTAAATTG GTTTCAGCAG AAACCAGGGA AAGCCCCTAA

201 GCTCCTGATC TATGCTGCAT CCGGTTTGAA GCGTGGGGTC CCATCACGGT

251 TCAGTGGTAG TGGATCTGGG ACAGATTTCA CTCTCACCAT CAGGACTCTG

301 CAACCTGATG ATTTTGCAAC TTACTCCTGT CACCAGAGTT ACAGTCTCCC

351 ATTCACTTTC GGCCCTGGGA CCAAAGTGGA TATCAAACGA ACTGTGGCTG

401 CACCATCTGT CTTCATCTTC CCGCCATCTG ATGAGCAGTT GAAATCTGGA

451 ACTGCCTCTG TTGTGTGCCT GCTGAATAAC TTCTATCCCA GAGAGGCCAA

501 AGTACAGTGG AAGGTGGATA ACGCCCTCCA ATCGGGTAAC TCCCAGGAGA

551 GTGTCACAGA GCAGGACAGC AAGGACAGCA CCTACAGCCT CAGCAGCACC

601 CTGACGCTGA GCAAAGCAGA CTACGAGAAA CACAAAGTCT ACGCCTGCGA

651 AGTCACCCAT CAGGGCCTGA GCTCGCCCGT CACAAAGAGC TTCAACAGGG

701 GAGAGTGTTA GTGA
```

6.34.2 Predicted Kappa Light Chain Protein Sequence

```
                                          SEQ ID NO. 20
  1 mdmrvpaqll gllllwlrga rcDIQMTQSP SSLSASVGDR VTITCRASQN

51 ISSYLNWFQQ KPGKAPKLLI YAASGLKRGV PSRFSGSGSG TDFTLTIRTL

101 QPDDFATYSC HQSYSLPFTF GPGTKVDIKR TVAAPSVFIF PPSDEQLKSG

151 TASVVCLLNN FYPREAKVQW KVDNALQSGN SQESVTEQDS KDSTYSLSST

201 LTLSKADYEK HKVYACEVTH QGLSSPVTKS FNRGEC
```

6.67.1 Heavy Chain Nucleotide Sequence

```
                                          SEQ ID NO. 21
   1 atgaaacacc tgtggttctt cctcctgctg gtggcagctc ccagatgggt 51 cctgtccCAG GTGCAGCTGC AGGAGTCGGG CCCAGGACTG GTGAAGCCTT

101 CGGAGACCCT GTCCCTCACC TGCACTGTCT CTGGTGACTC CATCAGTAGT

151 AACTATTGGA GCTGGATCCG GCAGCCCGCC GGGAAGGGAC TGGAGTGGAT

201 TGGGCGTATC TATACCAGTG GGGGCACCAA CTCCAACCCC TCCCTCAGGG

251 GTCGAGTCAC CATTTTAGCA GACACGTCCA AGAACCAGTT CTCTCTGAAA

301 CTGAGTTCTG TGACCGCCGC GGACACGGCC GTGTATTACT GTGCGAGAGA

351 TCGTATTACT ATAATTCGGG GACTTATTCC ATCCTTCTTT GACTACTGGG

401 GCCAGGGAAC CCTGGTCACC GTCTCCTCAG CTTCCACCAA GGGCCCATCC

451 GTCTTCCCCC TGGCGCCCTG CTCCAGGAGC ACCTCCGAGA GCACAGCCGC

501 CCTGGGCTGC CTGGTCAAGG ACTACTTCCC CGAACCGGTG ACGGTGTCGT

551 GGAACTCAGG CGCCCTGACC AGCGGCGTGC ACACCTTCCC GGCTGTCCTA

601 CAGTCCTCAG GACTCTACTC CCTCAGCAGC GTGGTGACCG TGCCCTCCAG

651 CAGCTTGGGC ACGAAGACCT ACACCTGCAA CGTAGATCAC AAGCCCAGCA

701 ACACCAAGGT GGACAAGAGA GTTGAGTCCA AATATGGTCC CCCATGCCCA

751 TCATGCCCAG CACCTGAGTT CCTGGGGGGA CCATCAGTCT TCCTGTTCCC

801 CCCAAAACCC AAGGACACTC TCATGATCTC CCGGACCCCT GAGGTCACGT

851 GCGTGGTGGT GGACGTGAGC CAGGAAGACC CCGAGGTCCA GTTCAACTGG

901 TACGTGGATG GCGTGGAGGT GCATAATGCC AAGACAAAGC CGCGGGAGGA

951 GCAGTTCAAC AGCACGTACC GTGTGGTCAG CGTCCTCACC GTCCTGCACC

1001 AGGACTGGCT GAACGGCAAG GAGTACAAGT GCAAGGTCTC CAACAAAGGC
```

```
1051 CTCCCGTCCT CCATCGAGAA AACCATCTCC AAAGCCAAAG GCAGCCCCG
1101 AGAGCCACAG GTGTACACCC TGCCCCCATC CCAGGAGGAG ATGACCAAGA
1151 ACCAGGTCAG CCTGACCTGC CTGGTCAAAG GCTTCTACCC CAGCGACATC
1201 GCCGTGGAGT GGGAGAGCAA TGGGCAGCCG GAGAACAACT ACAAGACCAC
1251 GCCTCCCGTG CTGGACTCCG ACGGCTCCTT CTTCCTCTAC AGCAGGCTAA
1301 CCGTGGACAA GAGCAGGTGG CAGGAGGGGA ATGTCTTCTC ATGCTCCGTG
1351 ATGCATGAGG CTCTGCACAA CCACTACACA CAGAAGAGCC TCTCCCTGTC
1401 TCTGGGTAAA TGA
```

6.67.1 Predicted Heavy Chain Protein Sequence

SEQ ID NO. 22

```
  1 mkhlwfflll vaaprwvlsQ VQLQESGPGL VKPSETLSLT CTVSGDSISS
 51 NYWSWIRQPA GKGLEWIGRI YTSGGTNSNP SLRGRVTILA DTSKNQFSLK
101 LSSVTAADTA VYYCARDRIT IIRGLIPSFF DYWGQGTLVT VSSASTKGPS
151 VFPLAPCSRS TSESTAALGC LVKDYFPEPV TVSWNSGALT SGVHTFPAVL
201 QSSGLYSLSS VVTVPSSSLG TKTYTCNVDH KPSNTKVDKR VESKYGPPCP
251 SCPAPEFLGG PSVFLFPPKP KDTLMISRTP EVTCVVVDVS QEDPEVQFNW
301 YVDGVEVHNA KTKPREEQFN STYRVVSVLT VLHQDWLNGK EYKCKVSNKG
351 LPSSIEKTIS KAKGQPREPQ VYTLPPSQEE MTKNQVSLTC LVKGFYPSDI
401 AVEWESNGQP ENNYKTTPPV LDSDGSFFLY SRLTVDKSRW QEGNVFSCSV
451 MHEALHNHYT QKSLSLSLGK
```

6.67.1 Kappa Light Chain Nucleotide Sequence

SEQ ID NO. 23

```
  1 atggtgttgc agacccaggt cttcatttct ctgttgctct ggatctctgg
 51 tgcctacggg GACATCGTGA TGACCCAGTC TCCAGACTCC CTGGCTGTGT
101 CTCTGGGCGA GAGGGCCACC ATCAACTGCA AGTCCAGCCA GAGTGTTTTA
151 TACAGCTCCA ACAATAAGAC CTACTTAGCT TGGTACCAAC AGAAACCAAG
201 ACAGCCTCCT AAATTGCTCA TTTACTGGGC ATCTATACGG GAATATGGGG
251 TCCCTGACCG ATTCAGTGGC AGCGGGTCTG GGACAGATTT CACTCTCACC
301 ATCAGCAGCC TGCAGGCTGA AGATGTGGCA GTTTATTTCT GTCAACAATA
351 TTATAGTATT CCTCCCCTCA CTTTCGGCGG AGGGACCAAG GTGGAGATCA
401 AACGAACTGT GGCTGCACCA TCTGTCTTCA TCTTCCCGCC ATCTGATGAG
451 CAGTTGAAAT CTGGAACTGC CTCTGTTGTG TGCCTGCTGA ATAACTTCTA
501 TCCCAGAGAG GCCAAAGTAC AGTGGAAGGT GGATAACGCC CTCCAATCGG
551 GTAACTCCCA GGAGAGTGTC ACAGAGCAGG ACAGCAAGGA CAGCACCTAC
601 AGCCTCAGCA GCACCCTGAC GCTGAGCAAA GCAGACTACG AGAAACACAA
651 AGTCTACGCC TGCGAAGTCA CCCATCAGGG CCTGAGCTCG CCCGTCACAA
701 AGAGCTTCAA CAGGGGAGAG TGTTAGTGA
```

6.67.1 Predicted Kappa Light Chain Protein Sequence

SEQ ID NO. 24

```
  1 mvlqtqvfis lllwisqayg DIVMTQSPDS LAVSLGERAT INCKSSQSVL
 51 YSSNNKTYLA WYQQKPRQPP KLLIYWASIR EYGVPDRFSG SGSGTDFTLT
101 ISSLQAEDVA VYFCQQYYSI PPLTFGGGTK VEIKRTVAAP SVFIFPPSDE
151 QLKSGTASVV CLLNNFYPRE AKVQWKVDNA LQSGNSQESV TEQDSKDSTY
201 SLSSTLTLSK ADYEKHKVYA CEVTHQGLSS PVTKSFNRGE C
```

6.73.2 Heavy Chain Nucleotide Sequence

SEQ ID NO. 25

```
   1 atggagtttg ggctgagctg gcttttcctt gtggctattt taaaaggtgt
  51 ccagtgtGAG GTGCAGCTGT TGGAGTCTGG GGGAGACTTG GTCCAGCCTG
 101 GGGGGTCCCT GAGACTCTCC TGTGCAGCCT CTGGATTCAC CTTTAGAAGT
 151 TATGCCATGA ACTGGGTCCG ACAGGCTCCA GGGAAGGGGC TGGAGTGGGT
 201 CTCAGTTATT AGTGGTCGTG GTGGTACTAC ATACTACGCA GACTCCGTGA
 251 AGGGCCGGTT CACCATCTCC AGAGACAATT CCAAGAACAC GCTGTATCTG
 301 CAAATGAACA GCCTGAGAGC CGAGGACGCG GCCGTATATT ACTGTGCGAA
 351 GATAGCAGTG GCTGGAGAGG GGCTCTACTA CTACTACGGT ATGGACGTCT
 401 GGGGCCAAGG GACCACGGTC ACCGTCTCCT CAGCTTCCAC CAAGGGCCCA
 451 TCCGTCTTCC CCTGGCGCC CTGCTCCAGG AGCACCTCCG AGAACACAGC
 501 CGCCCTGGGC TGCCTGGTCA AGGACTACTT CCCCGAACCG GTGACGGTGT
 551 CGTGGAACTC AGGCGCCCTG ACCAGCGGCG TGCACACCTT CCCGGCTGTC
 601 CTACAGTCCT CAGGACTCTA CTCCCTCAGC AGCGTGGTGA CCGTGCCCTC
 651 TAGCAGCTTG GGCACGAAGA CCTACACCTG CAACGTAGAT CACAAGCCCA
 701 GCAACACCAA GGTGGACAAG AGAGTTGAGT CCAAATATGG TCCCCCATGC
 751 CCATCATGCC CAGCACCTGA GTTCCTGGGG GGACCATCAG TCTTCCTGTT
 801 CCCCCCAAAA CCCAAGGACA CTCTCATGAT CTCCCGGACC CCTGAGGTCA
 851 CGTGCGTGGT GGTGGACGTG AGCCAGGAAG ACCCCGAGGT CCAGTTCAAC
 901 TGGTACGTGG ATGGCGTGGA GGTGCATAAT GCCAAGACAA AGCCGCGGGA
 951 GGAGCAGTTC AACAGCACGT ACCGTGTGGT CAGCGTCCTC ACCGTCCTGC
1001 ACCAGGACTG GCTGAACGGC AAGGAGTACA AGTGCAAGGT CTCCAACAAA
1051 GGCCTCCCGT CCTCCATCGA GAAAACCATC TCCAAAGCCA AAGGGCAGCC
1101 CCGAGAGCCA CAGGTGTACA CCCTGCCCCC ATCCCAGGAG GAGATGACCA
1151 AGAACCAGGT CAGCCTGACC TGCCTGGTCA AAGGCTTCTA CCCCAGCGAC
1201 ATCGCCGTGG AGTGGGAGAG CAATGGGCAG CCGGAGAACA ACTACAAGAC
1251 CACGCCTCCC GTGCTGGACT CCGACGGCTC CTTCTTCCTC TACAGCAGGC
1301 TAACCGTGGA CAAGAGCAGG TGGCAGGAGG GGAATGTCTT CTCATGCTCC
1351 GTGATGCATG AGGCTCTGCA CAACCACTAC ACACAGAAGA GCCTCTCCCT
1401 GTCTCTGGGT AAATGATAG
```

6.73.2 Predicted Heavy Chain Protein Sequence

SEQ ID NO. 26

```
  1 mefglswlfl vailkgvqcE VQLLESGGDL VQPGGSLRLS CAASGFTFRS
 51 YAMNWVRQAP GKGLEWVSVI SGRGGTTYYA DSVKGRFTIS RDNSKNTLYL
101 QMNSLRAEDA AVYYCAKIAV AGEGLYYYYG MDVWGQGTTV TVSSASTKGP
151 SVFPLAPCSR STSENTAALG CLVKDYFPEP VTVSWNSGAL TSGVHTFPAV
201 LQSSGLYSLS SVVTVPSSSL GTKTYTCNVD HKPSNTKVDK RVESKYGPPC
251 PSCPAPEFLG GPSVFLFPPK PKDTLMISRT PEVTCVVVDV SQEDPEVQFN
301 WYVDGVEVHN AKTKPREEQF NSTYRVVSVL TVLHQDWLNG KEYKCKVSNK
```

```
351 GLPSSIEKTI SKAKGQPREP QVYTLPPSQE EMTKNQVSLT CLVKGFYPSD

401 IAVEWESNGQ PENNYKTTPP VLDSDGSFFL YSRLTVDKSR WQEGNVFSCS

451 VMHEALHNHY TQKSLSLSLG K
```

6.73.2 Kappa Light Chain Nucleotide Sequence

SEQ ID NO. 27

```
  1 atggacatga gggtccccgc tcagctcctg gggctcctgc tactctggct 51 ccgaggtgcc agatgtGACA TCCAGATGAC CCAGTCTCCA TCCTCCCTGT

101 CTGCATCTGT AGGTGACAGA GTCACCTTCA CTTGCCGGGC AAGTCAGAAC

151 ATTACCAACT ATTTAAATTG GTATCAGCAG AAACCAGGGA AGGCCCCTAA

201 GCTCCTGATC TATGCTGCGT CCAGTTTGCC AAGAGGGGTC CCATCAAGGT

251 TCCGTGGCAG TGGATCTGGG ACAGATTTCA CTCTCACCAT CAGCAGTCTG

301 CAACCTGAAG ATTTTGCAAC TTACTACTGT CAACAGAGTT ACAGTAATCC

351 TCCGGAGTGC GGTTTTGGCC AGGGGACCAC GCTGGATATC AAACGAACTG

401 TGGCTGCACC ATCTGTCTTC ATCTTCCCGC CATCTGATGA GCAGTTGAAA

451 TCTGGAACTG CCTCTGTTGT GTGCCTGCTG AATAACTTCT ATCCCAGAGA

501 GGCCAAAGTA CAGTGGAAGG TGGATAACGC CCTCCAATCG GGTAACTCCC

551 AGGAGAGTGT CACAGAGCAG GACAGCAAGG ACAGCACCTA CAGCCTCAGC

601 AGCACCCTGA CGCTGAGCAA AGCAGACTAC GAGAACACA AAGTCTACGC

651 CTGCGAAGTC ACCCATCAGG GCCTGAGCTC GCCCGTCACA AAGAGCTTCA

701 ACAGGGGAGA GTGTTAGTGA
```

6.73.2 Predicted Kappa Light Chain Protein Sequence

SEQ ID NO. 28

```
  1 mdmrvpaqll qlllwlrga rcDIQMTQSP SSLSASVGDR VTFTCRASQN

51 ITNYLNWYQQ KPGKAPKLLI YAASSLPRGV PSRFRGSGSG TDFTLTISSL

101 QPEDFATYYC QQSYSNPPEC GFGQGTTLDI KRTVAAPSVF IFPPSDEQLK

151 SGTASVVCLL NNFYPREAKV QWKVDNALQS GNSQESVTEQ DSKDSTYSLS

201 STLTLSKADY EKHKVYACEV THQGLSSPVT KSFNRGEC
```

6.77.1 Heavy Chain Nucleotide Sequence

SEQ ID NO. 29

```
  1 atggaactgg ggctccgctg ggttttcctt gttgctattt tagaaggtgt 51 ccagtgtGAG GTGCAGCTGG TGGAGTCTGG GGGAGGCCTG GTCAAGCCTG

101 GGGGGTCCCT GAGACTCTCC TGTGCAGCCT CTGGATTCAC CTTCAGTAGC

151 TATAGCATGA ACTGGGTCCG CCAGGCTCCA GGGAAGGGGC TGGAGTGGGT

201 CTCATCCATT AGTAGTAGTA GTAGTTACAT ATACTACGCA GACTCAGTGA

251 AGGGCCGATT CACCATCTCC AGAGACAACG CCAAGAACTC ACTGTATCTG

301 CAAATGAACA GCCTGAGAGC CGAGGACACG GCTGTGTATT ACTGTGCGAG

351 AGATGGGTAT AGCAGTGGCT GGTCCTACTA CTACTACTAC GGTATGGACG

401 TCTGGGGCCA AGGGACCACG GTCACCGTCT CCTCAGCTTC CACCAAGGGC

451 CCATCCGTCT TCCCCCTGGC GCCCTGCTCC AGGAGCACCT CCGAGAGCAC

501 AGCCGCCCTG GGCTGCCTGG TCAAGGACTA CTTCCCCGAA CCGGTGACGG

551 TGTCGTGGAA CTCAGGCGCC CTGACCAGCG GCGTGCACAC CTTCCCGGCT

601 GTCCTACAGT CCTCAGGACT CTACTCCCTC AGCAGCGTGG TGACCGTGCC

651 CTCCAGCAGC TTGGGCACGA AGACCTACAC CTGCAACGTA GATCACAAGC

701 CCAGCAACAC CAAGGTGGAC AAGAGAGTTG AGTCCAAATA TGGTCCCCCA
```

```
 751 TGCCCATCAT GCCCAGCACC TGAGTTCCTG GGGGGACCAT CAGTCTTCCT
 801 GTTCCCCCCA AAACCCAAGG ACACTCTCAT GATCTCCCGG ACCCCTGAGG
 851 TCACGTGCGT GGTGGTGGAC GTGAGCCAGG AAGACCCCGA GGTCCAGTTC
 901 AACTGGTACG TGGATGGCGT GGAGGTGCAT AATGCCAAGA CAAAGCCGCG
 951 GGAGGAGCAG TTCAACAGCA CGTACCGTGT GGTCAGCGTC CTCACCGTCC
1001 TGCACCAGGA CTGGCTGAAC GGCAAGGAGT ACAAGTGCAA GGTCTCCAAC
1051 AAAGGCCTCC CGTCCTCCAT CGAGAAAACC ATCTCCAAAG CCAAAGGGCA
1101 GCCCCGAGAG CCACAGGTGT ACACCCTGCC CCCATCCCAG GAGGAGATGA
1151 CCAAGAACCA GGTCAGCCTG ACCTGCCTGG TCAAAGGCTT CTACCCCAGC
1201 GACATCGCCG TGGAGTGGGA GAGCAATGGG CAGCCGGAGA ACAACTACAA
1251 GACCACGCCT CCCGTGCTGG ACTCCGACGG CTCCTTCTTC CTCTACAGCA
1301 GGCTAACCGT GGACAAGAGC AGGTGGCAGG AGGGGAATGT CTTTTCACGC
1351 TCCGTGATGC ATGAGGCTCT GCACAACCAC TACACACAGA AGAGCCTCTC
1401 CCTGTCTCTG GGTAAATGAT AGGAATTCTG ATGA
```

6.77.1 Predicted Heavy Chain Protein Sequence

SEQ ID NO. 30

```
  1 melqlrwvfl vaileqvqcE VQLVESGGGL VKPGGSLRLS CAASGFTFSS
 51 YSMNWVRQAP GKGLEWVSSI SSSSSYIYYA DSVKGRFTIS RDNAKNSLYL
101 QMNSLRAEDT AVYYCARDGY SSGWSYYYYY GMDVWGQGTT VTVSSASTKG
151 PSVFPLAPCS RSTSESTAAL GCLVKDYFPE PVTVSWNSGA LTSGVHTFPA
201 VLQSSGLYSL SSVVTVPSSS LGTKTYTCNV DHKPSNTKVD KRVESKYGPP
251 CPSCPAPEFL GGPSVFLFPP KPKDTLMISR TPEVTCVVVD VSQEDPEVQF
301 NWYVDGVEVH NAKTKPREEQ FNSTYRVVSV LTVLHQDWLN GKEYKCKVSN
351 KGLPSSIEKT ISKAKGQPRE PQVYTLPPSQ EEMTKNQVSL TCLVKGFYPS
401 DIAVEWESNG QPENNYKTTP PVLDSDGSFF LYSRLTVDKS RWQEGNVFSR
451 SVMHEALHNH YTQKSLSLSL GK
```

6.77.1 Kappa Light Chain Nucleotide Sequence

SEQ ID NO. 31

```
  1 atgaggctcc ctgctcagct cctggggctg ctaatgctct ggatacctgg
 51 atccagtgca GATATTGTGA TGACCCAGAC TCCACTCTCT CTGTCCGTCA
101 CTCCTGGACA GCCGGCCTCC ATCTCCTGCA ACTCTAGTCA GAGCCTCCTG
151 CTTAGTGATG GAAAGACCTA TTTGAATTGG TACCTGCAGA AGCCCGGCCA
201 GCCTCCACAG CTCCTGATCT ATGAAGTTTC CAACCGGTTC TCTGGAGTGC
251 CAGACAGGTT CAGTGGCAGC GGGTCAGGGA CAGATTTCAC ACTGAAAATC
301 AGCCGGGTGG AGGCTGAGGA TGTTGGGGTT TATTCCTGCA TGCAAAGTAT
351 ACAGCTTATG TGCAGTTTTG GCCAGGGGAC CAAGCTGGAG ATCAAACGAA
401 CTGTGGCTGC ACCATCTGTC TTCATCTTCC CGCCATCTGA TGAGCAGTTG
451 AAATCTGGAA CTGCCTCTGT TGTGTGCCTG CTGAATAACT TCTATCCCAG
501 AGAGGCCAAA GTACAGTGGA AGGTGGATAA CGCCCTCCAA TCGGGTAACT
551 CCCAGGAGAG TGTCACAGAG CAGGACAGCA AGGACAGCAC CTACAGCCTC
```

```
601 AGCAGCACCC TGACGCTGAG CAAAGCAGAC TACGAGAAAC ACAAAGTCTA

651 CGCCTGCGAA GTCACCCATC AGGGCCTGAG CTCGCCCGTC ACAAAGAGCT

701 TCAACAGGGG AGAGTGTTAG TGA
```

6.77.1 Predicted Kappa Light Chain Protein Sequence

SEQ ID NO. 32

```
  1 mrlpaqllgl lmlwipgssa DIVMTQTPLS LSVTPGQPAS ISCNSSQSLL

51 LSDGKTYLNW YLQKPGQPPQ LLIYEVSNRF SGVPDRFSGS GSGTDFTLKI

101 SRVEAEDVGV YSCMQSIQLM CSFGQGTKLE IKRTVAAPSV FIFPPSDEQL

151 KSGTASVVCL LNNFYPREAK VQWKVDNALQ SGNSQESVTE QDSKDSTYSL

201 SSTLTLSKAD YEKHKVYACE VTHQGLSSPV TKSFNRGEC
```

7.16.6 Heavy Chain Nucleotide Sequence

SEQ ID NO. 33

```
   1 atggactgga cctggagcat ccttttcttg gtggcagcag caacaggtgc 51 ccactccCAG GTTCAGCTGG TGCAGTCTGG AGCTGAGGTG AAGAAGCCTG

101 GGGCCTCAGT GAAGGTCTCC TGCAAGGCTT CTGGTTACAC CTTTACCAGC

151 TATGGTATCA ACTGGGTGCG ACAGGCCCCT GGACAAGGGC TTGAGTGGAT

201 GGGATGGATC AGCGTTTACA GTGGTAACAC AAACTATGCA CAGAAGGTCC

251 AGGGCAGAGT CACCATGACC GCAGACACAT CCACGAGCAC AGCCTACATG

301 GACCTGAGGA GCCTGAGATC TGACGACACG GCCGTGTATT ACTGTGCGAG

351 AGAGGGTAGC AGCTCGTCCG GAGACTACTA TTACGGTATG GACGTCTGGG

401 GCCAAGGGAC CACGGTCACC GTCTCCTCAG CCTCCACCAA GGGCCCATCG

451 GTCTTCCCCC TGGCGCCCTG CTCCAGGAGC ACCTCCGAGA GCACAGCGGC

501 CCTGGGCTGC CTGGTCAAGG ACTACTTCCC CGAACCGGTG ACGGTGTCGT

551 GGAACTCAGG CGCTCTGACC AGCGGCGTGC ACACCTTCCC AGCTGTCCTA

601 CAGTCCTCAG GACTCTACTC CCTCAGCAGC GTGGTGACCG TGCCCTCCAG

651 CAACTTCGGC ACCCAGACCT ACACCTGCAA CGTAGATCAC AAGCCCAGCA

701 ACACCAAGGT GGACAAGACA GTTGAGCGCA AATGTTGTGT CGAGTGCCCA

751 CCGTGCCCAG CACCACCTGT GGCAGGACCG TCAGTCTTCC TCTTCCCCCC

801 AAAACCCAAG GACACCCTCA TGATCTCCCG GACCCCTGAG GTCACGTGCG

851 TGGTGGTGGA CGTGAGCCAC GAAGACCCCG AGGTCCAGTT CAACTGGTAC

901 GTGGACGGCG TGGAGGTGCA TAATGCCAAG ACAAAGCCAC GGGAGGAGCA

951 GTTCAACAGC ACGTTCCGTG TGGTCAGCGT CCTCACCGTT GTGCACCAGG

1001 ACTGGCTGAA CGGCAAGGAG TACAAGTGCA AGGTCTCCAA CAAAGGCCTC

1051 CCAGCCCCCA TCGAGAAAAC CATCTCCAAA ACCAAAGGGC AGCCCCGAGA

1101 ACCACAGGTG TACACCCTGC CCCCATCCCG GGAGGAGATG ACCAAGAACC

1151 AGGTCAGCCT GACCTGCCTG GTCAAAGGCT TCTACCCCAG CGACATCGCC

1201 GTGGAGTGGG AGAGCAATGG GCAGCCGGAG AACAACTACA AGACCACACC

1251 TCCCATGCTG GACTCCGACG GCTCCTTCTT CCTCTACAGC AAGCTCACCG

1301 TGGACAAGAG CAGGTGGCAG CAGGGGAACG TCTTCTCATG CTCCGTGATG

1351 CATGAGGCTC TGCACAACCA CTACACGCAG AAGAGCCTCT CCCTGTCTCC

1401 GGGTAAATGA
```

7.16.6 Predicted Heavy Chain Protein Sequence

SEQ ID NO. 34

```
  1 mdwtwsilfl vaaatqahsQ VQLVQSGAEV KKPGASVKVS CKASGYTFTS
 51 YGINWVRQAP GQGLEWMGWI SVYSGNTNYA QKVQGRVTMT ADTSTSTAYM
101 DLRSLRSDDT AVYYCAREGS SSSGDYYYGM DVWGQGTTVT VSSASTKGPS
151 VFPLAPCSRS TSESTAALGC LVKDYFPEPV TVSWNSGALT SGVHTFPAVL
201 QSSGLYSLSS VVTVPSSNFG TQTYTCNVDH KPSNTKVDKT VERKCCVECP
251 PCPAPPVAGP SVFLFPPKPK DTLMISRTPE VTCVVVDVSH EDPEVQFNWY
301 VDGVEVHNAK TKPREEQFNS TFRVVSVLTV VHQDWLNGKE YKCKVSNKGL
351 PAPIEKTISK TKGQPREPQV YTLPPSREEM TKNQVSLTCL VKGFYPSDIA
401 VEWESNGQPE NNYKTTPPML DSDGSFFLYS KLTVDKSRWQ QGNVFSCSVM
451 HEALHNHYTQ KSLSLSPGK
```

7.16.6 Kappa Light Chain Nucleotide Sequence

SEQ ID NO. 35

```
  1 atgaggctcc ctgctcagct cctggggctg ctaatgctct ggatacctgg
 51 atccagtgca GATATTGTGA TGACCCAGAC TCCACTCTCT CTGTCCGTCA
101 CCCCTGGACA GCCGGCCTCC ATCTCCTGCA AGTCTAGTCA GAGCCTCCTG
151 CATACTGATG GAACGACCTA TTTGTATTGG TACCTGCAGA AGCCAGGCCA
201 GCCTCCACAG CTCCTGATCT ATGAAGTTTC CAACCGGTTC TCTGGAGTGC
251 CAGATAGGTT CAGTGGCAGC GGGTCAGGGA CAGATTTCAC ACTGAAAATC
301 AGCCGGGTGG AGGCTGAGGA TGTTGGGATT TATTACTGCA TGCAAAATAT
351 ACAGCTTCCG TGGACGTTCG GCCAAGGGAC CAAGGTGGAA ATCAAACGAA
401 CTGTGGCTGC ACCATCTGTC TTCATCTTCC CGCCATCTGA TGAGCAGTTG
451 AAATCTGGAA CTGCCTCTGT TGTGTGCCTG CTGAATAACT TCTATCCCAG
501 AGAGGCCAAA GTACAGTGGA AGGTGGATAA CGCCCTCCAA TCGGGTAACT
551 CCCAGGAGAG TGTCACAGAG CAGGACAGCA AGGACAGCAC CTACAGCCTC
601 AGCAGCACCC TGACGCTGAG CAAAGCAGAC TACGAGAAAC ACAAAGTCTA
651 CGCCTGCGAA GTCACCCATC AGGGCCTGAG CTCGCCCGTC ACAAAGAGCT
701 TCAACAGGGG AGAGTGTTAG TGA
```

7.16.6 Kappa Light Chain Protein Sequence

SEQ ID NO. 36

```
  1 mrlpaqllgl lmlwipqssa DIVMTQTPLS LSVTPGQPAS ISCKSSQSLL
 51 HTDGTTYLYW YLQKPGQPPQ LLIYEVSNRF SGVPDRFSGS GSGTDFTLKI
101 SRVEAEDVGI YYCMQNIQLP WTFGQGTKVE IKRTVAAPSV FIFPPSDEQL
151 KSGTASVVCL LNNFYPREAK VQWKVDNALQ SGNSQESVTE QDSKDSTYSL
201 SSTLTLSKAD YEKHKVYACE VTHQGLSSPV TKSFNRGEC
```

7.20.5 Heavy Chain Nucleotide Sequence

SEQ ID NO. 37

```
  1 atgaaacacc tgtggttctt cctcctgctg gtggcagctc ccagatgggt
 51 cctgtccCAG GTGCAGCTGC AGGAGTCGGG CCCAGGACTG GTGAAGCCTT
101 CGGAGACCCT GTCCCTCACC TGCACTGTCT CTGGTAGCTC CATCAGTAGT
151 TACCACTGGA ACTGGATCCG GCAGCCCGCC GGGAAGGGAC TGGAGTGGAT
201 TGGGCGTATC TATACCAGTG GGAGCACCAA CTACAACCCC TCCCTCAAGA
251 GTCGAGTCAC CATGTCACTA GACACGTCCA AGAACCAGTT CTCCCTGAAG
301 CTGAGCTCTG TGACCGCCGC GGACACGGCC GTGTATTACT GTGCGAGAGA
```

```
 351 GGGGGTCAGG TATTACTATG CTTCGGGGAG TTATTACTAC GGTCTGGACG

401 TCTGGGGCCA AGGGACCACG GTCACCGTCT CCTCAGCCTC CACCAAGGGC

451 CCATCGGTCT TCCCCCTGGC GCCCTGCTCC AGGAGCACCT CCGAGAGCAC

501 AGCGGCCCTG GGCTGCCTGG TCAAGGACTA CTTCCCCGAA CCGGTGACGG

551 TGTCGTGGAA CTCAGGCGCT CTGACCAGCG GCGTGCACAC CTTCCCAGCT

601 GTCCTACAGT CCTCAGGACT CTACTCCCTC AGCAGCGTGG TGACCGTGCC

651 CTCCAGCAAC TTCGGCACCC AGACCTACAC CTGCAACGTA GATCACAAGC

701 CCAGCAACAC CAAGGTGGAC AAGACAGTTG AGCGCAAATG TTGTGTCGAG

751 TGCCCACCGT GCCCAGCACC ACCTGTGGCA GGACCGTCAG TCTTCCTCTT

801 CCCCCCAAAA CCCAAGGACA CCCTCATGAT CTCCCGGACC CCTGAGGTCA

851 CGTGCGTGGT GGTGGACGTG AGCCACGAAG ACCCCGAGGT CCAGTTCAAC

901 TGGTACGTGG ACGGCGTGGA GGTGCATAAT GCCAAGACAA AGCCACGGGA

951 GGAGCAGTTC AACAGCACGT TCCGTGTGGT CAGCGTCCTC ACCGTTGTGC

1001 ACCAGGACTG GCTGAACGGC AAGGAGTACA AGTGCAAGGT CTCCAACAAA

1051 GGCCTCCCAG CCCCCATCGA GAAAACCATC TCCAAAACCA AAGGGCAGCC

1101 CCGAGAACCA CAGGTGTACA CCCTGCCCCC ATCCCGGGAG GAGATGACCA

1151 AGAACCAGGT CAGCCTGACC TGCCTGGTCA AAGGCTTCTA CCCCAGCGAC

1201 ATCGCCGTGG AGTGGGAGAG CAATGGGCAG CCGGAGAACA ACTACAAGAC

1251 CACACCTCCC ATGCTGGACT CCGACGGCTC CTTCTTCCTC TACAGCAAGC

1301 TCACCGTGGA CAAGAGCAGG TGGCAGCAGG GGAACGTCTT CTCATGCTCC

1351 GTGATGCATG AGGCTCTGCA CAACCACTAC ACGCAGAAGA GCCTCTCCCT

1401 GTCTCCGGGT AAATGA
```

7.20.5 Predicted Heavy Chain Protein Sequence
```
                                              SEQ ID NO. 38
   1 mkhlwfflll vaaprwvlsQ VQLQESGPGL VKPSETLSLT CTVSGSSISS

51 YHWNWIRQPA GKGLEWIGRI YTSGSTNYNP SLKSRVTMSL DTSKNQFSLK

101 LSSVTAADTA VYYCAREGVR YYYASGSYYY GLDVWGQGTT VTVSSASTKG

151 PSVFPLAPCS RSTSESTAAL GCLVKDYFPE PVTVSWNSGA LTSGVHTFPA

201 VLQSSGLYSL SSVVTVPSSN FGTQTYTCNV DHKPSNTKVD KTVERKCCVE

251 CPPCPAPPVA GPSVFLFPPK PKDTLMISRT PEVTCVVVDV SHEDPEVQFN

301 WYVDGVEVHN AKTKPREEQF NSTFRVVSVL TVVHQDWLNG KEYKCKVSNK

351 GLPAPIEKTI SKTKGQPREP QVYTLPPSRE EMTKNQVSLT CLVKGFYPSD

401 IAVEWESNGQ PENNYKTTPP MLDSDGSFFL YSKLTVDKSR WQQGNVFSCS

451 VMHEALHNHY TQKSLSLSPG K
```

7.20.5 Kappa Light Chain Nucleotide Sequence
```
                                              SEQ ID NO. 39
   1 atgaggctcc ctgctcagct cctggggctg ctaatgctct gggtctctgg 51 atccagtggg GATATTGTGA TGACTCAGTC TCCACTCTCC CTGCCCGTCA

101 CCCCTGGAGA GCCGGCCTCC ATCTCCTGCA GGTCTAGTCA GAGCCTCCTG

151 CATGGTAATG GATACAACTA TTTGGATTGG TACCTGCAGA AGCCAGGGCA

201 GTCTCCACAG CTCCTGATCT ATTTGGGTTC TAATCGGGCC TCCGGGGTCC

251 CTGACAGGTT CAGTGGCAGT GGATCAGGCA CAGATTTTAC ACTGAAAATC
```

```
301 AGCAGAGTGG AGGCTGAGGA TGTTGGGGTT TATTACTGCA TGCAAGCTCT

351 ACAAACTCTC ACTTTCGGCG GAGGGACCAA GGTGGAGATC AAACGAACTG

401 TGGCTGCACC ATCTGTCTTC ATCTTCCCGC CATCTGATGA GCAGTTGAAA

451 TCTGGAACTG CCTCTGTTGT GTGCCTGCTG AATAACTTCT ATCCCAGAGA

501 GGCCAAAGTA CAGTGGAAGG TGGATAACGC CCTCCAATCG GGTAACTCCC

551 AGGAGAGTGT CACAGAGCAG GACAGCAAGG ACAGCACCTA CAGCCTCAGC

601 AGCACCCTGA CGCTGAGCAA AGCAGACTAC GAGAAACACA AAGTCTACGC

651 CTGCGAAGTC ACCCATCAGG GCCTGAGCTC GCCCGTCACA AAGAGCTTCA

701 ACAGGGGAGA GTGTTAGTGA
```

7.20.5 Predicted Kappa Light Chain Protein Sequence

SEQ ID NO. 40

```
  1 mrlpaqllgl lmlwvsgssg DIVMTQSPLS LPVTPGEPAS ISCRSSQSLL

51 HGNGYNYLDW YLQKPGQSPQ LLIYLGSNRA SGVPDRFSGS GSGTDFTLKI

101 SRVEAEDVGV YYCMQALQTL TFGGGTKVEI KRTVAAPSVF IFPPSDEQLK

151 SGTASVVCLL NNFYPREAKV QWKVDNALQS GNSQESVTEQ DSKDSTYSLS

201 STLTLSKADY EKHKVYACEV THQGLSSPVT KSFNRGEC
```

7.26.4 Heavy Chain Nucleotide Sequence

SEQ ID NO. 41

```
   1 atggactgga cctggagcat ccttttcttg gtggcagcag caacaggtgc 51 ccactccCAG GTTCAGCTGG TGCAGTCTGG AGCTGAGGTG AAGAAGCCTG

101 GGGCCTCAGT GAAGGTCTCC TGCGAGGCTT CTGGTTACAC CTTTACCAGC

151 TATGGTATCG ACTGGGTGCG ACAGGCCCCT GGACAAGGGC TTGAGTGGAT

201 GGGATGGATC AGCGTTTACA GTGGTAACAC AAACTATGCA CAGAAGCTCC

251 AGGGCAGAGT CACCATGTCC ACAGACACAT CCACGAGCAC AGCCTACATG

301 GAGCTGAGGA GCCTGAGATC TGACGACACG GCCGTGTATT ACTGTGCGAG

351 AGAGGGTAGC AGCTCGTCCG GAGACTACTA CTACGGTATG GACGTCTGGG

401 GCCAAGGGAC CACGGTCACC GTCTCCTCAG CCTCCACCAA GGGCCCATCG

451 GTCTTCCCCC TGGCGCCCTG CTCCAGGAGC ACCTCCGAGA GCACAGCGGC

501 CCTGGGCTGC CTGGTCAAGG ACTACTTCCC CGAACCGGTG ACGGTGTCGT

551 GGAACTCAGG CGCTCTGACC AGCGGCGTGC ACACCTTCCC AGCTGTCCTA

601 CAGTCCTCAG GACTCTACTC CCTCAGCAGC GTGGTGACCG TGCCCTCCAG

651 CAACTTCGGC ACCCAGACCT ACACCTGCAA CGTAGATCAC AAGCCCAGCA

701 ACACCAAGGT GGACAAGACA GTTGAGCGCA AATGTTGTGT CGAGTGCCCA

751 CCGTGCCCAG CACCACCTGT GGCAGGACCG TCAGTCTTCC TCTTCCCCCC

801 AAAACCCAAG GACACCCTCA TGATCTCCCG GACCCCTGAG GTCACGTGCG

851 TGGTGGTGGA CGTGAGCCAC GAAGACCCCG AGGTCCAGTT CAACTGGTAC

901 GTGGACGGCG TGGAGGTGCA TAATGCCAAG ACAAAGCCAC GGGAGGAGCA

951 GTTCAACAGC ACGTTCCGTG TGGTCAGCGT CCTCACCGTT GTGCACCAGG

1001 ACTGGCTGAA CGGCAAGGAG TACAAGTGCA AGGTCTCCAA CAAAGGCCTC

1051 CCAGCCCCCA TTGAGAAAAC CATCTCCAAA ACCAAAGGGC AGCCCCGAGA

1101 ACCACAGGTG TACACCCTGC CCCCATCCCG GGAGGAGATG ACCAAGAACC

1151 AGGTCAGCCT GACCTGCCTG GTCAAAGGCT TCTACCCCAG CGACATCGCC

1201 GTGGAGTGGG AGAGCAATGG GCAGCCGGAG AACAACTACA AGACCACACC
```

```
1251 TCCCATGCTG GACTCCGACG GCTCCTTCTT CCTCTACAGC AAGCTCACCG

1301 TGGACAAGAG CAGGTGGCAG CAGGGGAACG TCTTCTCATG CTCCGTGATG

1351 CATGAGGCTC TGCACAACCA CTACACGCAG AAGAGCCTCT CCCTGTCTCC

1402 GGGTAAATGA
```

7.26.4 Predicted Heavy Chain Protein Sequence

```
                                                    SEQ ID NO. 42
  1 mdwtwsilfl vaaatgahsQ VQLVQSGAEV KKPGASVKVS CEASGYTFTS

51 YGIDWVRQAP GQGLEWMGWI SVYSGNTNYA QKLQGRVTMS TDTSTSTAYM

101 ELRSLRSDDT AVYYCAREGS SSSGDYYYGM DVWGQGTTVT VSSASTKGPS

151 VFPLAPCSRS TSESTAALGC LVKDYFPEPV TVSWNSGALT SGVHTFPAVL

201 QSSGLYSLSS VVTVPSSNFG TQTYTCNVDH KPSNTKVDKT VERKCCVECP

251 PCPAPPVAGP SVFLFPPKPK DTLMISRTPE VTCVVVDVSH EDPEVQFNWY

301 VDGVEVHNAK TKPREEQFNS TFRVVSVLTV VHQDWLNGKE YKCKVSNKGL

351 PAPIEKTISK TKGQPREPQV YTLPPSREEM TKNQVSLTCL VKGFYPSDIA

401 VEWESNGQPE NNYKTTPPML DSDGSFFLYS KLTVDKSRWQ QGNVFSCSVM

451 HEALHNHYTQ KSLSLSPGK
```

7.26.4 Kappa Light Chain Nucleotide Sequence

```
                                                    SEQ ID NO. 43
  1 atgaggctcc ctgctcagct cctggggctg ctaatgctct ggatacctgg 51 atccagtgcg GATATTGTGA TGACCCAGAC TCCACTCTCT CTGTCCGTCA

101 CCCCTGGACA GCCGGCCTCC ATCTCCTGCA AGTCTAATCA GAGCCTCCTG

151 TATAGTGATG GAAAGACCTA TTTGTTTTGG TACCTGCAGA AGCCAGGCCA

201 GCCTCCACAG CTCCTGATCT ATGAAGTTTC CAACCGATTC TCTGGAGTGC

251 CAGATAGGTT CAGTGGCAGC GGGTCAGGGA CAGATTTCAC ACTGAAAATC

301 AGCCGGGTGG AGGCTGAGGA TGTTGGGGTT TATTACTGCA TGCAAAGTAT

351 ACAGCTTCCG TGGACGTTCG GCCAAGGGAC CAAGGTGGAA ATCAAACGAA

401 CTGTGGCTGC ACCATCTGTC TTCATCTTCC CGCCATCTGA TGAGCAGTTG

451 AAATCTGGAA CTGCCTCTGT TGTGTGCCTG CTGAATAACT TCTATCCCAG

501 AGAGGCCAAA GTACAGTGGA AGGTGGATAA CGCCCTCCAA TCGGGTAACT

551 CCCAGGAGAG TGTCACAGAG CAGGACAGCA AGGACAGCAC CTACAGCCTC

601 AGCAGCACCC TGACGCTGAG CAAAGCAGAC TACGAGAAAC ACAAAGTCTA

651 CGCCTGCGAA GTCACCCATC AGGGCCTGAG CTCGCCCGTC ACAAAGAGCT

701 TCAACAGGGG AGAGTGTTAG TGA
```

7.26.4 Predicted Kappa Light Chain Protein Sequence

```
                                                    SEQ ID NO. 44
  1 mrlpaqllql lmlwipqssa DIVMTQTPLS LSVTPGQPAS ISCKSNQSLL

51 YSDGKTYLFW YLQKPGQPPQ LLIYEVSNRF SGVPDRFSGS GSGTDFTLKI

101 SRVEAEDVGV YYCMQSIQLP WTFGQGTKVE IKRTVAAPSV FIFPPSDEQL

151 KSGTASVVCL LNNFYPREAK VQWKVDNALQ SGNSQESVTE QDSKDSTYSL

201 SSTLTLSKAD YEKHKVYACE VTHQGLSSPV TKSFNRGEC
```

9.8.2 Heavy Chain Nucleotide Sequence

```
                                                    SEQ ID NO. 45
  1 atggagtttg ggctgagctg gttttccctc gttgctcttt taagaggtgt 51 ccagtgtCAG GTGCAGCTGG TGGAGTCTGG GGGAGGCGTG GTCCAGCCTG
```

```
 101 GGAGGTCCCT GAGACTCTCC TGTGCAGCGT CTGGATTCAC CTTCAGTAGC
 151 TATGGCATGC ACTGGGTCCG CCAGGCTCCA GGCAAGGGGC TGGAGTGGGT
 201 GGCAGTTATA TGGTATGATG AAGTAATGA ATACTATGCA GACTCCGTGA
 251 AGGGCCGATT CACCATCTCC AGAGACAATT CCAAGAACAC GCTGTATCTG
 301 CAAATGAACA GCCTGAGAGC CGAGGACACG GCTGTGTATT ACTGTGCGAG
 351 GGGGGCGTAC CACTTTGCCT ACTGGGGCCA GGGAACCCTG GTCACCGTCT
 401 CCTCAGCTTC CACCAAGGGC CCATCCGTCT TCCCCCTGGC GCCCTGCTCC
 451 AGGAGCACCT CCGAGAGCAC AGCCGCCCTG GGCTGCCTGG TCAAGGACTA
 501 CTTCCCCGAA CCGGTGACGG TGTCGTGGAA CTCAGGCGCC CTGACCAGCG
 551 GCGTGCACAC CTTCCCGGCT GTCCTACAGT CCTCAGGACT CTACTCCCTC
 601 AGCAGCGTGG TGACCGTGCC CTCCAGCAGC TTGGGCACGA AGACCTACAC
 651 CTGCAACGTA GATCACAAGC CCAGCAACAC CAAGGTGGAC AAGAGAGTTG
 701 AGTCCAAATA TGGTCCCCCA TGCCCATCAT GCCCAGCACC TGAGTTCCTG
 751 GGGGGACCAT CAGTCTTCCT GTTCCCCCCA AAACCCAAGG ACACTCTCAT
 801 GATCTCCCGG ACCCCTGAGG TCACGTGCGT GGTGGTGGAC GTGAGCCAGG
 851 AAGACCCCGA GGTCCAGTTC AACTGGTACG TGGATGGCGT GGAGGTGCAT
 901 AATGCCAAGA CAAAGCCGCG GGAGGAGCAG TTCAACAGCA CGTACCGTGT
 951 GGTCAGCGTC CTCACCGTCC TGCACCAGGA CTGGCTGAAC GGCAAGGAGT
1001 ACAAGTGCAA GGTCTCCAAC AAAGGCCTCC CGTCCTCCAT CGAGAAAACC
1051 ATCTCCAAAG CCAAAGGGCA GCCCCGAGAG CCACAGGTGT ACACCCTGCC
1101 CCCATCCCAG GAGGAGATGA CCAAGAACCA GGTCAGCCTG ACCTGCCTGG
1151 TCAAAGGCTT CTACCCCAGC GACATCGCCG TGGAGTGGGA GAGCAATGGG
1201 CAGCCGGAGA ACAACTACAA GACCACGCCT CCCGTGCTGG ACTCCGACGG
1251 CTCCTTCTTC CTCTACAGCA GGCTAACCGT GGACAAGAGC AGGTGGCAGG
1301 AGGGGAATGT CTTCTCATGC TCCGTGATGC ATGAGGCTCT GCACAACCAC
1351 TACACACAGA AGAGCCTCTC CCTGTCTCTG GGTAAATGA
```

9.8.2 Predicted Heavy Chain Chain Protein Sequence

SEQ ID NO. 46

```
  1 mefglswvfl vallrgvqcQ VQLVESGGGV VQPGRSLRLS CAASGFTFSS
 51 YGMHWVRQAP GKGLEWVAVI WYDGSNEYYA DSVKGRFTIS RDNSKNTLYL
101 QMNSLRAEDT AVYYCARGAY HFAYWGQGTL VTVSSASTKG PSVFPLAPCS
151 RSTSESTAAL GCLVKDYFPE PVTVSWNSGA LTSGVHTFPA VLQSSGLYSL
201 SSVVTVPSSS LGTKTYTCNV DHKPSNTKVD KRVESKYGPP CPSCPAPEFL
251 GGPSVFLFPP KPKDTLMISR TPEVTCVVVD VSQEDPEVQF NWYVDGVEVH
301 NAKTKPREEQ FNSTYRVVSV LTVLHQDWLN GKEYKCKVSN KGLPSSIEKT
351 ISKAKGQPRE PQVYTLPPSQ EEMTKNQVSL TCLVKGFYPS DIAVEWESNG
401 QPENNYKTTP PVLDSDGSFF LYSRLTVDKS RWQEGNVFSC SVMHEALHNH
451 YTQKSLSLSL GK
```

9.8.2 Kappa Light Chain Nucleotide Sequence

SEQ ID NO. 47

```
  1 atggacatga gggtccctgc tcagctcctg gggctcctg tgctctggct
 51 ctcagtcgca ggtgccagat gtGACATCCA GATGACCCAG TCTCCATCCT
101 CCCTGTCTGC ATCTGTAGGA GACAGAGTCA CCATCACTTG CCAGGCGAGT
```

-continued

151 CAGGACATTA GCAACTATTT AAATTGGTAT CAGCAGAAAC CAGGGAAAGC

201 CCCTAAGCTC CTGATCTACG ATGCATCCAA TTTGGAAACA GGGGTCCCAT

251 CAAGGTTCAG TGGAAGTGGA TCTGGGACAG ATTTTACTTT CACCATCAGC

301 AGCCTGCAGC CTGAAGATAT TGCAACATAT TCCTGTCAAC ACTCTGATAA

351 TCTCTCGATC ACCTTCGGCC AGGGGACACG ACTGGAGATT AAACGAACTG

401 TGGCTGCACC ATCTGTCTTC ATCTTCCCGC CATCTGATGA GCAGTTGAAA

451 TCTGGAACTG CCTCTGTTGT GTGCCTGCTG AATAACTTCT ACCCCAGAGA

501 GGCCAAAGTA CAGTGGAAGG TGGATAACGC CCTCCAATCG GGTAACTCCC

551 AGGAGAGTGT CACAGAGCAG GACAGCAAGG ACAGCACCTA CAGCCTCAGC

601 AGCACCCTGA CGCTGAGCAA AGCAGACTAC GAGAAACACA AAGTCTACGC

651 CTGCGAAGTC ACCCATCAGG GCCTGAGCTC GCCCGTCACA AAGAGCTTCA

701 ACAGGGGAGA GTGTTAGTGA 9.8.2 Predicted Kappa Light Chain Protein Sequence

SEQ ID NO. 48

1 mdmrvpaqll glllwlsva garcDIQMTQ SPSSLSASVG DRVTITCQAS

51 QDISNYLNWY QQKPGKAPKL LIYDASNLET GVPSRFSGSG SGTDFTFTIS

101 SLQPEDIATY SCQHSDNLSI TFGQGTRLEI KRTVAAPSVF IFPPSDEQLK

151 SGTASVVCLL NNFYPREAKV QWKVDNALQS GNSQESVTEQ DSKDSTYSLS

201 STLTLSKADY EKHKVYACEV THQGLSSPVT KSFNRGEC

Nucleotide Sequence of cynomolgus MAdCAM $\alpha_4\beta_7$ binding domain

SEQ ID NO. 49

1 ATGGATCGGG GCCTGGCCCT CCTGCTGGCG GGGCTTCTGG GGCTCCTCCA

51 GCCGGGCTGC GGCCAGTCCC TCCAGGTGAA GCCCCTGCAG GTGGAGCCCC

101 CGGAGCCGGT GGTGGCCGTG GCCCTGGGCG CCTCTCGCCA GCTCACCTGC

151 CGCCTGGACT GCGCGGACGG CGGGGCCACG GTGCAGTGGC GGGGCCTGGA

201 CACCAGCCTG GGCGCGGTGC AGTCGGACGC GGGCCGCAGC GTCCTCACCG

251 TGCGCAACGC CTCGCTGTCG GCGGCCGGGA CCCGTGTGTG CGTGGGCTCC

301 TGCGGGGGCC GCACCTTCCA GCACACCGTG CGGCTCCTTG TGTACGCCTT

351 CCCGGACCAG CTGACCATCT CCCCGGCAGC CCTGGTGCCT GGTGACCCGG

401 AGGTGGCCTG TACGGCTCAC AAAGTCACGC CTGTGGACCC CAATGCGCTC

451 TCCTTCTCCC TGCTCCTGGG GGACCAGGAA CTGGAGGGGG CCCAGGCTCT

501 GGGCCCGGAG GTGGAGGAGG AGGAGGAGCC CCAGGAGGAG GAGGACGTGC

551 TGTTCAGGGT GACAGAGCGC TGGCGGCTGC CGACCCTGGC AACCCCTGTC

601 CTGCCCGCGC TCTACTGCCA GGCCACGATG AGGCTGCCTG GCTTGGAGCT

651 CAGCCACCGC CAGGCCATCC CGGTCCTGCA C

Amino acid sequence of cynomolgus MAdCAM $\alpha_4\beta_7$ binding domain

SEQ ID NO. 50

1 MDRGLALLLA GLLGLLQPGC GQSLQVKPLQ VEPPEPVVAV ALGASRQLTC

51 RLDCADGGAT VQWRGLDTSL GAVQSDAGRS VLTVRNASLS AAGTRVCVGS

101 CGGRTFQHTV RLLVYAFPDQ LTISPAALVP GDPEVACTAH KVTPVDPNAL

151 SFSLLLGDQE LEGAQALGPE VEEEEEPQEE EDVLFRVTER WRLPTLATPV

201 LPALYCQATM RLPGLELSHR QAIPVLH

-continued

Modified 6.22.2 Heavy Chain Nucleotide Sequence
SEQ ID NO. 51

```
   1 atggagtttg ggctgagctg ggttttcctc gttgctcttt taagaggtgt
  51 ccagtgtCAG GTGCAGCTGG TGGAGTCTGG GGGAGGCGTG GTCCAGCCTG
 101 GGAGGTCCCT GAGACTCTCC TGTGCAGCGT CTGGATTCAC CTTCAGTAGC
 151 GATGGCATGC ACTGGGTCCG CCAGGCTCCA GGCAAGGGGC TGGAGTGGGT
 201 GGCAATTATA TGGTATGATG GAAGTAATAA ATATTATGCA GACTCCGTGA
 251 AGGGCCGATT CACCATCTCC AGAGACAATT CCAAGAACAC GCTGTATCTG
 301 CAAATGAACA GCCTGAGAGC CGAGGACACG GCTGTATATT ACTGTGCGAG
 351 AGATCCCGGC TACTATTACG GTATGGACGT CTGGGGCCAA GGGACCACGG
 401 TCACCGTCTC CTCAGCTTCC ACCAAGGGCC CATCCGTCTT CCCCCTGGCG
 451 CCCTGCTCTA GAAGCACCTC CGAGAGCACA GCGGCCCTGG GCTGCCTGGT
 501 CAAGGACTAC TTCCCCGAAC CGGTGACGGT GTCGTGGAAC TCAGGCGCTC
 551 TGACCAGCGG CGTGCACACC TTCCCAGCTG TCCTACAGTC CTCAGGACTC
 601 TACTCCCTCA GCAGCGTGGT GACCGTGCCC TCCAGCAACT TCGGCACCCA
 651 GACCTACACC TGCAACGTAG ATCACAAGCC CAGCAACACC AAGGTGGACA
 701 AGACAGTTGA GCGCAAATGT TGTGTCGAGT GCCCACCGTG CCCAGCACCA
 751 CCTGTGGCAG GACCGTCAGT CTTCCTCTTC CCCCCAAAAC CCAAGGACAC
 801 CCTCATGATC TCCCGGACCC CTGAGGTCAC GTGCGTGGTG GTGGACGTGA
 851 GCCACGAAGA CCCCGAGGTC CAGTTCAACT GGTACGTGGA CGGCGTGGAG
 901 GTGCATAATG CCAAGACAAA GCCACGGGAG GAGCAGTTCA ACAGCACGTT
 951 CCGTGTGGTC AGCGTCCTCA CCGTTGTGCA CCAGGACTGG CTGAACGGCA
1001 AGGAGTACAA GTGCAAGGTC TCCAACAAAG CCCTCCCAGC CCCCATCGAG
1051 AAACCATCT CCAAAACCAA AGGGCAGCCC CGAGAACCAC AGGTGTACAC
1101 CCTGCCCCCA TCCCGGGAGG AGATGACCAA GAACCAGGTC AGCCTGACCT
1151 GCCTGGTCAA AGGCTTCTAC CCCAGCGACA TCGCCGTGGA GTGGGAGAGC
1201 AATGGGCAGC CGGAGAACAA CTACAAGACC ACACCTCCCA TGCTGGACTC
1251 CGACGGCTCC TTCTTCCTCT ACAGCAAGCT CACCGTGGAC AAGAGCAGGT
1301 GGCAGCAGGG GAACGTCTTC TCATGCTCCG TGATGCATGA GGCTCTGCAC
1351 AACCACTACA CGCAGAAGAG CCTCTCCCTG TCTCCGGGTA AATGATAG
```

Modified 6.22.2 Heavy Chain Amino Acid Sequence
SEQ ID NO. 52

```
   1 mefglswvfl vallrgvqcQ VQLVESGGGV VQPGRSLRLS CAASGFTFSS
  51 DGMHWVRQAP GKGLEWVAII WYDGSNKYYA DSVKGRFTIS RDNSKNTLYL
 101 QMNSLRAEDT AVYYCARDPG YYYGMDVWGQ GTTVTVSSAS TKGPSVFPLA
 151 PCSRSTSEST AALGCLVKDY FPEPVTVSWN SGALTSGVHT FPAVLQSSGL
 201 YSLSSVVTVP SSNFGTQTYT CNVDHKPSNT KVDKTVERKC CVECPPCPAP
 251 PVAGPSVFLF PPKPKDTLMI SRTPEVTCVV VDVSHEDPEV QFNWYVDGVE
 301 VHNAKTKPRE EQFNSTFRVV SVLTVVHQDW LNGKEYKCKV SNKGLPAPIE
 351 KTISKTKGQP REPQVYTLPP SREEMTKNQV SLTCLVKGFY PSDIAVEWES
 401 NGQPENNYKT TPPMLDSDGS FFLYSKLTVD KSRWQQGNVF SCSVMHEALH
 451 NHYTQKSLSL SPGK
```

Modified 6.22.2 Kappa Light Chain Nucleotide Sequence
SEQ ID NO. 53
```
  1 atgttgccat cacaactcat tgggtttctg ctgctctggg ttccagcttc
 51 caggggtGAA ATTGTGCTGA CTCAGTCTCC AGACTTTCAG TCTGTGACTC
101 CAAAAGAGAA AGTCACCATC ACCTGCCGGG CCAGTCAGAG AATTGGTAGT
151 AGCTTACACT GGTACCAGCA GAAACCAGAT CAGTCTCCAA AACTCCTCAT
201 CAAGTATGCT TCCCAGTCCT TCTCAGGGGT CCCCTCGAGG TTCAGTGGCA
251 GTGGATCTGG GACAGATTTC ACCCTCACCA TCAATAGCCT GGAAGCTGAA
301 GATGCTGCAA CTTATTACTG TCATCAGAGT GGTCGTTTAC CGCTCACTTT
351 CGGCGGAGGG ACCAAGGTGG AGATCAAACG AACTGTGGCT GCACCATCTG
401 TCTTCATCTT CCCGCCATCT GATGAGCAGT TGAAATCTGG AACTGCCTCT
451 GTTGTGTGCC TGCTGAATAA CTTCTATCCC AGAGAGGCCA AAGTACAGTG
501 GAAGGTGGAT AACGCCCTCC AATCGGGTAA CTCCCAGGAG AGTGTCACAG
551 AGCAGGACAG CAAGGACAGC ACCTACAGCC TCAGCAGCAC CCTGACGCTG
601 AGCAAAGCAG ACTACGAGAA ACACAAAGTC TACGCCTGCG AAGTCACCCA
651 TCAGGGCCTG AGCTCGCCCG TCACAAAGAG CTTCAACAGG GGAGAGTGTT
701 AGTGA
```

Modified 6.22.2 Kappa Light Chain Amino Acid Sequence
SEQ ID NO. 54
```
  1 mlpsqliqfl llwvpasrgE IVLTQSPDFQ SVTPKEKVTI TCRASQRIGS
 51 SLHWYQQKPD QSPKLLIKYA SQSFSGVPSR FSGSGSGTDF TLTINSLEAE
101 DAATYYCHQS GRLPLTFGGG TKVEIKRTVA APSVFIFPPS DEQLKSGTAS
151 VVCLLNNFYP REAKVQWKVD NALQSGNSQE SVTEQDSKDS TYSLSSTLTL
201 SKADYEKHKV YACEVTHQGL SSPVTKSFNR GEC
```

Modified 6.34.2 Heavy Chain Nucleotide Sequence
SEQ ID NO. 55
```
  1 atggagtttg ggctgagctg ggttttcctc gttgctcttt taagaggtgt
 51 ccagtgtCAG GTGCAGCTGG TGGAGTCTGG GGGAGGCGTG GTCCAGCCTG
101 GGAGGTCCCT GAGACTCTCC TGTGCAGCCT CTGGATTCAC CTTCAGTAGC
151 TATGGCATGC ACTGGGTCCG CCAGGCTCCA GGCAAGGGGC TGGAGTGGGT
201 GGCAGTTATA TCAAATGATG GAAATAATAA ATACTATGCA GACTCCGTGA
251 AGGGCCGATT CACCATCTCC AGAGACAATT CCAAAAACAC GCTGTATCTG
301 CAAATGAACA GCCTGCGCGC TGAGGACACG GCTGTGTATT ACTGTGCGAG
351 AGATAGTACG GCGATAACCT ACTACTACTA CGGAATGGAC GTCTGGGGCC
401 AAGGGACCAC GGTCACCGTC TCCTCAGCTT CCACCAAGGG CCCATCCGTC
451 TTCCCCCTGG CGCCCTGCTC TAGAAGCACC TCCGAGAGCA CAGCGGCCCT
501 GGGCTGCCTG GTCAAGGACT ACTTCCCCGA ACCGGTGACG GTGTCGTGGA
551 ACTCAGGCGC TCTGACCAGC GGCGTGCACA CCTTCCCAGC TGTCCTACAG
601 TCCTCAGGAC TCTACTCCCT CAGCAGCGTG GTGACCGTGC CCTCCAGCAA
651 CTTCGGCACC CAGACCTACA CCTGCAACGT AGATCACAAG CCCAGCAACA
701 CCAAGGTGGA CAAGACAGTT GAGCGCAAAT GTTGTGTCGA GTGCCCACCG
751 TGCCCAGCAC CACCTGTGGC AGGACCGTCA GTCTTCCTCT TCCCCCCAAA
801 ACCCAAGGAC ACCCTCATGA TCTCCCGGAC CCCTGAGGTC ACGTGCGTGG
851 TGGTGGACGT GAGCCACGAA GACCCCGAGG TCCAGTTCAA CTGGTACGTG
```

```
 901 GACGGCGTGG AGGTGCATAA TGCCAAGACA AAGCCACGGG AGGAGCAGTT

951 CAACAGCACG TTCCGTGTGG TCAGCGTCCT CACCGTTGTG CACCAGGACT

1001 GGCTGAACGG CAAGGAGTAC AAGTGCAAGG TCTCCAACAA AGGCCTCCCA

1051 GCCCCCATCG AGAAAACCAT CTCCAAAACC AAAGGGCAGC CCCGAGAACC

1101 ACAGGTGTAC ACCCTGCCCC CATCCCGGGA GGAGATGACC AAGAACCAGG

1151 TCAGCCTGAC CTGCCTGGTC AAAGGCTTCT ACCCCAGCGA CATCGCCGTG

1201 GAGTGGGAGA GCAATGGGCA GCCGGAGAAC AACTACAAGA CCACACCTCC

1251 CATGCTGGAC TCCGACGGCT CCTTCTTCCT CTACAGCAAG CTCACCGTGG

1301 ACAAGAGCAG GTGGCAGCAG GGGAACGTCT TCTCATGCTC CGTGATGCAT

1351 GAGGCTCTGC ACAACCACTA CACGCAGAAG AGCCTCTCCC TGTCTCCGGG

1401 TAAATGATAG
```

Modified 6.34.2 Heavy Chain Amino Acid Sequence
SEQ ID NO. 56
```
  1 mefglswvfl vallrqvqcQ VQLVESGGGV VQPGRSLRLS CAASGFTFSS

51 YGMHWVRQAP GKGLEWVAVI SNDGNNKYYA DSVKGRFTIS RDNSKNTLYL

101 QMNSLRAEDT AVYYCARDST AITYYYYGMD VWGQGTTVTV SSASTKGPSV

151 FPLAPCSRST SESTAALGCL VKDYFPEPVT VSWNSGALTS GVHTFPAVLQ

201 SSGLYSLSSV VTVPSSNFGT QTYTCNVDHK PSNTKVDKTV ERKCCVECPP

251 CPAPPVAGPS VFLFPPKPKD TLMISRTPEV TCVVVDVSHE DPEVQFNWYV

301 DGVEVHNAKT KPREEQFNST FRVVSVLTVV HQDWLNGKEY KCKVSNKGLP

351 APIEKTISKT KGQPREPQVY TLPPSREEMT KNQVSLTCLV KGFYPSDIAV

401 EWESNGQPEN NYKTTPPMLD SDGSFFLYSK LTVDKSRWQQ GNVFSCSVMH

451 EALHNHYTQK SLSLSPGK
```

Modified 6.34.2 Kappa Light Chain Nucleotide Sequence
SEQ ID NO. 57
```
  1 atggacatga gggtcccgc tcagctcctg gggctcctgc tactctggct 51 ccgaggtgcc agatgtGACA TCCAGATGAC CCAGTCTCCA TCCTCCCTGT

101 CTGCATCTGT CGGAGACAGA GTCACCATCA CTTGCCGGGC AAGTCAGAGT

151 ATTAGTAGCT ATTTAAATTG GTATCAGCAG AAACCAGGGA AAGCCCCTAA

201 GCTCCTGATC TATGCTGCAT CCGGTTTGAA GCGTGGGGTC CCATCACGGT

251 TCAGTGGTAG TGGATCTGGG ACAGATTTCA CTCTCACCAT CAGTTCTCTG

301 CAACCTGAGG ATTTTGCAAC TTACTACTGT CACCAGAGTT ACAGTCTCCC

351 ATTCACTTTC GGCCCTGGGA CCAAAGTGGA TATCAAACGA ACTGTGGCTG

401 CACCATCTGT CTTCATCTTC CCGCCATCTG ATGAGCAGTT GAAATCTGGA

451 ACTGCCTCTG TTGTGTGCCT GCTGAATAAC TTCTATCCCA GAGAGGCCAA

501 AGTACAGTGG AAGGTGGATA ACGCCCTCCA ATCGGGTAAC TCCCAGGAGA

551 GTGTCACAGA GCAGGACAGC AAGGACAGCA CCTACAGCCT CAGCAGCACC

601 CTGACGCTGA GCAAAGCAGA CTACGAGAAA CACAAAGTCT ACGCCTGCGA

651 AGTCACCCAT CAGGGCCTGA GCTCGCCCGT CACAAAGAGC TTCAACAGGG

701 GAGAGTGTTA GTGA
```

Modified 6.34.2 Kappa Light Chain Amino Acid Sequence
SEQ ID NO. 58
```
  1 mdmrvpaqll qllllwlrga rcDIQMTQSP SSLSASVGDR VTITCRASQS
 51 ISSYLNWYQQ KPGKAPKLLI YAASGLKRGV PSRFSGSGSG TDFTLTISSL
101 QPEDFATYYC HQSYSLPFTF GPGTKVDIKR TVAAPSVFIF PPSDEQLKSG
151 TASVVCLLNN FYPREAKVQW KVDNALQSGN SQESVTEQDS KDSTYSLSST
201 LTLSKADYEK HKVYACEVTH QGLSSPVTKS FNRGEC
```
Modified 6.67.1 Heavy Chain Nucleotide Sequence
SEQ ID NO. 59
```
   1 atgaaacacc tgtggttctt cctcctgctg gtggcagctc ccagatgggt
  51 cctgtccCAG GTGCAGCTGC AGGAGTCGGG CCCAGGACTG GTGAAGCCTT
 101 CGGAGACCCT GTCCCTCACC TGCACTGTCT CTGGTGACTC CATCAGTAGT
 151 AACTATTGGA GCTGGATCCG GCAGCCCGCC GGGAAGGGAC TGGAGTGGAT
 201 TGGGCGTATC TATACCAGTG GGGGCACCAA CTCCAACCCC TCCCTCAGGG
 251 GTCGAGTCAC CATGTCAGTA GACACGTCCA AGAACCAGTT CTCTCTGAAA
 301 CTGAGTTCTG TGACCGCCGC GGACACGGCC GTGTATTACT GTGCGAGAGA
 351 TCGTATTACT ATAATTCGGG GACTTATTCC ATCCTTCTTT GACTACTGGG
 401 GCCAGGGAAC CCTGGTCACC GTCTCCTCAG CTTCCACCAA GGGCCCATCC
 451 GTCTTCCCCC TGGCGCCCTG CTCTAGAAGC ACCTCCGAGA GCACAGCGGC
 501 CCTGGGCTGC CTGGTCAAGG ACTACTTCCC CGAACCGGTG ACGGTGTCGT
 551 GGAACTCAGG CGCTCTGACC AGCGGCGTGC ACACCTTCCC AGCTGTCCTA
 601 CAGTCCTCAG GACTCTACTC CCTCAGCAGC GTGGTGACCG TGCCCTCCAG
 651 CAACTTCGGC ACCCAGACCT ACACCTGCAA CGTAGATCAC AAGCCCAGCA
 701 ACACCAAGGT GGACAAGACA GTTGAGCGCA AATGTTGTGT CGAGTGCCCA
 751 CCGTGCCCAG CACCACCTGT GGCAGGACCG TCAGTCTTCC TCTTCCCCCC
 801 AAAACCCAAG GACACCCTCA TGATCTCCCG GACCCCTGAG GTCACGTGCG
 851 TGGTGGTGGA CGTGAGCCAC GAAGACCCCG AGGTCCAGTT CAACTGGTAC
 901 GTGGACGGCG TGGAGGTGCA TAATGCCAAG ACAAAGCCAC GGGAGGAGCA
 951 GTTCAACAGC ACGTTCCGTG TGGTCAGCGT CCTCACCGTT GTGCACCAGG
1001 ACTGGCTGAA CGGCAAGGAG TACAAGTGCA AGGTCTCCAA CAAAGGCCTC
1051 CCAGCCCCCA TCGAGAAAAC CATCTCCAAA ACCAAAGGGC AGCCCCGAGA
1101 ACCACAGGTG TACACCCTGC CCCCATCCCG GGAGGAGATG ACCAAGAACC
1151 AGGTCAGCCT GACCTGCCTG GTCAAAGGCT TCTACCCCAG CGACATCGCC
1201 GTGGAGTGGG AGAGCAATGG GCAGCCGGAG AACAACTACA AGACCACACC
1251 TCCCATGCTG GACTCCGACG GCTCCTTCTT CCTCTACAGC AAGCTCACCG
1301 TGGACAAGAG CAGGTGGCAG CAGGGGAACG TCTTCTCATG CTCCGTGATG
1351 CATGAGGCTC TGCACAACCA CTACACGCAG AAGAGCCTCT CCCTGTCTCC
1401 GGGTAAATGA TAG
```
Modified 6.67.1 Heavy Chain Amino Acid Sequence
SEQ ID NO. 60
```
  1 mkhlwfflll vaaprwvlsQ VQLQESGPGL VKPSETLSLT CTVSGDSISS
 51 NYWSWIRQPA GKGLEWIGRI YTSGGTNSNP SLRGRVTMSV DTSKNQFSLK
101 LSSVTAADTA VYYCARDRIT IIRGLIPSFF DYWGQGTLVT VSSASTKGPS
151 VFPLAPCSRS TSESTAALGC LVKDYFPEPV TVSWNSGALT SGVHTFPAVL
```

201 QSSGLYSLSS VVTVPSSNFG TQTYTCNVDH KPSNTKVDKT VERKCCVECP

251 PCPAPPVAGP SVFLFPPKPK DTLMISRTPE VTCVVVDVSH EDPEVQFNWY

301 VDGVEVHNAK TKPREEQFNS TFRVVSVLTV VHQDWLNGKE YKCKVSNKGL

351 PAPIEKTISK TKGQPREPQV YTLPPSREEM TKNQVSLTCL VKGFYPSDIA

401 VEWESNGQPE NNYKTTPPML DSDGSFFLYS KLTVDKSRWQ QGNVFSCSVM

451 HEALHNHYTQ KSLSLSPGK

Modified 6.67.1 Kappa Light Chain Nucleotide Sequence
SEQ ID NO. 61

1 atggtgttgc agacccaggt cttcatttct ctgttgctct ggatctctgg 51 tgcctacggg GACATCGTGA TGACCCAGTC TCCAGACTCC CTGGCTGTGT

101 CTCTGGGCGA GAGGGCCACC ATCAACTGCA AGTCCAGCCA GAGTGTTTTA

151 TACAGCTCCA ACAATAAGAA CTACTTAGCT TGGTACCAAC AGAAACCAGG

201 ACAGCCTCCT AAATTGCTCA TTTACTGGGC ATCTATACGG GAATATGGGG

251 TCCCTGACCG ATTCAGTGGC AGCGGGTCTG GACAGATTT CACTCTCACC

301 ATCAGCAGCC TGCAGGCTGA AGATGTGGCA GTTTATTTCT GTCAACAATA

351 TTATAGTATT CCTCCCCTCA CTTTCGGCGG AGGGACCAAG GTGGAGATCA

401 AACGAACTGT GGCTGCACCA TCTGTCTTCA TCTTCCCGCC ATCTGATGAG

451 CAGTTGAAAT CTGGAACTGC CTCTGTTGTG TGCCTGCTGA ATAACTTCTA

501 TCCCAGAGAG GCCAAAGTAC AGTGGAAGGT GGATAACGCC CTCCAATCGG

551 GTAACTCCCA GGAGAGTGTC ACAGAGCAGG ACAGCAAGGA CAGCACCTAC

601 AGCCTCAGCA GCACCCTGAC GCTGAGCAAA GCAGACTACG AGAAACACAA

651 AGTCTACGCC TGCGAAGTCA CCCATCAGGG CCTGAGCTCG CCCGTCACAA

701 AGAGCTTCAA CAGGGGAGAG TGTTAGTGA

Modified 6.67.1 Kappa Light Chain Amino Acid Sequence
SEQ ID NO. 62

1 mvlqtqvfis lllwisgayg DIVMTQSPDS LAVSLGERAT INCKSSQSVL

51 YSSNNKNYLA WYQQKPGQPP KLLIYWASIR EYGVPDRFSG SGSGTDFTLT

101 ISSLQAEDVA VYFCQQYYSI PPLTFGGGTK VEIKRTVAAP SVFIFPPSDE

151 QLKSGTASVV CLLNNFYPRE AKVQWKVDNA LQSGNSQESV TEQDSKDSTY

201 SLSSTLTLSK ADYEKHKVYA CEVTHQGLSS PVTKSFNRGE C

Modified 6.77.1 Heavy Chain Nucleotide Sequence
SEQ ID NO. 63

1 atggaactgg ggctccgctg ggttttcctt gttgctattt tagaaggtgt 51 ccagtgtGAG GTGCAGCTGG TGGAGTCTGG GGGAGGCCTG GTCAAGCCTG

101 GGGGGTCCCT GAGACTCTCC TGTGCAGCCT CTGGATTCAC CTTCAGTAGC

151 TATAGCATGA ACTGGGTCCG CCAGGCTCCA GGGAAGGGGC TGGAGTGGGT

201 CTCATCCATT AGTAGTAGTA GTAGTTACAT ATACTACGCA GACTCAGTGA

251 AGGGCCGATT CACCATCTCC AGAGACAACG CCAAGAACTC ACTGTATCTG

301 CAAATGAACA GCCTGAGAGC CGAGGACACG GCTGTGTATT ACTGTGCGAG

351 AGATGGGTAT AGCAGTGGCT GGTCCTACTA CTACTACTAC GGTATGGACG

401 TCTGGGGCCA AGGGACCACG GTCACCGTCT CCTCAGCTTC CACCAAGGGC

451 CCATCCGTCT TCCCCCTGGC GCCCTGCTCT AGAAGCACCT CCGAGAGCAC

501 AGCGGCCCTG GGCTGCCTGG TCAAGGACTA CTTCCCCGAA CCGGTGACGG

```
 551 TGTCGTGGAA CTCAGGCGCT CTGACCAGCG GCGTGCACAC CTTCCCAGCT

601 GTCCTACAGT CCTCAGGACT CTACTCCCTC AGCAGCGTGG TGACCGTGCC

651 CTCCAGCAAC TTCGGCACCC AGACCTACAC CTGCAACGTA GATCACAAGC

701 CCAGCAACAC CAAGGTGGAC AAGACAGTTG AGCGCAAATG TTGTGTCGAG

751 TGCCCACCGT GCCCAGCACC ACCTGTGGCA GGACCGTCAG TCTTCCTCTT

801 CCCCCCAAAA CCCAAGGACA CCCTCATGAT CTCCCGGACC CCTGAGGTCA

851 CGTGCGTGGT GGTGGACGTG AGCCACGAAG ACCCCGAGGT CCAGTTCAAC

901 TGGTACGTGG ACGGCGTGGA GGTGCATAAT GCCAAGACAA AGCCACGGGA

951 GGAGCAGTTC AACAGCACGT TCCGTGTGGT CAGCGTCCTC ACCGTTGTGC

1001 ACCAGGACTG GCTGAACGGC AAGGAGTACA AGTGCAAGGT CTCCAACAAA

1051 GGCCTCCCAG CCCCCATCGA GAAAACCATC TCCAAAACCA AGGGCAGCC

1101 CCGAGAACCA CAGGTGTACA CCCTGCCCCC ATCCCGGGAG GAGATGACCA

1151 AGAACCAGGT CAGCCTGACC TGCCTGGTCA AAGGCTTCTA CCCCAGCGAC

1201 ATCGCCGTGG AGTGGGAGAG CAATGGGCAG CCGGAGAACA ACTACAAGAC

1251 CACACCTCCC ATGCTGGACT CCGACGGCTC CTTCTTCCTC TACAGCAAGC

1301 TCACCGTGGA CAAGAGCAGG TGGCAGCAGG GGAACGTCTT CTCATGCTCC

1351 GTGATGCATG AGGCTCTGCA CAACCACTAC ACGCAGAAGA GCCTCTCCCT

1401 GTCTCCGGGT AAATGATAG
```

Modified 6.77.1 Heavy Chain Protein Sequence

SEQ ID NO. 64

```
  1 melqlrwvfl vaileqvqcE VQLVESGGGL VKPGGSLRLS CAASGFTFSS

51 YSMNWVRQAP GKGLEWVSSI SSSSSYIYYA DSVKGRFTIS RDNAKNSLYL

101 QMNSLRAEDT AVYYCARDGY SSGWSYYYYY GMDVWGQGTT VTVSSASTKG

151 PSVFPLAPCS RSTSESTAAL GCLVKDYFPE PVTVSWNSGA LTSGVHTFPA

201 VLQSSGLYSL SSVVTVPSSN FGTQTYTCNV DHKPSNTKVD KTVERKCCVE

251 CPPCPAPPVA GPSVFLFPPK PKDTLMISRT PEVTCVVVDV SHEDPEVQFN

301 WYVDGVEVHN AKTKPREEQF NSTFRVVSVL TVVHQDWLNG KEYKCKVSNK

351 GLPAPIEKTI SKTKGQPREP QVYTLPPSRE EMTKNQVSLT CLVKGFYPSD

401 IAVEWESNGQ PENNYKTTPP MLDSDGSFFL YSKLTVDKSR WQQGNVFSCS

451 VMHEALHNHY TQKSLSLSPG K
```

Modified 6.77.1 Kappa Light Chain Nucleotide Sequence

SEQ ID NO. 65

```
  1 atgaggctcc ctgctcagct cctggggctg ctaatgctct ggatacctgg 51 atccagtgca GATATTGTGA TGACCCAGAC TCCACTCTCT CTGTCCGTCA

101 CTCCTGGACA GCCGGCCTCC ATCTCCTGCA AGTCTAGTCA GAGCCTCCTG

151 CTTAGTGATG GAAAGACCTA TTTGAATTGG TACCTGCAGA AGCCCGGCCA

201 GCCTCCACAG CTCCTGATCT ATGAAGTTTC CAACCGGTTC TCTGGAGTGC

251 CAGACAGGTT CAGTGGCAGC GGGTCAGGGA CAGATTTCAC ACTGAAAATC

301 AGCCGGGTGG AGGCTGAGGA TGTTGGGGTT TATTACTGCA TGCAAAGTAT

351 ACAGCTTATG TGCAGTTTTG GCCAGGGGAC CAAGCTGGAG ATCAAACGAA

401 CTGTGGCTGC ACCATCTGTC TTCATCTTCC CGCCATCTGA TGAGCAGTTG

451 AAATCTGGAA CTGCCTCTGT TGTGTGCCTG CTGAATAACT TCTATCCCAG

501 AGAGGCCAAA GTACAGTGGA AGGTGGATAA CGCCCTCCAA TCGGGTAACT
```

-continued

```
551 CCCAGGAGAG TGTCACAGAG CAGGACAGCA AGGACAGCAC CTACAGCCTC

601 AGCAGCACCC TGACGCTGAG CAAAGCAGAC TACGAGAAAC ACAAAGTCTA

651 CGCCTGCGAA GTCACCCATC AGGGCCTGAG CTCGCCCGTC ACAAAGAGCT

701 TCAACAGGGG AGAGTGTTAG TGA
```

Modified 6.77.1 Kappa Light Chain Amino Acid Sequence

SEQ ID NO. 66

```
  1 mrlpaqllgl lmlwipgssa DIVMTQTPLS LSVTPGQPAS ISCKSSQSLL

51 LSDGKTYLNW YLQKPGQPPQ LLIYEVSNRF SGVPDRFSGS GSGTDFTLKI

101 SRVEAEDVGV YSCMQSIQLM SSFGQGTKLE IKRTVAAPSV FIFPPSDEQL

151 KSGTASVVCL LNNFYPREAK VQWKVDNALQ SGNSQESVTE QDSKDSTYSL

201 SSTLTLSKAD YEKHKVYACE VTHQGLSSPV TKSFNRGEC
```

Modified 7.26.4 Kappa Light Chain Nucleotide Sequence

SEQ ID NO. 67

```
  1 atgaggctcc ctgctcagct cctggggctg ctaatgctct ggatacctgg 51 atccagtgcg GATATTGTGA TGACCCAGAC TCCACTCTCT CTGTCCGTCA

101 CCCCTGGACA GCCGGCCTCC ATCTCCTGCA AGTCTAGTCA GAGCCTCCTG

151 TATAGTGATG GAAAGACCTA TTTGTTTTGG TACCTGCAGA AGCCAGGCCA

201 GCCTCCACAG CTCCTGATCT ATGAAGTTTC CAACCGATTC TCTGGAGTGC

251 CAGATAGGTT CAGTGGCAGC GGGTCAGGGA CAGATTTCAC ACTGAAAATC

301 AGCCGGGTGG AGGCTGAGGA TGTTGGGGTT TATTACTGCA TGCAAAGTAT

351 ACAGCTTCCG TGGACGTTCG GCCAAGGGAC CAAGGTGGAA ATCAAACGAA

401 CTGTGGCTGC ACCATCTGTC TTCATCTTCC CGCCATCTGA TGAGCAGTTG

451 AAATCTGGAA CTGCCTCTGT TGTGTGCCTG CTGAATAACT TCTATCCCAG

501 AGAGGCCAAA GTACAGTGGA AGGTGGATAA CGCCCTCCAA TCGGGTAACT

551 CCCAGGAGAG TGTCACAGAG CAGGACAGCA AGGACAGCAC CTACAGCCTC

601 AGCAGCACCC TGACGCTGAG CAAAGCAGAC TACGAGAAAC ACAAAGTCTA

651 CGCCTGCGAA GTCACCCATC AGGGCCTGAG CTCGCCCGTC ACAAAGAGCT

701 TCAACAGGGG AGAGTGTTAG TGA
```

Modified 7.26.4 Kappa Light Chain Amino Acid Sequence

SEQ ID NO. 68

```
  1 mrlpaqllgl lmlwipgssa DIVMTQTPLS LSVTPGQPAS ISCKSSQSLL

51 YSDGKTYLFW YLQKPGQPPQ LLIYEVSNRF SGVPDRFSGS GSGTDFTLKI

101 SRVEAEDVGV YYCMQSIQLP WTFGQGTKVE IKRTVAAPSV FIFPPSDEQL

151 KSGTASVVCL LNNFYPREAK VQWKVDNALQ SGNSQESVTE QDSKDSTYSL

201 SSTLTLSKAD YEKHKVYACE VTHQGLSSPV TKSFNRGEC
```

---

What is claimed is:

1. A method for producing a human monoclonal antibody that specifically binds MAdCAM, comprising the steps of:
   (a) immunizing a non-human transgenic animal that is capable of producing human antibodies with a MAdCAM-IgG$_1$ fusion protein, wherein the fusion protein comprises SEQ ID NO: 107 without the signal sequence; and
   (b) allowing the transgenic animal to mount an immune response to MAdCAM.

2. The method of claim 1, wherein the MadCAM-IgG$_1$ fusion protein is purified or present on a cell membrane.

3. The method of claim 1, further comprising the steps of:
   (c) isolating antibody-producing cells from the non-human transgenic animal;
   (d) immortalizing the antibody-producing cells;
   (e) creating individual monoclonal populations of immortalized antibody-producing cells; and
   (f) screening the immortalized antibody-producing cells or culture supernatants thereof to identify an antibody directed to MadCAM.

4. The method of claim 1, wherein the non-human transgenic animal is an engineered mouse strain that comprises fragments of human immunoglobulin loci and is deficient in mouse antibody production.

5. The method of claim 3, wherein the immortalizing the antibody-producing cells comprises fusion of spleen and lymph node lymphocytes with a myeloma cell line.

6. The method of claim 5 wherein the myeloma cell line is a non-secretory mouse myeloma.

7. The method of claim 6, wherein the non-secretory mouse myeloma is P3-X63-AG8-653.

8. The method of claim 3, wherein the screening the immortalized antibody-producing cells or culture supernatants thereof comprises an ELISA assay.

* * * * *

SEQUENCE LISTING

<160> NUMBER OF SEQ ID NOS: 147

<210> SEQ ID NO 1
<211> LENGTH: 1392
<212> TYPE: DNA
<213> ORGANISM: Homo sapiens

<400> SEQUENCE: 1
atggagtttg ggctgagctg gattttcctt gctgctattt taaaaggtgt ccagtgtgag     60

```
gtgcagctgg tggagtctgg gggaggcttg gtgaagcctg gggggtccct tagactctcc      120
tgtgtagcct ctggattcac tttcactaac gcctggatga tctgggtccg ccaggctcca      180
gggaaggggc tggagtgggt tggccgtatt aaaaggaaaa ctgatggtgg gacaacagac      240
tacgctgcac ccgtgaaagg cagattcacc atctcaagag atgattcaaa aaacacgctg      300
tatctgcaaa tgaacagcct gaaaaccgag gacacagccg tgtattactg taccacaggg      360
ggagtggctg aggactactg gggccaggga accctggtca ccgtctcctc agcctccacc      420
aagggcccat cggtcttccc cctggcgccc tgctccagga gcacctccga gagcacagcg      480
gccctgggct gcctggtcaa ggactacttc cccgaaccgg tgacggtgtc gtggaactca      540
ggcgctctga ccagcggcgt gcacaccttc ccagctgtcc tacagtcctc aggactctac      600
tccctcagca gcgtggtgac cgtgccctcc agcaacttcg gcacccagac ctacacctgc      660
aacgtagatc acaagcccag caacaccaag gtggacaaga cagttgagcg caaatgttgt      720
gtcgagtgcc caccgtgccc agcaccacct gtggcaggac cgtcagtctt cctcttcccc      780
ccaaaaccca aggacaccct catgatctcc cggacccctg aggtcacgtg cgtggtggtg      840
gacgtgagcc acgaagaccc cgaggtccag ttcaactggt acgtggacgg cgtggaggtg      900
cataatgcca agacaaagcc acgggaggag cagttcaaca gcacgttccg tgtggtcagc      960
gtcctcaccg ttgtgcacca ggactggctg aacggcaagg agtacaagtg caaggtctcc     1020
aacaaaggcc tcccagcccc catcgagaaa accatctcca aaaccaaagg cagccccga     1080
gaaccacagg tgtacaccct gcccccatcc cgggaggaga tgaccaagaa ccaggtcagc     1140
ctgacctgcc tggtcaaagg cttctacccc agcgacatcg ccgtggagtg ggagagcaat     1200
gggcagccgg agaacaacta caagaccaca cctcccatgc tggactccga cggctccttc     1260
ttcctctaca gcaagctcac cgtggacaag agcaggtggc agcaggggaa cgtcttctca     1320
tgctccgtga tgcatgaggc tctgcacaac cactacacgc agaagagcct ctccctgtct     1380
ccgggtaaat ga                                                          1392

<210> SEQ ID NO 2
<211> LENGTH: 463
<212> TYPE: PRT
<213> ORGANISM: Homo sapiens

<400> SEQUENCE: 2

Met Glu Phe Gly Leu Ser Trp Ile Phe Leu Ala Ala Ile Leu Lys Gly
  1               5                  10                  15

Val Gln Cys Glu Val Gln Leu Val Glu Ser Gly Gly Gly Leu Val Lys
                 20                  25                  30

Pro Gly Gly Ser Leu Arg Leu Ser Cys Val Ala Ser Gly Phe Thr Phe
             35                  40                  45

Thr Asn Ala Trp Met Ile Trp Val Arg Gln Ala Pro Gly Lys Gly Leu
         50                  55                  60

Glu Trp Val Gly Arg Ile Lys Arg Lys Thr Asp Gly Gly Thr Thr Asp
 65                  70                  75                  80

Tyr Ala Ala Pro Val Lys Gly Arg Phe Thr Ile Ser Arg Asp Asp Ser
                 85                  90                  95

Lys Asn Thr Leu Tyr Leu Gln Met Asn Ser Leu Lys Thr Glu Asp Thr
            100                 105                 110

Ala Val Tyr Tyr Cys Thr Thr Gly Gly Val Ala Glu Asp Tyr Trp Gly
        115                 120                 125
```

```
Gln Gly Thr Leu Val Thr Val Ser Ser Ala Ser Thr Lys Gly Pro Ser
        130                 135                 140
Val Phe Pro Leu Ala Pro Cys Ser Arg Ser Thr Ser Glu Ser Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
        195                 200                 205
Pro Ser Ser Asn Phe Gly Thr Gln Thr Tyr Thr Cys Asn Val Asp His
210                 215                 220
Lys Pro Ser Asn Thr Lys Val Asp Lys Thr Val Glu Arg Lys Cys Cys
225                 230                 235                 240
Val Glu Cys Pro Pro Cys Pro Ala Pro Pro Val Ala Gly Pro Ser Val
                245                 250                 255
Phe Leu Phe Pro Pro Lys Pro Lys Asp Thr Leu Met Ile Ser Arg Thr
            260                 265                 270
Pro Glu Val Thr Cys Val Val Val Asp Val Ser His Glu Asp Pro Glu
        275                 280                 285
Val Gln Phe Asn Trp Tyr Val Asp Gly Val Glu Val His Asn Ala Lys
290                 295                 300
Thr Lys Pro Arg Glu Glu Gln Phe Asn Ser Thr Phe Arg Val Val Ser
305                 310                 315                 320
Val Leu Thr Val Val His Gln Asp Trp Leu Asn Gly Lys Glu Tyr Lys
                325                 330                 335
Cys Lys Val Ser Asn Lys Gly Leu Pro Ala Pro Ile Glu Lys Thr Ile
            340                 345                 350
Ser Lys Thr Lys Gly Gln Pro Arg Glu Pro Gln Val Tyr Thr Leu Pro
        355                 360                 365
Pro Ser Arg Glu Glu Met Thr Lys Asn Gln Val Ser Leu Thr Cys Leu
370                 375                 380
Val Lys Gly Phe Tyr Pro Ser Asp Ile Ala Val Glu Trp Glu Ser Asn
385                 390                 395                 400
Gly Gln Pro Glu Asn Asn Tyr Lys Thr Thr Pro Pro Met Leu Asp Ser
                405                 410                 415
Asp Gly Ser Phe Phe Leu Tyr Ser Lys Leu Thr Val Asp Lys Ser Arg
            420                 425                 430
Trp Gln Gln Gly Asn Val Phe Ser Cys Ser Val Met His Glu Ala Leu
        435                 440                 445
His Asn His Tyr Thr Gln Lys Ser Leu Ser Leu Ser Pro Gly Lys
450                 455                 460

<210> SEQ ID NO 3
<211> LENGTH: 720
<212> TYPE: DNA
<213> ORGANISM: Homo sapiens

<400> SEQUENCE: 3
atgaggctcc ctgctcagct cctggggctg ctaatgctct gggtctctgg atccagtggg      60
gatattgtga tgactcagtc tccactctcc ctgcccgtca cccctggaga gccggcctcc     120
atctcctgca ggtctagtca gagcctcctg caaagtaatg gatacaacta tttggattgg     180
tacctgcaga agccagggca gtctccacag ctcctgatct atttgggttc taatcgggcc     240
```

```
tccgggtcc ctgacaggtt cagtggcagt ggatcaggca cagattttac actgaaaatc    300
agcagagtgg aggctgagga tgttggggtt tattactgca tgcaagctct acaaactatc    360
accttcggcc aagggacacg actggagatt aaacgaactg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca agtctacgc ctgcgaagtc    660 acccatcagg gcctgagctc gcccgtcaca aagagcttca caggggaga gtgttagtga    720
```

<210> SEQ ID NO 4
<211> LENGTH: 238
<212> TYPE: PRT
<213> ORGANISM: Homo sapiens

<400> SEQUENCE: 4

```
Met Arg Leu Pro Ala Gln Leu Leu Gly Leu Leu Met Leu Trp Val Ser
 1               5                  10                  15

Gly Ser Ser Gly Asp Ile Val Met Thr Gln Ser Pro Leu Ser Leu Pro
             20                  25                  30

Val Thr Pro Gly Glu Pro Ala Ser Ile Ser Cys Arg Ser Ser Gln Ser
         35                  40                  45

Leu Leu Gln Ser Asn Gly Tyr Asn Tyr Leu Asp Trp Tyr Leu Gln Lys
     50                  55                  60

Pro Gly Gln Ser Pro Gln Leu Leu Ile Tyr Leu Gly Ser Asn Arg Ala
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Val Gly Val Tyr Tyr
            100                 105                 110

Cys Met Gln Ala Leu Gln Thr Ile Thr Phe Gly Gln Gly Thr Arg Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 5
<211> LENGTH: 1392
<212> TYPE: DNA
<213> ORGANISM: Homo sapiens

<400> SEQUENCE: 5

```
atggagtttg ggctgagctg gatttttcctt gctgctattt taaaaggtgt ccagtgtgag     60
```

```
gtgcagctgg tggagtctgg gggaggcttg gtgaagcctg ggggggtccct tagactctcc    120
tgtgtagtct ctggattcac tttcactaac gcctggatga tctgggtccg ccaggctcca    180
gggaaggggc tggagtgggt tggccgtatt aaaaggaaaa ctgatggtgg gacaacagac    240
tacgctgcac ccgtgaaagg cagattcacc atctcaagag atgattcaaa aaacacgctg    300
tatctgcaaa tgaacagcct gaaaaccgag gacacagccg tgtattactg taccacaggg    360
ggagtggctg aggactactg gggccaggga accctggtca ccgtctcctc agcctccacc    420
aagggcccat cggtcttccc cctggcgccc tgctccagga gcacctccga gagcacagcg    480
gccctgggct gcctggtcaa ggactacttc cccgaaccgg tgacggtgtc gtggaactca    540
ggcgctctga ccagcggcgt gcacaccttc ccagctgtcc tacagtcctc aggactctac    600
tccctcagca gcgtggtgac cgtgccctcc agcaacttcg gcacccagac ctacacctgc    660
aacgtagatc acaagcccag caacaccaag gtggacaaga cagttgagcg caaatgttgt    720
gtcgagtgcc caccgtgccc agcaccacct gtggcaggac cgtcagtctt cctcttcccc    780
ccaaaaccca aggacaccct catgatctcc cggacccctg aggtcacgtg cgtggtggtg    840
gacgtgagcc acgaagaccc cgaggtccag ttcaactggt acgtggacgg cgtggaggtg    900
cataatgcca agacaaagcc acgggaggag cagttcaaca gcacgttccg tgtggtcagc    960
gtcctcaccg ttgtgcacca ggactggctg aacggcaagg agtacaagtg caaggtctcc   1020
aacaaaggcc tcccagcccc catcgagaaa accatctcca aaaccaaagg cagccccga    1080
gaaccacagg tgtacaccct gcccccatcc cgggaggaga tgaccaagaa ccaggtcagc   1140
ctgacctgcc tggtcaaagg cttctacccc agcgacatcg ccgtggagtg ggagagcaat   1200
gggcagccgg agaacaacta caagaccaca cctcccatgc tggactccga cggctccttc   1260
ttcctctaca gcaagctcac cgtggacaag agcaggtggc agcaggggaa cgtcttctca   1320
tgctccgtga tgcatgaggc tctgcacaac cactacacgc agaagagcct ctccctgtct   1380
ccgggtaaat ga                                                       1392
```

<210> SEQ ID NO 6
<211> LENGTH: 463
<212> TYPE: PRT
<213> ORGANISM: Homo sapiens

<400> SEQUENCE: 6

```
Met Glu Phe Gly Leu Ser Trp Ile Phe Leu Ala Ala Ile Leu Lys Gly
  1               5                  10                  15

Val Gln Cys Glu Val Gln Leu Val Glu Ser Gly Gly Gly Leu Val Lys
                 20                  25                  30

Pro Gly Gly Ser Leu Arg Leu Ser Cys Val Val Ser Gly Phe Thr Phe
             35                  40                  45

Thr Asn Ala Trp Met Ile Trp Val Arg Gln Ala Pro Gly Lys Gly Leu
         50                  55                  60

Glu Trp Val Gly Arg Ile Lys Arg Lys Thr Asp Gly Gly Thr Thr Asp
 65                  70                  75                  80

Tyr Ala Ala Pro Val Lys Gly Arg Phe Thr Ile Ser Arg Asp Asp Ser
                 85                  90                  95

Lys Asn Thr Leu Tyr Leu Gln Met Asn Ser Leu Lys Thr Glu Asp Thr
            100                 105                 110

Ala Val Tyr Tyr Cys Thr Thr Gly Gly Val Ala Glu Asp Tyr Trp Gly
        115                 120                 125

Gln Gly Thr Leu Val Thr Val Ser Ser Ala Ser Thr Lys Gly Pro Ser
```

```
                130             135             140
Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Val Asp Val Ser His Glu Asp Pro Glu
            275                 280                 285

Val Gln Phe Asn Trp Tyr Val Asp Gly Val Glu Val His Asn Ala Lys
        290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
                340                 345                 350

Ser Lys Thr Lys Gly Gln Pro Arg Glu Pro Gln Val Tyr Thr Leu Pro
            355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys
    450                 455                 460
```

<210> SEQ ID NO 7
<211> LENGTH: 720
<212> TYPE: DNA
<213> ORGANISM: Homo sapiens

<400> SEQUENCE: 7

```
atgaggctcc ctgctcagct cctggggctg ctaatgctct gggtctctgg atccagtggg    60
gatattgtga tgactcagtc tccactctcc ctgcccgtca cccctggaga gccggcctcc   120
atctcctgca ggtctagtca gagcctcctg caaagtaatg gattcaacta tttggattgg   180
tacctgcaga agccagggca gtctccacag ctcctgatct atttgggttc taatcgggcc   240
tccggggtcc ctgacaggtt cagtggcagt gggtcaggca cagatttac actgaaaatc   300
```

| | |
|---|---|
| agcagagtgg aggctgagga tgttggggtt tattactgca tgcaagctct acaaactatc | 360 |
| accttcggcc aagggacacg actggagatt aaacgaactg tggctgcacc atctgtcttc | 420 |
| atcttcccgc catctgatga gcagttgaaa tctggaactg cctctgttgt gtgcctgctg | 480 |
| aataacttct atcccagaga ggccaaagta cagtggaagg tggataacgc ctccaatcg | 540 |
| ggtaactccc aggagagtgt cacagagcag gacagcaagg acagcaccta cagcctcagc | 600 |
| agcaccctga cgctgagcaa agcagactac gagaaacaca agtctacgc ctgcgaagtc | 660 |
| acccatcagg gcctgagctc gcccgtcaca aagagcttca caggggaga gtgttagtga | 720 |

<210> SEQ ID NO 8
<211> LENGTH: 238
<212> TYPE: PRT
<213> ORGANISM: Homo sapiens

<400> SEQUENCE: 8

```
Met Arg Leu Pro Ala Gln Leu Leu Gly Leu Leu Met Leu Trp Val Ser
  1               5                  10                  15

Gly Ser Ser Gly Asp Ile Val Met Thr Gln Ser Pro Leu Ser Leu Pro
             20                  25                  30

Val Thr Pro Gly Glu Pro Ala Ser Ile Ser Cys Arg Ser Ser Gln Ser
         35                  40                  45

Leu Leu Gln Ser Asn Gly Phe Asn Tyr Leu Asp Trp Tyr Leu Gln Lys
     50                  55                  60

Pro Gly Gln Ser Pro Gln Leu Leu Ile Tyr Leu Gly Ser Asn Arg Ala
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Val Gly Val Tyr Tyr
            100                 105                 110

Cys Met Gln Ala Leu Gln Thr Ile Thr Phe Gly Gln Gly Thr Arg Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 9
<211> LENGTH: 1404
<212> TYPE: DNA
<213> ORGANISM: Homo sapiens

<400> SEQUENCE: 9

| | |
|---|---|
| atggagtttg ggctgagctg gcttttcctt gtggctattt taaaaggtgt ccagtgtgag | 60 |
| gtgcagctgt tggagtctgg gggaggcttg gtacagcctg gggggtccct gagactctcc | 120 |

```
tgtgcagcct ctggactcac ctttaacaat tctgccatga cctgggtccg ccaggctcca      180
gggaaggggc tggagtgggt ctcaactact agtggaagtg gtggtaccac atactacgca      240
gactccgtga agggccggtt caccatctcc agagactctc caagaacacg ctctatctg       300 caaatgaaca gcctgagagc cgaggacacg gccgtatatt actgtgcggc cgtggatac       360 agctatggta cgaccccta tgagtactgg ggccagggaa ccctggtcac cgtctcctca       420
gcttccacca agggcccatc cgtcttcccc ctggcgccct gttccaggag cacctccgag      480
agcacagccg ccctgggctg cctggtcaag gactacttcc ccgaaccggt gacggtgtcg      540
tggaactcag gcgccctgac cagcggcgtg cacaccttcc cggctgtcct acagtcctca      600
ggactctact ccctcagcag cgtggtgacc gtgccctcca gcagcttggg cacgaagacc      660
tacacctgca acgtagatca caagcccagc aacaccaagg tggacaagag agttgagtcc      720
aaatatggtc ccccatgccc atcatgccca gcacctgagt tcctgggggg accatcagtc      780
ttcctgttcc ccccaaaacc caaggacact ctcatgatct cccggacccc tgaggtcacg      840
tgcgtggtgg tggacgtgag ccaggaagac cccgaggtcc agttcaactg gtacgtggat      900
ggcgtggagg tgcataatgc caagacaaag ccgcgggagg agcagttcaa cagcacgtac      960
cgtgtggtca gcgtcctcac cgtcctgcac caggactggc tgaacggcaa ggagtacaag     1020
tgcaaggtct ccaacaaagg cctcccgtcc tccatcgaga aaaccatctc aaagccaaa      1080 gggcagcccc gagagccaca ggtgtacacc ctgcccccat cccaggagga gatgaccaag     1140
aaccaggtca gcctgacctg cctggtcaaa ggcttctacc ccagcgacat cgccgtggag     1200
tgggagagca atgggcagcc ggagaacaac tacaagacca cgcctcccgt gctggactcc     1260
gacggctcct tcttcctcta cagcaggcta accgtggaca agagcaggtg gcaggagggg     1320
aatgtcttct catgctccgt gatgcatgag gctctgcaca accactacac acagaagagc     1380
ctctccctgt ctctgggtaa atga                                            1404
```

<210> SEQ ID NO 10
<211> LENGTH: 467
<212> TYPE: PRT
<213> ORGANISM: Homo sapiens

<400> SEQUENCE: 10

```
Met Glu Phe Gly Leu Ser Trp Leu Phe Leu Val Ala Ile Leu Lys Gly
 1               5                  10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Leu Thr Phe
        35                  40                  45

Asn Asn Ser Ala Met Thr Trp Val Arg Gln Ala Pro Gly Lys Gly Leu
    50                  55                  60

Glu Trp Val Ser Thr Thr Ser Gly Ser Gly Thr Thr Tyr Tyr Ala
65                  70                  75                  80

Asp Ser Val Lys Gly Arg Phe Thr Ile Ser Arg Asp Ser Pro Lys Asn
                85                  90                  95

Thr Leu Tyr Leu Gln Met Asn Ser Leu Arg Ala Glu Asp Thr Ala Val
            100                 105                 110

Tyr Tyr Cys Ala Ala Arg Gly Tyr Ser Tyr Gly Thr Thr Pro Tyr Glu
        115                 120                 125

Tyr Trp Gly Gln Gly Thr Leu Val Thr Val Ser Ser Ala Ser Thr Lys
    130                 135                 140
```

-continued

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Ser Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
450                 455                 460

Leu Gly Lys
465

<210> SEQ ID NO 11
<211> LENGTH: 711
<212> TYPE: DNA
<213> ORGANISM: Homo sapiens

<400> SEQUENCE: 11
atggacatga gggtccccgc tcagctcctg gggctcctgc tactctggct ccgaggggcc      60
agatgtgaca tccagatgac ccagtctcca tcctccctgt ctgcatctgt aggagacaga     120
gtcaccatca cttgccgggc aagtcggagc attagcagct atttaaattg gtatcagcag     180
aaaccaggga agcccctaa gtcctgatc ttttttgtgt ccagtttgca aagtggggtc      240

```
ccatcaaggt tcagtggcag tggctctggg acagatttca ctctcaccat cagcagtctg    300
caacctgaag attttgcaac ttactactgt caacagaatt acattccccc tattaccttc    360
ggccagggga cacgactgga gatcagacga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta g             711
```

<210> SEQ ID NO 12
<211> LENGTH: 236
<212> TYPE: PRT
<213> ORGANISM: Homo sapiens

<400> SEQUENCE: 12

```
Met Asp Met Arg Val Pro Ala Gln Leu Leu Gly Leu Leu Leu Leu Trp
  1               5                  10                  15

Leu Arg Gly Ala Arg Cys Asp Ile Gln Met Thr Gln Ser Pro Ser Ser
                 20                  25                  30

Leu Ser Ala Ser Val Gly Asp Arg Val Thr Ile Thr Cys Arg Ala Ser
             35                  40                  45

Arg Ser Ile Ser Ser Tyr Leu Asn Trp Tyr Gln Gln Lys Pro Gly Lys
         50                  55                  60

Ala Pro Lys Val Leu Ile Phe Phe Val Ser Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
            100                 105                 110

Asn Tyr Ile Pro Pro Ile Thr Phe Gly Gln Gly Thr Arg Leu Glu Ile
        115                 120                 125

Arg Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 13
<211> LENGTH: 1398
<212> TYPE: DNA
<213> ORGANISM: Homo sapiens

<400> SEQUENCE: 13

```
atggagtttg ggctgagctg ggttttcctc gttgctcttt taagaggtgt ccagtgtcag    60
```

```
gtgcagctgg tggagtctgg gggaggcgtg gtccagcctg ggaggtccct gagactctcc    120
tgtgcagcgt ctggacacac cttcagtagc gatggcatgc actgggtccg ccaggctcca    180
ggcaaggggc tggagtgggt ggcaattata tggtatgatg gaagtaataa atattatgca    240
gactccgtga agggccgatt caccatctcc agagacaatt ccaagaacac gctgtatctg    300
caaatgaaca gcctgagagc cgaggacacg gctgtatatt actgtgcgag agatcccggc    360
tactattacg gtatggacgt ctggggccaa gggaccacgg tcaccgtctc ctcagcttcc    420
accaagggcc catccgtctt ccccctggcg ccctgctcca ggagcacctc cgagagcaca    480
gccgccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct tgggcacgaa gacctacacc    660
tgcaacgtag atcacaagcc cagcaacacc aaggtggaca gagagttga gtccaaatat    720 ggtcccccat gcccatcatg cccagcacct gagttcctgg ggggaccatc agtcttcctg    780
ttccccccaa acccaagga cactctcatg atctcccgga cccctgaggt cacgtgcgtg    840
gtggtggacg tgagccagga agaccccgag gtccagttca actggtacgt ggatggcgtg    900
gaggtgcata atgccaagac aaagccgcgg gaggagcagt tcaacagcac gtaccgtgtg    960
gtcagcgtcc tcaccgtcct gcaccaggac tggctgaacg gcaaggagta caagtgcaag   1020
gtctccaaca aaggcctccc gtcctccatc gagaaaacca tctccaaagc caaagggcag   1080
ccccgagagc cacaggtgta caccctgccc ccatcccagg aggagatgac caagaaccag   1140
gtcagcctga cctgcctggt caaaggcttc taccccagcg acatcgccgt ggagtgggag   1200
agcaatgggc agccggagaa caactacaag accgcgcctc ccgtgctgga ctccgacggc   1260
tccttcttcc tctacagcag gctaaccgtg gacaagagca ggtggcagga ggggaatgtc   1320
ttctcatgct ccgtgatgca tgaggctctg cacaaccact acacacagaa gagcctctcc   1380
ctgtctctgg gtaaatga                                                 1398
```

<210> SEQ ID NO 14
<211> LENGTH: 465
<212> TYPE: PRT
<213> ORGANISM: Homo sapiens

<400> SEQUENCE: 14

```
Met Glu Phe Gly Leu Ser Trp Val Phe Leu Val Ala Leu Leu Arg Gly
  1               5                  10                  15

Val Gln Cys Gln Val Gln Leu Val Glu Ser Gly Gly Gly Val Val Gln
             20                  25                  30

Pro Gly Arg Ser Leu Arg Leu Ser Cys Ala Ala Ser Gly His Thr Phe
         35                  40                  45

Ser Ser Asp Gly Met His Trp Val Arg Gln Ala Pro Gly Lys Gly Leu
     50                  55                  60

Glu Trp Val Ala Ile Ile Trp Tyr Asp Gly Ser Asn Lys Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Pro Gly Tyr Tyr Tyr Gly Met Asp Val Trp
        115                 120                 125
```

Gly Gln Gly Thr Thr Val Thr Val Ser Ser Ala Ser Thr Lys Gly Pro
130             135                 140

Ser Val Phe Pro Leu Ala Pro Cys Ser Arg Ser Thr Ser Glu Ser Thr
145             150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
210                 215                 220

His Lys Pro Ser Asn Thr Lys Val Asp Lys Arg Val Glu Ser Lys Tyr
225                 230                 235                 240

Gly Pro Pro Cys Pro Ser Cys Pro Ala Pro Glu Phe Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Ala Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
450                 455                 460

Lys
465

<210> SEQ ID NO 15
<211> LENGTH: 705
<212> TYPE: DNA
<213> ORGANISM: Homo sapiens

<400> SEQUENCE: 15
atgttgccat cacaactcat tgggtttctg ctgctctggg ttccagcttc caggggtgaa    60
attgtgctga ctcagtctcc agactttcag tctgtgactc caaaagagaa agtcaccatc   120
acctgccggg ccagtcagag aattggtagt agcttacact ggtaccagca gaaaccagat   180

```
cagtctccaa aactcctcat caagtatgct tcccagtcct tctcagggt  ccctcgagg      240 ttcagtggca gtggatctgg gacaaatttc accctcacca tcaatggcct ggaagctgaa      300
gatgctgcaa cttattactg tcatcagagt ggtcgtttac cgctcacttt cggcggaggg      360
accaaggtgg agatcaaacg aactgtggct gcaccatctg tcttcatctt cccgccatct      420
gatgagcagt tgaaatctgg aactgcctct gttgtgtgcc tgctgaataa cttctatccc      480
agagaggcca agtacagtg gaaggtggat aacgccctcc aatcgggtaa ctcccaggag       540
agtgtcacag agcaggacag caaggacagc acctacagcc tcagcagcac cctgacgctg      600
agcaaagcag actacgagaa acacaaagtc tacgcctgcg aagtcaccca tcagggcctg      660
agctcgcccg tcacaaagag cttcaacagg ggagagtgtt agtga                     705
```

<210> SEQ ID NO 16
<211> LENGTH: 233
<212> TYPE: PRT
<213> ORGANISM: Homo sapiens

<400> SEQUENCE: 16

```
Met Leu Pro Ser Gln Leu Ile Gly Phe Leu Leu Leu Trp Val Pro Ala
  1               5                  10                  15

Ser Arg Gly Glu Ile Val Leu Thr Gln Ser Pro Asp Phe Gln Ser Val
              20                  25                  30

Thr Pro Lys Glu Lys Val Thr Ile Thr Cys Arg Ala Ser Gln Arg Ile
          35                  40                  45

Gly Ser Ser Leu His Trp Tyr Gln Gln Lys Pro Asp Gln Ser Pro Lys
      50                  55                  60

Leu Leu Ile Lys Tyr Ala Ser Gln Ser Phe Ser Gly Val Pro Ser Arg
  65                  70                  75                  80

Phe Ser Gly Ser Gly Ser Gly Thr Asn Phe Thr Leu Thr Ile Asn Gly
                  85                  90                  95

Leu Glu Ala Glu Asp Ala Ala Thr Tyr Tyr Cys His Gln Ser Gly Arg
             100                 105                 110

Leu Pro Leu Thr Phe Gly Gly Gly Thr Lys Val Glu Ile Lys Arg Thr
         115                 120                 125

Val Ala Ala Pro Ser Val Phe Ile Phe Pro Pro Ser Asp Glu Gln Leu
     130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                 165                 170                 175

Asn Ser Gln Glu Ser Val Thr Glu Gln Asp Ser Lys Asp Ser Thr Tyr
             180                 185                 190

Ser Leu Ser Ser Thr Leu Thr Leu Ser Lys Ala Asp Tyr Glu Lys His
         195                 200                 205

Lys Val Tyr Ala Cys Glu Val Thr His Gln Gly Leu Ser Ser Pro Val
     210                 215                 220

Thr Lys Ser Phe Asn Arg Gly Glu Cys
225                 230
```

<210> SEQ ID NO 17
<211> LENGTH: 1410
<212> TYPE: DNA
<213> ORGANISM: Homo sapiens

<400> SEQUENCE: 17

```
atggagtttg gcctgagctg ggttttcctc gttgctcttt taagaggtgt ccagtgtcag      60
gtgcagctgg tggagtctgg gggaggcgtg gtccagcctg gaggtccct gagactctcc     120
tgtgcagcct ctggattcac cttcagtagc tatggcatgc actgggtccg ccaggctcca    180
ggcaaggggc tggagtgggt ggcagttata tcaaatgatg gaataataa atactatgca     240
gactccgtga agggccgatt caccatctcc agagacaatt ccaaaacac gctgtatctg     300
caaatgaaca gcctgagcgc tgaggacacg gctgtgtatt actgtgcgag agatagtacg    360
gcgataacct actactacta cggaatggac gtctggggcc aagggaccac ggtcaccgtc    420
tcctcagctt ccaccaaggg cccatccgtc ttccccctgg cgccctgctc caggagcacc    480
tccgagagca cagccgccct gggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacg    660
aagacctaca cctgcaacgt agatcacaag cccagcaaca ccaaggtgga caagagagtt    720
gagtccaaat atggtccccc atgcccatca tgcccagcac ctgagttcct ggggggacca    780
tcagtcttcc tgttccccc aaaacccaag gacactctca tgatctcccg gacccctgag    840
gtcacgtgcg tggtggtgga cgtgagccag gaagaccccg aggtccagtt caactggtac    900
gtggatggcg tggaggtgca taatgccaag acaaagccgc gggaggagca gttcaacagc    960
acgtaccgtg tggtcagcgt cctcaccgtc ctgcaccagg actggctgaa cggcaaggag   1020
tacaagtgca aggtctccaa caaaggcctc ccgtcctcca tcgagaaaac catctccaaa   1080
gccaaagggc agccccgaga gccacaggtg tacaccctgc ccccatccca ggaggagatg   1140
accaagaacc aggtcagcct gacctgcctg gtcaaaggct tctacccag cgacatcgcc   1200
gtggagtggg agagcaatgg acagccggag aacaactaca agaccacgcc tcccgtgctg   1260
gactccgacg gctccttctt cctctacagc aggctaaccg tggacaagag caggtggcag   1320
gaggggaatg tcttctcatg ctccgtgatg catgaggctc tgcacaacca ctacacacag   1380
aagagcctct ccctgtctct gggtaaatga                                    1410
```

<210> SEQ ID NO 18
<211> LENGTH: 469
<212> TYPE: PRT
<213> ORGANISM: Homo sapiens

<400> SEQUENCE: 18

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Ser Asn Asp Gly Asn Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Ser Ala Glu Asp Thr Ala Val
            100                 105                 110

Tyr Tyr Cys Ala Arg Asp Ser Thr Ala Ile Thr Tyr Tyr Tyr Tyr Gly

```
            115                 120                 125
Met Asp Val Trp Gly Gln Gly Thr Thr Val Thr Val Ser Ser Ala Ser
130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Lys Thr Tyr Thr
    210                 215                 220

Cys Asn Val Asp His Lys Pro Ser Asn Thr Lys Val Asp Lys Arg Val
225                 230                 235                 240

Glu Ser Lys Tyr Gly Pro Pro Cys Pro Ser Cys Pro Ala Pro Glu Phe
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser Gln Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Gly Leu Pro Ser
            340                 345                 350

Ser Ile Glu Lys Thr Ile Ser Lys Ala Lys Gly Gln Pro Arg Glu Pro
        355                 360                 365

Gln Val Tyr Thr Leu Pro Pro Ser Gln Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Arg Leu
            420                 425                 430

Thr Val Asp Lys Ser Arg Trp Gln Glu Gly Asn Val Phe Ser Cys Ser
        435                 440                 445

Val Met His Glu Ala Leu His Asn His Tyr Thr Gln Lys Ser Leu Ser
    450                 455                 460

Leu Ser Leu Gly Lys
465

<210> SEQ ID NO 19
<211> LENGTH: 714
<212> TYPE: DNA
<213> ORGANISM: Homo sapiens

<400> SEQUENCE: 19
atggacatga gggtccccgc tcagctcctg gggctcctgc tactctggct ccgaggtgcc      60
agatgtgaca tccagatgac ccagtctcca tcctccctgt ctgcatctgt cggagacaga     120
```

```
gtcaccatca cttgccgggc aagtcagaat attagtagct atttaaattg gtttcagcag    180
aaaccaggga agcccctaa gctcctgatc tatgctgcat ccggtttgaa gcgtggggtc    240
ccatcacggt tcagtggtag tggatctggg acagatttca ctctcaccat caggactctg    300
caacctgatg attttgcaac ttactcctgt caccagagtt acagtctccc attcactttc    360
ggccctggga ccaaagtgga tatcaaacga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta gtga          714
```

<210> SEQ ID NO 20
<211> LENGTH: 236
<212> TYPE: PRT
<213> ORGANISM: Homo sapiens

<400> SEQUENCE: 20

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asn Ile Ser Ser Tyr Leu Asn Trp Phe Gln Gln Lys Pro Gly Lys
    50                  55                  60

Ala Pro Lys Leu Leu Ile Tyr Ala Ala Ser Gly Leu Lys Arg Gly Val
65                  70                  75                  80

Pro Ser Arg Phe Ser Gly Ser Gly Ser Gly Thr Asp Phe Thr Leu Thr
                85                  90                  95

Ile Arg Thr Leu Gln Pro Asp Asp Phe Ala Thr Tyr Ser Cys His Gln
            100                 105                 110

Ser Tyr Ser Leu Pro Phe Thr Phe Gly Pro Gly Thr Lys Val Asp Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 21
<211> LENGTH: 1413
<212> TYPE: DNA
<213> ORGANISM: Homo sapiens

<400> SEQUENCE: 21

```
atgaaacacc tgtggttctt cctcctgctg gtggcagctc ccagatgggt cctgtcccag      60
gtgcagctgc aggagtcggg cccaggactg gtgaagcctt cggagaccct gtccctcacc     120
tgcactgtct ctggtgactc catcagtagt aactattgga gctggatccg gcagcccgcc     180
gggaagggac tggagtggat tgggcgtatc tataccagtg ggggcaccaa ctccaacccc     240
tccctcaggg gtcgagtcac catttttagca gacacgtcca agaaccagtt ctctctgaaa     300
ctgagttctg tgaccgccgc ggacacggcc gtgtattact gtgcgagaga tcgtattact     360
ataattcggg gacttattcc atccttcttt gactactggg gccagggaac cctggtcacc     420
gtctcctcag cttccaccaa gggcccatcc gtcttccccc tggcgccctg ctccaggagc     480
acctccgaga gcacagccgc cctgggctgc ctggtcaagg actacttccc cgaaccggtg     540
acggtgtcgt ggaactcagg cgccctgacc agcggcgtgc acaccttccc ggctgtccta     600
cagtcctcag gactctactc cctcagcagc gtggtgaccg tgccctccag cagcttgggc     660
acgaagacct acacctgcaa cgtagatcac aagcccagca acaccaaggt ggacaagaga     720
gttgagtcca aatatggtcc cccatgccca tcatgcccag cacctgagtt cctggggggga     780
ccatcagtct tcctgttccc cccaaaaccc aaggacactc tcatgatctc ccggacccct     840
gaggtcacgt gcgtggtggt ggacgtgagc caggaagacc ccgaggtcca gttcaactgg     900
tacgtggatg gcgtggaggt gcataatgcc aagacaaagc cgcgggagga gcagttcaac     960
agcacgtacc gtgtggtcag cgtcctcacc gtcctgcacc aggactggct gaacggcaag    1020
gagtacaagt gcaaggtctc caacaaaggc ctcccgtcct ccatcgagaa aaccatctcc    1080
aaagccaaag gcagccccg agagccacag gtgtacaccc tgcccccatc ccaggaggag    1140
atgaccaaga accaggtcag cctgacctgc ctggtcaaag gcttctaccc cagcgacatc    1200
gccgtggagt gggagagcaa tgggcagccg gagaacaact acaagaccac gcctcccgtg    1260
ctggactccg acggctcctt cttcctctac agcaggctaa ccgtggacaa gagcaggtgg    1320
caggagggga atgtcttctc atgctccgtg atgcatgagg ctctgcacaa ccactacaca    1380
cagaagagcc tctccctgtc tctgggtaaa tga                                 1413
```

<210> SEQ ID NO 22
<211> LENGTH: 470
<212> TYPE: PRT
<213> ORGANISM: Homo sapiens

<400> SEQUENCE: 22

```
Met Lys His Leu Trp Phe Phe Leu Leu Leu Val Ala Ala Pro Arg Trp
  1               5                  10                  15

Val Leu Ser Gln Val Gln Leu Gln Glu Ser Gly Pro Gly Leu Val Lys
             20                  25                  30

Pro Ser Glu Thr Leu Ser Leu Thr Cys Thr Val Ser Gly Asp Ser Ile
         35                  40                  45

Ser Ser Asn Tyr Trp Ser Trp Ile Arg Gln Pro Ala Gly Lys Gly Leu
     50                  55                  60

Glu Trp Ile Gly Arg Ile Tyr Thr Ser Gly Gly Thr Asn Ser Asn Pro
 65                  70                  75                  80

Ser Leu Arg Gly Arg Val Thr Ile Leu Ala Asp Thr Ser Lys Asn Gln
                 85                  90                  95

Phe Ser Leu Lys Leu Ser Ser Val Thr Ala Ala Asp Thr Ala Val Tyr
            100                 105                 110
```

```
Tyr Cys Ala Arg Asp Arg Ile Thr Ile Ile Arg Gly Leu Ile Pro Ser
        115                 120                 125

Phe Phe Asp Tyr Trp Gly Gln Gly Thr Leu Val Thr Val Ser Ser Ala
130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
        165                 170                 175

Pro Glu Pro Val Thr Val Ser Trp Asn Ser Gly Ala Leu Thr Ser Gly
        180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Lys Thr Tyr
        210                 215                 220

Thr Cys Asn Val Asp His Lys Pro Ser Asn Thr Lys Val Asp Lys Arg
225                 230                 235                 240

Val Glu Ser Lys Tyr Gly Pro Pro Cys Pro Ser Cys Pro Ala Pro Glu
                245                 250                 255

Phe Leu Gly Gly Pro Ser Val Phe Leu Phe Pro Pro Lys Pro Lys Asp
        260                 265                 270

Thr Leu Met Ile Ser Arg Thr Pro Glu Val Thr Cys Val Val Val Asp
        275                 280                 285

Val Ser Gln Glu Asp Pro Glu Val Gln Phe Asn Trp Tyr Val Asp Gly
        290                 295                 300

Val Glu Val His Asn Ala Lys Thr Lys Pro Arg Glu Glu Gln Phe Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Gly Leu Pro
        340                 345                 350

Ser Ser Ile Glu Lys Thr Ile Ser Lys Ala Lys Gly Gln Pro Arg Glu
        355                 360                 365

Pro Gln Val Tyr Thr Leu Pro Pro Ser Gln Glu Met Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Arg
                420                 425                 430

Leu Thr Val Asp Lys Ser Arg Trp Gln Glu Gly Asn Val Phe Ser Cys
        435                 440                 445

Ser Val Met His Glu Ala Leu His Asn His Tyr Thr Gln Lys Ser Leu
        450                 455                 460

Ser Leu Ser Leu Gly Lys
465                 470

<210> SEQ ID NO 23
<211> LENGTH: 729
<212> TYPE: DNA
<213> ORGANISM: Homo sapiens

<400> SEQUENCE: 23
atggtgttgc agacccaggt cttcatttct ctgttgctct ggatctctgg tgcctacggg    60
```

```
gacatcgtga tgacccagtc tccagactcc ctggctgtgt ctctgggcga gagggccacc    120
atcaactgca agtccagcca gagtgtttta tacagctcca acaataagac ctacttagct    180
tggtaccaac agaaaccaag acagcctcct aaattgctca tttactgggc atctatacgg    240
gaatatgggg tccctgaccg attcagtggc agcgggtctg ggacagattt cactctcacc    300
atcagcagcc tgcaggctga agatgtggca gtttatttct gtcaacaata ttatagtatt    360
cctcccctca ctttcggcgg agggaccaag gtggagatca aacgaactgt ggctgcacca    420
tctgtcttca tcttcccgcc atctgatgag cagttgaaat ctggaactgc ctctgttgtg    480
tgcctgctga ataacttcta tcccagagag gccaaagtac agtggaaggt ggataacgcc    540
ctccaatcgg gtaactccca ggagagtgtc acagagcagg acagcaagga cagcacctac    600
agcctcagca gcaccctgac gctgagcaaa gcagactacg agaaacacaa agtctacgcc    660
tgcgaagtca cccatcaggg cctgagctcg cccgtcacaa agagcttcaa caggggagag    720
tgttagtga                                                           729
```

<210> SEQ ID NO 24
<211> LENGTH: 241
<212> TYPE: PRT
<213> ORGANISM: Homo sapiens

<400> SEQUENCE: 24

```
Met Val Leu Gln Thr Gln Val Phe Ile Ser Leu Leu Leu Trp Ile Ser
 1               5                  10                  15

Gly Ala Tyr Gly Asp Ile Val Met Thr Gln Ser Pro Asp Ser Leu Ala
             20                  25                  30

Val Ser Leu Gly Glu Arg Ala Thr Ile Asn Cys Lys Ser Ser Gln Ser
         35                  40                  45

Val Leu Tyr Ser Ser Asn Asn Lys Thr Tyr Leu Ala Trp Tyr Gln Gln
     50                  55                  60

Lys Pro Arg Gln Pro Pro Lys Leu Leu Ile Tyr Trp Ala Ser Ile Arg
 65                  70                  75                  80

Glu Tyr Gly Val Pro Asp Arg Phe Ser Gly Ser Gly Ser Gly Thr Asp
                 85                  90                  95

Phe Thr Leu Thr Ile Ser Ser Leu Gln Ala Glu Asp Val Ala Val Tyr
            100                 105                 110

Phe Cys Gln Gln Tyr Tyr Ser Ile Pro Pro Leu Thr Phe Gly Gly Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys
```

<210> SEQ ID NO 25
<211> LENGTH: 1419
<212> TYPE: DNA
<213> ORGANISM: Homo sapiens

<400> SEQUENCE: 25

```
atggagtttg ggctgagctg gcttttctt gtggctattt taaaaggtgt ccagtgtgag      60
gtgcagctgt tggagtctgg gggagacttg gtccagcctg gggggtccct gagactctcc     120
tgtgcagcct ctggattcac ctttagaagt tatgccatga actgggtccg acaggctcca     180
gggaaggggc tggagtgggt ctcagttatt agtggtcgtg gtggtactac atactacgca     240
gactccgtga agggccggtt caccatctcc agagacaatt ccaagaacac gctgtatctg     300
caaatgaaca gcctgagagc cgaggacgcg gccgtatatt actgtgcgaa gatagcagtg     360
gctggagagg ggctctacta ctactacggt atggacgtct ggggccaagg gaccacggtc     420
accgtctcct cagcttccac caagggccca tccgtcttcc cctggcgcc ctgctccagg     480
agcacctccg agaacacagc cgccctgggc tgcctggtca aggactactt ccccgaaccg     540
gtgacggtgt cgtggaactc aggcgccctg accagcggcg tgcacacctt cccggctgtc     600
ctacagtcct caggactcta ctccctcagc agcgtggtga ccgtgccctc tagcagcttg     660
ggcacgaaga cctacacctg caacgtagat cacaagccca gcaacaccaa ggtggacaag     720
agagttgagt ccaaatatgg tcccccatgc ccatcatgcc cagcacctga gttcctgggg     780
ggaccatcag tcttcctgtt ccccccaaaa cccaaggaca ctctcatgat ctcccggacc     840
cctgaggtca cgtgcgtggt ggtggacgtg agccaggaag accccgaggt ccagttcaac     900
tggtacgtgg atggcgtgga ggtgcataat gccaagacaa agccgcggga ggagcagttc     960
aacagcacgt accgtgtggt cagcgtcctc accgtcctgc accaggactg gctgaacggc    1020
aaggagtaca agtgcaaggt ctccaacaaa ggcctcccgt cctccatcga gaaaaccatc    1080
tccaaagcca agggcagcc ccgagagcca caggtgtaca ccctgccccc atcccaggag    1140
gagatgacca gaaccaggt cagcctgacc tgcctggtca aaggcttcta ccccagcgac    1200
atcgccgtgg agtgggagag caatgggcag ccggagaaca actacaagac cacgcctccc    1260
gtgctggact ccgacggctc cttcttcctc tacagcaggc taaccgtgga caagagcagg    1320
tggcaggagg ggaatgtctt ctcatgctcc gtgatgcatg aggctctgca caaccactac    1380
acacagaaga gcctctcct gtctctgggt aaatgatag                            1419
```

<210> SEQ ID NO 26
<211> LENGTH: 471
<212> TYPE: PRT
<213> ORGANISM: Homo sapiens

<400> SEQUENCE: 26

```
Met Glu Phe Gly Leu Ser Trp Leu Phe Leu Val Ala Ile Leu Lys Gly
  1               5                  10                  15

Val Gln Cys Glu Val Gln Leu Leu Glu Ser Gly Gly Asp Leu Val Gln
                 20                  25                  30

Pro Gly Gly Ser Leu Arg Leu Ser Cys Ala Ala Ser Gly Phe Thr Phe
             35                  40                  45

Arg Ser Tyr Ala Met Asn Trp Val Arg Gln Ala Pro Gly Lys Gly Leu
         50                  55                  60

Glu Trp Val Ser Val Ile Ser Gly Arg Gly Gly Thr Thr Tyr Tyr Ala
 65                  70                  75                  80
```

Asp Ser Val Lys Gly Arg Phe Thr Ile Ser Arg Asp Asn Ser Lys Asn
            85                  90                  95

Thr Leu Tyr Leu Gln Met Asn Ser Leu Arg Ala Glu Asp Ala Ala Val
            100                 105                 110

Tyr Tyr Cys Ala Lys Ile Ala Val Ala Gly Glu Gly Leu Tyr Tyr Tyr
            115                 120                 125

Tyr Gly Met Asp Val Trp Gly Gln Gly Thr Thr Val Thr Val Ser Ser
130                 135                 140

Ala Ser Thr Lys Gly Pro Ser Val Phe Pro Leu Ala Pro Cys Ser Arg
145                 150                 155                 160

Ser Thr Ser Glu Asn Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Ser Leu Gly Thr Lys Thr
210                 215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Cys Pro Ser Cys Pro Ala Pro
                245                 250                 255

Glu Phe Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser Gln Glu Asp Pro Glu Val Gln Phe Asn Trp Tyr Val Asp
290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
            355                 360                 365

Glu Pro Gln Val Tyr Thr Leu Pro Pro Ser Gln Glu Glu Met Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Arg Leu Thr Val Asp Lys Ser Arg Trp Gln Glu Gly Asn Val Phe Ser
            435                 440                 445

Cys Ser Val Met His Glu Ala Leu His Asn His Tyr Thr Gln Lys Ser
450                 455                 460

Leu Ser Leu Ser Leu Gly Lys
465                 470

<210> SEQ ID NO 27
<211> LENGTH: 720

<212> TYPE: DNA
<213> ORGANISM: Homo sapiens

<400> SEQUENCE: 27

```
atggacatga gggtccccgc tcagctcctg gggctcctgc tactctggct ccgaggtgcc    60
agatgtgaca tccagatgac ccagtctcca tcctccctgt ctgcatctgt aggtgacaga   120
gtcaccttca cttgccgggc aagtcagaac attaccaact atttaaattg gtatcagcag   180
aaaccaggga aggcccctaa gctcctgatc tatgctgcgt ccagtttgcc aagaggggtc   240
ccatcaaggt tccgtggcag tggatctggg acagatttca ctctcaccat cagcagtctg   300
caacctgaag attttgcaac ttactactgt caacagagtt acagtaatcc tccggagtgc   360
ggttttggcc aggggaccac gctggatatc aaacgaactg tggctgcacc atctgtcttc   420
atcttcccgc catctgatga gcagttgaaa tctggaactg cctctgttgt gtgcctgctg   480
aataacttct atcccagaga ggccaaagta cagtggaagg tggataacgc cctccaatcg   540
ggtaactccc aggagagtgt cacagagcag gacagcaagg acagcaccta cagcctcagc   600
agcaccctga cgctgagcaa agcagactac gagaaacaca agtctacgc ctgcgaagtc   660
acccatcagg gcctgagctc gcccgtcaca aagagcttca caggggaga gtgttagtga   720
```

<210> SEQ ID NO 28
<211> LENGTH: 238
<212> TYPE: PRT
<213> ORGANISM: Homo sapiens

<400> SEQUENCE: 28

```
Met Asp Met Arg Val Pro Ala Gln Leu Leu Gly Leu Leu Leu Leu Trp
 1               5                  10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Phe Thr Cys Arg Ala Ser
        35                  40                  45

Gln Asn Ile Thr Asn Tyr Leu Asn Trp Tyr Gln Gln Lys Pro Gly Lys
    50                  55                  60

Ala Pro Lys Leu Leu Ile Tyr Ala Ala Ser Ser Leu Pro Arg Gly Val
65                  70                  75                  80

Pro Ser Arg Phe Arg Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
           100                 105                 110

Ser Tyr Ser Asn Pro Pro Glu Cys Gly Phe Gly Gln Gly Thr Thr Leu
       115                 120                 125

Asp Ile Lys Arg Thr Val Ala Ala Pro Ser Val Phe Ile Phe Pro Pro
   130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
           180                 185                 190

Lys Asp Ser Thr Tyr Ser Leu Ser Ser Thr Leu Thr Leu Ser Lys Ala
       195                 200                 205

Asp Tyr Glu Lys His Lys Val Tyr Ala Cys Glu Val Thr His Gln Gly
   210                 215                 220
```

Leu Ser Ser Pro Val Thr Lys Ser Phe Asn Arg Gly Glu Cys
225                 230                 235

<210> SEQ ID NO 29
<211> LENGTH: 1434
<212> TYPE: DNA
<213> ORGANISM: Homo sapiens

<400> SEQUENCE: 29

| | | | | |
|---|---|---|---|---|
| atggaactgg ggctccgctg ggttttcctt gttgctattt tagaaggtgt ccagtgtgag | | | | 60 |
| gtgcagctgg tggagtctgg gggaggcctg gtcaagcctg gggggtccct gagactctcc | | | | 120 |
| tgtgcagcct ctggattcac cttcagtagc tatagcatga actgggtccg ccaggctcca | | | | 180 |
| gggaaggggc tggagtgggt ctcatccatt agtagtagta gtagttacat atactacgca | | | | 240 |
| gactcagtga agggccgatt caccatctcc agagacaacg ccaagaactc actgtatctg | | | | 300 |
| caaatgaaca gcctgagagc cgaggacacg gctgtgtatt actgtgcgag agatgggtat | | | | 360 |
| agcagtggct ggtcctacta ctactactac ggtatggacg tctggggcca agggaccacg | | | | 420 |
| gtcaccgtct cctcagcttc caccaagggc ccatccgtct tccccctggc gccctgctcc | | | | 480 |
| aggagcacct ccgagagcac agccgccctg ggctgcctgg tcaaggacta cttccccgaa | | | | 540 |
| ccggtgacgg tgtcgtggaa ctcaggcgcc ctgaccagcg gcgtgcacac cttcccggct | | | | 600 |
| gtcctacagt cctcaggact ctactccctc agcagcgtgg tgaccgtgcc ctccagcagc | | | | 660 |
| ttgggcacga agacctacac ctgcaacgta gatcacaagc ccagcaacac caaggtggac | | | | 720 |
| aagagagttg agtccaaata tggtccccca tgcccatcat gcccagcacc tgagttcctg | | | | 780 |
| gggggaccat cagtcttcct gttcccccca aaacccaagg acactctcat gatctcccgg | | | | 840 |
| acccctgagg tcacgtgcgt ggtggtggac gtgagccagg aagaccccga ggtccagttc | | | | 900 |
| aactggtacg tggatggcgt ggaggtgcat aatgccaaga caaagccgcg ggaggagcag | | | | 960 |
| ttcaacagca cgtaccgtgt ggtcagcgtc ctcaccgtcc tgcaccagga ctggctgaac | | | | 1020 |
| ggcaaggagt acaagtgcaa ggtctccaac aaaggcctcc cgtcctccat cgagaaaacc | | | | 1080 |
| atctccaaag ccaaagggca gccccgagag ccacaggtgt acaccctgcc cccatcccag | | | | 1140 |
| gaggagatga ccaagaacca ggtcagcctg acctgcctgg tcaaaggctt ctaccccagc | | | | 1200 |
| gacatcgccg tggagtggga gagcaatggg cagccggaga caactacaa gaccacgcct | | | | 1260 |
| cccgtgctgg actccgacgg ctccttcttc ctctacagca ggctaaccgt ggacaagagc | | | | 1320 |
| aggtggcagg aggggaatgt cttttcacgc tccgtgatgc atgaggctct gcacaaccac | | | | 1380 |
| tacacacaga gagcctctc cctgtctctg ggtaaatgat aggaattctg atga | | | | 1434 |

<210> SEQ ID NO 30
<211> LENGTH: 472
<212> TYPE: PRT
<213> ORGANISM: Homo sapiens

<400> SEQUENCE: 30

Met Glu Leu Gly Leu Arg Trp Val Phe Leu Val Ala Ile Leu Glu Gly
1               5                   10                  15

Val Gln Cys Glu Val Gln Leu Val Glu Ser Gly Gly Gly Leu Val Lys
                20                  25                  30

Pro Gly Gly Ser Leu Arg Leu Ser Cys Ala Ala Ser Gly Phe Thr Phe
            35                  40                  45

Ser Ser Tyr Ser Met Asn Trp Val Arg Gln Ala Pro Gly Lys Gly Leu
        50                  55                  60

```
Glu Trp Val Ser Ser Ile Ser Ser Ser Ser Tyr Ile Tyr Tyr Ala
 65                  70                  75                  80

Asp Ser Val Lys Gly Arg Phe Thr Ile Ser Arg Asp Asn Ala Lys Asn
             85                  90                  95

Ser Leu Tyr Leu Gln Met Asn Ser Leu Arg Ala Glu Asp Thr Ala Val
            100                 105                 110

Tyr Tyr Cys Ala Arg Asp Gly Tyr Ser Ser Gly Trp Ser Tyr Tyr Tyr
            115                 120                 125

Tyr Tyr Gly Met Asp Val Trp Gly Gln Gly Thr Thr Val Thr Val Ser
            130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Lys
            210                 215                 220

Thr Tyr Thr Cys Asn Val Asp His Lys Pro Ser Asn Thr Lys Val Asp
225                 230                 235                 240

Lys Arg Val Glu Ser Lys Tyr Gly Pro Pro Cys Pro Ser Cys Pro Ala
                245                 250                 255

Pro Glu Phe Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
            275                 280                 285

Val Asp Val Ser Gln Glu Asp Pro Glu Val Gln Phe Asn Trp Tyr Val
            290                 295                 300

Asp Gly Val Glu Val His Asn Ala Lys Thr Lys Pro Arg Glu Glu Gln
305                 310                 315                 320

Phe Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Gly
            340                 345                 350

Leu Pro Ser Ser Ile Glu Lys Thr Ile Ser Lys Ala Lys Gly Gln Pro
            355                 360                 365

Arg Glu Pro Gln Val Tyr Thr Leu Pro Pro Ser Gln Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Arg Leu Thr Val Asp Lys Ser Arg Trp Gln Glu Gly Asn Val Phe
            435                 440                 445

Ser Arg Ser Val Met His Glu Ala Leu His Asn His Tyr Thr Gln Lys
            450                 455                 460

Ser Leu Ser Leu Ser Leu Gly Lys
465                 470
```

```
<210> SEQ ID NO 31
<211> LENGTH: 723
<212> TYPE: DNA
<213> ORGANISM: Homo sapiens

<400> SEQUENCE: 31
atgaggctcc ctgctcagct cctggggctg ctaatgctct ggatacctgg atccagtgca      60
gatattgtga tgacccagac tccactctct ctgtccgtca ctcctggaca gccggcctcc     120
atctcctgca actctagtca gagcctcctg cttagtgatg gaaagaccta tttgaattgg     180
tacctgcaga agcccggcca gcctccacag ctcctgatct atgaagtttc caaccggttc     240
tctggagtgc cagacaggtt cagtggcagc gggtcaggga cagatttcac actgaaaatc     300
agccgggtgg aggctgagga tgttggggtt tattcctgca tgcaaagtat acagcttatg     360
tgcagttttg gccaggggac caagctggag atcaaacgaa ctgtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct tcaacagggg agagtgttag     720
tga                                                                   723

<210> SEQ ID NO 32
<211> LENGTH: 239
<212> TYPE: PRT
<213> ORGANISM: Homo sapiens

<400> SEQUENCE: 32

Met Arg Leu Pro Ala Gln Leu Leu Gly Leu Leu Met Leu Trp Ile Pro
  1               5                  10                  15

Gly Ser Ser Ala Asp Ile Val Met Thr Gln Thr Pro Leu Ser Leu Ser
                 20                  25                  30

Val Thr Pro Gly Gln Pro Ala Ser Ile Ser Cys Asn Ser Ser Gln Ser
             35                  40                  45

Leu Leu Leu Ser Asp Gly Lys Thr Tyr Leu Asn Trp Tyr Leu Gln Lys
         50                  55                  60

Pro Gly Gln Pro Pro Gln Leu Leu Ile Tyr Glu Val Ser Asn Arg Phe
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Val Gly Val Tyr Ser
            100                 105                 110

Cys Met Gln Ser Ile Gln Leu Met Cys Ser Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205
```

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 33
<211> LENGTH: 1410
<212> TYPE: DNA
<213> ORGANISM: Homo sapiens

<400> SEQUENCE: 33

```
atggactgga cctggagcat ccttttcttg gtggcagcag caacaggtgc ccactcccag       60
gttcagctgg tgcagtctgg agctgaggtg aagaagcctg ggcctcagt gaaggtctcc      120
tgcaaggctt ctggttacac ctttaccagc tatggtatca actgggtgcg acaggcccct      180
ggacaaggc ttgagtggat gggatggatc agcgtttaca gtggtaacac aaactatgca      240
cagaaggtcc agggcagagt caccatgacc gcagacacat ccacgagcac agcctacatg      300
gacctgagga gcctgagatc tgacgacacg gccgtgtatt actgtgcgag agagggtagc      360
agctcgtccg gagactacta ttacggtatg gacgtctggg gccaagggac cacggtcacc      420
gtctcctcag cctccaccaa gggcccatcg gtcttccccc tggcgccctg ctccaggagc      480
acctccgaga gcacagcggc cctgggctgc ctggtcaagg actacttccc cgaaccggtg      540
acggtgtcgt ggaactcagg cgctctgacc agcggcgtgc acaccttccc agctgtccta      600
cagtcctcag gactctactc cctcagcagc gtggtgaccg tgccctccag caacttcggc      660
acccagacct acacctgcaa cgtagatcac aagcccagca acaccaaggt ggacaagaca      720
gttgagcgca aatgttgtgt cgagtgccca ccgtgcccag caccacctgt ggcaggaccg      780
tcagtcttcc tcttcccccc aaaacccaag gacaccctca tgatctcccg gacccctgag      840
gtcacgtgcg tggtggtgga cgtgagccac gaagaccccg aggtccagtt caactggtac      900
gtggacggcg tggaggtgca taatgccaag acaaagccac gggaggagca gttcaacagc      960
acgttccgtg tggtcagcgt cctcaccgtt gtgcaccagg actggctgaa cggcaaggag     1020
tacaagtgca aggtctccaa caaaggcctc ccagccccca tcgagaaaac catctccaaa     1080
accaaagggc agccccgaga accacaggtg tacaccctgc ccccatcccg ggaggagatg     1140
accaagaacc aggtcagcct gacctgcctg gtcaaaggct tctacccag cgacatcgcc     1200
gtggagtggg agagcaatgg gcagccggag aacaactaca agaccacacc tcccatgctg     1260
gactccgacg gctccttctt cctctacagc aagctcaccg tggacaagag caggtggcag     1320
caggggaacg tcttctcatg ctccgtgatg catgaggctc tgcacaacca ctacacgcag     1380
aagagcctct ccctgtctcc gggtaaatga                                     1410
```

<210> SEQ ID NO 34
<211> LENGTH: 469
<212> TYPE: PRT
<213> ORGANISM: Homo sapiens

<400> SEQUENCE: 34

Met Asp Trp Thr Trp Ser Ile Leu Phe Leu Val Ala Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
        35                  40                  45

-continued

```
Thr Ser Tyr Gly Ile Asn Trp Val Arg Gln Ala Pro Gly Gln Gly Leu
     50                  55                  60

Glu Trp Met Gly Trp Ile Ser Val Tyr Ser Gly Asn Thr Asn Tyr Ala
 65                  70                  75                  80

Gln Lys Val Gln Gly Arg Val Thr Met Thr Ala Asp Thr Ser Thr Ser
                 85                  90                  95

Thr Ala Tyr Met Asp Leu Arg Ser Leu Arg Ser Asp Asp Thr Ala Val
            100                 105                 110

Tyr Tyr Cys Ala Arg Glu Gly Ser Ser Ser Gly Asp Tyr Tyr Tyr Tyr
        115                 120                 125

Gly Met Asp Val Trp Gly Gln Gly Thr Thr Val Thr Val Ser Ser Ala
130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Asn Phe Gly Thr Gln Thr Tyr
210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Gln Phe Asn Trp Tyr Val Asp Gly Val
290                 295                 300

Glu Val His Asn Ala Lys Thr Lys Pro Arg Glu Glu Gln Phe Asn Ser
305                 310                 315                 320

Thr Phe Arg Val Val Ser Val Leu Thr Val Val His Gln Asp Trp Leu
                325                 330                 335

Asn Gly Lys Glu Tyr Lys Cys Lys Val Ser Asn Lys Gly Leu Pro Ala
            340                 345                 350

Pro Ile Glu Lys Thr Ile Ser Lys Thr Lys Gly Gln Pro Arg Glu Pro
        355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Met Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460
```

Leu Ser Pro Gly Lys
465

<210> SEQ ID NO 35
<211> LENGTH: 723
<212> TYPE: DNA
<213> ORGANISM: Homo sapiens

<400> SEQUENCE: 35

| | | |
|---|---|---|
| atgaggctcc ctgctcagct cctggggctg ctaatgctct ggatacctgg atccagtgca | 60 |
| gatattgtga tgacccagac tccactctct ctgtccgtca cccctggaca gccggcctcc | 120 |
| atctcctgca gtctagtca gagcctcctg catactgatg gaacgaccta tttgtattgg | 180 |
| tacctgcaga agccaggcca gcctccacag ctcctgatct atgaagtttc caaccggttc | 240 |
| tctggagtgc cagataggtt cagtggcagc gggtcaggga cagatttcac actgaaaatc | 300 |
| agccgggtgg aggctgagga tgttgggatt tattactgca tgcaaaatat acagcttccg | 360 |
| tggacgttcg gccaagggac caaggtggaa atcaaacgaa ctgtggctgc accatctgtc | 420 |
| ttcatcttcc cgccatctga tgagcagttg aaatctggaa ctgcctctgt tgtgtgcctg | 480 |
| ctgaataact tctatcccag agaggccaaa gtacagtgga aggtggataa cgccctccaa | 540 |
| tcgggtaact cccaggagag tgtcacagag caggacagca aggacagcac ctacagcctc | 600 |
| agcagcaccc tgacgctgag caaagcagac tacgagaaac acaaagtcta cgcctgcgaa | 660 |
| gtcacccatc agggcctgag ctcgcccgtc acaaagagct tcaacagggg agagtgttag | 720 |
| tga | 723 |

<210> SEQ ID NO 36
<211> LENGTH: 239
<212> TYPE: PRT
<213> ORGANISM: Homo sapiens

<400> SEQUENCE: 36

Met Arg Leu Pro Ala Gln Leu Leu Gly Leu Leu Met Leu Trp Ile Pro
1               5                   10                  15

Gly Ser Ser Ala Asp Ile Val Met Thr Gln Thr Pro Leu Ser Leu Ser
            20                  25                  30

Val Thr Pro Gly Gln Pro Ala Ser Ile Ser Cys Lys Ser Ser Gln Ser
        35                  40                  45

Leu Leu His Thr Asp Gly Thr Thr Tyr Leu Tyr Trp Tyr Leu Gln Lys
    50                  55                  60

Pro Gly Gln Pro Pro Gln Leu Leu Ile Tyr Glu Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Ile Tyr Tyr
            100                 105                 110

Cys Met Gln Asn Ile Gln Leu Pro Trp Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp

```
                180                 185                 190
Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
        210                 215                 220

Gly Leu Ser Ser Pro Val Thr Lys Ser Phe Asn Arg Gly Glu Cys
225                 230                 235
```

<210> SEQ ID NO 37
<211> LENGTH: 1416
<212> TYPE: DNA
<213> ORGANISM: Homo sapiens

<400> SEQUENCE: 37

```
atgaaacacc tgtggttctt cctcctgctg gtggcagctc ccagatgggt cctgtcccag    60
gtgcagctgc aggagtcggg cccaggactg gtgaagcctt cggagaccct gtccctcacc   120
tgcactgtct ctggtagctc catcagtagt taccactgga actggatccg gcagcccgcc   180
gggaagggac tggagtggat tgggcgtatc tataccagtg ggagcaccaa ctacaacccc   240
tccctcaaga gtcgagtcac catgtcacta gacacgtcca agaaccagtt ctccctgaag   300
ctgagctctg tgaccgccgc ggacacggcc gtgtattact gtgcgagaga gggggtcagg   360
tattactatg cttcggggag ttattactac ggtctggacg tctggggcca agggaccacg   420
gtcaccgtct cctcagcctc caccaagggc ccatcggtct tccccctggc gccctgctcc   480
aggagcacct ccgagagcac agcggccctg ggctgcctgg tcaaggacta cttccccgaa   540
ccggtgacgg tgtcgtggaa ctcaggcgct ctgaccagcg gcgtgcacac cttcccagct   600
gtcctacagt cctcaggact ctactccctc agcagcgtgg tgaccgtgcc ctccagcaac   660
ttcggcaccc agacctacac ctgcaacgta gatcacaagc ccagcaacac caaggtggac   720
aagacagttg agcgcaaatg ttgtgtcgag tgcccaccgt gcccagcacc acctgtggca   780
ggaccgtcag tcttcctctt ccccccaaaa cccaaggaca cctcatgat ctcccggacc    840
cctgaggtca cgtgcgtggt ggtggacgtg agccacgaag accccgaggt ccagttcaac   900
tggtacgtgg acggcgtgga ggtgcataat gccaagacaa agccacggga ggagcagttc   960
aacagcacgt tccgtgtggt cagcgtcctc accgttgtgc accaggactg gctgaacggc  1020
aaggagtaca gtgcaaggt ctccaacaaa ggcctcccag cccccatcga aaaaccatc   1080
tccaaaacca agggcagcc cgagaacca caggtgtaca ccctgccccc atcccgggag  1140
gagatgacca gaaccaggt cagcctgacc tgcctggtca aaggcttcta ccccagcgac  1200
atcgccgtgg agtgggagag caatgggcag ccggagaaca actacaagac cacacctccc  1260
atgctggact ccgacggctc cttcttcctc tacagcaagc tcaccgtgga caagagcagg  1320
tggcagcagg ggaacgtctt ctcatgctcc gtgatgcatg aggctctgca caaccactac  1380
acgcagaaga gcctctccct gtctccgggt aaatga                            1416
```

<210> SEQ ID NO 38
<211> LENGTH: 471
<212> TYPE: PRT
<213> ORGANISM: Homo sapiens

<400> SEQUENCE: 38

```
Met Lys His Leu Trp Phe Phe Leu Leu Leu Val Ala Ala Pro Arg Trp
 1               5                  10                  15

Val Leu Ser Gln Val Gln Leu Gln Glu Ser Gly Pro Gly Leu Val Lys
```

```
            20                  25                  30
Pro Ser Glu Thr Leu Ser Leu Thr Cys Thr Val Ser Gly Ser Ser Ile
            35                  40                  45

Ser Ser Tyr His Trp Asn Trp Ile Arg Gln Pro Ala Gly Lys Gly Leu
            50                  55                  60

Glu Trp Ile Gly Arg Ile Tyr Thr Ser Gly Ser Thr Asn Tyr Asn Pro
 65                  70                  75                  80

Ser Leu Lys Ser Arg Val Thr Met Ser Leu Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Glu Gly Val Arg Tyr Tyr Ala Ser Gly Ser Tyr
            115                 120                 125

Tyr Tyr Gly Leu Asp Val Trp Gly Gln Gly Thr Thr Val Thr Val Ser
            130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Asn Phe Gly Thr Gln
            210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Gln Phe Asn Trp Tyr Val Asp
            290                 295                 300

Gly Val Glu Val His Asn Ala Lys Thr Lys Pro Arg Glu Glu Gln Phe
305                 310                 315                 320

Asn Ser Thr Phe Arg Val Val Ser Val Leu Thr Val Val His Gln Asp
                325                 330                 335

Trp Leu Asn Gly Lys Glu Tyr Lys Cys Lys Val Ser Asn Lys Gly Leu
            340                 345                 350

Pro Ala Pro Ile Glu Lys Thr Ile Ser Lys Thr Lys Gly Gln Pro Arg
            355                 360                 365

Glu Pro Gln Val Tyr Thr Leu Pro Pro Ser Arg Glu Glu Met Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Met Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445
```

Cys Ser Val Met His Glu Ala Leu His Asn His Tyr Thr Gln Lys Ser
        450                 455                 460

Leu Ser Leu Ser Pro Gly Lys
465                 470

<210> SEQ ID NO 39
<211> LENGTH: 720
<212> TYPE: DNA
<213> ORGANISM: Homo sapiens

<400> SEQUENCE: 39
atgaggctcc ctgctcagct cctggggctg ctaatgctct gggtctctgg atccagtggg    60
gatattgtga tgactcagtc tccactctcc ctgcccgtca cccctggaga gccggcctcc   120
atctcctgca ggtctagtca gagcctcctg catggtaatg gatacaacta tttggattgg   180
tacctgcaga agccagggca gtctccacag ctcctgatct atttgggttc taatcgggcc   240
tccggggtcc ctgacaggtt cagtggcagt ggatcaggca cagattttac actgaaaatc   300
agcagagtgg aggctgagga tgttggggtt tattactgca tgcaagctct acaaactctc   360
actttcggcg gagggaccaa ggtggagatc aaacgaactg tggctgcacc atctgtcttc   420
atcttcccgc catctgatga gcagttgaaa tctggaactg cctctgttgt gtgcctgctg   480
aataacttct atcccagaga ggccaaagta cagtggaagg tggataacgc cctccaatcg   540
ggtaactccc aggagagtgt cacagagcag gacagcaagg acagcaccta cagcctcagc   600
agcaccctga cgctgagcaa agcagactac gagaaacaca agtctacgc ctgcgaagtc   660 acccatcagg gcctgagctc gcccgtcaca aagagcttca caggggaga gtgttagtga   720

<210> SEQ ID NO 40
<211> LENGTH: 238
<212> TYPE: PRT
<213> ORGANISM: Homo sapiens

<400> SEQUENCE: 40

Met Arg Leu Pro Ala Gln Leu Leu Gly Leu Leu Met Leu Trp Val Ser
  1               5                  10                  15

Gly Ser Ser Gly Asp Ile Val Met Thr Gln Ser Pro Leu Ser Leu Pro
                 20                  25                  30

Val Thr Pro Gly Glu Pro Ala Ser Ile Ser Cys Arg Ser Ser Gln Ser
             35                  40                  45

Leu Leu His Gly Asn Gly Tyr Asn Tyr Leu Asp Trp Tyr Leu Gln Lys
         50                  55                  60

Pro Gly Gln Ser Pro Gln Leu Leu Ile Tyr Leu Gly Ser Asn Arg Ala
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Val Gly Val Tyr Tyr
            100                 105                 110

Cys Met Gln Ala Leu Gln Thr Leu Thr Phe Gly Gly Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
              180                 185                 190

Lys Asp Ser Thr Tyr Ser Leu Ser Ser Thr Leu Thr Leu Ser Lys Ala
          195                 200                 205

Asp Tyr Glu Lys His Lys Val Tyr Ala Cys Glu Val Thr His Gln Gly
      210                 215                 220

Leu Ser Ser Pro Val Thr Lys Ser Phe Asn Arg Gly Glu Cys
225                 230                 235

<210> SEQ ID NO 41
<211> LENGTH: 1410
<212> TYPE: DNA
<213> ORGANISM: Homo sapiens

<400> SEQUENCE: 41
atggactgga cctggagcat ccttttcttg gtggcagcag caacaggtgc ccactcccag      60
gttcagctgg tgcagtctgg agctgaggtg aagaagcctg ggcctcagt gaaggtctcc     120 tgcgaggctt ctggttacac ctttaccagc tatggtatcg actgggtgcg acaggcccct    180
ggacaagggc ttgagtggat gggatggatc agcgtttaca gtggtaacac aaactatgca    240
cagaagctcc agggcagagt caccatgtcc acagacacat ccacgagcac agcctacatg    300
gagctgagga gcctgagatc tgacgacacg gccgtgtatt actgtgcgag agagggtagc    360
agctcgtccg gagactacta ctacggtatg gacgtctggg gccaagggac cacggtcacc    420
gtctcctcag cctccaccaa gggcccatcg gtcttccccc tggcgccctg ctccaggagc    480
acctccgaga gcacagcggc cctgggctgc ctggtcaagg actacttccc cgaaccggtg    540
acggtgtcgt ggaactcagg cgctctgacc agcggcgtgc acaccttccc agctgtccta    600
cagtcctcag gactctactc cctcagcagc gtggtgaccg tgccctccag caacttcggc    660
acccagacct acacctgcaa cgtagatcac aagcccagca acaccaaggt ggacaagaca    720
gttgagcgca aatgttgtgt cgagtgccca ccgtgcccag caccacctgt ggcaggaccg    780
tcagtcttcc tcttcccccc aaaacccaag gacaccctca tgatctcccg gacccctgag    840
gtcacgtgcg tggtggtgga cgtgagccac gaagaccccg aggtccagtt caactggtac    900
gtggacggcg tggaggtgca taatgccaag acaaagccac gggaggagca gttcaacagc    960
acgttccgtg tggtcagcgt cctcaccgtt gtgcaccagg actggctgaa cggcaaggag   1020
tacaagtgca aggtctccaa caaaggcctc ccagccccca ttgagaaaac catctccaaa   1080
accaaagggc agccccgaga accacaggtg tacaccctgc ccccatcccg ggaggagatg   1140
accaagaacc aggtcagcct gacctgcctg gtcaaaggct tctacccag cgacatcgcc   1200 gtggagtggg agagcaatgg gcagccggag aacaactaca agaccacacc tcccatgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga                                     1410

<210> SEQ ID NO 42
<211> LENGTH: 469
<212> TYPE: PRT
<213> ORGANISM: Homo sapiens

<400> SEQUENCE: 42

Met Asp Trp Thr Trp Ser Ile Leu Phe Leu Val Ala Ala Ala Thr Gly
  1               5                  10                  15

Ala His Ser Gln Val Gln Leu Val Gln Ser Gly Ala Glu Val Lys Lys
            20                  25                  30

Pro Gly Ala Ser Val Lys Val Ser Cys Glu Ala Ser Gly Tyr Thr Phe
            35                  40                  45

Thr Ser Tyr Gly Ile Asp Trp Val Arg Gln Ala Pro Gly Gln Gly Leu
    50                  55                  60

Glu Trp Met Gly Trp Ile Ser Val Tyr Ser Gly Asn Thr Asn Tyr Ala
65                  70                  75                  80

Gln Lys Leu Gln Gly Arg Val Thr Met Ser Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Glu Gly Ser Ser Ser Gly Asp Tyr Tyr Tyr Tyr
            115                 120                 125

Gly Met Asp Val Trp Gly Gln Gly Thr Thr Val Thr Val Ser Ser Ala
130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Phe Arg Val Val Ser Val Leu Thr Val Val His Gln Asp Trp Leu
                325                 330                 335

Asn Gly Lys Glu Tyr Lys Cys Lys Val Ser Asn Lys Gly Leu Pro Ala
            340                 345                 350

Pro Ile Glu Lys Thr Ile Ser Lys Thr Lys Gly Gln Pro Arg Glu Pro
            355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Met Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
    435                 440                 445

Val Met His Glu Ala Leu His Asn His Tyr Thr Gln Lys Ser Leu Ser
    450                 455                 460

Leu Ser Pro Gly Lys
465

<210> SEQ ID NO 43
<211> LENGTH: 723
<212> TYPE: DNA
<213> ORGANISM: Homo sapiens

<400> SEQUENCE: 43

```
atgaggctcc ctgctcagct cctggggctg ctaatgctct ggatacctgg atccagtgcg    60
gatattgtga tgacccagac tccactctct ctgtccgtca cccctggaca gccggcctcc   120
atctcctgca agtctaatca gagcctcctg tatagtgatg aaagacctac tttgttttgg   180
tacctgcaga agccaggcca gcctccacag ctcctgatct atgaagtttc caaccgattc   240
tctggagtgc cagataggtt cagtggcagc gggtcaggga cagatttcac actgaaaatc   300
agccgggtgg aggctgagga tgttggggtt tattactgca tgcaaagtat acagcttccg   360
tggacgttcg gccaagggac caaggtggaa atcaaacgaa ctgtggctgc accatctgtc   420
ttcatcttcc cgccatctga tgagcagttg aaatctggaa ctgcctctgt tgtgtgcctg   480
ctgaataact tctatcccag agaggccaaa gtacagtgga aggtggataa cgccctccaa   540
tcgggtaact cccaggagag tgtcacagag caggacagca aggacagcac ctacagcctc   600
agcagcaccc tgacgctgag caaagcagac tacgagaaac acaaagtcta cgcctgcgaa   660
gtcacccatc agggcctgag ctcgcccgtc acaaagagct tcaacagggg agagtgttag   720
tga                                                                723
```

<210> SEQ ID NO 44
<211> LENGTH: 239
<212> TYPE: PRT
<213> ORGANISM: Homo sapiens

<400> SEQUENCE: 44

Met Arg Leu Pro Ala Gln Leu Leu Gly Leu Leu Met Leu Trp Ile Pro
  1               5                  10                  15

Gly Ser Ser Ala Asp Ile Val Met Thr Gln Thr Pro Leu Ser Leu Ser
                20                  25                  30

Val Thr Pro Gly Gln Pro Ala Ser Ile Ser Cys Lys Ser Asn Gln Ser
            35                  40                  45

Leu Leu Tyr Ser Asp Gly Lys Thr Tyr Leu Phe Trp Tyr Leu Gln Lys
        50                  55                  60

Pro Gly Gln Pro Pro Gln Leu Leu Ile Tyr Glu Val Ser Asn Arg Phe
 65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ser Ile Gln Leu Pro Trp Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu

```
                    145                 150                 155                 160
Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 45
<211> LENGTH: 1389
<212> TYPE: DNA
<213> ORGANISM: Homo sapiens

<400> SEQUENCE: 45
```

| | |
|---|---|
| atggagtttg ggctgagctg ggttttcctc gttgctcttt taagaggtgt ccagtgtcag | 60 |
| gtgcagctgg tggagtctgg gggaggcgtg gtccagcctg gaggtccct gagactctcc | 120 |
| tgtgcagcgt ctggattcac cttcagtagc tatggcatgc actgggtccg ccaggctcca | 180 |
| ggcaaggggc tggagtgggt ggcagttata tggtatgatg aagtaatga atactatgca | 240 |
| gactccgtga agggccgatt caccatctcc agagacaatt ccaagaacac gctgtatctg | 300 |
| caaatgaaca gcctgagagc cgaggacacg gctgtgtatt actgtgcgag ggggcgtac | 360 |
| cactttgcct actggggcca gggaaccctg gtcaccgtct cctcagcttc caccaagggc | 420 |
| ccatccgtct tccccctggc gccctgctcc aggagcacct ccgagagcac agccgccctg | 480 |
| ggctgcctgg tcaaggacta cttccccgaa ccggtgacgg tgtcgtggaa ctcaggcgcc | 540 |
| ctgaccagcg gcgtgcacac cttcccggct gtcctacagt cctcaggact ctactccctc | 600 |
| agcagcgtgg tgaccgtgcc ctccagcagc ttgggcacga gacctacac tgcaacgta | 660 |
| gatcacaagc ccagcaacac caaggtggac aagagagttg agtccaaata tggtccccca | 720 |
| tgcccatcat gcccagcacc tgagttcctg gggggaccat cagtcttcct gttccccca | 780 |
| aaacccaagg acactctcat gatctcccgg acccctgagg tcacgtgcgt ggtggtggac | 840 |
| gtgagccagg aagacccga ggtccagttc aactggtacg tggatggcgt ggaggtgcat | 900 |
| aatgccaaga caaagccgcg ggaggagcag ttcaacagca cgtaccgtgt ggtcagcgtc | 960 |
| ctcaccgtcc tgcaccagga ctggctgaac ggcaaggagt acaagtgcaa ggtctccaac | 1020 |
| aaaggcctcc cgtcctccat cgagaaaacc atctccaaag ccaaagggca gccccgagag | 1080 |
| ccacaggtgt acaccctgcc cccatcccag gaggagatga ccaagaacca ggtcagcctg | 1140 |
| acctgcctgg tcaaaggctt ctaccccagc gacatcgccg tggagtggga gagcaatggg | 1200 |
| cagccggaga caactacaa gaccacgcct cccgtgctgg actccgacgg ctccttcttc | 1260 |
| ctctacagca ggctaaccgt ggacaagagc aggtggcagg aggggaatgt cttctcatgc | 1320 |
| tccgtgatgc atgaggctct gcacaaccac tacacacaga gagcctctc cctgtctctg | 1380 |
| ggtaaatga | 1389 |

```
<210> SEQ ID NO 46
<211> LENGTH: 462
<212> TYPE: PRT
<213> ORGANISM: Homo sapiens
```

```
<400> SEQUENCE: 46

Met Glu Phe Gly Leu Ser Trp Val Phe Leu Val Ala Leu Leu Arg Gly
 1               5                  10                  15

Val Gln Cys Gln Val Gln Leu Val Glu Ser Gly Gly Gly Val Val Gln
             20                  25                  30

Pro Gly Arg Ser Leu Arg Leu Ser Cys Ala Ala Ser Gly Phe Thr Phe
         35                  40                  45

Ser Ser Tyr Gly Met His Trp Val Arg Gln Ala Pro Gly Lys Gly Leu
     50                  55                  60

Glu Trp Val Ala Val Ile Trp Tyr Asp Gly Ser Asn Glu Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Gly Ala Tyr His Phe Ala Tyr Trp Gly Gln Gly
        115                 120                 125

Thr Leu Val Thr Val Ser Ser Ala Ser Thr Lys Gly Pro Ser Val Phe
130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Lys Thr Tyr Thr Cys Asn Val Asp His Lys Pro
210                 215                 220

Ser Asn Thr Lys Val Asp Lys Arg Val Glu Ser Lys Tyr Gly Pro Pro
225                 230                 235                 240

Cys Pro Ser Cys Pro Ala Pro Glu Phe Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Gly Leu Pro Ser Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Gln Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415
```

```
Gly Ser Phe Phe Leu Tyr Ser Arg Leu Thr Val Asp Lys Ser Arg Trp
                420                 425                 430

Gln Glu Gly Asn Val Phe Ser Cys Ser Val Met His Glu Ala Leu His
            435                 440                 445

Asn His Tyr Thr Gln Lys Ser Leu Ser Leu Ser Leu Gly Lys
        450                 455                 460
```

<210> SEQ ID NO 47
<211> LENGTH: 720
<212> TYPE: DNA
<213> ORGANISM: Homo sapiens

<400> SEQUENCE: 47

```
atggacatga gggtccctgc tcagctcctg gggctcctgc tgctctggct ctcagtcgca      60
ggtgccagat gtgacatcca gatgacccag tctccatcct ccctgtctgc atctgtagga    120
gacagagtca ccatcacttg ccaggcgagt caggacatta gcaactattt aaattggtat    180
cagcagaaac cagggaaagc ccctaagctc ctgatctacg atgcatccaa tttgaaaaca    240
ggggtcccat caaggttcag tggaagtgga tctgggacag attttacttt caccatcagc    300
agcctgcagc ctgaagatat tgcaacatat tcctgtcaac actctgataa tctctcgatc    360
accttcggcc agggacacg actggagatt aaacgaactg tggctgcacc atctgtcttc    420
atcttcccgc catctgatga gcagttgaaa tctggaactg cctctgttgt gtgcctgctg    480
aataacttct accccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca agtctacgc ctgcgaagtc    660
acccatcagg gcctgagctc gcccgtcaca aagagcttca caggggagag tgttagtga    720
```

<210> SEQ ID NO 48
<211> LENGTH: 238
<212> TYPE: PRT
<213> ORGANISM: Homo sapiens

<400> SEQUENCE: 48

```
Met Asp Met Arg Val Pro Ala Gln Leu Leu Gly Leu Leu Leu Leu Trp
  1               5                  10                  15

Leu Ser Val Ala Gly Ala Arg Cys Asp Ile Gln Met Thr Gln Ser Pro
             20                  25                  30

Ser Ser Leu Ser Ala Ser Val Gly Asp Arg Val Thr Ile Thr Cys Gln
         35                  40                  45

Ala Ser Gln Asp Ile Ser Asn Tyr Leu Asn Trp Tyr Gln Gln Lys Pro
     50                  55                  60

Gly Lys Ala Pro Lys Leu Leu Ile Tyr Asp Ala Ser Asn Leu Glu Thr
 65                  70                  75                  80

Gly Val Pro Ser Arg Phe Ser Gly Ser Gly Ser Gly Thr Asp Phe Thr
                 85                  90                  95

Phe Thr Ile Ser Ser Leu Gln Pro Glu Asp Ile Ala Thr Tyr Ser Cys
            100                 105                 110

Gln His Ser Asp Asn Leu Ser Ile Thr Phe Gly Gln Gly Thr Arg Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160
```

Asn Asn Phe Tyr Pro Arg Glu Ala Lys Val Gln Trp Lys Val Asp Asn
            165                 170                 175

Ala Leu Gln Ser Gly Asn Ser Gln Glu Ser Val Thr Glu Gln Asp Ser
        180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235

<210> SEQ ID NO 49
<211> LENGTH: 681
<212> TYPE: DNA
<213> ORGANISM: Macaca fascicularis

<400> SEQUENCE: 49

```
atggatcggg gcctggccct cctgctggcg gggcttctgg ggctcctcca gccgggctgc     60
ggccagtccc tccaggtgaa gcccctgcag gtggagcccc cggagccggt ggtggccgtg    120
gccctgggcg cctctcgcca gctcacctgc cgcctggact gcgcggacgg cggggccacg    180
gtgcagtggc ggggcctgga caccagcctg ggcgcggtgc agtcggacgc gggccgcagc    240
gtcctcaccg tgcgcaacgc ctcgctgtcg gcggccggga cccgtgtgtg cgtgggctcc    300
tgcgggggcc gcaccttcca gcacaccgtg cggctccttg tgtacgcctt cccggaccag    360
ctgaccatct ccccggcagc cctggtgcct ggtgaccccg gaggtggcctg tacggctcac    420 aaagtcacgc ctgtggaccc caatgcgctc tccttctccc tgctcctggg ggaccaggaa    480
ctggaggggg cccaggctct gggcccggag gtggaggagg aggaggagcc ccaggaggag    540
gaggacgtgc tgttcagggt gacagagcgc tggcggctgc cgaccctggc aaccccctgtc    600 ctgcccgcgc tctactgcca ggccacgatg aggctgcctg gcttggagct cagccaccgc    660
caggccatcc cggtcctgca c                                              681
```

<210> SEQ ID NO 50
<211> LENGTH: 227
<212> TYPE: PRT
<213> ORGANISM: Macaca fascicularis

<400> SEQUENCE: 50

Met Asp Arg Gly Leu Ala Leu Leu Ala Gly Leu Leu Gly Leu Leu
1               5                   10                  15

Gln Pro Gly Cys Gly Gln Ser Leu Gln Val Lys Pro Leu Gln Val Glu
                20                  25                  30

Pro Pro Glu Pro Val Val Ala Val Ala Leu Gly Ala Ser Arg Gln Leu
        35                  40                  45

Thr Cys Arg Leu Asp Cys Ala Asp Gly Gly Ala Thr Val Gln Trp Arg
    50                  55                  60

Gly Leu Asp Thr Ser Leu Gly Ala Val Gln Ser Asp Ala Gly Arg Ser
65                  70                  75                  80

Val Leu Thr Val Arg Asn Ala Ser Leu Ser Ala Ala Gly Thr Arg Val
                85                  90                  95

Cys Val Gly Ser Cys Gly Gly Arg Thr Phe Gln His Thr Val Arg Leu
            100                 105                 110

Leu Val Tyr Ala Phe Pro Asp Gln Leu Thr Ile Ser Pro Ala Ala Leu
        115                 120                 125

```
Val Pro Gly Asp Pro Glu Val Ala Cys Thr Ala His Lys Val Thr Pro
    130                 135                 140

Val Asp Pro Asn Ala Leu Ser Phe Ser Leu Leu Gly Asp Gln Glu
145                 150                 155                 160

Leu Glu Gly Ala Gln Ala Leu Gly Pro Glu Val Glu Glu Glu Glu
                165                 170                 175

Pro Gln Glu Glu Glu Asp Val Leu Phe Arg Val Thr Glu Arg Trp Arg
                180                 185                 190

Leu Pro Thr Leu Ala Thr Pro Val Leu Pro Ala Leu Tyr Cys Gln Ala
        195                 200                 205

Thr Met Arg Leu Pro Gly Leu Glu Leu Ser His Arg Gln Ala Ile Pro
    210                 215                 220

Val Leu His
225

<210> SEQ ID NO 51
<211> LENGTH: 1398
<212> TYPE: DNA
<213> ORGANISM: Artificial Sequence
<220> FEATURE:
<223> OTHER INFORMATION: Description of Artificial Sequence: Modified
      human monoclonal antibody heavy chain nucleotide sequence

<400> SEQUENCE: 51
atggagtttg ggctgagctg ggttttcctc gttgctcttt taagaggtgt ccagtgtcag    60
gtgcagctgg tggagtctgg gggaggcgtg gtccagcctg gaggtccct gagactctcc    120 tgtgcagcgt ctggattcac cttcagtagc gatggcatgc actgggtccg ccaggctcca    180 ggcaagggc tggagtgggt ggcaattata tggtatgatg aagtaataa atattatgca    240 gactccgtga agggccgatt caccatctcc agagacaatt ccaagaacac gctgtatctg    300
caaatgaaca gcctgagagc cgaggacacg gctgtatatt actgtgcgag agatcccggc    360
tactattacg gtatggacgt ctggggccaa gggaccacgg tcaccgtctc ctcagcttcc    420
accaagggcc catccgtctt ccccctggcg ccctgctcta agcacctc cgagagcaca    480 gcggccctgg gctgcctggt caaggactac ttccccgaac cggtgacggt gtcgtggaac    540
tcaggcgctc tgaccagcgg cgtgcacacc ttcccagctg tcctacagtc ctcaggactc    600
tactccctca gcagcgtggt gaccgtgccc tccagcaact tcggcaccca gacctacacc    660
tgcaacgtag atcacaagcc cagcaacacc aaggtggaca agacagttga gcgcaaatgt    720
tgtgtcgagt gcccaccgtg cccagcacca cctgtggcag accgtcagt cttcctcttc    780 cccccaaaac ccaaggacac cctcatgatc tcccggaccc ctgaggtcac gtgcgtggtg    840
gtggacgtga gccacgaaga ccccgaggtc cagttcaact ggtacgtgga cggcgtggag    900
gtgcataatg ccaagacaaa gccacgggag gagcagttca acagcacgtt ccgtgtggtc    960
agcgtcctca ccgttgtgca ccaggactgg ctgaacggca aggagtacaa gtgcaaggtc   1020
tccaacaaag gcctcccagc ccccatcgag aaaaccatct ccaaaaccaa agggcagccc   1080
cgagaaccac aggtgtacac cctgccccca tcccgggagg agatgaccaa gaaccaggtc   1140
agcctgacct gcctggtcaa aggcttctac cccagcgaca tcgccgtgga gtgggagagc   1200
aatgggcagc cggagaacaa ctacaagacc acacctccca tgctggactc cgacggctcc   1260
ttcttcctct acagcaagct caccgtggac aagagcaggt ggcagcaggg gaacgtcttc   1320
tcatgctccg tgatgcatga ggctctgcac aaccactaca cgcagaagag cctctccctg   1380
```
tctccgggta aatgatag 1398

<210> SEQ ID NO 52
<211> LENGTH: 464
<212> TYPE: PRT
<213> ORGANISM: Artificial Sequence
<220> FEATURE:
<223> OTHER INFORMATION: Description of Artificial Sequence: Modified human monoclonal antibody heavy chain amino acid sequence

<400> SEQUENCE: 52

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Asp Gly Met His Trp Val Arg Gln Ala Pro Gly Lys Gly Leu
    50                  55                  60

Glu Trp Val Ala Ile Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Pro Gly Tyr Tyr Tyr Gly Met Asp Val Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
    355                 360                 365

Pro Pro Ser Arg Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 53
<211> LENGTH: 705
<212> TYPE: DNA
<213> ORGANISM: Artificial Sequence
<220> FEATURE:
<223> OTHER INFORMATION: Description of Artificial Sequence: Modified
      human monoclonal antibody light chain nucleotide sequence

<400> SEQUENCE: 53
atgttgccat cacaactcat tgggtttctg ctgctctggg ttccagcttc caggggtgaa       60
attgtgctga ctcagtctcc agactttcag tctgtgactc caaaagagaa agtcaccatc      120
acctgccggg ccagtcagag aattggtagt agcttacact ggtaccagca gaaaccagat      180
cagtctccaa aactcctcat caagtatgct tcccagtcct ctcagggggt cccctcgagg      240
ttcagtggca gtggatctgg gacagatttc accctcacca tcaatagcct ggaagctgaa      300
gatgctgcaa cttattactg tcatcagagt ggtcgtttac cgctcacttt cggcggaggg      360
accaaggtgg agatcaaacg aactgtggct gcaccatctg tcttcatctt cccgccatct      420
gatgagcagt tgaaatctgg aactgcctct gttgtgtgcc tgctgaataa cttctatccc      480
agagaggcca agtacagtg gaaggtggat aacgccctcc aatcgggtaa ctcccaggag       540
agtgtcacag agcaggacag caaggacagc acctacagcc tcagcagcac cctgacgctg      600
agcaaagcag actacgagaa acacaaagtc tacgcctgcg aagtcaccca tcagggcctg      660
agctcgcccg tcacaaagag cttcaacagg ggagagtgtt agtga                      705

<210> SEQ ID NO 54
<211> LENGTH: 233
<212> TYPE: PRT
<213> ORGANISM: Artificial Sequence
<220> FEATURE:
<223> OTHER INFORMATION: Description of Artificial Sequence: Modified
      human monoclonal antibody light chain amino acid sequence

<400> SEQUENCE: 54

Met Leu Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Arg Ile
        35                  40                  45

Gly Ser Ser Leu His Trp Tyr Gln Gln Lys Pro Asp Gln Ser Pro Lys
    50                  55                  60

```
Leu Leu Ile Lys Tyr Ala Ser Gln Ser Phe Ser Gly Val Pro Ser Arg
 65                  70                  75                  80

Phe Ser Gly Ser Gly Ser Gly Thr Asp Phe Thr Leu Thr Ile Asn Ser
                 85                  90                  95

Leu Glu Ala Glu Asp Ala Ala Thr Tyr Tyr Cys His Gln Ser Gly Arg
            100                 105                 110

Leu Pro Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

```
<210> SEQ ID NO 55
<211> LENGTH: 1410
<212> TYPE: DNA
<213> ORGANISM: Artificial Sequence
<220> FEATURE:
<223> OTHER INFORMATION: Description of Artificial Sequence: Modified
      human monoclonal antibody heavy chain nucleotide sequence

<400> SEQUENCE: 55
atggagtttg ggctgagctg ggttttcctc gttgctcttt taagaggtgt ccagtgtcag      60
gtgcagctgg tggagtctgg gggaggcgtg gtccagcctg ggaggtccct gagactctcc     120
tgtgcagcct ctggattcac cttcagtagc tatggcatgc actgggtccg ccaggctcca     180 ggcaagggc tggagtgggt ggcagttata tcaaatgatg gaaataataa atactatgca      240
gactccgtga agggccgatt caccatctcc agagacaatt ccaaaaacac gctgtatctg     300
caaatgaaca gcctgcgcgc tgaggacacg gctgtgtatt actgtgcgag atatagtacg     360
gcgataacct actactacta cggaatggac gtctggggcc aagggaccac ggtcaccgtc     420
tcctcagctt ccaccaaggg cccatccgtc ttccccctgg cgccctgctc tagaagcacc     480
tccgagagca gcgcggccct gggctgcctg gtcaaggact acttccccga accggtgacg     540
gtgtcgtgga actcaggcgc tctgaccagc ggcgtgcaca ccttcccagc tgtcctacag     600
tcctcaggac tctactccct cagcagcgtg gtgaccgtgc cctccagcaa cttcggcacc     660
cagacctaca cctgcaacgt agatcacaag cccagcaaca ccaaggtgga caagacagtt     720
gagcgcaaat gttgtgtcga gtgcccaccg tgcccagcac cacctgtggc aggaccgtca     780
gtcttcctct tccccccaaa acccaaggac accctcatga tctcccggac ccctgaggtc     840
acgtgcgtgg tggtggacgt gagccacgaa gaccccgagg tccagttcaa ctggtacgtg     900
gacggcgtgg aggtgcataa tgccaagaca aagccacggg aggagcagtt caacagcacg     960
ttccgtgtgg tcagcgtcct caccgttgtg caccaggact ggctgaacgg caaggagtac    1020
aagtgcaagg tctccaacaa aggcctccca gcccccatcg agaaaaccat ctccaaaacc    1080
```

-continued

```
aaagggcagc cccgagaacc acaggtgtac accctgcccc catcccggga ggagatgacc    1140
aagaaccagg tcagcctgac ctgcctggtc aaaggcttct accccagcga catcgccgtg    1200
gagtgggaga gcaatgggca gccggagaac aactacaaga ccacacctcc catgctggac    1260
tccgacggct ccttcttcct ctacagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaatgatag                                     1410
```

<210> SEQ ID NO 56
<211> LENGTH: 468
<212> TYPE: PRT
<213> ORGANISM: Artificial Sequence
<220> FEATURE:
<223> OTHER INFORMATION: Description of Artificial Sequence: Modified
      human monoclonal antibody heavy chain amino acid sequence

<400> SEQUENCE: 56

```
Met Glu Phe Gly Leu Ser Trp Val Phe Leu Val Ala Leu Leu Arg Gly
 1               5                  10                  15

Val Gln Cys Gln Val Gln Leu Val Glu Ser Gly Gly Gly Val Val Gln
             20                  25                  30

Pro Gly Arg Ser Leu Arg Leu Ser Cys Ala Ala Ser Gly Phe Thr Phe
         35                  40                  45

Ser Ser Tyr Gly Met His Trp Val Arg Gln Ala Pro Gly Lys Gly Leu
     50                  55                  60

Glu Trp Val Ala Val Ile Ser Asn Asp Gly Asn Asn Lys Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Ser Thr Ala Ile Thr Tyr Tyr Tyr Tyr Gly
        115                 120                 125

Met Asp Val Trp Gly Gln Gly Thr Thr Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Gln Phe Asn Trp Tyr Val Asp Gly Val Glu
```

```
                          290                 295                 300
Val His Asn Ala Lys Thr Lys Pro Arg Glu Glu Gln Phe Asn Ser Thr
305                 310                 315                 320

Phe Arg Val Val Ser Val Leu Thr Val Val His Gln Asp Trp Leu Asn
                325                 330                 335

Gly Lys Glu Tyr Lys Cys Lys Val Ser Asn Lys Gly Leu Pro Ala Pro
                    340                 345                 350

Ile Glu Lys Thr Ile Ser Lys Thr Lys Gly Gln Pro Arg Glu Pro Gln
                355                 360                 365

Val Tyr Thr Leu Pro Pro Ser Arg Glu Glu Met Thr Lys Asn Gln Val
                370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                    405                 410                 415

Pro Met Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
                435                 440                 445

Met His Glu Ala Leu His Asn His Tyr Thr Gln Lys Ser Leu Ser Leu
                450                 455                 460

Ser Pro Gly Lys
465

<210> SEQ ID NO 57
<211> LENGTH: 714
<212> TYPE: DNA
<213> ORGANISM: Artificial Sequence
<220> FEATURE:
<223> OTHER INFORMATION: Description of Artificial Sequence: Modified
      human monoclonal antibody light chain nucleotide sequence

<400> SEQUENCE: 57
atggacatga gggtccccgc tcagctcctg gggctcctgc tactctggct ccgaggtgcc      60
agatgtgaca tccagatgac ccagtctcca tcctccctgt ctgcatctgt cggagacaga     120
gtcaccatca cttgccgggc aagtcagagt attagtagct atttaaattg gtatcagcag     180
aaaccaggga aagcccctaa gctcctgatc tatgctgcat ccggtttgaa agtgggggtc     240
ccatcacggt tcagtggtag tggatctggg acagatttca ctctcaccat cagttctctg     300
caacctgagg attttgcaac ttactactgt caccagagtt acagtctccc attcactttc     360
ggccctggga ccaaagtgga tatcaaacga actgtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgtta gtga           714

<210> SEQ ID NO 58
<211> LENGTH: 236
<212> TYPE: PRT
<213> ORGANISM: Artificial Sequence
<220> FEATURE:
<223> OTHER INFORMATION: Description of Artificial Sequence: Modified
      human monoclonal antibody light chain amino acid sequence
```

<400> SEQUENCE: 58

```
Met Asp Met Arg Val Pro Ala Gln Leu Leu Gly Leu Leu Leu Leu Trp
  1               5                  10                  15

Leu Arg Gly Ala Arg Cys Asp Ile Gln Met Thr Gln Ser Pro Ser Ser
             20                  25                  30

Leu Ser Ala Ser Val Gly Asp Arg Val Thr Ile Thr Cys Arg Ala Ser
         35                  40                  45

Gln Ser Ile Ser Ser Tyr Leu Asn Trp Tyr Gln Lys Pro Gly Lys
     50                  55                  60

Ala Pro Lys Leu Leu Ile Tyr Ala Ala Ser Gly Leu Lys Arg Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys His Gln
            100                 105                 110

Ser Tyr Ser Leu Pro Phe Thr Phe Gly Pro Gly Thr Lys Val Asp Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 59
<211> LENGTH: 1413
<212> TYPE: DNA
<213> ORGANISM: Artificial Sequence
<220> FEATURE:
<223> OTHER INFORMATION: Description of Artificial Sequence: Modified
      human monoclonal antibody heavy chain nucleotide sequence

<400> SEQUENCE: 59

```
atgaaacacc tgtggttctt cctcctgctg gtggcagctc ccagatgggt cctgtcccag    60
gtgcagctgc aggagtcggg cccaggactg gtgaagcctt cggagaccct gtccctcacc   120
tgcactgtct ctggtgactc catcagtagt aactattgga gctggatccg gcagcccgcc   180
gggaagggac tggagtggat tgggcgtatc tataccagtg gggcaccaa ctccaacccc    240 tccctcaggg gtcgagtcac catgtcagta gacacgtcca agaaccagtt ctctctgaaa   300
ctgagttctg tgaccgccgc ggacacggcc gtgtattact gtgcgagaga tcgtattact   360
ataattcggg gacttattcc atccttcttt gactactggg gccagggaac cctggtcacc   420
gtctcctcag cttccaccaa gggcccatcc gtcttccccc tggcgccctg ctctagaagc   480
acctccgaga gcacagcggc cctgggctgc ctggtcaagg actacttccc cgaaccggtg   540
acggtgtcgt ggaactcagg cgctctgacc agcggcgtgc acaccttccc agctgtccta   600
cagtcctcag gactctactc cctcagcagc gtggtgaccg tgccctccag caacttcggc   660
```

```
acccagacct acacctgcaa cgtagatcac aagcccagca acaccaaggt ggacaagaca      720
gttgagcgca aatgttgtgt cgagtgccca ccgtgcccag caccacctgt ggcaggaccg      780
tcagtcttcc tcttcccccc aaaacccaag gacaccctca tgatctcccg gacccctgag      840
gtcacgtgcg tggtggtgga cgtgagccac gaagaccccg aggtccagtt caactggtac      900
gtggacggcg tggaggtgca taatgccaag acaaagccac gggaggagca gttcaacagc      960
acgttccgtg tggtcagcgt cctcaccgtt gtgcaccagg actggctgaa cggcaaggag     1020
tacaagtgca aggtctccaa caaaggcctc ccagccccca tcgagaaaac catctccaaa     1080 accaagggc agccccgaga accacaggtg tacaccctgc ccccatcccg ggaggagatg      1140
accaagaacc aggtcagcct gacctgcctg gtcaaaggct tctacccag cgacatcgcc      1200 gtggagtggg agagcaatgg gcagccggag aacaactaca agaccacacc tcccatgctg     1260
gactccgacg gctccttctt cctctacagc aagctcaccg tggacaagag caggtggcag     1320
caggggaacg tcttctcatg ctccgtgatg catgaggctc tgcacaacca ctacacgcag     1380
aagagcctct ccctgtctcc gggtaaatga tag                                  1413
```

<210> SEQ ID NO 60
<211> LENGTH: 469
<212> TYPE: PRT
<213> ORGANISM: Artificial Sequence
<220> FEATURE:
<223> OTHER INFORMATION: Description of Artificial Sequence: Modified
      human monoclonal antibody heavy chain amino acid sequence

<400> SEQUENCE: 60

```
Met Lys His Leu Trp Phe Phe Leu Leu Leu Val Ala Ala Pro Arg Trp
 1               5                   10                  15

Val Leu Ser Gln Val Gln Leu Gln Glu Ser Gly Pro Gly Leu Val Lys
                20                  25                  30

Pro Ser Glu Thr Leu Ser Leu Thr Cys Thr Val Ser Gly Asp Ser Ile
            35                  40                  45

Ser Ser Asn Tyr Trp Ser Trp Ile Arg Gln Pro Ala Gly Lys Gly Leu
        50                  55                  60

Glu Trp Ile Gly Arg Ile Tyr Thr Ser Gly Gly Thr Asn Ser Asn Pro
65                  70                  75                  80

Ser Leu Arg Gly Arg Val Thr Met Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Arg Ile Thr Ile Ile Arg Gly Leu Ile Pro Ser
        115                 120                 125

Phe Phe Asp Tyr Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Asn Phe Gly Thr Gln Thr Tyr
    210                 215                 220
```

```
Thr Cys Asn Val Asp His Lys Pro Ser Asn Thr Lys Val Asp Lys Thr
225                 230                 235                 240

Val Glu Arg Lys Cys Val Glu Cys Pro Pro Cys Pro Ala Pro Pro
            245                 250                 255

Val Ala Gly Pro Ser Val Phe Leu Phe Pro Pro Lys Pro Lys Asp Thr
        260                 265                 270

Leu Met Ile Ser Arg Thr Pro Glu Val Thr Cys Val Val Val Asp Val
        275                 280                 285

Ser His Glu Asp Pro Glu Val Gln Phe Asn Trp Tyr Val Asp Gly Val
        290                 295                 300

Glu Val His Asn Ala Lys Thr Lys Pro Arg Glu Gln Phe Asn Ser
305                 310                 315                 320

Thr Phe Arg Val Val Ser Val Leu Thr Val Val His Gln Asp Trp Leu
                325                 330                 335

Asn Gly Lys Glu Tyr Lys Cys Lys Val Ser Asn Lys Gly Leu Pro Ala
            340                 345                 350

Pro Ile Glu Lys Thr Ile Ser Lys Thr Lys Gly Gln Pro Arg Glu Pro
        355                 360                 365

Gln Val Tyr Thr Leu Pro Pro Ser Arg Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Met Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 61
<211> LENGTH: 729
<212> TYPE: DNA
<213> ORGANISM: Artificial Sequence
<220> FEATURE:
<223> OTHER INFORMATION: Description of Artificial Sequence: Modified
      human monoclonal antibody light chain nucleotide sequence

<400> SEQUENCE: 61
atggtgttgc agacccaggt cttcatttct ctgttgctct ggatctctgg tgcctacggg     60
gacatcgtga tgacccagtc tccagactcc ctggctgtgt ctctgggcga gagggccacc    120
atcaactgca gtccagcca gagtgtttta tacagctcca acaataagaa ctacttagct    180
tggtaccaac agaaaccagg acagcctcct aaattgctca tttactgggc atctatacgg    240
gaatatgggg tccctgaccg attcagtggc agcgggtctg ggacagattt cactctcacc    300
atcagcagcc tgcaggctga agatgtggca gtttatttct gtcaacaata ttatagtatt    360
cctcccctca ctttcggcgg agggaccaag gtggagatca aacgaactgt ggctgcacca    420
tctgtcttca tcttcccgcc atctgatgag cagttgaaat ctggaactgc ctctgttgtg    480
tgcctgctga taacttcta tcccagagag gccaaagtac agtggaaggt ggataacgcc    540
ctccaatcgg gtaactccca ggagagtgtc acagagcagg acagcaagga cagcacctac    600
```

```
agcctcagca gcaccctgac gctgagcaaa gcagactacg agaaacacaa agtctacgcc      660
tgcgaagtca cccatcaggg cctgagctcg cccgtcacaa agagcttcaa caggggagag      720
tgttagtga                                                              729
```

<210> SEQ ID NO 62
<211> LENGTH: 241
<212> TYPE: PRT
<213> ORGANISM: Artificial Sequence
<220> FEATURE:
<223> OTHER INFORMATION: Description of Artificial Sequence: Modified human monoclonal antibody light chain amino acid sequence

<400> SEQUENCE: 62

```
Met Val Leu Gln Thr Gln Val Phe Ile Ser Leu Leu Trp Ile Ser
 1               5                  10                  15

Gly Ala Tyr Gly Asp Ile Val Met Thr Gln Ser Pro Asp Ser Leu Ala
                20                  25                  30

Val Ser Leu Gly Glu Arg Ala Thr Ile Asn Cys Lys Ser Ser Gln Ser
        35                  40                  45

Val Leu Tyr Ser Ser Asn Asn Lys Asn Tyr Leu Ala Trp Tyr Gln Gln
    50                  55                  60

Lys Pro Gly Gln Pro Pro Lys Leu Leu Ile Tyr Trp Ala Ser Ile Arg
65                  70                  75                  80

Glu Tyr Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Phe Cys Gln Gln Tyr Tyr Ser Ile Pro Pro Leu Thr Phe Gly Gly Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys
```

<210> SEQ ID NO 63
<211> LENGTH: 1419
<212> TYPE: DNA
<213> ORGANISM: Artificial Sequence
<220> FEATURE:
<223> OTHER INFORMATION: Description of Artificial Sequence: Modified human monoclonal antibody heavy chain nucleotide sequence

<400> SEQUENCE: 63

```
atggaactgg ggctccgctg gtttttcctt gttgctattt tagaaggtgt ccagtgtgag      60
gtgcagctgg tggagtctgg gggaggcctg gtcaagcctg gggggtccct gagactctcc     120
```

```
tgtgcagcct ctggattcac cttcagtagc tatagcatga actgggtccg ccaggctcca    180
gggaagggc tggagtgggt ctcatccatt agtagtagta gtagttacat atactacgca     240
gactcagtga agggccgatt caccatctcc agagacaacg ccaagaactc actgtatctg    300
caaatgaaca gcctgagagc cgaggacacg gctgtgtatt actgtgcgag agatgggtat    360
agcagtggct ggtcctacta ctactactac ggtatggacg tctggggcca agggaccacg    420
gtcaccgtct cctcagcttc caccaagggc ccatccgtct tccccctggc gccctgctct    480
agaagcacct ccgagagcac agcggccctg ggctgcctgg tcaaggacta cttccccgaa    540
ccggtgacgg tgtcgtggaa ctcaggcgct ctgaccagcg gcgtgcacac cttcccagct    600
gtcctacagt cctcaggact ctactccctc agcagcgtgg tgaccgtgcc ctccagcaac    660
ttcggcaccc agacctacac ctgcaacgta gatcacaagc ccagcaacac caaggtggac    720
aagacagttg agcgcaaatg ttgtgtcgag tgcccaccgt gcccagcacc acctgtggca    780
ggaccgtcag tcttcctctt ccccccaaaa cccaaggaca cctcatgat ctcccggacc     840
cctgaggtca cgtgcgtggt ggtggacgtg agccacgaag accccgaggt ccagttcaac    900
tggtacgtgg acggcgtgga ggtgcataat gccaagacaa agccacggga ggagcagttc    960
aacagcacgt tccgtgtggt cagcgtcctc accgttgtgc accaggactg gctgaacggc   1020
aaggagtaca agtgcaaggt ctccaacaaa ggcctcccag cccccatcga gaaaaccatc   1080
tccaaaacca agggcagcc ccgagaacca caggtgtaca ccctgccccc atcccgggag    1140
gagatgacca gaaccaggt cagcctgacc tgcctggtca aaggcttcta cccagcgac    1200
atcgccgtgg agtgggagag caatgggcag ccggagaaca actacaagac cacacctccc   1260
atgctggact ccgacggctc cttcttcctc tacagcaagc tcaccgtgga caagagcagg   1320
tggcagcagg ggaacgtctt ctcatgctcc gtgatgcatg aggctctgca caaccactac   1380
acgcagaaga gcctctccct gtctccgggt aaatgatag                           1419
```

<210> SEQ ID NO 64
<211> LENGTH: 471
<212> TYPE: PRT
<213> ORGANISM: Artificial Sequence
<220> FEATURE:
<223> OTHER INFORMATION: Description of Artificial Sequence: Modified
      human monoclonal antibody heavy chain amino acid sequence

<400> SEQUENCE: 64

Met Glu Leu Gly Leu Arg Trp Val Phe Leu Val Ala Ile Leu Glu Gly
 1               5                  10                  15

Val Gln Cys Glu Val Gln Leu Val Glu Ser Gly Gly Gly Leu Val Lys
                20                  25                  30

Pro Gly Gly Ser Leu Arg Leu Ser Cys Ala Ala Ser Gly Phe Thr Phe
            35                  40                  45

Ser Ser Tyr Ser Met Asn Trp Val Arg Gln Ala Pro Gly Lys Gly Leu
        50                  55                  60

Glu Trp Val Ser Ser Ile Ser Ser Ser Ser Tyr Ile Tyr Tyr Ala
 65                 70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Asp Gly Tyr Ser Ser Gly Trp Ser Tyr Tyr Tyr
        115                 120                 125

Tyr Tyr Gly Met Asp Val Trp Gly Gln Gly Thr Thr Val Thr Val Ser
130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Asn Phe Gly Thr Gln
210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Gln Phe Asn Trp Tyr Val Asp
290                 295                 300

Gly Val Glu Val His Asn Ala Lys Thr Lys Pro Arg Glu Glu Gln Phe
305                 310                 315                 320

Asn Ser Thr Phe Arg Val Val Ser Val Leu Thr Val Val His Gln Asp
                325                 330                 335

Trp Leu Asn Gly Lys Glu Tyr Lys Cys Lys Val Ser Asn Lys Gly Leu
            340                 345                 350

Pro Ala Pro Ile Glu Lys Thr Ile Ser Lys Thr Lys Gly Gln Pro Arg
        355                 360                 365

Glu Pro Gln Val Tyr Thr Leu Pro Pro Ser Arg Glu Glu Met Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Met Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 65
<211> LENGTH: 723
<212> TYPE: DNA
<213> ORGANISM: Artificial Sequence
<220> FEATURE:
<223> OTHER INFORMATION: Description of Artificial Sequence: Modified
      human monoclonal antibody light chain nucleotide sequence

<400> SEQUENCE: 65
atgaggctcc ctgctcagct cctggggctg ctaatgctct ggataccctgg atccagtgca    60

```
gatattgtga tgacccagac tccactctct ctgtccgtca ctcctggaca gccggcctcc    120
atctcctgca agtctagtca gagcctcctg cttagtgatg aaagaccta tttgaattgg    180 tacctgcaga agcccggcca gcctccacag ctcctgatct atgaagtttc aaccggttc    240 tctggagtgc cagacaggtt cagtggcagc gggtcaggga cagatttcac actgaaaatc    300
agccgggtgg aggctgagga tgttggggtt tattactgca tgcaaagtat acagcttatg    360
tgcagttttg gccaggggac caagctggag atcaaacgaa ctgtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct tcaacagggg agagtgttag    720
tga                                                                 723
```

```
<210> SEQ ID NO 66
<211> LENGTH: 239
<212> TYPE: PRT
<213> ORGANISM: Artificial Sequence
<220> FEATURE:
<223> OTHER INFORMATION: Description of Artificial Sequence: Modified
      human monoclonal antibody light chain amino acid sequence

<400> SEQUENCE: 66
```

Met Arg Leu Pro Ala Gln Leu Leu Gly Leu Leu Met Leu Trp Ile Pro
 1               5                  10                  15

Gly Ser Ser Ala Asp Ile Val Met Thr Gln Thr Pro Leu Ser Leu Ser
            20                  25                  30

Val Thr Pro Gly Gln Pro Ala Ser Ile Ser Cys Lys Ser Gln Ser
        35                  40                  45

Leu Leu Leu Ser Asp Gly Lys Thr Tyr Leu Asn Trp Tyr Leu Gln Lys
    50                  55                  60

Pro Gly Gln Pro Pro Gln Leu Leu Ile Tyr Glu Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Ser
            100                 105                 110

Cys Met Gln Ser Ile Gln Leu Met Ser Ser Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys

<210> SEQ ID NO 67
<211> LENGTH: 723
<212> TYPE: DNA
<213> ORGANISM: Artificial Sequence
<220> FEATURE:
<223> OTHER INFORMATION: Description of Artificial Sequence: Modified
      human monoclonal antibody light chain nucleotide sequence

<400> SEQUENCE: 67

```
atgaggctcc ctgctcagct cctggggctg ctaatgctct ggatacctgg atccagtgcg    60
gatattgtga tgacccagac tccactctct ctgtccgtca cccctggaca gccggcctcc   120
atctcctgca agtctagtca gagcctcctg tatagtgatg gaaagaccta tttgttttgg   180
tacctgcaga agccaggcca gcctccacag ctcctgatct atgaagtttc caaccgattc   240
tctggagtgc cagataggtt cagtggcagc gggtcaggga cagatttcac actgaaaatc   300
agccgggtgg aggctgagga tgttggggtt tattactgca tgcaaagtat acagcttccg   360
tggacgttcg gccaagggac caaggtggaa atcaaacgaa ctgtggctgc accatctgtc   420
ttcatcttcc cgccatctga tgagcagttg aaatctggaa ctgcctctgt tgtgtgcctg   480
ctgaataact tctatcccag agaggccaaa gtacagtgga aggtggataa cgccctccaa   540
tcgggtaact cccaggagag tgtcacagag caggacagca aggacagcac ctacagcctc   600
agcagcaccc tgacgctgag caaagcagac tacgagaaac acaaagtcta cgcctgcgaa   660
gtcacccatc agggcctgag ctcgcccgtc acaaagagct tcaacagggg agagtgttag   720
tga                                                                 723
```

<210> SEQ ID NO 68
<211> LENGTH: 239
<212> TYPE: PRT
<213> ORGANISM: Artificial Sequence
<220> FEATURE:
<223> OTHER INFORMATION: Description of Artificial Sequence: Modified
      human monoclonal antibody light chain amino acid sequence

<400> SEQUENCE: 68

```
Met Arg Leu Pro Ala Gln Leu Leu Gly Leu Leu Met Leu Trp Ile Pro
1               5                   10                  15

Gly Ser Ser Ala Asp Ile Val Met Thr Gln Thr Pro Leu Ser Leu Ser
            20                  25                  30

Val Thr Pro Gly Gln Pro Ala Ser Ile Ser Cys Lys Ser Ser Gln Ser
        35                  40                  45

Leu Leu Tyr Ser Asp Gly Lys Thr Tyr Leu Phe Trp Tyr Leu Gln Lys
    50                  55                  60

Pro Gly Gln Pro Pro Gln Leu Leu Ile Tyr Glu Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ser Ile Gln Leu Pro Trp Thr Phe Gly Gly Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160
```

```
Leu Asn Asn Phe Tyr Pro Arg Glu Ala Lys Val Gln Trp Lys Val Asp
            165                 170                 175

Asn Ala Leu Gln Ser Gly Asn Ser Gln Glu Ser Val Thr Glu Gln Asp
        180                 185                 190

Ser Lys Asp Ser Thr Tyr Ser Leu Ser Ser Thr Leu Thr Leu Ser Lys
    195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 69
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Ser Gln Ser Leu Leu Gln Ser Asn Gly Tyr Asn Tyr Leu
1               5                   10

<210> SEQ ID NO 70
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tatctaagct tctagactcg agcgccacca tggactggac ctggagcatc ctt          53

<210> SEQ ID NO 71
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
tatctaagct tctagactcg agcgccacca tggagtttgg gctgagctgg att          53

<210> SEQ ID NO 72
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tatctaagct tctagactcg agcgccacca tggaactggg gctccgctgg gtt          53

<210> SEQ ID NO 73
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
```
tatctaagct tctagactcg agcgccacca tggagtttgg gctgagctgg ctt        53

<210> SEQ ID NO 74
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tatctaagct tctagactcg agcgccacca tggagtttgg gctgagctgg gtt        53

<210> SEQ ID NO 75
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tatctaagct tctagactcg agcgccacca tggagtttgg gctgagctgg gtt        53

<210> SEQ ID NO 76
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tatctaagct tctagactcg agcgccacca tgaaacacct gtggttcttc ctc        53

<210> SEQ ID NO 77
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tatctaagct tctagacccg ggcgccacca tgaggctccc tgctcagctc ctg        53

<210> SEQ ID NO 78
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tatctaagct tctagacccg ggcgccacca tgttgccatc acaactcatt ggg        53

<210> SEQ ID NO 79
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tatctaagct tctagacccg ggcgccacca tggtgttgca gacccaggtc ttc    53

<210> SEQ ID NO 80
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tatctaagct tctagacccg ggcgccacca tggacatgag ggtccccgct cag    53

<210> SEQ ID NO 81
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tatctaagct tctagacccg ggcgccacca tggacatgag ggtccctgct cag    53

<210> SEQ ID NO 82
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ttctctgatc agaattccta tcatttaccc ggagacaggg agag    44

<210> SEQ ID NO 83
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ttctttgatc agaattctca ctaacactct ccctgttga agc    43

<210> SEQ ID NO 84
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ttctctgatc agaattccta tcatttaccc agagacaggg agag    44

<210> SEQ ID NO 85
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ggatctggga cagatttcac cctcaccatc aatagcctgg aagc    44

<210> SEQ ID NO 86
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gcttccaggc tattgatggt gagggtgaaa tctgtcccag atcc                    44

<210> SEQ ID NO 87
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gcagcgtctg gattcacctt cagtagc                                       27

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gctactgaag gtgaatccag acgctgc                                       27

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
cggaggtgct tctagagcag ggcg                                          24

<210> SEQ ID NO 90
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gcaagtcaga gtattagtag ctatttaaat tggtatcagc agaaacc                 47

<210> SEQ ID NO 91
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ggtttctgct gataccaatt taaatagcta ctaatactct gacttgc                 47

<210> SEQ ID NO 92
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ccatcagttc tctgcaacct gaggattttg caacttacta ctgtcacc                48

<210> SEQ ID NO 93
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ggtgacagta gtaagttgca aaatcctcag gttgcagaga actgatgg                48

<210> SEQ ID NO 94
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gcaaatgaac agcctgcgcg ctgaggacac g                                  31

<210> SEQ ID NO 95
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cgtgtcctca gcgcgcaggc tgttcatttg c                                  31

<210> SEQ ID NO 96
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
caataagaac tacttagctt ggtaccaaca gaaaccagga cagcc                   45

<210> SEQ ID NO 97
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ggctgtcctg gtttctgttg gtaccaagct aagtagttct tattg                   45

<210> SEQ ID NO 98
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 98
ccctcagggg tcgagtcacc atgtcagtag acacgtccaa gaacc            45

<210> SEQ ID NO 99
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 99
ggttcttgga cgtgtctact gacatggtga ctcgacccct gaggg            45

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 100
attctagagc agggcgccag g                                       21

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 101
ccatctcctg caagtctagt cagagcctcc                              30

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 102
ggaggctctg actagacttg caggagatgg                              30

<210> SEQ ID NO 103
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
ggtttattac tgcatgcaaa gtatacagct tatgtccagt tttggcc           47

<210> SEQ ID NO 104

```
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
ggccaaaact ggacataagc tgtatacttt gcatgcagta ataaacc                47

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
cctgcaagtc tagtcagagc ctcc                                         24

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ggaggctctg actagacttg cagg                                         24

<210> SEQ ID NO 107
<211> LENGTH: 543
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107
```

Met Asp Phe Gly Leu Ala Leu Leu Leu Ala Gly Leu Leu Gly Leu Leu
 1               5                  10                  15

Leu Gly Gln Ser Leu Gln Val Lys Pro Leu Gln Val Glu Pro Pro Glu
                20                  25                  30

Pro Val Val Ala Val Ala Leu Gly Ala Ser Arg Gln Leu Thr Cys Arg
            35                  40                  45

Leu Ala Cys Ala Asp Arg Gly Ala Ser Val Gln Trp Arg Gly Leu Asp
        50                  55                  60

Thr Ser Leu Gly Ala Val Gln Ser Asp Thr Gly Arg Ser Val Leu Thr
    65                  70                  75                  80

Val Arg Asn Ala Ser Leu Ser Ala Ala Gly Thr Arg Val Cys Val Gly
                85                  90                  95

Ser Cys Gly Gly Arg Thr Phe Gln His Thr Val Gln Leu Leu Val Tyr
               100                 105                 110

Ala Phe Pro Asp Gln Leu Thr Val Ser Pro Ala Ala Leu Val Pro Gly
           115                 120                 125

Asp Pro Glu Val Ala Cys Thr Ala His Lys Val Thr Pro Val Asp Pro
       130                 135                 140

Asn Ala Leu Ser Phe Ser Leu Leu Val Gly Gly Gln Glu Leu Glu Gly
   145                 150                 155                 160

Ala Gln Ala Leu Gly Pro Glu Val Gln Glu Glu Glu Glu Glu Pro Gln 165                 170                 175
Gly Asp Glu Asp Val Leu Phe Arg Val Thr Glu Arg Trp Arg Leu Pro
            180                 185                 190

Pro Leu Gly Thr Pro Val Pro Pro Ala Leu Tyr Cys Gln Ala Thr Met
        195                 200                 205

Arg Leu Pro Gly Leu Glu Leu Ser His Arg Gln Ala Ile Pro Val Leu
    210                 215                 220

His Ser Pro Thr Ser Pro Glu Pro Pro Asp Thr Thr Ser Pro Glu Ser
225                 230                 235                 240

Pro Asp Thr Thr Ser Pro Glu Ser Pro Asp Thr Thr Ser Gln Glu Pro
            245                 250                 255

Pro Asp Thr Thr Ser Gln Glu Pro Pro Asp Thr Thr Ser Gln Glu Pro
        260                 265                 270

Pro Asp Thr Thr Ser Pro Glu Pro Pro Asp Lys Thr Ser Pro Glu Pro
    275                 280                 285

Ala Pro Gln Gln Gly Ser Thr His Thr Pro Arg Ser Pro Gly Ser Thr
290                 295                 300

Arg Thr Arg Arg Pro Glu Ile Gln Pro Lys Ser Cys Asp Lys Thr His
305                 310                 315                 320

Thr Cys Pro Pro Cys Pro Ala Pro Glu Leu Leu Gly Gly Pro Ser Val
            325                 330                 335

Phe Leu Phe Pro Pro Lys Pro Lys Asp Thr Leu Met Ile Ser Arg Thr
        340                 345                 350

Pro Glu Val Thr Cys Val Val Val Asp Val Ser His Glu Asp Pro Glu
    355                 360                 365

Val Lys Phe Asn Trp Tyr Val Asp Gly Val Glu Val His Asn Ala Lys
370                 375                 380

Thr Lys Pro Arg Glu Glu Gln Tyr Asn Ser Thr Tyr Arg Val Val Ser
385                 390                 395                 400

Val Leu Thr Val Leu His Gln Asp Trp Leu Asn Gly Lys Glu Tyr Lys
            405                 410                 415

Cys Lys Val Ser Asn Lys Ala Leu Pro Ala Pro Ile Glu Lys Thr Ile
        420                 425                 430

Ser Lys Ala Lys Gly Gln Pro Arg Glu Pro Gln Val Tyr Thr Leu Pro
    435                 440                 445

Pro Ser Arg Asp Glu Leu Thr Lys Asn Gln Val Ser Leu Thr Cys Leu
450                 455                 460

Val Lys Gly Phe Tyr Pro Ser Asp Ile Ala Val Glu Trp Glu Ser Asn
465                 470                 475                 480

Gly Gln Pro Glu Asn Asn Tyr Lys Ala Thr Pro Pro Val Leu Asp Ser
            485                 490                 495

Asp Gly Ser Phe Phe Leu Tyr Ser Lys Leu Thr Val Asp Lys Ser Arg
        500                 505                 510

Trp Gln Gln Gly Asn Val Phe Ser Cys Ser Val Met His Glu Ala Leu
    515                 520                 525

His Asn His Tyr Thr Gln Lys Ser Leu Ser Leu Ser Pro Gly Lys
530                 535                 540

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<220> FEATURE:
<221> NAME/KEY: modified_base
<222> LOCATION: (21)
<223> OTHER INFORMATION: Inosine

<400> SEQUENCE: 108
caggtgcagc tggagcagtc ngg                                              23

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gctgagggag tagagtcctg agga                                             24

<210> SEQ ID NO 110
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gctgagggag tagagtcctg aggactgt                                         28

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
agcatggatc ggggcctggc c                                                21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gtgcaggacc gggatggcct g                                                21

<210> SEQ ID NO 113
<211> LENGTH: 116
<212> TYPE: PRT
<213> ORGANISM: Homo sapiens

<400> SEQUENCE: 113

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
```

```
            50                  55                  60
Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Val Ala Asp Tyr Trp Gly Gln Gly Thr Leu Val Thr
                100                 105                 110

Val Ser Ser Ala
        115

<210> SEQ ID NO 114
<211> LENGTH: 116
<212> TYPE: PRT
<213> ORGANISM: Homo sapiens

<400> SEQUENCE: 114

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Gly Tyr Ser Tyr Gly Tyr Trp Gly Gln Gly Thr Leu Val Thr
                100                 105                 110

Val Ser Ser Ala
        115

<210> SEQ ID NO 115
<211> LENGTH: 117
<212> TYPE: PRT
<213> ORGANISM: Homo sapiens

<400> SEQUENCE: 115

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Tyr Tyr Gly Met Asp Val Trp Gly Gln Gly Thr Thr Val
                100                 105                 110

Thr Val Ser Ser Ala
        115
```

<210> SEQ ID NO 116
<211> LENGTH: 122
<212> TYPE: PRT
<213> ORGANISM: Homo sapiens

<400> SEQUENCE: 116

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Val Val Thr Tyr Tyr Tyr Tyr Gly Met Asp Val Trp Gly
            100                 105                 110

Gln Gly Thr Thr Val Thr Val Ser Ser Ala
        115                 120

<210> SEQ ID NO 117
<211> LENGTH: 120
<212> TYPE: PRT
<213> ORGANISM: Homo sapiens

<400> SEQUENCE: 117

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ile Thr Met Val Arg Gly Val Ile Phe Asp Tyr Trp Gly Gln Gly
            100                 105                 110

Thr Leu Val Thr Val Ser Ser Ala
        115                 120

<210> SEQ ID NO 118
<211> LENGTH: 121
<212> TYPE: PRT
<213> ORGANISM: Homo sapiens

<400> SEQUENCE: 118

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Ala Val Ala Tyr Tyr Tyr Gly Met Asp Val Trp Gly Gln
                100                 105                 110

Gly Thr Thr Val Thr Val Ser Ser Ala
            115                 120

<210> SEQ ID NO 119
<211> LENGTH: 125
<212> TYPE: PRT
<213> ORGANISM: Homo sapiens

<400> SEQUENCE: 119

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
                 20                  25                  30

Ser Met Asn Trp Val Arg Gln Ala Pro Gly Lys Gly Leu Glu Trp Val
             35                  40                  45

Ser Ser Ile Ser Ser Ser Ser Tyr Ile Tyr Tyr Ala Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Ser Ser Gly Trp Tyr Tyr Tyr Tyr Gly Met Asp
                100                 105                 110

Val Trp Gly Gln Gly Thr Thr Val Thr Val Ser Ser Ala
            115                 120                 125

<210> SEQ ID NO 120
<211> LENGTH: 121
<212> TYPE: PRT
<213> ORGANISM: Homo sapiens

<400> SEQUENCE: 120

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Gly Ile Ser Trp Val Arg Gln Ala Pro Gly Gln Gly Leu Glu Trp Met
             35                  40                  45

Gly Trp Ile Ser Ala Tyr Asn Gly Asn Thr Asn Tyr Ala Gln Lys Leu
            50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ser Ser Ser Tyr Tyr Tyr Gly Met Asp Val Trp Gly Gln
                100                 105                 110

Gly Thr Thr Val Thr Val Ser Ser Ala
            115                 120

<210> SEQ ID NO 121
<211> LENGTH: 122
<212> TYPE: PRT
<213> ORGANISM: Homo sapiens

<400> SEQUENCE: 121

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Tyr Tyr Gly Ser Gly Ser Tyr Tyr Gly Met Asp Val Trp Gly
            100                 105                 110

Gln Gly Thr Thr Val Thr Val Ser Ser Ala
        115                 120

<210> SEQ ID NO 122
<211> LENGTH: 112
<212> TYPE: PRT
<213> ORGANISM: Homo sapiens

<400> SEQUENCE: 122

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Phe Asp Tyr Trp Gly Gln Gly Thr Leu Val Thr Val Ser Ser Ala
            100                 105                 110

<210> SEQ ID NO 123
<211> LENGTH: 112
<212> TYPE: PRT
<213> ORGANISM: Homo sapiens

<400> SEQUENCE: 123

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Gln Ser
            20                  25                  30

Asn Gly Tyr Asn Tyr Leu Asp Trp Tyr Leu Gln Lys Pro Gly Gln Ser
        35                  40                  45

```
Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Ile Thr Phe Gly Gln Gly Thr Arg Leu Glu Ile Lys Arg
            100                 105                 110
```

<210> SEQ ID NO 124
<211> LENGTH: 107
<212> TYPE: PRT
<213> ORGANISM: Homo sapiens

<400> SEQUENCE: 124

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Val Leu Ile
            35                  40                  45

Phe Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Arg Leu Glu Ile Lys Arg
            100                 105
```

<210> SEQ ID NO 125
<211> LENGTH: 106
<212> TYPE: PRT
<213> ORGANISM: Homo sapiens

<400> SEQUENCE: 125

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
                20                  25                  30

Leu His Trp Tyr Gln Gln Lys Pro Asp Gln Ser Pro Lys Leu Leu Ile
            35                  40                  45

Lys Tyr Ala Ser Gln Ser Phe Thr Gly Val Pro Ser Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Thr Phe
                85                  90                  95

Gly Gly Gly Thr Lys Val Glu Ile Lys Arg
            100                 105
```

<210> SEQ ID NO 126
<211> LENGTH: 108
<212> TYPE: PRT
<213> ORGANISM: Homo sapiens

<400> SEQUENCE: 126

```
Asp Ile Gln Met Thr Gln Ser Pro Ser Ser Leu Ser Ala Ser Val Gly
```

```
            1               5                  10                 15
Asp Arg Val Thr Ile Thr Cys Arg Ala Ser Gln Ser Ile Ser Ser Tyr
                        20                 25                 30

Leu Asn Trp Tyr Gln Gln Lys Pro Gly Lys Ala Pro Lys Leu Leu Ile
                35                 40                 45

Tyr Ala Ala Ser Ser Leu Ser Gln Gly Val Pro Ser Arg Phe Ser Gly
         50                 55                 60

Ser Gly Ser Gly Thr Asp Phe Thr Leu Thr Ile Ser Ser Leu Gln Pro
65                  70                 75                 80

Glu Asp Phe Ala Thr Tyr Tyr Cys Gln Gln Ser Tyr Ser Thr Pro Phe
                85                 90                 95

Thr Phe Gly Pro Gly Thr Lys Val Asp Ile Lys Arg
                100                105
```

<210> SEQ ID NO 127
<211> LENGTH: 114
<212> TYPE: PRT
<213> ORGANISM: Homo sapiens

<400> SEQUENCE: 127

```
Asp Ile Val Met Thr Gln Ser Pro Asp Ser Leu Ala Val Ser Leu Gly
1               5                  10                 15

Glu Arg Ala Thr Ile Asn Cys Lys Ser Ser Gln Ser Val Leu Tyr Ser
                20                 25                 30

Ser Asn Asn Lys Asn Tyr Leu Ala Trp Tyr Gln Gln Lys Pro Gly Gln
            35                 40                 45

Pro Pro Lys Leu Leu Ile Tyr Trp Ala Ser Thr Arg Glu Ser Gly Val
    50                 55                 60

Pro Asp Arg Phe Ser Gly Ser Gly Ser Gly Thr Asp Phe Thr Leu Thr
65                 70                 75                 80

Ile Ser Ser Leu Gln Ala Glu Asp Val Ala Val Tyr Tyr Cys Gln Gln
                85                 90                 95

Tyr Tyr Ser Thr Pro Leu Thr Phe Gly Gly Gly Thr Lys Val Glu Ile
                100                105                110

Lys Arg
```

<210> SEQ ID NO 128
<211> LENGTH: 106
<212> TYPE: PRT
<213> ORGANISM: Homo sapiens

<400> SEQUENCE: 128

```
Asp Ile Gln Met Thr Gln Ser Pro Ser Ser Leu Ser Ala Ser Val Gly
1               5                  10                 15

Asp Arg Val Thr Ile Thr Cys Arg Ala Ser Gln Ser Ile Ser Ser Tyr
                20                 25                 30

Leu Asn Trp Tyr Gln Gln Lys Pro Gly Lys Ala Pro Lys Leu Leu Ile
                35                 40                 45

Tyr Ala Ala Ser Ser Leu Gln Ser Gly Val Pro Ser Arg Phe Ser Gly
         50                 55                 60

Ser Gly Ser Gly Thr Asp Phe Thr Leu Thr Ile Ser Ser Leu Gln Pro
65                  70                 75                 80

Glu Asp Phe Ala Thr Tyr Tyr Cys Gln Gln Ser Tyr Ser Thr Pro Phe
                85                 90                 95

Gly Gln Gly Thr Thr Leu Asp Ile Lys Arg
                100                105
```

```
<210> SEQ ID NO 129
<211> LENGTH: 110
<212> TYPE: PRT
<213> ORGANISM: Homo sapiens

<400> SEQUENCE: 129

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Phe Gly Gln Gly Thr Lys Leu Glu Ile Lys Arg
            100                 105                 110

<210> SEQ ID NO 130
<211> LENGTH: 113
<212> TYPE: PRT
<213> ORGANISM: Homo sapiens

<400> SEQUENCE: 130

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Trp Thr Phe Gly Gln Gly Thr Lys Val Glu Ile Lys
            100                 105                 110

Arg

<210> SEQ ID NO 131
<211> LENGTH: 112
<212> TYPE: PRT
<213> ORGANISM: Homo sapiens

<400> SEQUENCE: 131

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Gly
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
```

```
                    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Leu Thr Phe Gly Gly Gly Thr Lys Val Glu Ile Lys Arg
            100                 105                 110
```

<210> SEQ ID NO 132
<211> LENGTH: 107
<212> TYPE: PRT
<213> ORGANISM: Homo sapiens

<400> SEQUENCE: 132

```
Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Ile Thr
                 85                  90                  95

Phe Gly Gln Gly Thr Arg Leu Glu Ile Lys Arg
            100                 105
```

<210> SEQ ID NO 133
<211> LENGTH: 125
<212> TYPE: PRT
<213> ORGANISM: Homo sapiens

<400> SEQUENCE: 133

```
Gln Val Gln Leu Val Gln Ser Gly Ala Glu Val Lys Lys Pro Gly Ala
  1               5                  10                  15

Ser Val Lys Val Ser Cys Glu Ala Ser Gly Tyr Thr Phe Thr Ser Tyr
                 20                  25                  30

Gly Ile Asp Trp Val Arg Gln Ala Pro Gly Gln Gly Leu Glu Trp Met
             35                  40                  45

Gly Trp Ile Ser Val Tyr Ser Gly Asn Thr Asn Tyr Ala Gln Lys Leu
 50                  55                  60

Gln Gly Arg Val Thr Met Ser Thr Asp Thr Ser Thr Ser Thr Ala Phe
 65                  70                  75                  80

Phe Leu Leu Arg Ser Leu Arg Ser Asp Thr Ala Val Tyr Tyr Cys
                 85                  90                  95

Ala Arg Glu Gly Ser Ser Ser Gly Asp Tyr Tyr Gly Met Asp
            100                 105                 110

Val Trp Gly Gln Gly Thr Thr Val Thr Val Ser Ser Ala
        115                 120                 125
```

<210> SEQ ID NO 134
<211> LENGTH: 11
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 134

Cys Lys Pro Leu Gln Val Glu Pro Pro Glu Pro
 1               5                   10

<210> SEQ ID NO 135
<211> LENGTH: 8
<212> TYPE: PRT
<213> ORGANISM: Homo sapiens

<400> SEQUENCE: 135

Thr Phe Asn Asn Ser Ala Met Thr
 1               5

<210> SEQ ID NO 136
<211> LENGTH: 9
<212> TYPE: PRT
<213> ORGANISM: Homo sapiens

<400> SEQUENCE: 136

Cys Lys Ser Asn Gln Ser Leu Leu Tyr
 1               5

<210> SEQ ID NO 137
<211> LENGTH: 9
<212> TYPE: PRT
<213> ORGANISM: Homo sapiens

<400> SEQUENCE: 137

Ser Gly Thr Asn Phe Thr Leu Thr Ile
 1               5

<210> SEQ ID NO 138
<211> LENGTH: 9
<212> TYPE: PRT
<213> ORGANISM: Homo sapiens

<400> SEQUENCE: 138

Ala Ser Gln Asn Ile Ser Ser Tyr Leu
 1               5

<210> SEQ ID NO 139
<211> LENGTH: 9
<212> TYPE: PRT
<213> ORGANISM: Homo sapiens

<400> SEQUENCE: 139

Ser Ser Asn Asn Lys Thr Tyr Leu Ala
 1               5

<210> SEQ ID NO 140
<211> LENGTH: 8
<212> TYPE: PRT
<213> ORGANISM: Homo sapiens

<400> SEQUENCE: 140

Arg Ala Ser Gln Asn Ile Thr Asn
 1               5

<210> SEQ ID NO 141
<211> LENGTH: 8
<212> TYPE: PRT
<213> ORGANISM: Homo sapiens

```
<400> SEQUENCE: 141

Ser Cys Asn Ser Ser Gln Ser Leu
 1               5

<210> SEQ ID NO 142
<211> LENGTH: 8
<212> TYPE: PRT
<213> ORGANISM: Homo sapiens

<400> SEQUENCE: 142

His Ser Asp Asn Leu Ser Ile Thr
 1               5

<210> SEQ ID NO 143
<211> LENGTH: 7
<212> TYPE: PRT
<213> ORGANISM: Homo sapiens

<400> SEQUENCE: 143

Leu Gln Ser Asn Gly Tyr Asn
 1               5

<210> SEQ ID NO 144
<211> LENGTH: 7
<212> TYPE: PRT
<213> ORGANISM: Homo sapiens

<400> SEQUENCE: 144

Leu Gln Ser Asn Gly Tyr Asn
 1               5

<210> SEQ ID NO 145
<211> LENGTH: 7
<212> TYPE: PRT
<213> ORGANISM: Homo sapiens

<400> SEQUENCE: 145

His Gly Asn Gly Tyr Asn Tyr
 1               5

<210> SEQ ID NO 146
<211> LENGTH: 8
<212> TYPE: PRT
<213> ORGANISM: Homo sapiens

<400> SEQUENCE: 146

Leu Thr Ile Asn Gly Leu Glu Ala
 1               5

<210> SEQ ID NO 147
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 147

Gly Gly Gly Gly Ser Gly Gly Gly Ser Gly Gly Gly Gly Ser
 1               5                  10                  15
```